United States Patent [19]
Ali et al.

[11] Patent Number: 5,977,101
[45] Date of Patent: Nov. 2, 1999

[54] BENZIMIDAZOLES/IMIDAZOLES LINKED TO A FIBRINOGEN RECEPTOR ANTAGONIST TEMPLATE HAVING VITRONECTIN RECEPTOR ANTAGONIST ACTIVITY

[75] Inventors: Fadia El-Fehail Ali, Cherry Hill, N.J.; William Bondinell, Wayne, Pa.; William Francis Huffman, Malvern, Pa.; M. Amparo Lago, Audubon, Pa.; Richard McCulloch Keenan, Malvern, Pa.; Chet Kwon, King of Prussia, Pa.; William Henry Miller, Schwenksville, Pa.; Thomas Nguyen, King of Prussia, Pa.; Dennis T. Takata, Flourtown, Pa.

[73] Assignee: SmithKline Beecham Corporation, Philadelphia, Pa.

[21] Appl. No.: 08/505,171

[22] PCT Filed: Jun. 29, 1995

[86] PCT No.: PCT/US95/08306

§ 371 Date: Dec. 20, 1996

§ 102(e) Date: Dec. 20, 1996

[87] PCT Pub. No.: WO96/00730

PCT Pub. Date: Jan. 11, 1996

[51] Int. Cl.⁶ .......................... A61K 31/55; C07D 403/06; C07D 403/14
[52] U.S. Cl. .......................... 514/221; 514/218; 514/220; 540/542; 540/553; 540/559; 540/562; 540/568; 540/570; 540/575
[58] Field of Search .................................. 514/218, 220, 514/221; 540/542, 553, 559, 562, 568, 570, 575

[56] References Cited

U.S. PATENT DOCUMENTS

| | | | |
|---|---|---|---|
| 4,297,346 | 10/1981 | Rips et al. | 424/177 |
| 4,322,346 | 3/1982 | Korosi et al. | 540/487 |
| 4,327,026 | 4/1982 | Branca et al. | 424/244 |
| 4,339,583 | 7/1982 | Cross et al. | 546/256 |
| 4,361,511 | 11/1982 | Branca et al. | 424/244 |

(List continued on next page.)

FOREIGN PATENT DOCUMENTS

| | | | |
|---|---|---|---|
| 045 451 | of 1982 | European Pat. Off. . | |
| 048 045 | of 1982 | European Pat. Off. . | |
| 167 920 | of 1986 | European Pat. Off. | 540/570 |
| 0167920 | 1/1986 | European Pat. Off. | 540/570 |
| 275 748 | of 1988 | European Pat. Off. . | |

(List continued on next page.)

OTHER PUBLICATIONS

T. Green, et al, "Protective Groups In Organic Synthesis" 1991 by J. Wiley; pp. 309–315.

Chemical Abstracts, vol. 119, No. 3, Jul. 19, 1993, Graham et al, "HIV Protease Inhibitors with n–Terminal Polyether Substituents", p. 840, abstract No. 27838.

Chemical Abstracts, vol. 118, No. 19, issued May 10, 1993, Kempf et al, "Amino Acid Derivatives as HIV–1 Protease Inhibitors and Mthods for Their Synthesis", p. 1013, abstract No. 192283.

Chemical Abstracts, vol. 112, No. 7, issued Feb. 12, 1990, Ogawa et al, "One–Step Preparation of D–Penicillamine from Benzylpenicillin", p. 720, abstract No. 55358.

Chemical Abstracts, vol. 110, No. 24, issued Jun. 12, 1989, Katritzky et al, "Azlactones as Polymer Components and Intermediates", p. 11, abstract No. 213529.

Chemical Abstracts, vol. 101, No. 21, issued Nov. 19, 1984, Gakhar et al, "Substituted Benimidazole[2,1–h]pteridine–2, 4–diones", p. 764, abstract No. 191852.

(List continued on next page.)

*Primary Examiner*—Yogendra N. Gupta
*Attorney, Agent, or Firm*—Mary E. McCarthy; Stephen Venetianer; Charles M. Kinzig

[57] ABSTRACT

Vitronectin receptor antagonists having the formula:

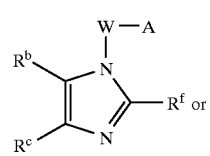

(I)

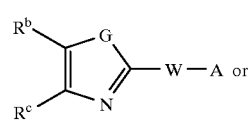

(II)

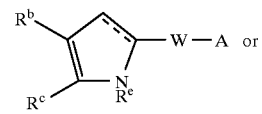

(III)

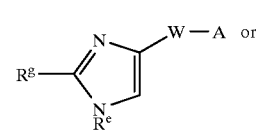

(IV)

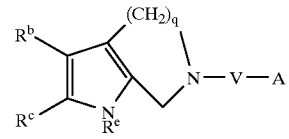

(V)

which are useful for the treatment of inflammation, cancer and cardiovascular disorders, such as atherosclerosis and restenosis, and diseases wherein bone resorption is a factor, such as osteoporsis.

18 Claims, No Drawings

U.S. PATENT DOCUMENTS

| | | | |
|---|---|---|---|
| 4,377,522 | 3/1983 | Branca et al. | 540/487 |
| 4,410,520 | 10/1983 | Watthey et al. | 424/244 |
| 4,497,740 | 2/1985 | Zeugner et al. | 540/573 |
| 4,556,660 | 12/1985 | Janssens et al. | 514/272 |
| 4,604,389 | 8/1986 | Reiffen et al. | 514/213 |
| 4,737,495 | 4/1988 | Bomhard et al. | 514/213 |
| 4,808,713 | 2/1989 | Attwood et al. | 540/487 |
| 4,820,834 | 4/1989 | Evans | 540/504 |
| 4,873,237 | 10/1989 | Crossley | 514/222.8 |
| 5,008,263 | 4/1991 | Cooper et al. | 514/220 |
| 5,017,571 | 5/1991 | Hansen et al. | 540/594 |
| 5,043,447 | 8/1991 | Pascal et al. | 540/575 |
| 5,059,688 | 10/1991 | Effland et al. | 540/594 |
| 5,096,900 | 3/1992 | George et al. | 514/213 |
| 5,149,699 | 9/1992 | Ellingboe et al. | 514/258 |
| 5,185,351 | 2/1993 | Finkelstein et al. | 514/341 |
| 5,241,065 | 8/1993 | Berger et al. | 540/523 |
| 5,250,679 | 10/1993 | Blackburn et al. | 540/490 |
| 5,300,668 | 4/1994 | Dasilva Jardine. | 556/441 |
| 5,403,836 | 4/1995 | Blackburn et al. | 514/213 |
| 5,438,118 | 8/1995 | Callahan et al | 530/330 |
| 5,470,849 | 11/1995 | Callahan et al. | 514/212 |
| 5,565,449 | 10/1996 | Blackburn et al. | 514/219 |
| 5,663,166 | 9/1997 | Blackburn et al. | 514/213 |
| 5,674,863 | 10/1997 | Blackburn et al. | 514/211 |
| 5,674,865 | 10/1997 | Blackburn et al. | 514/213 |
| 5,693,636 | 12/1997 | Bondinell et al. | 514/221 |

FOREIGN PATENT DOCUMENTS

| | | |
|---|---|---|
| 341 915 | of 1989 | European Pat. Off.. |
| WO 89/05150 | of 1989 | European Pat. Off.. |
| 372 486 | of 1990 | European Pat. Off.. |
| 381 033 | of 1990 | European Pat. Off.. |
| 447 857 | of 1991 | European Pat. Off.. |
| 478 328 | of 1992 | European Pat. Off.. |
| 478 362 | of 1992 | European Pat. Off.. |
| 478 363 | of 1992 | European Pat. Off.. |
| 479 481 | of 1992 | European Pat. Off.. |
| 512 829 | of 1992 | European Pat. Off.. |
| 523 845 | of 1993 | European Pat. Off.. |
| 3702755 | of 1988 | Germany . |
| WO 92/07568 | of 1992 | WIPO . |
| WO 92/09297 | of 1992 | WIPO . |
| WO 93/08174 | of 1993 | WIPO . |
| WO 93/00095 | 1/1993 | WIPO . |
| WO 93/08174 | 4/1993 | WIPO . |
| WO 94/11360 | of 1994 | WIPO . |
| WO 94/14776 | of 1994 | WIPO . |
| WO 95/04057 | of 1995 | WIPO . |
| WO 96/00574 | of 1996 | WIPO . |

OTHER PUBLICATIONS

Chemical Abtracts, vol. 100, No. 17, issued Apr. 23, 1984, Buess et al, "Nitrogen–14 and Chlorine–35 Nuclear Quadrupole Resonance Data for Nitrogen Mustards: Attempted Correlations with Chemical and Biological Activities", p. 18, abstract No. 132092.

Chemical Abstracts, vol. 100, No. 15, issued Apr. 9, 1984, Wilson et al., "Iminodiacetic Acid Derivatives of Benimidazole. Synthesis of N–(benzimidazol–2–ylmethyl)iminodiacetic acids", p. 584, abstract No. 120962.

Chemical Abstracts, vol. 99, No. 5, issued Aug. 1, 1983, Erhardt et al, "Ultra–short–acting .beta.–Adrenergic Receptor Blocking Agents. 3. Ethylenediamine Derivatives of (Aryloxy)propanolamines Having Esters on the Aryl Function", p. 117, abstract No. 32768.

Chemical Abstracts, vol. 78, No. 7, issued Feb. 19, 1973, Botta, "(Aminoalkyl) benzimidazoles, –thiazoles, andoxazoles", p. 493, abstract No. 43476.

Chemical Abstracts, vol. 123, No. 17, issued Oct. 2, 1995, Calderwood et al, "Imidazole Derivatives as Therapeutic Agents", p. 32, abstract No. 198799.

Chemical Abstracts, vol. 123, No. 5, issued May 3, 1995, Devadas et al, "Design and Syntheses of Potent and Selective Dipeptide Inhibitors of *Candida albicans* Myristoyl–CoA: Protein N–Myristoyltransferase", pp. 1837–1840, abstract No. 56550.

Chemical Abstracts, vol. 122, No. 7, issued Feb. 13, 1995, Silvestri et al, "Non–steriodal Antiinflammatory Agents. Synthesis and Enzyme Inhibition of 2–[4–(Heteroarylmethyl)phenul]propanoic Acids and Analogs", p. 24, abstract No. 71355.

Chemical Abstracts, vol. 122, No. 3, issued Jan. 16, 1995, DaDilva Jardine et al, "Benzylimidazolepyridine Derivatives as Angiotensin II Receptor Antagonists", p. 940, abstract No. 31518.

Chemical Abstracts, vol. 121, No. 17, issued Oct. 24, 1994, Mueller–Gliemann et al, "Substituted Imidazol[4,5–b]pyridines and Benzimidazoles", p. 1180, abstract No. 205394.

Chemical Abstracts, vol. 121, No. 15, issued Oct. 10, 1994, Hirata et al, "Manufacture of 4–(1–Imidazolylmethyl)cinnamic Acid", p. 1082, abstract No. 179589.

Chemical Abstracts, vol. 120, No. 21, issued May 23, 1994, Bryan et al, "[(Benzodioxolyl)methyl]propenoates and Their Use as Endotheline Receptor Antagonists", p. 1078, abstract No. 270460.

Chemical Abstracts, vol. 120, No. 19, issued May 9, 1994, Krantz et al, "Preparation of Cyclic Amides of 3–Amino–2–hydroxycarboxylic Acids as HIV Protease Inhibitors", p. 1125, abstract No. 245776.

Chemical Abstracts, vol. 120, No. 11, issued Mar. 14, 1994, Hamanaka et al, "heterocyclic Phenoxyacetic Acid Derivatives Antithrombotic and Antihypertensive Agents", p. 1041, abstract No. 134462.

Chemical Abstracts, vol. 120, No. 9, issued Feb. 28, 1994, Hauel et al, "Substituted Biphenyl Derivatives, Therapeutic Agents Containing Them and Process for Their Preparation", p. 1172, abstract No. 107067.

Chemical Abstracts, vol. 120, No. 9, issued Feb. 28, 1994, Clegg et al, "1–[(Arylalkyl)aminoalkyl]imidazoles with Antiinflammatory and Antiallergic Properties", p. 1164, abstract No. 107002.

Chemical Abstracts, vol. 119, No. 25, issued Dec. 20, 1993, Ito et al, "Preparation of Imidazoles as TXA2 Synthetase Inhibitors", p. 999, abstract No. 271164.

Chemical Abstracts, vol. 119, No. 6, issued Aug. 9, 1994, Chen et al, "Synthesis and Properties of a New Color Reagent BIACAB", p. 911, abstract No. 61801.

Chemical Abstracts, vol. 118, No. 23, issued Jun. 7, 1994, Mueller et al, "Preparation of (Azolylalkyl)phenylacetates and Related Compounds as Angiotensin II Antagonists", p. 1004, abstract No. 234063.

Chemical Abstracts, vol. 118, No. 19, issued May 10, 1993, Sprague et al, "OKY–046 Prevents Increase in LTB4 and Pulmonary Edema in Phorbol Ester–Induced Lung Injury in Dogs", p. 182, abstract No. 184200.

Chemical Abstracts, vol. 118, No. 11, issued Mar. 15, 1993, Dickinson et al, "5–alkyl–3–[(pyridyl)alkyl]benzenepropanoatesand 5–alkyl–3–[(imidazolyl)alkyl]benzenepropanoates, a Method for Their Preparation and Their Use as Thromboxane A2 Antagonists", p. 835, abstract No. 101812.

Chemical Abstracts, vol. 117, No. 19, issued Nov. 9, 1992, Meanwell et al, "Nonprostanoid Prostacyclin Mimetics. 3. Structural Variations of the Diphenyl Heterocycle Moiety", p. 800, abstract No. 191813.

Chemical Abstracts, vol. 117, No. 13, issued Sep. 28, 1992, Artico et al, "Aromatic Hydrazides as Specific Inhibitors of Bovine Serum Amine Oxidase", p. 739, abstract No. 131127.

Chemical Abstracts, vol. 116, No. 25, issued Jun. 22, 1992, Cooper et al, "Preparation of 6,7–Dihydroimidazo[1,5,4–ef][1,5]benzodiazepin–6–ones as Platelet Activating Factor Antagonists", p. 796, abstract No. 255646.

Chemical Abstracts, vol. 122, No. 13, issued Mar. 27, 1995, Chiku et al, "Pharmocokinetics of a New Benzimidazole Sulfoxide Derivative, E3810(2): Absorption, Distribution, Metabolism and Excretion in Rats", pp. 612–627, abstract No. 150780.

Chemical Abstracts, vol. 121, No. 25, issued Dec. 19, 1994, Yasuda et al, "Pharmacokinetic Properties of E3810, a New Proton Pump Inhibitor, in Healthy Male Volunteers", pp. 466–473, abstract No. 291924.

Chemical Abstracts, vol. 105, No. 23, issued Dec. 8, 1986, Hasegawa et al, "(Diazolylmethyl)pyridine Derivatives for Circulatory Diseases", p. 596, abstract No. 208885.

Chemical Abstracts, vol. 114, No. 13, issued Apr. 1, 1991, Strehlke et al, "Preparation of Imidazolyl–and Triazolylakylcycloketones as Aromatase Inhibitors", p. 801, abstract No. 122382.

Chemical Abstracts, vol. 98, No. 19, issued May 9, 1983, Lautenschlaeger et al, "Omega–[5–(1–imidazolylmethyl)thien–2–yl]alkanecarboxylic Acids, Their Derivatives and Pharmaceutical Preparations Containing Them", p. 515, abstract No. 160721.

Chemical Abstracts, vol. 96, No. 15, issued Apr. 12, 1982, "1–Substituted Imidazole Derivatives", p. 702, abstract No. 122794.

Chemical Abstracts, vol. 118, No. 11, issued Mar. 15, 1993, Hallinan et al, "Preparation of Dibenz[b,f][1,4]oxazepines and Related Compounds as Analgesics and Prostaglandin Antagonists", p. 858, abstract No. 102002.

Chemical Abstracts, vol. 115, No. 21, issued Nov. 25, 1991, Kmonicel et al, "Synthesis of a Series of 5–Methyl–1H–imidazol–4–ylmethyl Sulfides", p. 937, abstract No. 232128.

Sternbach, L.H., *J. Med Chem.*, 22, 2 (1979).

Friedinger, R.M., Cholecystokinin and Gastrin Antagonists, *Med. Res. Rev.*, 9, 271 (1989).

Mori et al., New Synthesis of Diazepinone Skeleton Using Palladium Catalyzed Carbonylation, *Heterocycles*, 16 (1981).

Muller et al., Synthese von 1,2–annelierten 1,4–Benzodiazepinen und 4,1–Benzoxazepinen, *Helv. Chim. Acta*, 65, 2118 (1982).

Heindel et al., Synthesis, Transformation and General Pharmacologic Activity in 1,4–Benzodiazepine–3,5–Diones, *J. Med. Chem.*, 14, 1233 (1971).

Pauwells et al., Potent and Selective Inhibition of HIV–1 Replication in vitro by a Novel Series of TIBO Derivatives, *Nature*, 343, 470 (1990).

Nichols et al., *J. Pharm. Exp. Ther.*, 270, 614 (1994).

Coller, *Coronary Artery Disease*, 3, 1016 (1992).

Topol et al. *Thrombosis and Haemostasis*, 70, 94 (1993).

Nichols et al., *TIPS*, 13, 413 (Nov. 1991).

Tighneanu et al., Double Cyclisation of Phenyglycine–o–carboxylic Acids–I, *Tetrahedron*, 36, 1385 (1980).

Callahan et al., *Peptide Chemistry 1992: Proceedings of the 2nd Japanese Symposium on Peptides Chemistry*, p. 495 (1993).

Ku et al., *J. Am. Chem. Soc.*, 115, 8861 (1993).

Tidwell et al., *Thrombosis Research*, vol. 19, pp. 339–349 (1980).

Ku et al., *J. Med. Chem.*, 38(1), pp. 9–12 (1995).

BENZIMIDAZOLES/IMIDAZOLES LINKED TO A FIBRINOGEN RECEPTOR ANTAGONIST TEMPLATE HAVING VITRONECTIN RECEPTOR ANTAGONIST ACTIVITY

FIELD OF THE INVENTION

This invention relates to pharmaceutically active compounds which inhibit the vitronectin receptor and are useful for the treatment of inflammation, cancer and cardiovascular disorders, such as atherosclerosis and restenosis, and diseases wherein bone resorption is a factor, such as osteoporosis.

BACKGROUND OF THE INVENTION

Integrins are a superfamily of cell adhesion receptors, which are transmembrane glycoproteins expressed on a variety of cells. These cell surface adhesion receptors include gpIIb/IIIa, the fibrinogen receptor, and $\alpha_v\beta_3$, the vitronectin receptor. The fibrinogen receptor gpIIb/IIIa is expressed on the platelet surface and it mediates platelet aggregation and the formation of a hemostatic clot at the site of a bleeding wound. Philips, et al, *Blood.*, 1988, 71, 831. The vitronectin receptor $\alpha_v\beta_3$ is expressed on a number of cells, including endothelial, smooth muscle, osteoclast, and tumor cells, and, thus, it has a variety of functions. The $\alpha_v\beta_3$ receptor expressed on the membrane of osteoclast cells mediates the bone resorption process and contributes to the development of osteoporosis. Ross, et al., *J. Biol Chem.*, 1987, 262, 7703. The $\alpha_v\beta_3$ receptor expressed on human aortic smooth muscle cells stimulates their migration into neointima, which leads to the formation of atherosclerosis and restenosis after angioplasty. Brown, et al, *Cardiovascular Res.*, 1994, 28, 1815. Additionally, a recent study has shown that a $\alpha_v\beta_3$ antagonist is able to promote tumor regression by inducing apoptosis of angiogenic blood vessels. Brooks, et al, *Cell*, 1994, 79, 1157. Thus, agents that would block the vitronectin receptor would be useful in treating diseases mediated by this receptor, such as osteoporosis, atherosclerosis, restenosis and cancer.

The vitronectin receptor is known to bind to bone matrix proteins, such as osteopontin, bone sialoprotein and thrombospondin, which contain the tri-peptide Arg-Gly-Asp (or RGD) motif. Thus, Horton, et al., *Exp. Cell Res.* 1991, 195, 368, disclose that RGD-containing peptides and an anti-vitronectin receptor antibody (23C6) inhibit dentine resorption and cell spreading by osteoclasts. In addition, Sato, et al., *J. Cell Biol.* 1990, 111, 1713 disclose that echistatin, a snake venom peptide which contains the RGD sequence, is a potent inhibitor of bone resorption in tissue culture, and inhibits attachment of osteoclasts to bone. Fisher, et al., *Endocrinology* 1993, 132, 1411, has further shown that echistatin inhibits bone resorption in vivo in the rat. Bertolini et al., *J. Bone Min. Res.*, 6, Sup. 1, S146, 252 have shown that cylco-S,S-$N^\alpha$-acetyl-cysteinyl-$N^\alpha$-methyl-argininyl-glycyl-aspartyl-penicillamine inhibits osteoclast attachment to bone. EP 528 587 and 528 586 report substituted phenyl derivatives which inhibit osteoclast mediated bone resorption.

Alig et al., EP 0 381 033, Hartman, et al., EP 0 540,334, Blackburn, et al., WO 93/08174, Bondinell, et al., WO 93/00095, Blackburn, et al. WO 95/04057, Egbertson, et al, EP 0 478 328, Sugihara, et al. EP 529,858, Porter, et al., EP 0 542 363, and Fisher, et al., EP 0 635 492 disclose certain compounds that are useful for inhibiting the fibrinogen receptor. It has now been discovered that certain appropriately substituted compounds are potent inhibitors of the vitronectin receptor. In particular, it has been discovered that such compounds are more potent inhibitors of the vitronectin receptor than the fibrinogen receptor and such compounds contain a fibrinogen receptor antagonist template.

SUMMARY OF THE INVENTION

This invention comprises compounds of the formula (I)–(V) as described hereinafter, which have pharmacological activity for the inhibition of the vitronection receptor and are useful in the treatment of inflammation, cancer and cardiovascular disorders, such as atherosclerosis and restenosis, and diseases wherein bone resorption is a factor, such as osteoporosis.

This invention is also a pharmaceutical composition comprising a compound according to formula (I)–(V) and a pharmaceutically carrier.

This invention is also a method of treating diseases which are mediated by the vitronectin receptor. In a particular aspect, the compounds of this invention are useful for treating atherosclerosis, restenosis, inflammation, cancer and diseases wherein bone resorption is a factor, such as osteoporosis.

DETAILED DESCRIPTION

This invention comprises novel compounds which are more potent inhibitors of the vitronectin receptor than the fibrinogen receptor. The compounds of the instant invention comprise a fibrinogen receptor antagonist template that is linked to a nitrogen-containing five-membered ring, which is optionally fused to an aromatic six-membered ring. The fibrinogen receptor antagonist template is substituted by an aliphatic substituent which contains an acidic moiety. It is preferred that about fourteen intervening covalent bonds via the shortest intramolecular path will exist between the acidic group of the fibrinogen receptor antagonist template and the nitrogen of the optionally fused five-membered ring.

As used herein, the term "fibrinogen receptor antagonist template" means the core structure of a fibrinogen receptor antagonist, said core being substituted by an acidic group and said core being linked to an organic group substituted with a basic nitrogen moiety. A fibrinogen receptor antagonist is an agent that inhibits the binding of fibrinogen to the platelet-bound fibrinogen receptor GPIIb–IIIa. It is an object of this invention that a fibrinogen receptor antagonist is converted to a vitronectin receptor antagonist by replacing the organic group substituted with a basic nitrogen moiety in a fibrinogen receptor antagonist with an optionally fused nitrogen-containing five-membered ring, preferably an imidazole ring and, most preferably, a benzimidazole ring.

This invention comprises compounds of formula (I)–(V):

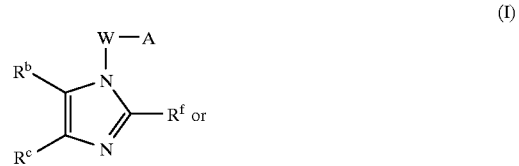

(I)

-continued

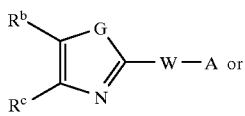
(II)

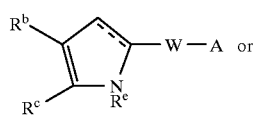
(III)

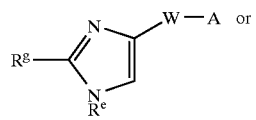
(IV)

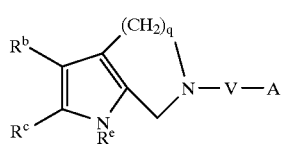
(V)

wherein:

W is $CHR^g{}_a$—U—$CHR^g{}_b$—V— or

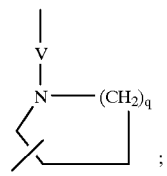
;

A is a fibrinogen receptor antagonist template;
U and V are absent or CO, $CR^g{}_2$, $C(=CR^g{}_2)$, $S(O)_k$, O, $NR^g$, $CR^gOR^g$, $CR^g(OR^k)CR^g{}_2$, $CR^g{}_2CR^g(OR^k)$, $C(O)CR^g{}_2$, $CR^g{}_2C(O)$, $CONR^i$, $NR^iCO$, $OC(O)$, $C(O)O$, $C(S)O$, $OC(S)$, $C(S)NR^g$, $NR^gC(S)$, $S(O)_2NR^g$, $NR^gS(O)_2$ $N=N$, $NR^gNR^g$, $NR^gCR^g{}_2$, $NR^gCR^g{}_2$, $CR^g{}_2O$, $OCR^g{}_2$, $C\equiv C$ or $CR^g=CR^g$;

G is $NR^e$, S or O;

$R^g$ is H, $C_{1-6}$alkyl, Het-$C_{0-6}$alkyl, $C_{3-7}$cycloalkyl-$C_{0-6}$alkyl or Ar—$C_{0-6}$alkyl;

$R^k$ is $R^g$, —$C(O)R^g$, or —$C(O)OR^f$;

$R^i$ is H, $C_{1-6}$alkyl, Het-$C_{0-6}$alkyl, $C_{3-7}$cycloalkyl-$C_{0-6}$alkyl, Ar—$C_{0-6}$alkyl, or $C_{1-6}$alkyl substituted by one to three groups chosed from halogen, CN, $NR^g{}_2$, $OR^g$, $SR^g$, $CO_2R^g$, and $CON(R^g)_2$;

$R^f$ is H, $C_{1-6}$alkyl or Ar—$C_{1-6}$alkyl;

$R^e$ is H, $C_{1-6}$alkyl, Ar—$C_{1-6}$alkyl, Het-$C_{1-6}$alkyl, $C_{3-7}$cycloalkyl-$C_{1-6}$alkyl, or $(CH_2)_kCO_2R^g$;

k is 0, 1 or 2;
q is 1 or 2;
a is 0, 1 or 2;
b is 0, 1 or 2;
$R^b$ and $R^c$ are independently selected from H, $C_{1-6}$alkyl, Ar—$C_{0-6}$alkyl, Het-$C_{0-6}$alkyl, or $C_{3-6}$cycloalkyl-$C_{0-6}$alkyl, halogen, $CF_3$, $OR^f$, $S(O)_kR^f$, $COR^f$, $NO_2$, $N(R^f)_2$, $CO(NR^f)_2$, $CH_2N(R^f)_2$, or $R^b$ and $R^c$ are joined together to form a five or six membered aromatic or non-aromatic carbocyclic or heterocyclic ring, optionally substituted by up to three substituents chosen from halogen, $CF_3$, $C_{1-4}$alkyl, $OR^f$, $S(O)_kR^f$, $COR^f$, $CO_2R^f$ OH, $NO_2$, $N(R^f)_2$, $CO(NR^f)_2$, and $CH_2N(R^f)_2$; or methylenedioxy;

or a pharmaceutically acceptable salt thereof, with the proviso that:

(i) when A is 1,2,4,5-tetrahydro-3-oxo-4-(2-phenylethyl)-1H-1,4-benzodiazepine-2-acetic acid, then W is not —$(CH_2)_{2-3}$NHCO— attached at the 1-position of an imidazole ring; and (ii) when A is 1,2,4,5-tetrahydro-3-oxo-4-(2-phenylethyl)-1H-1,4-benzodiazepine-2-acetic acid, then W is not —$(CH_2)_2$ NHCO— attached at the 4(5)-position of an imidazole ring.

Also included in this invention are pharmaceutically acceptable addition salts, complexes or prodrugs of the compounds of this invention. Prodrugs are considered to be any covalently bonded carriers which release the active parent drug according to formula (I) in vivo. In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. In cases wherein compounds may exist in tautomeric forms, such as keto-enol tautomers, such as

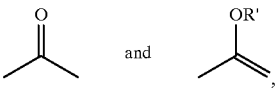

and each tautomeric form is contemplated as being included within this invention whether existing in equilibrium or locked in one form by appropriate substitution with R'.

The compounds of formula (I)–(V) inhibit the binding of vitronectin and other RGD-containing peptides to the vitronectin ($\alpha_v\beta_3$) receptor. Inhibition of the vitronectin receptor on osteoclasts inhibits osteoclastic bone resorption and is useful in the treatment of diseases wherein bone resorption is associated with pathology, such as osteoporosis. Additionally, since the compounds of the instant invention inhibit vitronectin receptors on a number of different types of cells, said compounds would be useful in the treatment of inflammation and cardiovascular diseases, such as atherosclerosis and restenosis, and would be useful as antimetastatic and antitumor agents.

In a particuar embodiment, the compounds of this invention are of the formula (II), wherein $R^b$ and $R^c$ are joined to form an aromatic ring containing up to two nitrogen atoms. In a preferred embodiment $R^b$ and $R^c$ are joined to form an optionally substituted phenyl ring according to formula (IIa):

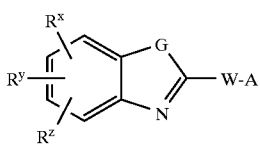
(IIa)

wherein G is N—$R^e$, S, CH or O.

Suitably W is —$(CHR^g)_aNR^iCO$— or

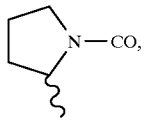

or, when G is CH, W is —$CH_2CH_2NR^iCO$— wherein $R^i$ is a methylene group attached to G.

Preferably W is —$CHR^gNR^iCO$—.

Suitably $R^i$ is H, $C_{1-6}$alkyl, $C_{3-7}$cycloalkyl, Ar or $C_{1-6}$alkyl substituted by one to three groups chosen from halogen, CN, $NR^g_2$, $OR^g$, $SR^g$, $CO_2R^g$, and $CON(R^g)_2$, Ar, Het or $C_{3-7}$cycloalkyl. In particular, $R^i$ is H, methyl, butyl, cyanomethyl, carboxymethyl, phenylethyl or benzimidazolylmethyl.

Suitably $R^x$, $R^y$ and $R^z$ are independently chosen from $C_{1-6}$alkyl, methoxy, nitro, trifluoromethyl, fluoro, chloro, amino or $R^x$ and $R^y$ are adjacent to one another and are joined to form a methylenedioxy group.

Preferably G is $NR^e$.

Suitably $R^e$ is H, $C_{1-4}$alkyl, Ar, Het or $C_{1-4}$alkyl substituted by Ar or Het. More suitably, $R^e$ is H, methyl or benzimidazolylmethyl.

In another specific embodiment, $R^b$ and $R^c$ form a six membered aromatic ring containing one or two nitrogen atoms according to formulas (IIb–d):

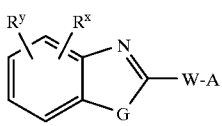
(IIb)

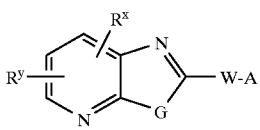
(IIc)

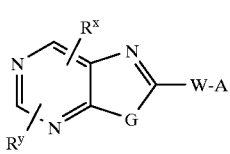
(IId)

wherein G, $R^x$ and $R^y$ are as above for formula (IIa).

In another aspect this invention is an intermediate compound of formula XXX:

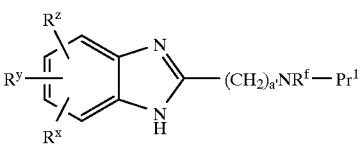
(XXX)

wherein $Pr^1$ is a nitrogen protecting group, $R^f$ is H, $C_{1-6}$alkyl or $ArC_{1-6}$alkyl, a' is 1–3, and $R^x$, $R^y$ and $R^z$ are independently chosen from H, halogen, $SR^f$, $OR^f$, $CF_3$, $N(R^f)_2$, $NO_2$ and $C_{1-6}$alkyl. Preferred nitrogen protecting groups are alkyl and aryl carboxylic acid groups, and alkyloxycarbonyl or arylmethyloxycarbonyl groups, such as the acetyl, BOC and Cbz group. Typically $R^g$ is H or methyl.

Specifically, the compounds of this invention are comprised of a nitrogen-containing optionally fused five-membered ring, a linking group W, and a fibrinogen receptor antagonist template A. In particular, the fibrinogen receptor antagonist template A is as defined in Bondinell, et al., WO 93/00095, published Jan. 7, 1993, of the sub-formula (VI):

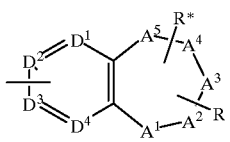
(VI)

$A^1$ to $A^5$ form an accessible substituted seven-membered ring, which may be saturated or unsaturated, optionally containing up to two heteroatoms chosen from the group of O, S and N wherein S and N may be optionally oxidized;

$D^1$ to $D^4$ form an accessible substituted six membered ring, optionally containing up to two nitrogen atoms;

R is at least one substituent chosen from the group of $R^7$, or Q-$C_{1-4}$alkyl, Q-$C_{2-4}$alkenyl, Q-$C_{2-4}$alkynyl, optionally substituted by one or more of =O, $R^{11}$ or $R^7$;

R* is H, Q-$C_{1-6}$alkyl, Q-$C_{1-6}$oxoalkyl, Q-$C_{2-6}$alkenyl, Q-$C_{3-4}$oxoalkenyl, Q-$C_{3-4}$oxoalkynyl, Q-$C_{2-4}$alkynyl, $C_{3-6}$cycloalkyl, Ar or Het, optionally substituted by one or more of $R^{11}$;

Q is H, $C_{3-6}$cycloalkyl, Het or Ar;

$R^7$ is —$COR^8$, —$COCR'_2R^9$, —$C(S)R^8$, —$S(O)_mOR'$, —$S(O)_mNR'R''$, —$PO(OR')$, —$PO(OR')_2$, —$B(OR')_2$, —$NO_2$ and Tet;

$R^8$ is —OR—, —NR'R'', —$NR'SO_2R'$, —NR'OR', $OCR'_2C(O)OR'$, —$OCR'_2OC(O)$—R', —$OCR'_2C(O)NR'_2$, $CF_3$ or $AA^1$;

$R^9$ is —OR', —CN, —$S(O)_rR'$, $S(O)_mNR'_2$, —$C(O)R'$ $C(O)NR'_2$ or —$CO_2R'$;

$R^{11}$ is H, halo, —$OR^{12}$, —CN, —$NR'R^{12}$, —$NO_2$, —$CF_3$, $CF_3S(O)_r$, —$CO_2R'$, —$CONR'_2$, Q-$C_{0-6}$alkyl-, Q-$C_{1-6}$oxoalkyl-, Q-$C_{2-6}$alkenyl-, Q-$C_{2-6}$alkynyl-, Q-$C_{0-6}$alkyloxy-, Q-$C_{0-6}$alkylamino- or Q-$C_{0-6}$alkyl-S(O)$_r$—;

$R^{12}$ is R', —C(O)R', —C(O)NR'$_2$, —C(O)OR$^{15}$, —S(O)$_m$R' or S(O)$_m$NR'$_2$;

$R^{13}$ is R', —CF$_3$, —SR', or —OR';

$R^{14}$ is R', C(O)R', CN, NO$_2$, SO$_2$R' or C(O)OR$^{15}$;

$R^{15}$ is H, C$_{1-6}$alkyl or Ar—C$_{0-4}$alkyl;

R' is H, C$_{1-6}$alkyl, C$_{3-7}$cycloalkyl-C$_{0-4}$alkyl or Ar—C$_{0-4}$alkyl;

R" is R', —C(O)R' or —C(O)OR$^{15}$;

R'" is R" or AA2;

AA1 is an amino acid attached through its amino group and having its carboxyl group optionally protected, and AA$_2$ is an amino acid attached through its carboxyl group, and having its amino group optionally protected;

m is 1 or 2;

n is 0 to 3;

p is 0 or 1; and t is 0 to 2; or pharmaceutically acceptable salts thereof, with the proviso that:

(i) when A is 1,2,4,5-tetrahydro-3-oxo-4-(2-phenylethyl)-1H-1,4-benzodiazepine-2-acetic acid, then W is not —(CH$_2$)$_{2-3}$NHCO— attached at the 1-position of an imidazole ring; and (ii) when A is 1,2,4,5-tetrahydro-3-oxo-4-(2-phenylethyl)-1H-1,4-benzodiazepine-2-acetic acid, then W is not —(CH$_2$)$_2$NHCO— attached at the 4(5)-position of an imidazole ring.

With reference to formula (VI), suitably, $A^1$ is CR$^1$R$^{1'}$, CR$^1$, NR$^1$, N, O or S(O)$_x$;

$A^2$ is CR$^2$R$^{2'}$, CR$^2$, NR$^2$;

$A^3$ is CR$^3$R$^{3'}$, CR$^3$, NR$^3$, N, O or S(O)$_x$;

$A^4$ is CR$^4$R$^{4'}$, CR$^4$, NR$^4$, or N;

$A^5$ is CR$^5$R$^{5'}$, CR$^5$, NR$^5$, N, O or S(O)$_x$;

$D^1$–$D^4$ are CR$^{11}$, CR$^6$ or N;

$R^1$ and $R^{1'}$ are R* or R, or together are =O;

$R^2$ and $R^{2'}$ are R*, R or =O;

$R^3$ and $R^{3'}$ are R*, R or =O;

$R^4$ and $R^{4'}$ are R*, R or =O;

$R^5$ and $R^{5'}$ are R*, R or =O; and x is 0 to 2.

More suitably, $A^1$ is CR$^1$R$^{1'}$, CR$^1$, NR$^1$, N, O or S; $A^2$ is CR$^2$R$^{2'}$, NR$^2$ or CR$^2$; $A^3$ is CR$^3$R$^{3'}$; $A^4$ is CR$^4$R$^{4'}$, CR$^4$, NR$^4$, or N; $A^5$ is CR$^5$R$^{5'}$, CR$^5$, NR$^5$, N, O; $D^1$–$D^4$ are CH; $R^2$ or $R^4$ are R; $R^3,R^{3'}$ and $R^5,R^{5'}$ are =O or R*,H.

Preferably, $A^1$ is CHR$^1$, CR$^1$, NR", N or S; $A^2$ is CR$^2$ or CR$^2$R$^{2'}$; $A^3$ is CR$^3$R$^{3'}$; $A^4$ is CR$^4$R$^{4'}$ or NR$^4$; $A^5$ is CR$^5$R$^{5'}$, and $D^1$–$D^4$ are CH.

In one embodiment, $A^1$ is CR$^1$, $A^2$ is CR$^2$, $A^3$ is C=O, $A^4$ is NR$^4$ and $A^5$ are CHR$^5$.

In another embodiment, $A^1$ is NR$^1$, $A^2$ is CHCR$^2$, $A^3$ is CR$^3$R$^{3'}$, $A^4$ is NR$^4$, and $A^5$ are C=O.

In yet another embodiment, $A^1$ and $A^4$ are C=O, $A^2$ is NR$^2$, $A^3$ is CHR$^{3'}$ and $A^5$ is NR$^5$.

In a preferred embodiment, $A^1$ is NR$^1$, $A^2$ is CHR$^2$, $A^3$ is C=O, $A^4$ is NR' and $A^5$ is CHR$^5$.

Representative sub-formulas of (VI) are given by each of formulas (VIa)–(VIi) below:

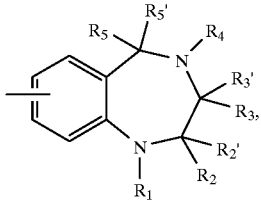

(VIa)

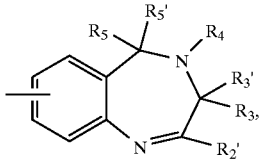

(VIb)

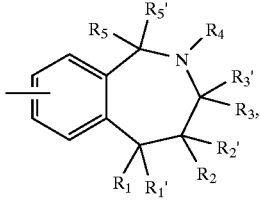

(VIc)

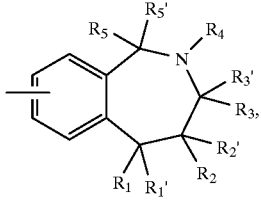

(VId)

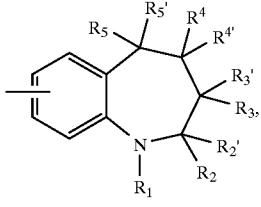

(VIe)

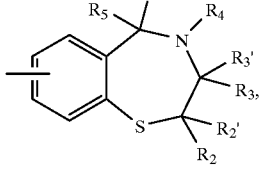

(VIf)

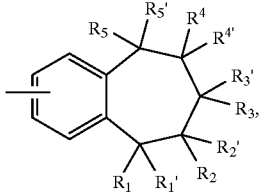

(VIg)

-continued (VIh)

(VIi)

Specific embodiments of this invention wherein the fibrinogen receptor antagonist template A is of the sub-formula (VI) are named in Examples 1–75.

Preferred compounds of this invention are:

(2S)-7-[[[N-(2-benzimidazolyl)methyl-N-methyl]amino] carbonyl]-4-methyl-3-oxo-2,3,4,5-tetrahydro-1H-1,4-benzodiazepine-2-acetic acid;

-7-[[[2-(4-aza-5-methylbenzimidazolyl)methyl]-methylamino]carbonyl]4-methyl-3-oxo-2,3,4,5-tetrahydro-1H-1,4-benzodiazepine-2-acetic acid;

(±)-7-[[[2-(4-Azabenzimidazolyl)methyl]methylamino] carbonyl]-4-(2-methoxyethyl)-3-oxo-2,3,4,5-tetrahydro-1H-1,4-benzodiazepine-2-acetic acid;

(±)-7-[[[2-(benzimidazolyl)methyl]methylamino]carbonyl]-4-(2-methoxyethyl)-3-oxo-2,3,4,5-tetrahydro-1H-1,4-benzodiazepine-2-acetic acid;

-7-[[[2-(4-azabenzimidazolyl)methyl]methylamino] carbonyl]-4-methyl-3-oxo-2,3,4,5-tetrahydro-1H-1,4-benzodiazepine-2-acetic acid;

(2S)-7-[[[N-butyl-N-benzimidazol-2-yl)methyl]amino] carbonyl]-3-oxo-4-methyl-2,3,4,5-tetrahydro-1H-1,4-benzodiazepine-2-acetic acid;

-7-[[[(2-benzimidazolyl)methyl]methylamino]carbonyl]-3-oxo-4-(2-phenylethyl)-2,3,4,5-tetrahydro-1H-1,4-benzodiazepine-2-acetic acid;

-7-[[[N-(2-benzimidazolyl)methyl-N-(2-phenylethyl)] amino]carbonyl]-4-methyl-3-oxo-2,3,4,5-tetrahydro-1H-1,4-benzodiazepine-2-acetic acid;

(±)-7-[[[2-(benzimidazolyl)methyl]amino]carbonyl-4-[2-(3,4-methylenedioxyphenyl)ethyl]-3-oxo-2,3,4,5-tetrahydro-1H-1,4-benzodiazepine-2-acetic acid; and (±)-7-[[[N-(2-benzimidazolyl)methyl-N-methyl]amino] carbonyl]-3-oxo-4-(2-phenylethyl)-2,3,4,5-tetrahydro-1H-1,4-benzodiazepine-2-acetic acid.

The most preferred fibrinogen receptor antagonist template is of the sub-formula (VIa), wherein $CR^2R^{2'}$ is $CHCH_2CO_2H$, $CR^3R^{3'}$ is C=O, and $CR^5R^{5'}$ is $C_2$. Vitronectin fibrinogen receptor antagonism is particularly pronounced when the A-W- substituent is attached to the 7-position of the 3-oxo-2,3,4,5-tetrahydro-1H-1,4-benzodiazepine ring system. (±)-8-[[[(2-Benzimidazolyl) methyl]amino]-carbonyl]-4-methyl-3-oxo-2,3,4,5-tetrahydro-1H-1,4-benzodiazepine-2-acetic acid has a Ki of greater than 50 micromolar in the in vitro vitronectin binding assay described hereinbelow. In the formula below the definitions for the substituents are as defined in formulas (I)–(IV), unless specified otherwise.

Another embodiment of a preferred fibrinogen receptor template A is represented by the 1,4-benzodiazepine 2,5-dione of sub-formula (VII);

(VII)

wherein:

Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy, CN, $CO_2R^f$, $OC(O)R^f$, or $NHC(O)R^f$; and $R^h$ is $(CH_2)_qCO_2R^f$.

The preparation and the use of this sub-structure in preparing fibrinogen receptor antagonists of this sub-formula is detailed in Bondinell, et al., WO 93/00095 published Jan. 7, 1993 and Blackburn, et al., WO 93/08174, published Apr. 29, 1993.

Table I, below, summaries other preferred fibrinogen receptor templates that are included within the scope of the present invention. Such templates are:

TABLE 1

(VIII)

A is or wherein:

$R^{21}$ and $R^{22}$ independently are H or $-Z-CO_2R^f$ or Z-CON $(R^f)2$ with the proviso that one of $A^1$ or $A^2$ is $-Z-CO_2R^f$ or $Z-CON(R^f)2$;

Z is $-CH_2-$, $-O(CH_2)_q-$, $-NR^f(CH_2)_q-$, $-S(CH_2)_q$, $-CH_2CH_2-$, $-CH(CH_3)CH_2-$, $-(CH_2)_3-$, $-CH=CH-$, $-C(CH_3)=CH-$, $CH_2-CH=CH-$ or $CH=CHCH_2$; and Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy or $Z-CO-R^f$, in Alig, et al., EP 0 381 033, published Aug. 8, 1990.

The preferred fibrinogen receptor template A in formula (VIII) is

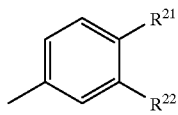

Specific embodiments of this aspect of the invention are:

4-[2-[[[1-[(Benzimidazol2-yl)methyl]benzimidazol-2-yl]methylamino]acetyl] phenoxyacetic acid;

(±)-4-[[2-[(Benzimidazo-2-yl)methyl]methylamino]-1-hydroxyethyl]-1,2-phenylene dioxydiacetic acid;

4-[2-[[(Benzimidazo-2-yl)methyl]methylamino]acetyl]-1,2-phenylenedioxydiacetic acid; or 3-[[4-[[[(Benzimidazol-2-yl)methy]amino]carbonyl]phenyl]amino]propionic acid.

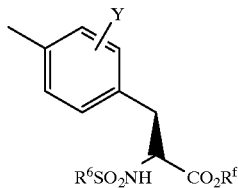

(IX)

wherein:

$R^6$ is aryl, $C_{1-10}$alkyl, $C_{3-6}$cycloalkyl, $C_{4-10}$aralkyl, $C_{1-10}$alkoxyalkyl, $C_{1-10}$alkaryl, $C_{1-10}$alkylthioalkyl, $C_{1-10}$alkoxythioalkyl, $C_{1-10}$alkylamino, $C_{4-10}$aralkylamino, $C_{1-10}$alkanoylamino, $C_{4-10}$aralkanoylamino, $C_{1-10}$alkanoyl, $C_{4-10}$aralkanoyl, or $C_{1-10}$carboxyalkyl; and Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy, CN, $CO_2R^f$, $OC(O)R^f$, or $NHC(O)R^f$, in Egbertson, et al., EP 0 478 328, published Apr. 1, 1992.

The preferred compounds of formula (IX) are those wherein $R^6$ is aryl, $C_{1-10}$alkyl, $C_{3-6}$cycloalkyl, or $C_{4-10}$aralkyl. A specific embodiment of this aspect of the invention is (S)-(2-butylsulfonyl-amnino)-3-[4-(3-benzimidazo-2-yl)propyloxy)]phenylpropionic.

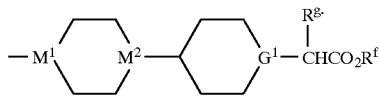

(X)

wherein:

$M^1$ is CH or N;

$M^2$ is CH or N, with the proviso that when $M^1$ is CH, $M^2$ is N; and

G' is N or $N^{\oplus}R''$, in Eldred, et al., EP 0542 363, published May 19, 1993.

Preferred embodiments of the vitronectin receptor antagonists containing the substructure of formula (X) are those wherein G' is N an $M^1$ is N. A compound containing this substructure, namely 4-[4-[1-(2-methylbenzimidazolyl)piperidinyl]]-piperidineacetic acid, has a Ki of greater than 50 micromolar in the in vitro vitronectin binding assay described hereinbelow.

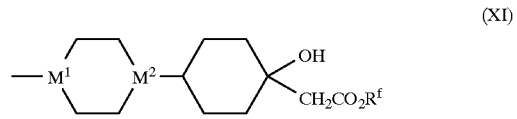

(XI)

wherein:

$M^1$ is CH or N; and $M^2$ is CH or N, with the proviso that when $M^1$ is CH, $M^2$ is N, in Porter, et al., EP 0 537 980, published Apr. 21, 1993.

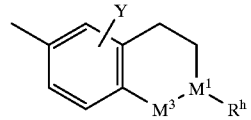

(XII)

wherein:

$M^1$ is CH or N;

Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy, CN, $CO_2R^f$, $OC(O)R^f$, or $NHC(O)R^f$;

$D^3$ is $CH_2$, or C=O; and $R^h$ is $(CH_2)_qCO_2R^f$, in Klinnick, et al., EP 0 635,492, published Jan. 25, 1995.

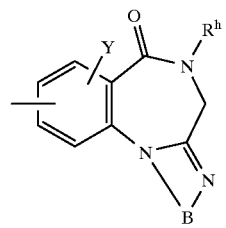

(XIII)

wherein:

Y is H, $C_{1-4}$alkyl, $C_{1-4}$alkoxy, $C_{1-4}$alkoxycarbonyl, F, Cl, Br, I, $CF_3$, $OR^f$, $S(O)_kR^f$, $COR^f$, $NO_2$, $N(R^f)_2$, $CO(NR^f)_2$, $CH_2N(R^f)_2$, methylenedioxy, CN, $CO_2R^f$, $OC(O)R^f$, or $NHC(O)R^f$;

$R^h$ is $(CH_2)_nCO_2R^f$; and

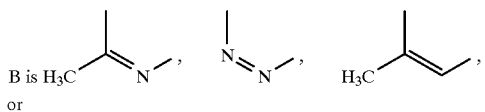

or

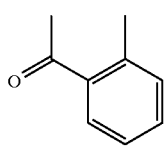

in Blackburn, et al., WO 95/04057, published Feb. 9, 1995.

(XIV)

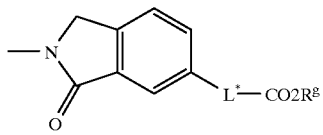

wherein:
L* is —C(O)NR$^g$—(CH$_2$)—, —C(O)—(CH$_2$)$_q$—, NR$^g$—(CH$_2$)$_q$—, —O—(CH$_2$)$_q$—, or S(O)$_k$—(CH$_2$)$_q$—, in Hartman, et al., EP 0 540 331, published May 5, 1993.

(XV)

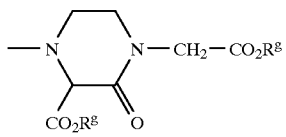

in Sugihara, et al., EP 0 529,858, published Mar. 3, 1993.

(XVI)

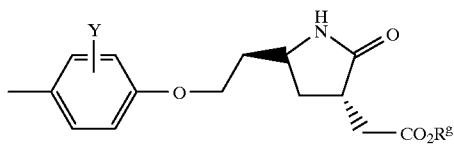

wherein:
Y is H, C$_{1-4}$alkyl, C$_{1-4}$alkoxy, C$_{1-4}$alkoxycarbonyl, F, Cl, Br, I, CF$_3$, OR$^f$, S(O)$_k$R$^f$, COR$^{f1}$, NO$_2$, N(R$^f$)$_2$, CO(NR$^f$)$_2$, CH$_2$N(R$^f$)$_2$, methylenedioxy, CN, CO$_2$R$^f$, OC(O)R$^f$, or NHC(O)R$^f$, in Himmeisbach, et al., EP 0 483 667, published May 6, 1992.

(XVII)

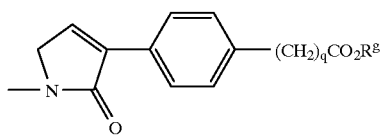

in Linz, et al., EP 0 567 968, published Nov. 3, 1993.

(XVIII)

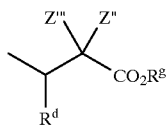

wherein:
R$^d$ is Het-C$_{0-6}$alkyl; and
Z", Z'" independently are hydrogen, C$_{1-4}$alkyl, halo, OR$^f$, CN, S(O)$_k$R$^f$, CO$_2$R$^f$, or OH, in Bovy, et al., EP 0 539 343, published Apr. 28, 1993.

The above descriptions of fibrinogen receptor templates for use in the present invention were taken from pending published patent applications. Reference should be made to such patent applications for their full disclosures, including the methods of preparing said templates and specific compounds using said templates, the entire disclosure of such patent applications being incorporated herein by reference.

Table II, below, describes other fibrinogen receptor antagonists, whose core structures would be useful in carrying out the instant invention. Reference should be made to the patent applications and other publications for their full disclosures, including the methods of preparing said templates and specific compounds using said templates, the entire disclosure of the noted patent applications and other publications being incorporated herein by reference. Since it is contemplated that any fibrinogen receptor antagonist that is linked to an optionally fused nitrogen-containing five-membered ring will possess the novel utility described herein, the list below does not limit the scope of the present invention.

Table II

Adir et Compagnie
FR 928004, Jun. 30, 1992, Fauchere, J. L., et al.
EP 0578535, Jun. 29, 1993, Fauchere, J-L, et al.: Describes X-RGDW-OH analogs, where X contains a cationic amine.
CA 2128560, Jan. 24, 1995, Godfroid, J-J, et al., substituted piperazines.

Asahi Breweries, Ltd.
JP 05239030, Sep. 17, 1993, aminomethyltetrahydroisoquinolines.

Asahi Glass
WO 90/02751, Ohba, M. et al.: Sep. 8, 1989: Describes cyclic RGD-containing peptides.
WO 90/115950, Mar. 22, 1990, Ohba, M., et al.
EP 0406428, Jan. 9, 1991: Describes cyclic RGD-containing peptides
WO 92/09627, Isoai, A. et al.: Nov. 29, 1991: Describes cyclic RGD-containing peptides.

Cassella AG
DE 4207254, (Der 93-289298/37) Mar. 7, 1992, Zoller, G., et al.: Describes guanidinopropyl-4-oxo-2-thioimidazolidin-3-yl-Asp-X analogs
EP 93904010, Feb. 24, 1993, Zoller, G., 4-oxo-2-Thioxoirnidazolidine Derivatives.
EP 0565896, Mar. 18, 1993, Klinger, O, et al.: Describes guanidinoethylphenyloxyacetyl-Asp-X analogs.
EP 0566919, (Der 93-338002/43) Apr. 3, 1993, Zoller, G., et al.: Describes guanidinopropyl-4-oxo-2-thioimidazolidin-3-yl-Asp-X analogs.
EP 580008, (Der 94-027663/04) Jul. 6, 1993, Zoller, G., et al.: Describes 5-m-guanidinophenyl-2,4-dioxoimidazolidin-3yl)acetyl-Asp-Phg.
DE 224414, Jul. 6, 1993, Zoller, G., et al.: Describes 5-m-guanidinophenyl-2,4-dioxoimidazolidin-3yl)acetyl-Asp-Phg.
EP 584694, (Der 94-067259/09) Apr. 2, 1994, Zoller, G., et al.: Describes 5-m-guanidinophenyl-2,4-dioxoimidazolidin-3yl)acetyl-Asp-Phg.
DE 4301747, (Der 94-235891/29) Jul. 28, 1994, Zoller, G., et al.: Describes 5-m-guanidinophenyl-2,4-dioxoimidazolidin-3yl)acetyl-Asp-Phg analogs.
DE 4308034, (Der 94-286666/36) Sep. 15, 1994, Klinger, O. et al.: Describes 5-m-guanidinophenyl-2,4-dioxoimidazolidin-3yl)acetyl-Asp-Phg analogs.
DE 4309867, Sep. 29, 1994, Klingler, O, et al.: Describes 5-m-guanidinophenyl-2,4-dioxoimidazolidin-3yl)acetyl-Asp-Phg.

Chiron
WO 93/07169, (Der 93-134382/16), Mar. 15, 1993, Devlin, J. J., et al.: Describes RGD peptides.

Ciba Geigy
EP 0452210, (Der 91-305246/42) Apr. 5, 1990, describes aminoalkanoyl-GDF analogs.
EP 0452257, Mar. 26, 1991, Allen, M. C., et al.: Describes aminoalkanoylAsp-Phe analogs.
COR Therapeutics
WO 90/15620, Jun. 15, 1990: Describes cyclic RGD-containing peptides.
EP 0477295, Apr. 1, 1992: Scarborough, R. M. et al.
WO 92/08472, May 29, 1992, Scarborough, R. M. et al.
WO 93/223356, Apr. 27, 1993, Swift, R. L., et al.: Describes cyclic RGD-containing peptides.
EP 0557442, Sep. 1, 1993, Scarborough, R. M., et al.
Scarborough, R. M.; Rose, J. W.; Hsu, M. A.; Phillips, D. R.; Fried, V. A.; Campbell, A. M.; Nunnizzi, L.; Charo, I. F., Barbourin, A GPIIb–IIIa-Specific Integrin Antagonist from the Venom of Sistrurus M. Barbouri, *J. Biol. Chem.*, 266, 9359, 1991.
Daiichi Pharm Co Ltd.
JP 05078344-A, (Der 93-140339/17) Mar. 30, 1993: Describes Bis-amidinoheterocycles, eg. benzofurans.
DuPont Merck
WO 93/07170, Apr. 15, 1993: Describes cyclic-RGD-containing peptides.
WO 94/11398, May 26, 1994: Wells, G. J. et al. Describes cyclic RGD containing peptides.
IL 109237, Jul. 31, 1994.
WO 94/22909, (Der 94-333113/41) Oct. 13, 1994: DeGrado W. F., et al.
WO 94/22910, (Der 94-333114/41 Oct. 13, 1994: DeGrado W. F., et al. Prodrugs.
WO 94/22494, (Der 94-332838/41) Oct. 13, 1994: DeGrado W. F., et al. Cyclic peptides
EP 625164, Nov. 23, 1994: Degrado, W. F., et al. Cyclic peptides.
Mousa, S. A.; Bozarth, J. M.; Forsythe, M. S.; Jackson, S. M.; Leamy, A.; Diemer, M. M.; Kapil, R. P.; Knabb, R. M.; Mayo, M. C.; Pierce, S. K.; al., e., Antiplatelet and Antithrombotic Efficacy of DMP 728, a Novel Platelet GPIIb/IIIa Receptor Antagonist, *Circulation*, 89, 3, 1994.
Jackson, S.; DeGrado, W.; Dwivedi, A.; Parthasarathy, A.; Higley, A.; Krywko, J.; Rockwell, A.; Markwalder, J.; Wells, G.; Wexler, R.; Mousa, S.; Harlow, R., Template-Constrained Cyclic Peptides: Design of High-Affinity Ligands for GPIIb/IIIa, *J. Amer. Chem. Soc.*, 116, 3220, 1994.
Ellem Ind Farna Spa
GB 2207922, Aug. 3, 1988, describes linear RGD analogs.
Farmitalia Erba SRL Carlo
EP 611765 (Der 94-265375/33), Aug. 24, 1994: Cozzi, P., et al. Describes 5-(2-pyrazinylmethyl-2-imidazol-1-yl)-1-cyclohexylethylidene)aminoxypentanoic acid.
Fuji Photo Film
JP 04208296-A (Der. 92-303598/38), Nov. 30, 1990, Describes RGD peptides.
JP 04213311-A (Der. 92-305482/38), Nov. 27, 1990, Describes multimeric RGD peptides.
JP 04217693-A, (Der 92-312284/38), Oct. 23, 1990, Describes multimeric RGD peptides.
JP 04221394-A (Der. 92-313678/38), Oct. 26, 1990, Describes multimeric RGD peptides.
JP 04221395-A (Der. 92-313679/38), Oct. 26, 1990, Describes multimeric RGD peptides.
JP 04221396-A (Der. 92-313680/38), Oct. 26, 1990, Describes multimeric RGD peptides.
JP 04221397-A (Der. 92-313681/38), Dec. 20, 1990, Describes multimeric RGD peptides.
EP 0482649 A2, Apr. 29, 1992, Kojima, M. et al.: Describes RGD peptides.
EP 0488258A2, Jun. 3, 1992, Komazawa, H., et al: Describes RGD peptides.
EP 503301-A2, Feb. 14, 1991, Kitaguchi, H. et al.: Describes RGD peptides.
JP 05222092, May 21, 1993, Nishikawa, N., et al.: DescribesLinear X-RGDS.
JP 06239885, (Der 94-313705/39), Aug. 30, 1993, Nishikawa, N. et al.: Describes multimeric RGD peptides.
WO 9324448, (Der 93-405663/50), Dec. 9, 1993, Nishikawa, N., et al.: Describes multimeric retro-inverseo RGD peptides.
JP 06228189, (Der 94-299801/37), Aug. 16, 1994. Describes RGD peptides.
EP 619118, (Der 94-311647/39), Oct. 12, 1994, Nishikawa, N. et al.: Describes linear RGD peptides.
Fujisawa
EP 0513675, May 8, 1992, N. Umekita, et al.: Describes amidinophenyloxyalkanoyl-Asp-Val-OH analogs.
WO 9409030-A1, Apr. 28, 1994, Takasugi, H., et al.: Describes Amnidinophenoycbutanoyl-Asp-Val-OH analogs.
EP 0513675, (Der 92-383589/47): Describes Amidinophenyloxybutyri-Asp-Val analogs.
WO 9500502, Jan. 5, 1995, Oku, T., et al.,: Describes "aminopiperazine derivatives."
FR 144633: Thromb Haem. 69, 706, 1993.
Cox, D.; Aoki, T.; Seki, J.; Motoyama, Y.; Yoshida, K., Pentamnidine: A Specific Nonpeptide GPIIb/IIIa Antagonist, *Thromb. Haem.*, 69, 707, 1993.
Genentech
WO 90/15072 (Der 91007159): Describes RGD-containing peptides:
WO 91/01331 (Der 91058116), Jul. 5, 1990, P. L. Barker, et al.: Describes cyclic RGD-containing peptides
WO 91/04247, Sep. 24, 1990, T. R. Webb: Describes (guanidinoalkyl)Pro-GD analogs.
WO 91/11458 (Der 91252610), Jan. 28, 1991, P. L. Barker, et al.: Describes cyclic RGD-containing peptides
WO 92/07870, Oct. 24, 1991 J. P. Burnier, et al.: Describes cyclic RGD-containing peptides.
WO 92/17492, Oct. 15, 1992, Burnier, J. P. et al.: Describes cyclic RGD-containing peptides.
CA 2106314, Oct. 6, 1992, Burnier, J. P. et al.
WO 93/08174, Oct. 15, 1991, B. K. Blackburn, et al.: Describes 2,5-dioxo-1,4-benzodiazepines.
CA 2106314, Oct. 6, 1992, Burnier, J. P., et al.
EP 0555328, Aug. 18, 1993, J. P. Burnier, et al.
WO 95/04057, Feb. 9, 1995, Blackburn, B. K., et al.: Describes 1,4-benzodiazepines containing a heterocyclic at positions 1,2.
Scarborough, R. M., Naughton, M. A., Teng, W., Rose, J. W., Phillips, D. R., Nannizzi, L, Arfsten, A., Campbell, A. M., and Charo, I. F., J. Biol. Chem. 268, 1066, 1993.
Dennis, M. S.; Henzel, W. J.; Pitti, R. M.; T., L. M.; Napier, M. A.; Deisher, T. A.; Bunting, S.; Lazarus, R., Platelet Glycoprotein IIb-IIIa Protein Antagonists from Snake Venoms: Evidence for a Family of Platelet-Aggregation Inhibitors, *Proc. Natl. Acad. Sci. USA*, 87, 2471, 1989.
Barker, P. L.; Bullens, S.; Bunting, S.; Burdick, D. J.; Chan, K. S.; Deisher, T.; Eigenbrot, C.; Gadek, T. R.; Gantzos, R.; Lipari, M. T.; Muir, C. D.; Napier, M. A.; Pitti, R. M.; Padua, A.; Quan, C.; Stanley, M.; Struble, M.; Tom, J. Y. K.; Burnier, J., P., Cyclic RGD Peptide Analogues as Antiplatelet Antithrombotics, *J. Med. Chem.*, 35, 2040, 1992.

McDowell, R. S.; Gadek, T. R., Structural Studies of Potent Constrained RGD Peptides, *J. Amer. Chem. Soc.*, 114, 9245, 1992.

Glaxo

EP 537980, Oct. 13, 1992, B. Porter, et al.: Describes six cis-4-[4-(4-amidinophenyl)-1-piperazinyl]-1-hydroxycyclohexaneacetic acid analogs.

EO 0542363, Nov. 10, 1992, Porter, B., et al.: Describes 4-[-4-amidinophenyl-piperazinyl]-piperidine-1-acetic acid analogs.

WO 93/22303, Jan. 11, 1993, Middlemiss, D., et al.: Describes amidinophenyl-arylpiperazineacetic acid analogs.

WO 93/22303, Jan. 11, 1993, Middlemiss, D., et al.: Describes amidinophenyl-arylpiperazineacetic acid analogs.

WO 93/14077, Jan. 15, 1993, B. Porter, et al.: Describes amidinophenyl-piperizinyl-piperidine-acetic acid analogs.

EP 609282 A1, Aug. 10, 1994, Porter, B. et al.: Describes cyclohexane acetic acid derivatives.

EP 612313, Aug. 31, 1994, Porter, B., et al. Describes alpha-alkylpiperidineacetic acid derivatives.

EP 93911769, Apr. 20, 1994, Midlemiss, D., et al.

EP 637304 A1, Feb. 8, 1995, Middlemiss, D., et al. Piperazine Acetic acid Derivatives.

Hann, M. M.; Carter, B.; Kitchin, J.; Ward, P.; Pipe, A.; Broomhead, J.; Hornby, E.; Forster, M.; Perry, C., An Investigation of the Bioactive Conformation of ARG-GLY-ASP Containing Cyclic Peptides and Snake Venom Peptides Which Inhibit Human Platelet Aggregation, In *Molecular Recognition: Chemical and Biochemical Problems II*, S. M. Roberts, Ed., The Royal Society of Chemistry, Cambridge, 1992.

Ross, B. C. Nonpeptide Fibrinogen Receptor Antagonists", (SAR leading to the discovery of GR 144053), In Seventh RSC-SCI Medicinal Chemistry Symposium, The Royal Society of Chemistry Fine Chemicals and Medicinals Group and SCI Fine Chemicals Group, Churchill College, Cambridge, 1993, L20.

Pike, N. B.; Foster, M. R.; Hornby, E. J.; Lumley, P., Effect of the Fibrinogen Receptor Antagonist GR144053 Upon Platelet Aggregation Ex Vivo Following Intravenous and Oral Administration to the Marmoset and Cynomologous Monkey, *Thromb. Haem.*, 69, 1071, 1993.

Hoechst

DE 4009506, Mar. 24, 1990, Konig, W., et al.: Describes Hydantoin-(Arg-Gly)-Asp-X analogs.

Hoffmann-La Roche

AU 9344935, (Der 94-118783/15), Mar. 10, 1994,: Describes Cyclic RGD analogs.

EP 0592791, Apr. 20, 1994, Bannwarth. W. et al.: Describes Cyclic RGD analogs.

Kogyo Gijutsuin

JP 06179696, Jun. 28, 1994, Maruyama, S., et al.: Describes Gly-Pro-Arg-Pro-Pro and analogs.

Kyowa Hakko Kogyo KK

JP 05078244-A, Mar. 30, 1993: Describes dibenzo(b,e) oxepine derivatives.

Laboratoire Chauvin

WO 9401456, Jan. 20, 1994, Regnouf, D. V. J. et al.: Describes Ac-Arg-Gly-Asp-NHBn analogs.

La Jolla Cancer Res. Fndn

WO 9500544, Jan. 5, 1994, Pierschbacher, M. D. et al.

US 079441, Jan 5, 1994, Pierschbacher, M. D. et al.: Describes RGD Peptides.

Lilly/COR

EP 0635492, Jan. 25, 1995, Fisher, M. J., Happ, A. M., Jakubowski, J. A., Kinnick, M. D., Kline, A. D., Morin, Jr., J. M., Sall, M. A., Vasileff, R. T.,: Describes compounds with 6,6-templates.

Medical University of South Carolina

EP 587770, Mar. 23, 1994 Halushka, P. V., Spicer, K. M.

Merck

EP 0368486 (Der 90-149427/20), Nov. 10, 1988: Describes X-R-Tyr-D-Y analogs.

EP 0382451 (Der 90248531): Descirbes RGD-containing snake venom inhibitors.

EP 0382538 (Der 90248420): Descirbes RGD-containing snake venom inhibitors.

EP 0410537, Jul. 23, 1990, R. F. Nutt, et al.: Describes cyclic RGD-containing peptides.

EP 0410539, Jul. 25, 1990, R. F. Nutt, et al.: Describes cyclic RGD-containing peptides.

EP 0410540, Jul. 25, 1990, R. F. Nutt, et al.: Describes cyclic RGD-containing peptides.

EP 0410541, Jul. 25, 1990, R. F. Nutt, et al.: Describes cyclic RGD-containing peptides.

EP 0410767, Jul. 26, 1990, R. F. Nutt, et al.: Describes linear RGD-containing peptides.

EP 0411833, Jul. 26, 1990, R. F. Nutt, et al.: Describes cyclic RGD-containing peptides.

EP 0422937, Oct. 11, 1990, R. F. Nutt, et al.: Describes cyclic RGD-containing peptides.

EP 0422938, Oct. 11, 1990, R. F. Nutt, et al.: Describes cyclic RGD-containing peptides.

EP 0487238, Oct. 13, 1991, T. M. Connolly, et al.: Describes Linear RGD-containing.

EP 0437367 (Der 91209968), M. Sato et al.: Describes cyclic RGD-containing peptides, as inhibitors of osteoclast-mediated bone resorption.

EP 576898, Jan. 5, 1994, Jonczyk, A., et al.: Describes linear RGD peptide analogs for use in inhibition of cell adhesion.

WO 9409029, Apr. 28, 1994, Nutt, R. F. and Veber, D. F., describes piperidinylethylpyrrolidinylacetyl-Asp-Trp (tetrazoles).

EP 618225, (Der 94-304404/38) Oct. 5, 1994, Describes RGD peptide analogs as antimetastatic compounds.

DE 4310643, (Der 94-311172/39), Oct. 6, 1994, Jonczyk, A. et al.,: Describes cyclic RGD analogs as antimetastatic agents.

NO 9404093, Oct. 27, 1994, Jonczyk, A. et al.

EP 0632053, Jan. 4, 1995, Jonczyk, A. et al.,: Describes cyclic RGD analogs as antimetastatic agents.

EP 0479481, Sep. 25, 1991, M. E. Duggan et al.: Describes X-GlyAsp-Y linear semipeptides.

EP 0478328, Sep. 26, 1991, M. S. Egbertson, et al.: Describes tyrosine derivatives.

EP 0478362, Sep. 27, 1991 M. E. Duggan et al.: Describes X-Gly-(3-phenethyl)βAla analogs.

EP 0478363, Sep. 27, 1991, W. L. Laswell, et al.: Describes Tyrosine sulfonamides.

EP 0512829, May, 7, 1992, Duggan, M. E., et al.: Describes chiral 3-hydroxy-6-(4-piperidinyl)heptanoyl-β-X-β-Ala-OH analogs, with variations on X and the central alkanoyl chain.

EP 0512831, May, 7, 1992, Duggan, M. E., et al.: Describes chiral 2-oxo-3-(Piperidinylethyl)piperidinylacetyl-β-X-β-Ala-OH analogs, with variations on X and the central piperidinyl ring.

EP 0528586, Aug. 5, 1992, M. S. Egbertson, et al.: Describes tyrosine sulfonamides as inhibitors of osteoclast-mediated bone resorption.

EP 0528587, Aug. 5, 1992, M. S. Egbertson, et al.: Describes tyrosine sulfonamides as inhibitors of osteoclast-mediated bone resorption.

EP 0540334, Oct. 29, 1992, G. D. Hartman, et al.: Describes benzimidazoles.

US 5227490, Feb. 21, 1992, G. D. Hartman, et al.: Describes Tyrosine sulfonamides.

CA 2088518, Feb. 10, 1993, Egbertson, M. S., et la. aminoalkyl-phenyl derivs. as bone resorption inhibts.

US 5206373-A, (Der 93-151790/18) Apr. 27, 1993, Chung, J. Y. L., et al.: Describes MK-383-type compounds.

WO 9316994, (Der 93-288324/36), Sep. 2, 1993, Chung, J. Y. L., et al.: Describes pyridinylbutyl-L-Tyrbutylsulfonamide.

US 5264420-A, Nov. 23, 1993, Describes piperidinylalkyl-Gly-betaAla analogs.

US 5272158, Dec. 21, 1993, Hartman, G. D. et al.,: Describes piperidinylethylisoinole analogs.

US 5281585, Jan. 25, 1994, Ihle, N., et al.,: Describes 3-(piperidinylethyl)-piperidinone analogs.

GB 945317 A, Mar. 17, 1994 (Priority US 34042A, Mar. 22, 1993).

GB 2271567 A, Apr. 20, 1994, Hartman, G. D. et al.: Describes compounds replacing Tyr with beta-phenylsuccinate.

US 5294616, (Der 94-091561/11) Mar. 15, 1994, Egbertson, M. S., et al.

US 5292756, (Der 94-082364) Apr. 8, 1994, Hartman, G. D. et al.

WO 9408577, Apr. 28, 1994, Hartman, G. D., et al.

WO 9408962, Apr. 28, 1994, Hartman, G. D., et al.

WO 9409029, (Der 94-151241/18) Apr. 28, 1994, Hartman, G. D., et al. Describes piperidinylpyrrolinylacetyl-Asp-Trp-tetrazoles.

US 5312923, May 17, 1994, Chung, J. Y. L. et al.

HU 9400249, May 30, 1994, Gante, J. et al.,: Describes piperazine analogs.

WO 9412181, (Der 94-199942/24), Jun. 9, 1994, Egbertson, M. S. et al.,: Describes piperidinylethyloxyphenyl acetic acid analogs US 5321034, Jun. 14, 1994, Duggan, M. E., et al.: Describes Piperidinylalkyl-betaamino acids.

US 5334596, Aug. 2, 1994, Hartman, G. D. et al.

EP 0608759 A, Aug. 3, 1994, GAnte, J. P. et al.: Describes amidinopiperazinyl compounds.

WO 9418981, (Der 94-2293975/36) Sep. 1, 1994, Claremon, D. A. et al.: Describes Many different amine surrogate.

GB 2276384, (Der 94-2287743/36) Sep. 28, 1994, Claremon, D. A., Liverton, N.,: Describes piperidinylethylquinazoline analogs.

WO 9422825, Oct. 13, 1994, Claremon, D. A. Liverton, N. J.,: Describes piperidinylethyl-retro-benzodiazepine analogs.

EP 0623615A, Nov. 9, 1994, Raddatz, P. et al: Describes amidinophenyloxazolidinylmethyl-piperidine-4-carboxylic acid and analogs.

WO 9504531, Feb. 16, 1995, Hartman, G D., et al.: Describes piperidinylalkylheterocycles.

Nutt, R. F.; Brady, S. F.; Colton, C. D.; Sisko, J. T.; Ciccarone, T. M.; Levy, M. R.; Duggan, M. E.; Imagire, I. S.; Gould, R. J.; Anderson, P. S.; Veber, D. F., Development of Novel, Highly Selective Fibrinogen Receptor Antagonists as Potentially Useful Antithrombotic Agents, In *Peptides, Chemistry and Biology, Proc. 12th Amer. Peptide Symp.*, J. A. Smith and J. E. Rivier, Ed., ESCOM, Leiden, 1992; 914.

Hartmnan, G. D.; Egbertson, M. S.; Halszenko, W.; Laswell, W. L.; Duggan, M. E.; Smith, R. L.; Naylor, A. M.; Manno, P. D.; Lynch, R. J.; Zhang, G.; Chang, C. T. C.; Gould, R. J., Non-peptide Fibrinogen Receptor Antagonists. 1. Discovery and Design of Exosite Inhibitors, *J. Med. Chem.*, 35, 4640, 1992.

Gould, R. J.; Barrett, S.; Ellis, J. D.; Holahan, M. A.; Stranieri, M. T.; Theoharides, A. D.; Lynch, J. J.; Friedman, P. A.; Duggan, M. E.; Ilie, N. C.; Anderson, P. S.; Hartman, G. D., Characterization of L-703,014, A Novel Fibrinogen Receptor Antagonist, Following Oral Administration to Dogs, *Thromb. Haem.*, 69, 539, 1993.

Merrell Dow

WO 93/24520, May 14, 1993, Harbeson, S. L., et al.: Describes cyclic RGD peptides.

WO 9324520, Dec. 9, 1993, Harbeson, Bitonti,J., A.,: Describes cyclic RGD analogs as antimetastatic agents.

WO 9429349, Dec. 22, 1994, Harbeson, Bitonti,J., A.,: Describes cyclic RGD analogs as antimetastatic agents.

Nippon Steel Corp

WO 9405696, Mar. 17, 1993, Sato, Y., et al.,

EP 628571, Dec. 14, 1994, Sato, Y. et al.

WO 9501371, Jan. 12, 1995, Sato, Y. et al.: Describes RWSRGDW analogs.

ONO Pharmaceuticals

JP 05286922 (Der 93-383035/48), Describes guanidinophenol alkylbenzoic acid esters.

Roche

EP 038,362, Feb. 19, 1990, M. Muller, et al.: Describes X-NHCHYCO-Gly-Asp-NHCHZCO2H analogs.

EP 0372486, Jun. 13, 1990, Allig, L., et al.

EP 0381033, Jul., 8, 1990, Allig, L., et al.

EP 0384362, Aug. 29, 1990, Allig, L. et al.: Describes amidinophenyl-linked Gly-Asp-X semipeptides.

EP 0445796, Sep. 11, 1991, Allig, L. et al.: Describes amidinophenyl-linked Gly-Asp-X semipeptides.

EP 0505868, Sep. 30, 1992, Allig, L. et al.: Describes N-acyl-alphaamino acid derivatives, ie. analogs from EP0381003 with variations in the phenyloxyacetic acid group.

US 5273982-A, (Der 94-006713/01) Dec. 28, 1993: Describes amidinophenyl-linked Gly-Asp-X semipeptides.

Alig, L.; Edenhofer, A.; Hadvary, P.; Hurzeler, M.; Knopp, D.; Muller, M.; Steiner, B.; Trzeciak, A.; Weller, T., Low Molecular Weight, Non-peptide Fibrinogen Receptor Antagonists, *J. Med. Chem.*, 35, 4393, 1992.

Rhone-Poulenc Rorer

US 4952562, Sep. 29, 1989, S. I. Klein et al.: Describes X-Gly-Asp-Val-OH analogs.

US 5064814, (Der 91-353169/48) Apr. 5, 1990: Describes Piperidinyl-azetidinyl-Asp-X analogs.

WO 9104746, Sep. 25, 1990, S. I. Klein et al.: Describes X-Asp-Val-OH analogs.

WO 91/05562, Oct. 10, 1989, S. I. Klein et al.: Describes X-Gly-Asp-Val-OH analogs.

WO 91/07976, (Der 91-192965) Nov. 28, 1990, S. I. Klein et al.: Describes X-cycloAA-Asp-Val-OH analogs.

WO 91/04746, S. I. Klein et al.: Describes des-AminoArginine RGD analogs.

WO 92/18117, Apr. 11, 1991, S. I. Klein et al.: Describes X-Asp-Val-OH analogs.

US 5086069, (Der 92-064426/08) Apr. 2, 1992, : Describes X-Gly-Asp-Val-OH analogs.

WO 92/17196, Mar. 30, 1992, S. I. Klein et al.: Describes X-Gly-Asp-Val-OH analogs.

US 5328900, (Der 94-2221950/27) Jul. 12, 1992, : Describes X-azetidinyl-Asp-Val-OH analogs.

US 5332726, (Der 94-2241043/29) Jul. 26, 1994, : Describes guanidinoalkanoyl-(N-alkyl)Gly-Asp-Val-OH analogs.
WO 93/11759, Dec. 7, 1992, S. I. Klein et al.: Describes Bis-guanidinoaklanoic acid analogs.
EP 0577775, Jan. 12, 1994, Klein, S. I. et al.
CA 2107088, Sep. 29, 1992, Klein, S.I. et al.
Sandoz
EP 0560730, Mar. 8, 1993 G. Kottirisch and R. Metternich: Describes amnidinophenylalkanamid-S-α-acetic acid analogs.
G. Kottirisch, et al. Biorg. Med. Chem. Lett 3, 1675–1680, 1993, Describes amiidinophenylacetyl-(Gly-Asp-γ-lactam mimetic)analogs.
Schering AG
E 530937, Mar. 10, 1993, Noeski-Jungblut, C., et al. "Collagen Induced Platelet Aggregation Inbitor."
Searle/Monsanto
EP 0319506, (Der 89-3195506) Dec. 2, 1988, S. P. Adams, et al.: Describes RGD-X analogs.
EP 0462,960, Jun. 19.1991, Tjoeng, F. S., et al.: Describes guanidinooctanoyl-Asp-Phe analogs.
US 4857508, S. P. Adams, et al.: Describes RGD analogs.
EP 0502536, (Der 92-301855) Mar. 3, 1991, R. B. Garland, et al.: Describes amidinophenylalkanoyl-Asp-Phe analogs.
EP 0319506, Dec. 2, 1988, S. P. Adams et al.: Describes RGDX analogs.
US 4992463, Aug. 18, 1989: Describes guanidinoalkanoyl-Asp-X analogs.
US 5037808, Apr. 23, 1990: Describes guanidinoalkanoyl-Asp-X analogs.
EP 0454651 A2, Oct. 30, 199 1, Tjoeng, F. S., et al.: Describes amidinoalkanoyl-Asp-X analogs.
US 4879313, Jul. 20, 1988: Describes guanidinoalkanoyl-Asp-X analogs.
WO 93/12074, Nov. 19, 1991, N . Abood, et al.: Describes amidinophenylalkanoyl-β-X-AlaOH analogs.
WO 93/12103, Dec. 11, 1991, P. R. Bovy, et al.: Describes ainidinophenylalkanoyl-β-X-lactone analogs.
US 5091396, Feb. 25, 1992, Tjoeng, F. S., et al.: Describes amidinoalkanoyl-Asp-X analogs.
WO 92/15607, Mar. 5, 1992, Garland, R. B., et al.: Describes amidinophenylalkanoyl-Asp-X analogs.
WO 93/07867, Apr. 29, 1993, P. R. Bovy, et al.: Describes amidinophenyl-amidopropionyl-β-X-AlaOH analogs.
US 888686, May 22, 1992, Bovy, P. R. et al.
CA 2099994, Sep. 7, 1992, Garland, R. B., et al.
US 5254573, Oct. 6, 1992, Bovy, P. R., et al.: Describes amidinophenylamidopropionyl-β-X-β-Ala-OH.
(PF54C06), EP 0539343, Oct. 14, 1992, P. R. Bovy et al.: Describes amidinophenylamidopropionyl-β-X-β-Ala-OH.
WO 93/12074, Nov. 27, 1992, N. A. Abood, et al.: Describes amidinophenylalkylamido-(R)-Asp-(i.e. retro-Asp)-alkyl and aryl amides and sulfonamides.
WO 93/12103, Dec. 11, 1992, P. R. Bovy et al.: Describes amidinophenylalkanoyl-Asp-X lactones
EP 0 539343, Apr. 28, 1993, Bovy, P. R., et al.
EP 0542708, May, 19, 1993, Bovy. P. R., et al.
WO 94/00424, Jun. 23, 1993, Abood, N. A., et al.: Describes amidinophenylalkanoic acid lactones related to previous compounds.
WO 93/16038, Aug. 16, 1993, Miyano. M. et al.: Describes amidinophenylpentanoyl-β-arylsulfonamidomethyl-β-Ala-OH analogs.
WO 93US7975, Aug. 17, 1993, Zablocki, J. A., Tjoeng, F. S.

WO 93/18058, Sep. 16, 1993, Bovy, P. R. et al.: Describes amidinophenylamidoproionoyl-Asp-X-OH analogs.
US 5254573, Oct. 19, 1993, Bovy, P. R., et al., Describes amidinophenylpropionyl-amino acid dervs.
US, 5272162, Dec. 21, 1993, Tjoeng, F. S., et al.: Describes amidinophenyl-X-NHCO-β-Y-β-Ala-OH analogs.
EP 0574545, Dec. 22, 1993, Garland, R. B., et al.: AmidinophenylX-Asp Analogs.
WO 9401396, Jan. 20, 1994, Tjoeng, F. S., et al., Describes amidinophenylalkylamido-amino acid derivatives.
WO 9405694, (Der 94-101119/12) Mar. 17, 1994, Zablocki, et al.: Describes amidinophenylalkylamido-amino acid derivatives.
US 5314902, May 24, 1994, Adams, S. P. et al.: Describes amidinophenylamidoalkanoyl derivatives.
WO 9418162, Aug, 18, 1994, Adams, S. P., et al.: Describes amidinophenylalkanoyl-amino acid derivatives.
WO 9419341, Sep. 1, 1994, Tjoeng, F. S., et al.: Describes amidinophenylnipecotic acid derivatives.
US 5344837, (Der 94-2285503/35), Sep. 6, 1994, Zablocki, J. A., et al.
EP 614360, Sep. 14, 1994, Bovy, P. R., et al.
WO 9420457, (Der 94-2302907/37) Sep. 15, 1994, Tjoeng, F. S. et al. Amindinophenyl compounds with central ring.
WO 9421602, (Der 94-2316876/39), Sep. 29, 1994, Tjoeng, F. S., et al. Describes guanidinoalkylarninocarbonylanrinoacid derivatives.
WO 9422820, Oct. 13, 1994, Abood, N. A., et al.: Describes amidinophenylpyrollidinonyl-β-Ala derivatives.
EP 630366, Dec. 28, 1994, Bovy, P. R., et al.
US 5378727, Jan. 3, 1995, Bovy, P. R. et al.
K. F. Fok, et al., Int. J. Peptide Prot. Res., 38, 124–130, 1991, SAR of RGDY analogs.
J. A. Zablocki, et al. J. Med. Chem. 35, 4914–4917, 1992, SAR summary of guanidinoalkanoyl-Asp-Phe analogs.
Tjoeng, F. S.; Fok, K. F.; Zupec, M. E.; Garland, R. B.; Miyano, M.; Panzer-Knodle, S.; King, L. W.; Taite, B. B.; Nicholson, N. S.; Feigen, L. P.; Adams, S. P., Peptide Mimetics of the RGD Sequence, In Peptides, Chem. and Biol. Proc. 12th Amer. Peptide Symp., J. A. Smith and J. E. Rivier, Ed., ESCOM, Leiden, 1992; 752.
Nicholson, N.; Taite, B.; Panzer-Knodle, S.; Salyers, A.; Haas, N.; Szalony, J.; Zablocki, J.; Feigen, L.; Glenn, K.; Keller, B.; Broschat, K.; Herin, M.; Jacqmin, P.; lesne, M., An Orally Active Glycoprotein IIb/IIIa Antagonist—SC-54684, Thromb. Haem., 69, 975, 1993.
Sumitomo Pharm. Co. Ltd.
WO 9501336, Jun. 6, 1994, Ikeda, Y., et at., Describes piperidinyloxyacetyl-Tyr-piperidinyloxyacetic acid derivatives.
Sumitomo Seiyaku KK
JP 06025290, (Der 94-077374/10) Feb. 1, 1994. Describes multimeric RGDT.
Taisho Pharm. (Teijin, Ltd)
JP 05230009, (Der 93-317431/40, Feb. 24, 1992: Describes amidino-Cbz-meta-aminophenylpropionate.
JP 9235479, Feb. 24, 1992: Describes Amidinophenylcarbamates.
(PFD4C06), WO 94/17804, Aug. 18, 1994, Mizushima, Y. Pharm. Comp for Treating Cerebral Thrombosis.
(EP 634171), Jan. 18, 1995, Nizushima, M. Pharm. Comp for Treating Cerebral Thrombosis. Prostaglandins
Takeda
EP 0529858, Apr. 3, 1993, H. Sugihara, et al.: Describes amidinobenzoyl-Gly-Piperazinone analogs.
EP 606881, Jul. 20, 1994, Cyclic peptides with beta and gamma turns.

EP 614664, Sep. 14, 1994, Miyake, A., et al: Quinolonecarboxylic Acids as cell adhesion inhibitors.
Tanabe
WO 89/07609, T. J. Lobl, et al.: Describes RGD analogs.
WO 92/00995, Jul. 9, 1991, T. J. Lobl, et al.: Describes cyclic RGD analogs.
WO 93/08823, Nov. 6, 1991, T. C. McKenzie: Describes guanidinoalkanoyl-Gly-Asp-X analogs.
CA 2087021, Jan. 10, 1991, Lobl, T. J., et al: Describes cyclic RGD analogs.
WO 92/08464, Nov. 15, 1991, T. C. McKenzie, et al.: Describes.
Telios/La Jolla Cancer Research
US. 4578079, Nov. 22, 1983, E. Ruoslahti, and M. Pierschbacher: Describes X-RGD-Y analogs.
US. 4614517, Jun. 17, 1985, E. Ruoslahti, and M. Pierschbacher: Describes X-RGD-Y analogs.
US. 4792,525, Jun. 17, 1985, E. Ruoslahti, and M. Pierschbacher: Describes X-RGD-Y analogs.
US 4879237, (Der 90-154405/20) May, 24, 1985, Describes X-RGD-Y analogs.
WO 91/15515, (Der 91-325173/44) Apr. 6, 1990, describes cyclic RGD analogs.
US. 5041380, 1991, E. Ruoslahti, and M. Pierschbacher: Describes RGD-X analogs.
WO 95/00544 Jan. 5, 1995, Craig, W. S., et. al.
Cheng, S.; Craig, W. S.; Mullen, D.; Tschopp, J. F.; Dixon, D.; Pierschbacher, M. F., Design and Synthesis of Novel Cyclic RGD-Containing Peptides as Highly Potent and Selective Integrin $\alpha_{IIb}\beta_3$ Antagonists, *J. Medicin. Chem.*, 37, 1, 1994.
Collen, D.; Lu, H. R.; Stassen, J.-M.; Vreys, I.; Yasuda, T.; Bunting, S.; Gold, H. K., Antithrombotic Effects and Bleeding Time Prolongation with Synthetic Platelet GPIIb/IIIa Inhibitors in Animal Models of Platelet-Mediated Thrombosis, *Thrombosis and Haemostasis*, 71, 95, 1994.
Temple U.
WO 9409036, (Der 94-151248/18), Apr. 28, 1994, Describes disintegrin peptides.
Terumo KK
JP 6279389, Oct. 4, 1994, Obama, H., et al.: Describes 3-(4-amidinophenyloxymethyl)phenylamidopropionic acid analogs (ala Roche I-35).
Karl Thomae/Boehringer Ingelheim
EP 0483667, May 6, 1992, Himmelsbach, F., et al.: Describes amidinobiphenyl-oxymethyl-2-pyrrolidinone-acetic acid.
EP 0496378, Jan. 22, 1992, Himmelsbach, F., et al.: Describes arnidinobiphenyl-aminocarbonylcyclohexylcarboxylic acid analogs.
EP 0503548, Sep. 16, 1992, Himmelsbach, F., et al.: Describes amidinophenyl-pyrrolidinone-phenylpropionic acid analogs.
AU A-86926/91, May 7, 1992, Himmelsbach, F. et al.: Describes amidinophenyl compounds.
EP 0528369, Feb. 24, 1993, Austel, V., et al.: Describes amidinobiphenyl-oxymethy-2-pyrrolidinone-acetic acid.
EP 0537696, Apr. 21, 1993 Linz, G., et al.: Describes amidinophenyl-pyridazine analogs.
DE 4124942, Jan. 28, 1993, Himmelsbach, F. et al.: Describes amidino-triarylproionic acid analogs.
DE 4129603, Mar. 11, 1993, Pieper, H, et al.: Describes amidinobiphenyl-benzimidazole.
EP 0547517 A1, (Der 93-198544) Jun. 23, 1993, Soyka, R., et al.: Describes pyridyl compounds.
EP 0567966, Nov. 3, 1993, Himmelsbach, F., et al.: Describes arnidinobiphenyl-oxymethy-2-pyrrolidinone-acetic acid.
EP 0567967, Nov. 3 1993, Weisenberger, J., et al.: Describes amidinobiphenyl-oxymethyl2-pyrrolidinone-acetic acid.
EP 0567968, Nov. 3, 1993, Linz, G., et al.: Describes amidinobiphenyl-lactam-acetic acid and amidinophenyl-lactamphenylpropionic acid analogs.
EP 0574808, Jun. 11, 1993, Pieper, H., et al.: Describes amidinobiphenyl-X-acetic acid ester analogs.
Der 93-406657/51, Austel, V., et al.: Describes amidinobiphenyl analogs.
EP 587134, (Der 94-085077/11) Mar. 16, 1994, Himmerlsbach, F. D. D., et al., Describes amidinophenyl-triazolone analogs.
EP 589874, Apr. 6, 1994, Grell, W., et al.
(P534005), DE 4234295, Apr. 14, 1994, Pieper, H., et al., Describes heteroaryl-azacyclohexylcarboxylic acid analogs.
EP 0592949, Apr. 20, 1994, Pieper, H. D., et al., Describes amidinophenyl-4piperidinamido-4-cyclohexylcarboxylic acid analogs.
EP 596326, May, 11, 1994, Maier, R. et al.
DE 4241632, Jun. 15, 1994, Himmelsbach, F., et al., Describes piperidinophenylamido-phenylpropionyl analogs.
EP 0604800 A, Jul. 6, 1994, Himmelsbach, F. et al., Describes piperidinophenylamido-phenylalanine derivatives.
DE 4302051, (Der 94-2235999/29) Jul., 28, 1994, describes compounds containing a 2H-pyrazo-5-one.
EP 0608858 A, Aug. 3, 1994, Linz, G. D., et al., Describes amidino-biphenyl compounds.
DE 4304650, (Der 94-2256165/32), Aug. 18, 1994, Austel, V., et al., describes compounds with a 5,6 template.
EP 611660, Aug. 24, 1994, Austel, V., et al., Describes tricyclic template.
DE 4305388, (Der 94-2264904/33), Aug. 25, 1994, Himmelsbach, F., et al., Describes 6,6 and 7,6 templates.
(P5D4005), EP 612741, (Der 94-2265886/33), Aug. 31, 1994, Himmelsbach, F., et al., Describes 6,6 and 7,6 templates.
EP 0639575 A, Feb. 22, 1995, Linz, G., et al.: Describes tetrahydrothiazolo-[5,4,c]pyridine cation replacements.
DE 4324580, Jan. 26, 1995, Linz, G. et al.
EP 0638553, Feb. 15, 1995, Himmelsbach, F., et al.
F. Hiummelsbach, V. Austel, G. Kruger, H. Pieper, H. Weisenberger, T. H. Muller, and W. G. Eisert, in XIIth Int. Symp. on Med. Chem. Basel, Book of Abstracts, 47, 1992.
V. Austel, W. Eisert, F. Himmelsbach, G. Kruger, G. Linz, T. Muller, H. Pieper, and J. Weisenberger, Natl. Mtg. Amer. Chem. Soc. Book of Abstracts, Denver, Div. Med. Chem., 1993.
Muller, T. H.; Schurer, H.; Waldmann, L.; Bauer, E.; Himmelsbach, F.; Binder, K., Orally Activity of BIBU 104, a Prodrug of the Non-peptide Fibrinogen Receptor Antagonist BIBU 52, in Mice and Monkeys, *Thromb. Haem.*, 69, 975, 1993.
Univ. California
WO 94/14848, Jul., 7, 1994, Zanetti, M. RGD peptides from CDR.
Univ. New York
WO 94/00144, Jun. 29, 1993, Ojima, I. et al.: Describes RGD peptide multimers.
Yeda Res. and Dev. Co.
WO 93/09795, (Der 93-182236/22), Lido, O. et al.: Describes Guanidinopentanoic acid analogs.
Zeneca
WO 9422834, Oct. 13, 1994, Wayne, M. G., et al. Describes pyridinopiperazino-phenylcarbonyl-amino acids.

WO 9422835, Oct. 13, 1994, Wayne, M. G., et al. Describes pyridinopiperidino-amidophenylacetic acids.

EP 632016, Jan. 4, 1995, Brewster, A. G., et al. Describes pyridinopropionylhydrazinylbenzoyl analogs.

EO 632019, Jan. 4, 1995, Brown, G., Shute, R. E.

EO 632020, Jan. 4, 1995, Brown, G., Shute, R. E.

In cases wherein the compounds of this invention may have one or more chiral centers, unless specified, this invention includes each unique nonracemic compound which may be synthesized and resolved by conventional techniques. In cases in which compounds have unsaturated carbon-carbon double bonds, both the cis (Z) and trans (E) isomers are within the scope of this invention. The meaning of any substituent at any one occurrence is independent of its meaning, or any other substituent's meaning, at any other occurrence.

Abbreviations and symbols commonly used in the peptide and chemical arts are used herein to describe the compounds of this invention. In general, the amino acid abbreviations follow the IUPAC-IUB Joint Commission on Biochemical Nomenclature as described in *Eur. J. Biochem.*, 158, 9 (1984).

$C_{1-4}$alkyl as applied herein means an optionally substituted alkyl group of 1 to 4 carbon atoms, and includes methyl, ethyl, n-propyl, isopropyl, n-butyl, isobutyl and t-butyl. $C_{1-6}$alkyl additionally includes pentyl, n-pentyl, isopentyl, neopentyl and hexyl and the simple aliphatic isomers thereof $C_{0-4}$alkyl and $C_{0-6}$alkyl additionally indicates that no alkyl group need be present (e.g., that a covalent bond is present).

Any $C_{1-4}$alkyl or $C_{1-6}$ alkyl, $C_{2-6}$ alkenyl, $C_{2-6}$ alkynyl or $C_{1-6}$ oxoalkyl may be optionally substituted with the group $R^x$, which may be on any carbon atom that results in a stable structure and is available by conventional synthetic techniques. Suitable groups for $R^x$ are $C_{1-4}$alkyl, $OR^1$, $SR^1$, $C_{1-4}$alkyl, $C_{1-4}$alkylsulfonyl, $C_{1-4}$alkylsulfoxyl, —CN, $N(R^1)_2$, $CH_2N(R^1)_2$, —$NO_2$, —$CF_3$, —$CO_2R^{'3}$ —$CON(R^1)_2$, —$COR^1$, —$NR^1C(O)R^1$, OH, F, Cl, Br, I, or $CF_3S(O)_r$—, wherein r is 0 to 2.

Ar, or aryl, as applied herein, means phenyl or naphthyl, or phenyl or naphthyl substituted by one to three substituents, such as those defined above for alkyl, especially $C_{1-4}$alkyl, $C_{1-4}$alkoxy, $C_{1-4}$alkthio, trifluoroalkyl, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazole, benzopyran, benzothiophene, furan, imidazole, indoline, morpholine, piperidine, piperazine, pyrrole, pyrrolidine, tetrahydropyridine, pyridine, thiazole, thiophene, quinoline, isoquinoline, and tetra- and perhydro-quinoline and isoquinoline. Any accessible combination of up to three substituents on the Het ring, such as those defined above for alkyl that are available by chemical synthesis and are stable are within the scope of this invention.

$C_{3-7}$cycloalkyl refers to an optionally substituted carbocyclic system of three to seven carbon atoms, which may contain up to two unsaturated carbon-carbon bonds. Typical of $C_{3-7}$cycloalkyl are cyclopropyl, cyclobutyl, cyclopentyl, cyclopentenyl, cyclohexyl, cyclohexenyl and cycloheptyl. Any combination of up to three substituents, such as those defined above for alkyl, on the cycloalkyl ring that is available by conventional chemical synthesis and is stable, is within the scope of this invention.

When $R^b$ and $R^c$ are joined together to form a five- or six-membered aromatic or non-aromatic carbocyclic or heterocyclic ring fused to the ring to which $R^b$ and $R^c$ are attached, the ring formed will generally be a five- or six-membered heterocycle selected from those listed above for Het, or will be a phenyl, cyclohexyl or cyclopentyl ring. Preferably $R_b$ and $R_c$ will be —D1=D2—D3=D4 wherein D1–D4 are independently CH, N or C—$R_x$ with the proviso that no more than two of D1–D4 are N. Most preferably, when $R^b$ and $R^c$ are joined together they form the group —CH=CH—CH=CH—.

Certain radical groups are abbreviated herein. t-Bu refers to the tertiary butyl radical, Boc refers to the t-butyloxycarbonyl radical, Fmoc refers to the fluorenylmethoxycarbonyl radical, Ph refers to the phenyl radical, Cbz refers to the benzyloxycarbonyl radical, BrZ refers to the o-bromobenzyloxycarbonyl radical, ClZ refers to the o-chlorobenzyloxycarbonyl radical, Bzl refers to the benzyl radical, 4-MBzl refers to the 4-methyl benzyl radical, Me refers to methyl, Et refers to ethyl, Ac refers to acetyl, Alk refers to $C_{1-4}$alkyl, Nph refers to 1- or 2-naphthyl and cHex refers to cyclohexyl. Tet refers to 5-tetrazolyl.

Certain reagents are abbreviated herein. DCC refers to dicyclohexylcarbodiimide, DMAP refers to dimethylaminopyridine, DIEA refers to diisopropylethyl amine, EDC refers to 1-(3-dimethylaminopropyl)-3-ethylcarbodiimide, hydrochloride. HOBt refers to 1-hydroxybenzotriazole, THF refers to tetrahydrofuran, DIEA refers to diisopropylethylamine, DME refers to dimethoxyethane, DMF refers to dimethylformamide, NBS refers to N-bromosuccinimide, Pd/C refers to a palladium on carbon catalyst, PPA refers to 1-propanephosphonic acid cyclic anhydride, DPPA refers to diphenylphosphoryl azide, BOP refers to benzotriazol-1-yloxy-tris(dimethyl-amino) phosphonium hexafluorophosphate, HF refers to hydrofluoric acid, TEA refers to triethylamine, TFA refers to trifluoroacetic acid, PCC refers to pyridinium chlorochromate.

Compounds of the formula (I)–(V) are prepared, for example, by reacting a compound of formula (XIX) with a compound of formula (XX), wherein $L^1$ and $L^2$ are groups which may react to form a covalent bond in the moiety W, by methods generally known in the art.

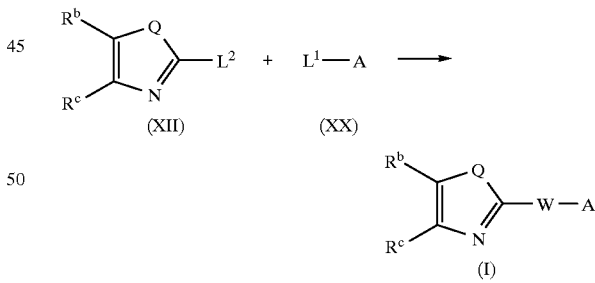

Typical methods include coupling to form amide bonds, nucleophilic displacement reactions and palladium catalyzed couplings. For instance, when W contains an ether or amine linkage, the bond may be formed by a displacement reaction, and one of $L^1$ and $L^2$ will contain an amino or hydroxy group and the other will contain a displaceable group, such as a chloro, bromo or iodo group. When W contains an amide bond, typically one of $L^1$ and $L^2$ will contain an amino group, and the other will contain a carboxylic acid group. In another approach, $L^1$ may be an aryl or heteroaryl bromide, iodide or trifluoromethylsulfonyloxy derivative and $L^2$ may contain an amino group and the amide linkage may be formed by palladium-catalyzed aminocarbonylation with carbon monoxide in a suitable solvent such as dimethylformamide or toluene.

It will be apparent that the precise identity of $L^1$ and $L^2$ will be dependent upon the site of the linkage being formed. General methods for preparing the linkage —(CHR")$_r$—U—(CHR")$_s$—V— are described, for example, in EP-A 0372 486 and EP-A 0 381 033 and EP-A 0 478 363, which are incorporated herein by reference.

For instance, if V is CONH, $L^1$ may be —NH$_2$, $L^2$ may be OH (as in an acid) or Cl (as in an acid chloride), and $R^{6"}$ may be W—(CR'$_2$)$_q$—Z—(CR'R$^{10}$)$_r$—U—(CR'$_2$)$_s$—C(O), with any functional groups optionally protected. For example, $R^{6'}$ may be (benzyloxycarbonyl-amidino)benzoyl- or ($N^\alpha$-Boc,$N^{guan}$-Tos)arginyl-. When $L^2$ is OH, a coupling agent is used.

Similarly, if V is NHCO, $L^1$ may be —CO$_2$H or CO—Cl, $L^2$ may be —NH$_2$, and $R^{6"}$ may be W—(CR'$_2$)$_q$—Z—(CR'R$^{10}$)$_r$—U—(CR'$_2$)$_s$—. For example, $R^{6"}$ may be (benzyloxycarbonyl-amidino)phenyl, (benzyloxycarbonylamino)methylbenzyl- or 6-(benzyloxycarbonylamino)hexyl-.

Where V is NHSO$_2$, $L^1$ may be SO$_2$Cl, $L^2$ may be —NH$_2$ and $R^{6"}$ may be as above. Where V is SO$_2$NH, $L^1$ may be —NH$_2$ and $L^2$ may be SO$_2$Cl. Methods to prepare such sulfonyl chlorides are disclosed, for instance, in *J. Org. Chem.*, 23, 1257 (1958).

If V is CH=CH, $L^1$ may be —CHO, $L^2$ may be CH=P—Ph$_3$ and $R^{6"}$ may be W—(CR'$_2$)$_q$—Z—(CR'R$^{10}$)$_r$—U—(CR'$_2$)$_s$—. Alternately, $L^1$ may be CH=P—Ph$_3$, $L^2$ may be CHO, e.g., $R^{6"}$ may be W—(CR'$_2$)$_q$—Z—(CR'R$^{10}$)$_r$—U—(CR'$_2$)$_{s-1}$—CHO.

Where V is CH$_2$CH$_2$ may be obtained by reduction of a suitably protected compound wherein V is CH=CH.

Where V is CH$_2$O, CH$_2$N or C≡C, $L^1$ may be —OH, —NH or —C≡C H, respectively; $L^2$ may be —Br; and $R^{6"}$ may be W—(CR'$_2$)$_q$—Z—(CR'R$^{10}$)$_r$—U—(CR'$_2$)$_s$—. For example, $R^{6"}$ may be (benzyloxycarbonylamino)-methylbenzyl- or 2-(N-benzyl-4-piperidinyl)-ethyl. Similarly where U or V is OCH$_2$, NR'CH$_2$ or C≡C, $L^1$ may be —CH$_2$Br and $L^2$ may be —OH, —NH or —C≡C H, respectively. Alternately, when U or V is C≡C, $L^1$ may be Br, I or CF$_3$SO$_3$, $L^2$ may be C≡C H and the coupling may be catalyzed by palladium and a base.

Compounds wherein V is CHOHCH$_2$ may be prepared from a suitably protected compound where V is CH=CH by the procedure disclosed in *J. Org. Chem.*, 54, 1354 (1989).

Compounds wherein V is CH$_2$CHOH may be obtained from a suitably protected compound where V is CH=CH by hydroboration and basic oxidation as disclosed in *Tet. Lett.*, 31, 231 (1990).

Compounds of the formula (I)–(V), wherein the fibrinogen receptor antagonist template is of the formula (VI) are prepared by the general methods described in Schemes I–III.

Scheme I

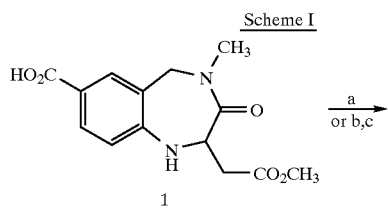

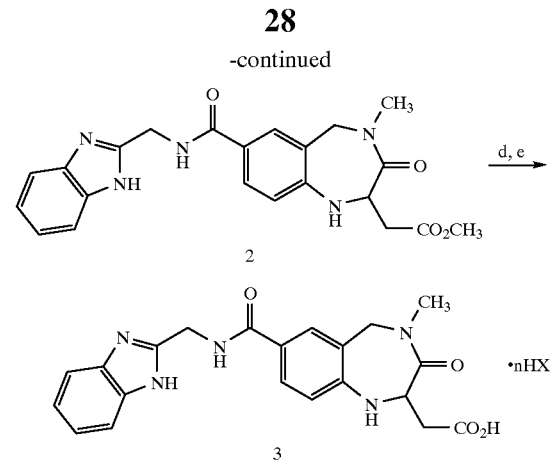

Methyl (±)-7-carboxy4-methyl-3-oxo-2,3,4,5-tetrahydro-1H-1,4-benzodiazepine-2-acetate (I-1), prepared as described by Bondinell, et al. (WO 93/00095), is converted to an activated form of the carboxylic acid using, for example, EDC and HOBT or SOCl$_2$, and the activated form is subsequently reacted with an appropriate amine to afford the corresponding amide I-2. Many additional methods for converting a carboxylic acid to an amide are known, and can be found in standard reference books, such as "Compendium of Organic Synthetic Methods", Vol. I–VI (published by Wiley-Interscience). The methyl ester of I-2 is hydrolyzed using aqueous base, for example, aqueous LiOH in THF or aqueous NaOH in methanol, and the intermediate carboxylate salt is acidified with a suitable acid, for instance TFA or HCl, to afford the carboxylic acid I-3. Alternatively, the intermediate carboxylate salt can be isolated, if desired.

Scheme II

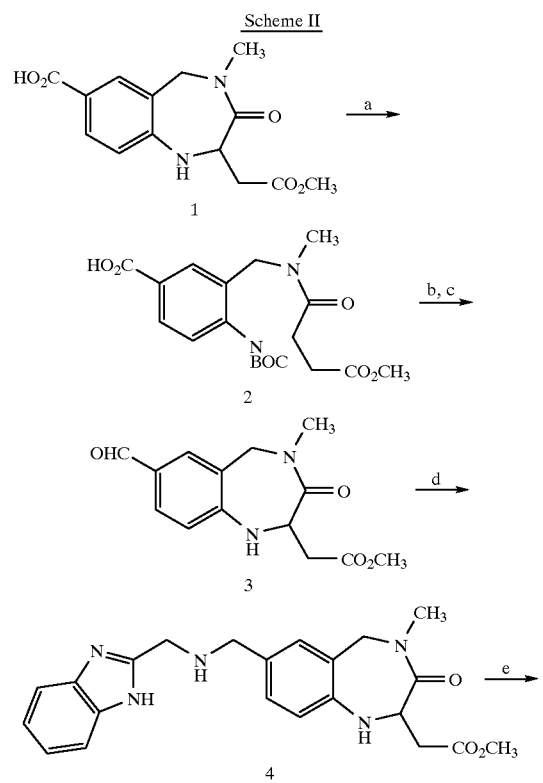

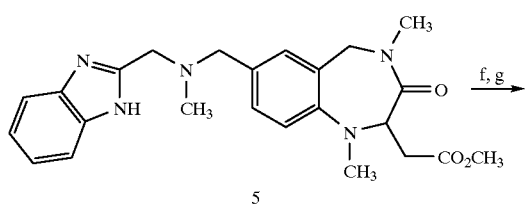

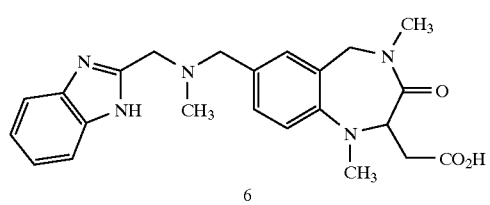

a) (BOC)₂O, DMAP, CH₃CN;
b) SOCl₂, toluene, 70° C.;
c) H₂, 10% Pd/C, 2, 6-lutidine, THF;
d) 2-(aminomethyl)benzimidazole, NaBH₃CN, MeOH;
e) formaldehyde, NaBH₃CN, AcOH, CH₃CN;
f) LiOH, THF, H₂O;
g) acidification.

Conversion of the carboxylic acid moiety of 1-Scheme II to an aldehyde can be accomplished by standard methodology, as described in "Compendium of Organic Synthetic Methods" (published by Wiley-Interscience). For example, after protection of the aniline nitrogen as its tert-butyl carbamate, the carboxylic acid is converted to the corresponding acid chloride with a suitable reagent, such as thionyl chloride. The tert-butyl carbamate is lost under these conditions. The resulting acid chloride is then reduced to aldehyde 3-Scheme II by hydrogenation over a suitable catalyst, for instance palladium on carbon in the presence of 2,6-lutidine. The aldehyde 3-Scheme II is then converted to the amine 4-Scheme II by reaction with 2-(aminomethyl) benzimidazole in the presence of a suitable reducing agent, such as sodium cyanoborohydride. Alternative methods for converting an aldehyde to an amine are described in "Compendium of Organic Synthetic Methods" (published by Wiley-Interscience). The basic nitrogen atoms of 4-Scheme II are methylated under modified Eschweiler-Clarke conditions (Sondengam, B. L. et al, *Tetrahedron Letters* 1973, 261; Borsch, R. F.; Hassid, A. I. *J. Org. Chem.* 1972, 37, 1673). Thus, reaction of 4-Scheme II with formaldehyde in the presence of a suitable reducing agent, such as sodium cyanoborohydride, gives 5-Scheme II. Saponification of the methyl ester of 5-Scheme II by the methods described earlier gives 6-Scheme II. The methyl ester of 4-Scheme II can be cleaved similarly.

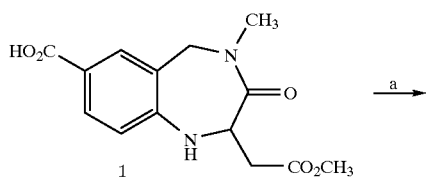

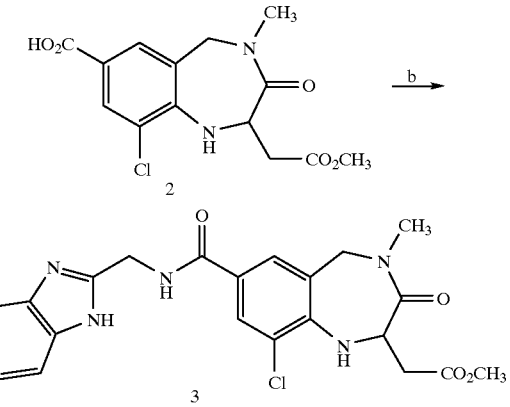

a) NCS, DMF, 80° C.;
b) see Scheme 1.

Halogenation of the aromatic moiety of 1-Scheme III can be accomplished with an appropriate electrophilic halogenating reagent, such as N-chlorosuccinimide. The resulting chlorinated derivative, 2-Scheme III, is then conveted to 3-Scheme III by the methods described in Scheme I.

The core 6-7 fused ring system is prepared of formula (VI) by methods well known in the art, e.g., Hynes, et al., *J. Het. Chem.*, 1988, 25, 1173; Muller, et al., *Helv. Chim. Acta.*, 1982, 65, 2118; Mori, et al., *Heterocycles*, 1981, 16, 1491. Similarly, methods for preparing benzazepines, 1,4-benzothiazepines, 1,4-benzoxazepines and 1,4-benzodiazepines are known and are disclosed, for instance, in Bondinell, et al., International Patent Application WO 93/00095.

A representative method for preparing the benzodiazepine nucleus is given by Schemes IV and V. A representative method for preparing a benzazepine nucleus is given by Scheme VI. A representative method for preparing a benzothiazepine is given by Scheme VII. An benzoxazepine nucleus may be prepared in the same manner as Scheme VII, except substting a benzyl alcohol for a benzyl thiol.

Scheme IV

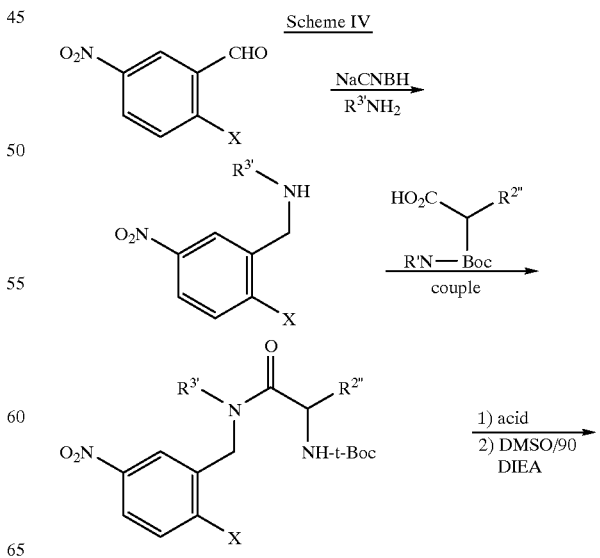

31
-continued

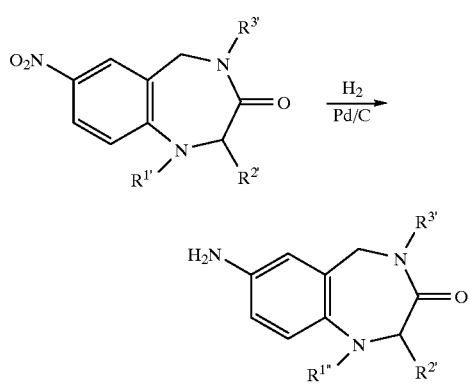

32
-continued

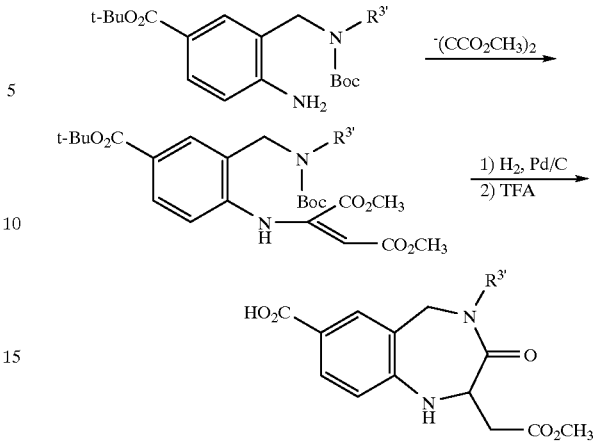

Scheme V

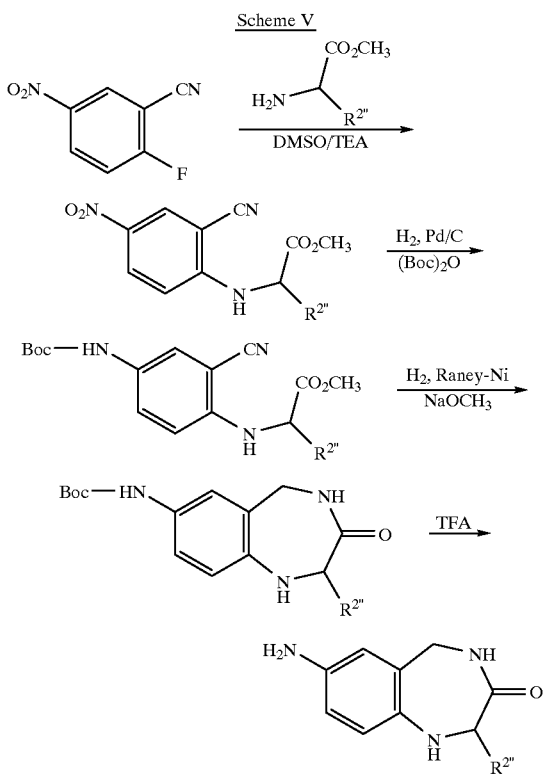

Scheme VII

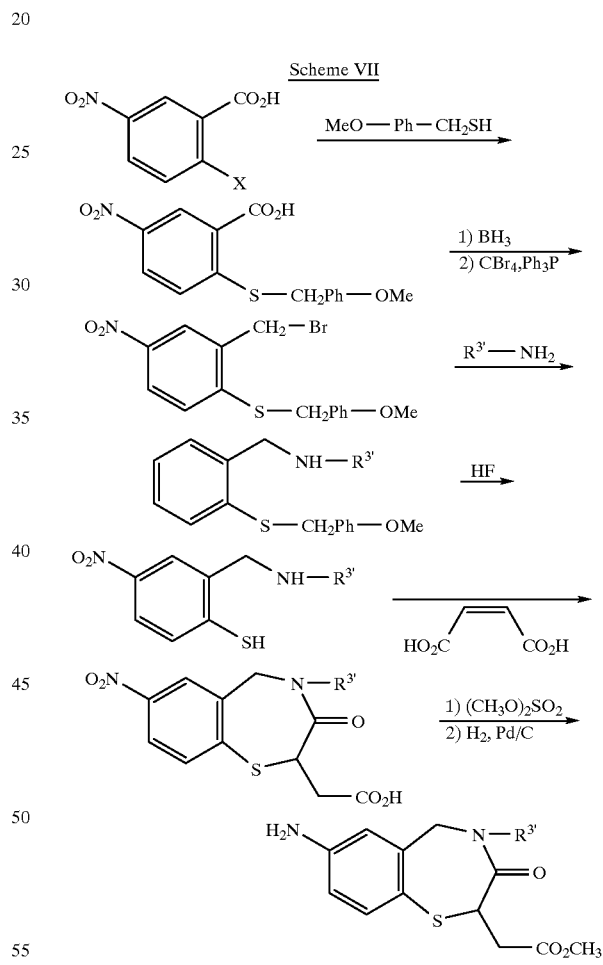

Scheme VI

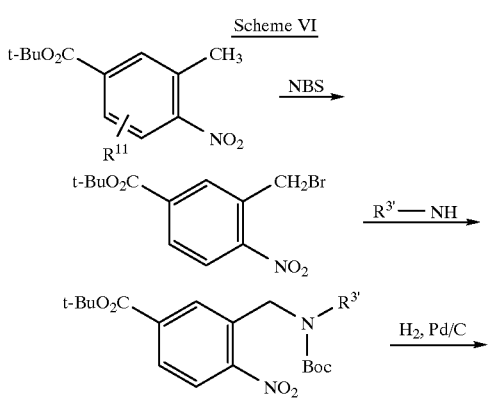

The simple tri-substituted benzene starting materials are commercially available or prepared by routine methods well known in the art.

Schemes VIII–XI are illustrative of the methods for preparing certain compounds of the instant invention. In schemes VIII–X, a covalent bond of the group W is prepared by a nucleophilic displacement reaction.

In Scheme VIII, 4-[2-(methylamino)acetyl]phenol hydrochloride (*Recl. Trav. Chim. Pays-Bas* 1949, 68, 960) is N-protected with a suitable nitrogen protecting group, such as a tert-butoxycarbonyl (BOC) group, to provide the N-protected derivative 2-Scheme VIII.

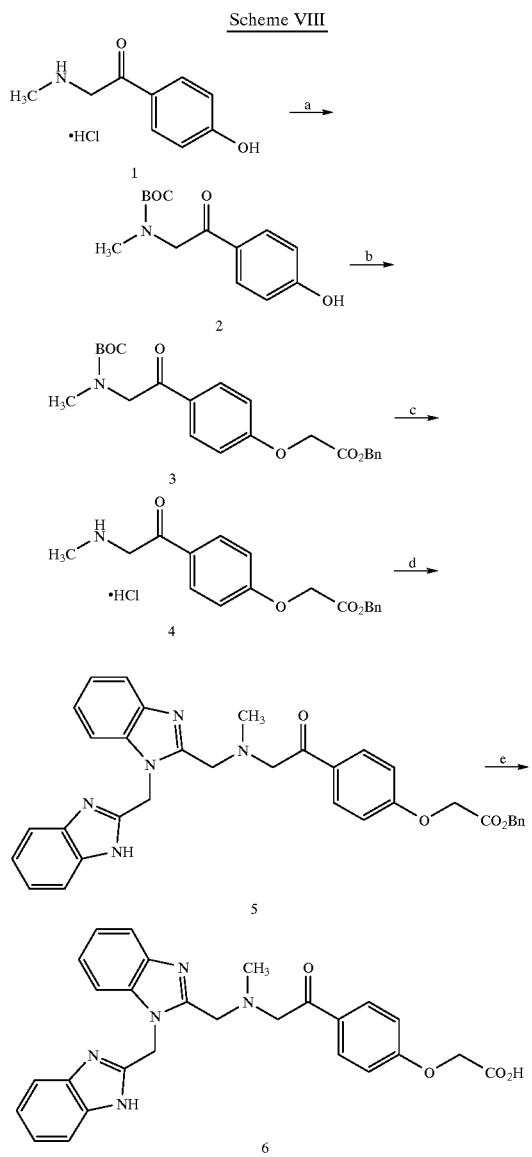

a) (BOC)₂O, NaOH, 1,4-dioxane, H₂O;
b) BrCH₂CO₂Bn, K₂CO₃, acetone;
c) 4 MHCl in 1,4-dioxane;
d) 2-(chloromethyl)benzimidazole, Et₃N, CH₃CN, CH₂Cl₂;
e) H₂, 5% Pd/C, MeOH.

Other standard nitrogen protecting groups, such as those described in Greene "Protective Groups in Organic Synthesis", may be chosen such that the protecting group employed is compatible with the subsequent chemistry and can be removed selectively under conditions which will not interfere with other functionality in the molecule. Alkylation of the phenol moiety of compound 2-Scheme VIII to afford the aryloxyacetic acid derivative 3-Scheme VIII can be accomplished by reaction with a haloacetic acid ester, for instance benzyl bromoacetate, under basic conditions in a neutral solvent. Generally, $K_2CO_3$ in refluxing acetone or 2-butanone gives acceptable results, but other bases, such as $Li_2CO_3$ or $Cs_2CO_3$, and other solvents, such as DMF, THF, or DME, might also be used. The nitrogen protecting group of 3-Scheme VIII is removed under conditions appropriate for selective deprotection of the specific protecting group employed. For example, the BOC group of 3-Scheme VIII can be removed under acidic conditions, such as 4 M HCl in 1,4-dioxane or TFA in $CH_2Cl_2$, to afford amine 4-Scheme VIII as the corresponding ammonium salt. Conversion of compound 4-Scheme VIII to the bis-benzimidazole derivative 5-Scheme VIII can be accomplished by alkylation with 2-(chloromethyl)benzimidazole in a solvent mixture of $CH_3CN$ and $CH_2Cl_2$ in the presence of $Et_3N$. Subsequent removal of the ester group of compound 5-Scheme VIII under appropriate conditions gives compound 6-Scheme VIII. The conditions selected for ester removal must be appropriate for the specific ester present as well as compatible with the other functionality in the molecule. For instance, the benzyl ester of 5-Scheme VIII can be removed by hydrogenolysis in the presence of a suitable catalyst, such as Pd on carbon, in an inert solvent, generally MeOH, EtOH, or acetic acid, to afford 6-Scheme VIII.

In Scheme IX, commercially available andrenolone hydrochloride (1-Scheme 2) is N-protected as discussed in Scheme 1 to provide the Cbz derivative 2-Scheme 2.

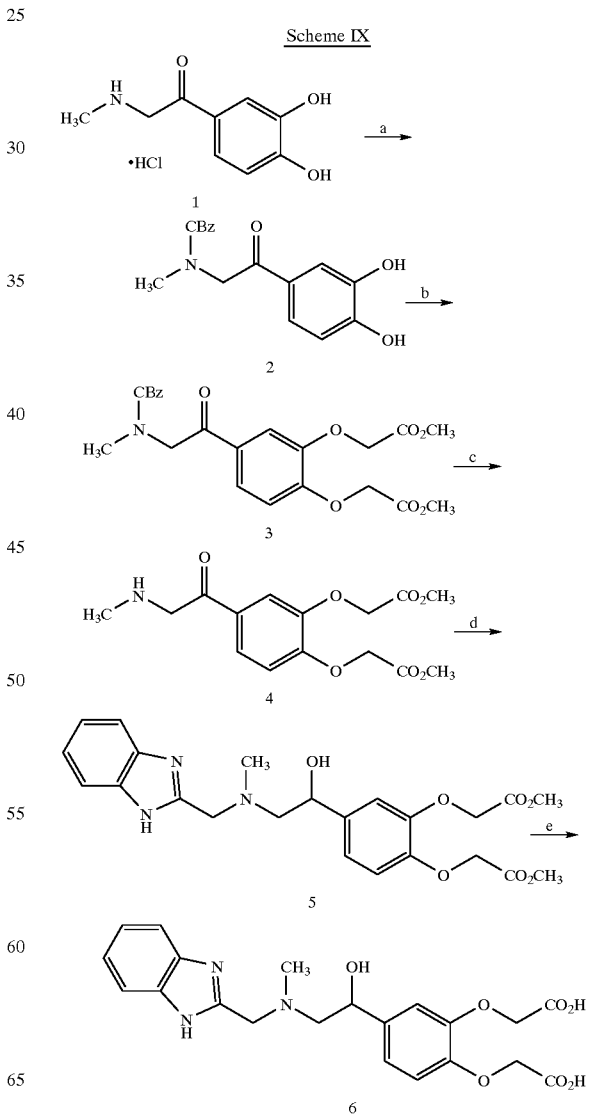

-continued a) CbzCl, NaOH, toluene, H₂O;
b) BrCH₂CO₂CH₃, K₂CO₃, acetone;
c) H₂, 10%Pd/C, EtOAc, MeOH;
d) 2-(chloromethyl)benzimidazole, Et₃N, CH₃CN, CH₂Cl₂;
e) 1.0 N LiOH, THF, H₂O.

Dialkylation of 2-Scheme IX by reaction with a haloacetic acid ester, for instance methyl bromoacetate, under basic conditions in a neutral solvent, provides the 1,2-phenylenedioxydiacetic acid derivative 3-Scheme IX. K₂CO₃ in refluxing acetone generally gives acceptable results, but other bases and solvents, such as those discussed in Scheme VIII, might also be used. Removal of the nitrogen protecting group of 3-Scheme IX by hydrogenolysis over a Pd/C catalyst in a solvent mixture of EtOAc and MeOH is accompanied by concomitant reduction of the ketone to afford aminoalcohol 4-Scheme IX. N-alkylation of compound 4-Scheme IX with 2-(chloromethyl)benzimidazole in a solvent mixture of CH₃CN and CH₂Cl₂ in the presence of Et₃N gives the mono-benzimidazole derivative 5-Scheme IX. Subsequent removal of the ester group of 5-Scheme IX under appropriate conditions, as discussed in Scheme VIII, gives compound 6-Scheme IX. Generally, a methyl ester, such as that present in 5-Scheme IX, is removed by hydrolysis in the presence of an alkali metal hydroxide, such as LiOH, NaOH, or KOH, in an aqueous solvent, typically MeOH, EtOH, or THF.

In Scheme X, commercially available andrenolone hydrochloride (1-Scheme X) is N-protected as described in Scheme VIII to provide the BOC derivative 2-Scheme X.

Scheme X

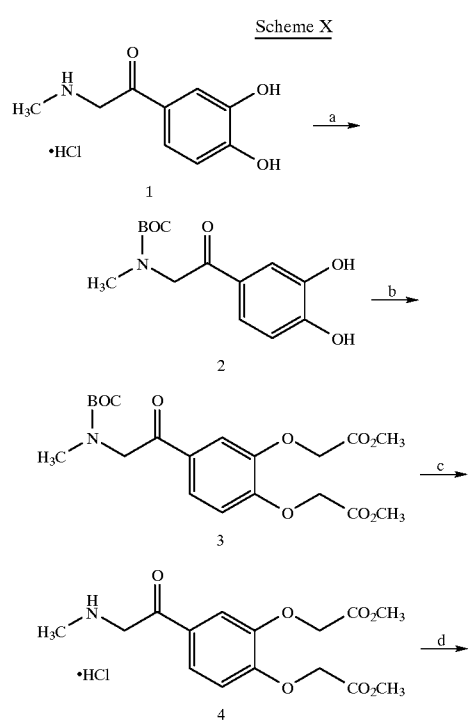

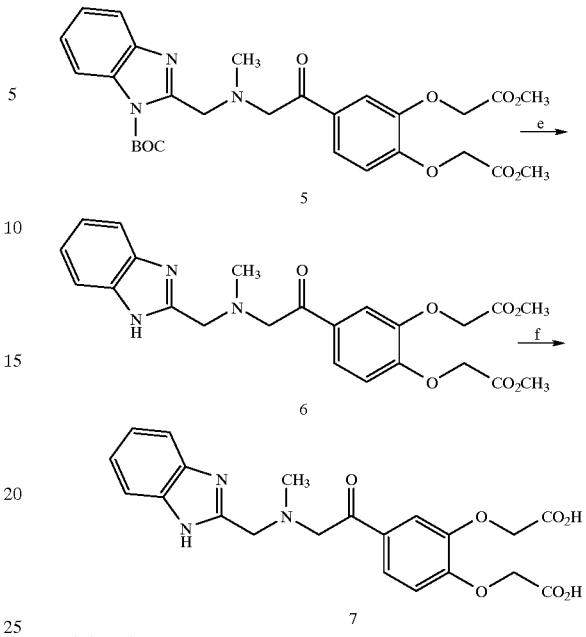

a) (BOC)₂O, NaOH, 1,4-dioxane, H₂O;
b) BrCH₂CO₂CH3, K₂CO₃, acetone;
c) 4 M HCl in 1,4-dioxane;
d) 1-(BOC)-2-(bromethyl)benzimidazole, Et₃N, THF,CH₂Cl₂;
e) TFA, CH₂Cl₂;
f) 1.0 N LiOH, THF, H₂O.

Dialkylation of 2-Scheme X as discussed in Scheme IX affords 3-Scheme X. The nitrogen protecting group of 3-Scheme X is removed as discussed in Scheme VIII to afford amine 4-Scheme X as the corresponding ammonium salt. Alkylation of 4-Scheme X with 1-BOC-2-(bromomethyl)benzimidazole in a solvent mixture of THF and CH₂Cl₂ in the presence of Et₃N gives the mono-benzimidazole derivative 5-Scheme X. Subsequent removal of the BOC group of 5-Scheme X as discussed in Scheme VIII delivers 6-Scheme X. Removal of the ester group of 6-Scheme X as discussed in Schemes 1 and 2 gives 7-Scheme IX. Alternatively, the ester group of 5-Scheme X might be removed first, followed by removal of the BOC group.

In Scheme XI, the moiety W is prepared by an amide coupling reaction.

Scheme XI

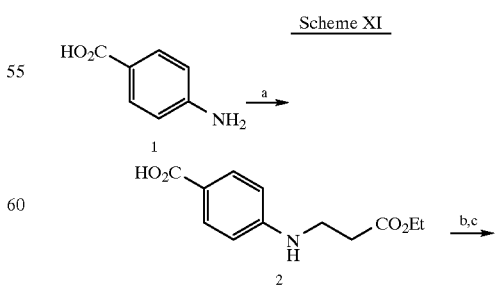

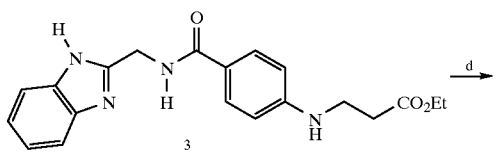

a) ethyl acrylate, HOAc;
b) SOCl$_2$;
c) 2-(aminomethyl)benzimidazole, DIEA, CH$_2$Cl$_2$;
d) NaOH, H$_2$O, MeOH.

Initially, ethyl 3-[4-(carboxy)phenyl]amino]propionic acid (2-Scheme XI) is prepared by Michael-type addition of 4-(carboxy)aniline (1-Scheme XI) to ethyl acrylate in acetic acid as described in *Chem. Ber.*, 91, 2239, 1958. The carboxyl in compound 2-Scheme XI is converted to the acid chloride with thionyl chloride, and the acid chloride is condensed with 2-(aminomethyl)benzimidazole dihydrochloride hydrate with diisopropylethylamine in dichloromethane to form compound 3-Scheme XI. The ethyl ester 3-Scheme XI is saponified with sodium hydroxide in aqueous methanol to give compound 4-Scheme XI; alternatively the ester can be converted to the carboxylic acid with other metal hydroxides or carbonates in a suitable solvent.

Scheme XII

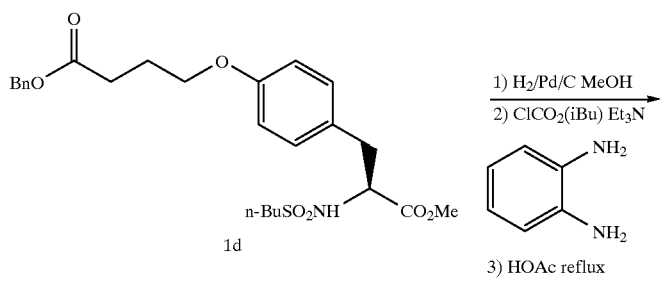

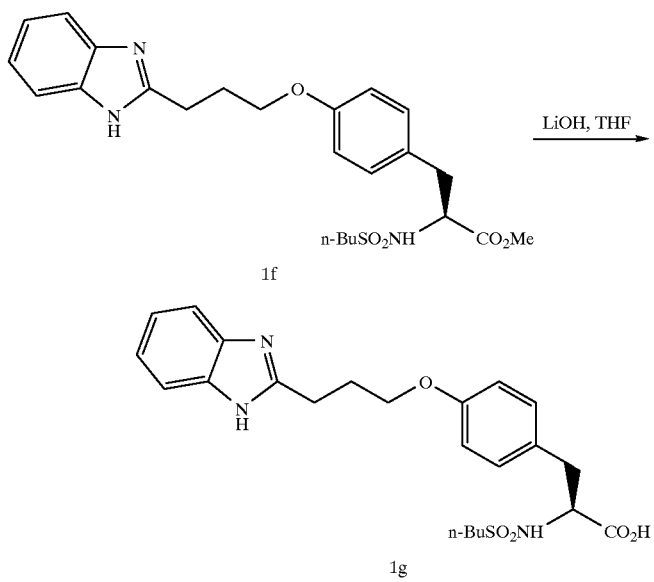

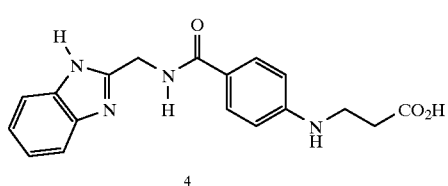

The starting material for the formula 1g-Scheme XII compounds are prepared following the procedures in Egbertson et al., J. Med. Chem., 1994, 37, 2537–3551 which discloses general methods to alkylate the phenol of an N-protected tyrosine derivative, remove the N-protecting group, and sulfonylate the amine. Using benzyl 4-bromobutyrate as the alkylating agent, intermediate 1d-Scheme XII was prepared. Removal of the benzyl ester and reaction with ortho-phenylenediamine under standard conditions afforded the benzimidazole 1f-Scheme XII. Finally, saponification of the methyl ester yielded the target compound 1 g-Scheme XII.

Intermediate compounds of formula (XXX) may be prepared from suitably protected amino acids and phenyl-1,2-diamines or 2-nitro-anilines which are commercially available or prepared by methods available to those skilled in the art according to the Scheme (XIII) and (XIV).

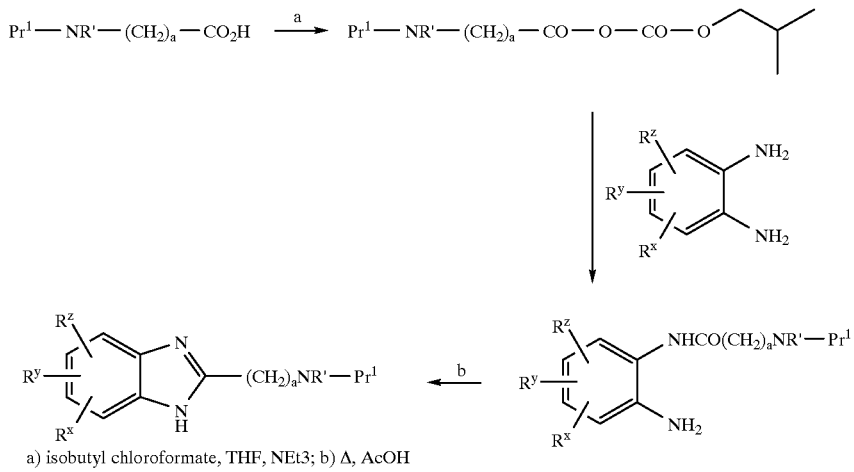

Scheme XIII a) isobutyl chloroformate, THF, NEt3; b) Δ, AcOH

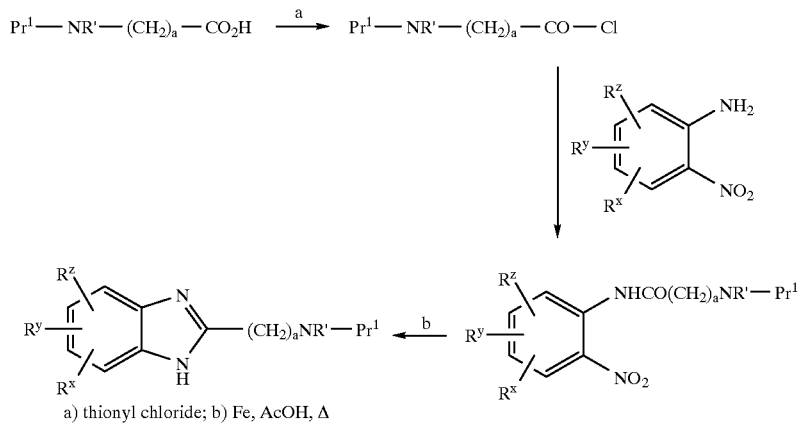

Scheme XIV a) thionyl chloride; b) Fe, AcOH, Δ

Amide coupling reagents as used herein denote reagents which may be used to form peptide bonds. Typical coupling methods employ carbodiimides, activated anhydrides and esters and acyl halides. Reagents such as EDC, DCC, DPPA, PPA, BOP reagent, HOBt, N-hydroxysuccinirnide and oxalyl chloride are typical.

Coupling methods to form peptide bonds are generally well known to the art. The methods of peptide synthesis generally set forth by Bodansky et al., THE PRACTICE OF PEPTIDE SYNTHESIS, Springer-Verlag, Berlin, 1984, Ali et al., in *J. Med. Chem.*, 29, 984 (1986) and *J. Med. Chem.*, 30, 2291 (1987) are generally illustrative of the technique and are incorporated herein by reference.

Typically, the amine or aniline is coupled via its free amino group to an appropriate carboxylic acid substrate using a suitable carbodiimide coupling agent, such as N,N' dicyclohexyl carbodiimide (DCC), optionally in the presence of catalysts such as 1-hydroxybenzotriazole (HOBt) and dimethylamino pyridine (DMAP). Other methods, such as the formation of activated esters, anhydrides or acid halides, of the free carboxyl of a suitably protected acid substrate, and subsequent reaction with the free amine of a suitably protected amine, optionally in the presence of a base, are also suitable. For example, a protected Boc-amino acid or Cbz-amidino benzoic acid is treated in an anhydrous solvent, such as methylene chloride or tetrahydrofuran (THF), in the presence of a base, such as N-methyl morpholine, DMAP or a trialkylamine, with isobutyl chloroformate to form the "activated anhydride", which is subsequently reacted with the free amine of a second protected amino acid or aniline.

The compounds of formula (XIX) and (XX) are commercially available or are prepared by methods known in the art such as illustrated herein disclosed in standard reference books, like the COMPENDIUM OF ORGANIC SYNTHETIC METHODS, Vol. I–VI (Wiley-Interscience). A generally applicable route to benzimidazoles is disclosed in Nestor et al, *J. Med. Chem.* 1984, 27, 320. Representative methods for preparing compounds of formula (XX) are also common to the art and may be found, for instance, in EP-A 0 381 033.

Acid addition salts of the compounds are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic. Certain of the compounds form inner salts or zwitterions which may be acceptable. Cationic salts are prepared by treating the parent compound with an excess of an alkaline reagent, such as a hydroxide, carbonate or alkoxide, containing the appropriate cation; or with an appropriate organic amine. Cations such as $Li^+$, $Na^+$, $K^+$, $Ca^{++}$, $Mg^{++}$ and $NH_4^+$ are specific examples of cations present in pharmaceutically acceptable salts.

This invention also provides a pharmaceutical composition which comprises a compound according to formula (I)–(V) and a pharmaceutically acceptable carrier. Accordingly, the compounds of formula (I)–(V) may be used in the manufacture of a medicament. Pharmaceutical compositions of the compounds of formula (I)–(V) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, these compounds may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

For rectal administration, the compounds of this invention may also be combined with excipients such as cocoa butter, glycerin, gelatin or polyethylene glycols and molded into a suppository.

The compounds described herein are antagonists of the vitronectin receptor, and are useful for treating diseases wherein the underlying pathology is attributable to ligand or cell which interacts with the vitronectin receptor. For instance, these compounds are useful for the treatment of diseases wherein loss of the bone matrix creates pathology. Thus, the instant compounds are useful for the treatment of ostoeporosis, hyperparathyroidism, Paget's disease, hypercalcernia of malignancy, osteolytic lesions produced by bone metastasis, bone loss due to immobilization or sex hormone deficiency. The compounds of this invention are also believed to have utility as antitumor, anti-angiogenic, antiinflammatory and anti-metastatic agents, and be useful in the treatment of atherosclerosis and restenosis.

The compound is administered either orally or parenterally to the patient, in a manner such that the concentration of drug is sufficient to inhibit bone resorption, or other such indication. The pharmaceutical composition containing the peptide is administered at an oral dose of between about 0.1 to about 50 mg/kg in a manner consistent with the condition of the patient. Preferably the oral dose would be about 0.5 to about 20 mg/kg. For acute therapy, parenteral administration is preferred. An intravenous infusion of the peptide in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg. The compounds are administered one to four times daily at a level to achieve a total daily dose of about 0.4 to about 400 mg/kg/day. The precise level and method by which the compounds are administered is readily determined by one routinely skilled in the art by comparing the blood level of the agent to the concentration required to have a therapeutic effect.

The compounds may be tested in one of several biological assays to determine the concentration of compound which is required to have a given pharmacological effect.

Inhibition of Vitronectin Binding

Solid-Phase [$^3$H]-SK&F-107260 Binding to $\alpha_v\beta_3$: Human placenta or human platelet $\alpha_v\beta_3$ (0.1–0.3 mg/mL) in buffer T (containing 2 mM $CaCl_2$ and 1% octylglucoside) was diluted with buffer T containing 1 mM $CaCl_2$, 1 mM $MnCl_2$, 1 mM $MgCl_2$ (buffer A) and 0.05% $NaN_3$, and then immediately added to 96-well ELISA plates (Corning, New York, N.Y.) at 0.1 mL per well. 0.1–0.2 µg of $\alpha_v\beta_3$ was added per well. The plates were incubated overnight at 4° C. At the time of the experiment, the wells were washed once with buffer A and were incubated with 0.1 mL of 3.5% bovine serum albumin in the same buffer for 1 hr at room temperature. Following incubation the wells were aspirated completely and washed twice with 0.2 mL buffer A.

Compounds were dissolved in 100% DMSO to give a 2 mM stock solution, which was diluted with binding buffer (15 mM Tris-HCl (pH 7.4), 100 mM NaCl, 1 mM $CaCl_2$, 1 mM $MnCl_2$, 1 mM $MgCl_2$) to a final compound concentration of 100 µM. This solution is then diluted to the required final compound concentration. Various concentrations of unlabeled antagonists (0.001–100 µM) were added to the wells in triplicates, followed by the addition of 5.0 nM of [$^3$H]-SK&F-107260 (65–86 Ci/mmol).

The plates were incubated for 1 hr at room temperature. Following incubation the wells were aspirated completely and washed once with 0.2 mL of ice cold buffer A in a well-to-well fashion. The receptors were solubilized with 0.1 mL of 1% SDS and the bound [$^3$H]-SK&F-107260 was determined by liquid scintillation counting with the addition of 3 mL Ready Safe in a Beckman LS Liquid Scintillation Counter, with 40% efficiency. Nonspecific binding of [$^3$H]-SK&F-107260 was determined in the presence of 2 µM SK&F-107260 and was consistently less than 1% of total radioligand input. The $IC_{50}$ (concentration of the antagonist to inhibit 50% binding of [$^3$H]-SK&F-107260) was determined by a nonlinear, least squares curve-fitting routine, which was modified from the LUNDON-2 program. The $K_i$ (dissociation constant of the antagonist) was calculated according to the equation: $K_i=IC_{50}(1+L/K_d)$, where L and $K_d$ were the concentration and the dissociation constant of [$^3$H]-SK&F-107260, respectively.

Compounds of the present invention inhibit vitronectin binding to SK&F 107260 in the concentration range of about 0.001 to 50 micromolar.

Compounds of this invention are also tested for in vitro and in vivo bone resorption in assays standard in the art for evaluating inhibition of bone formation, such as the pit formation assay disclosed in EP 528 587, which may also be performed using human osteoclasts in place of rat osteoclasts, and the ovarectomized rat model, described by Wronski et al., Cells and Materials 1991, Sup. 1, 69–74.

Vascular Smooth Muscle Cell Migration Assay

Rat or human aortic smooth muscle cells were used. The cell migration was monitored in a Transwell cell culture chamber by using a polycarbonate membrane with pores of 8 um (Costar). The lower surface of the filter was coated with vitronectin. Cells were suspended in DMEM supplemented with 0.2% bovine serum albumin at a concentration of $2.5–5.0 \times 10^6$ cells/mL, and were pretreated with test compound at various concentrations for 20 min at 20° C. The solvent alone was used as control. 0.2 mL of the cell suspension was placed in the upper compartment of the chamber. The lower compartment contained 0.6 mL of DMEM supplemented with 0.2% bovine serum albumin. Incubation was carried out at 37° C. in an atmosphere of 95% air/5% $CO_2$ for 24 hr. After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

PARATHYROIDECTOMIZED RAT MODEL

Each experimental group consists of 5–6 male Sprague-Dawley rats. The rats are parathyroidectomized (by the vendor, Taconic Farms) 7 days prior to use. Twenty four hours prior to use, circulating ionized calcium levels are measured in whole blood immediately after it has been withdrawn by tail venipuncture into heparinized tubes. Rats are included if ionized Ca level (measured with a Ciba-Corning model 634 calcium pH analyzer) is _1.2 mM/L. The rats are then put on a diet of calcium-free chow and deionized water. At the start of the experiment the rats weigh approximately 100 g. Baseline Ca levels are measured and the rats are administered control vehicle (saline) or compound (dissolved in saline) as a single intravenous (tail vein) bolus injection followed immediately by a single subcutaneous injection of either human parathyroid hormone 1-34 peptide (hPTH1-34, dose 0.2 mg/kg in saline/0.1% bovine serum albumen, Bachem, Ca) or the PTH vehicle. The calcemic response to PTH (and any effect of compound on this response) is measured 2 h after compound/PTH administration.

RAT ULNA DRIFT MODEL

Each experimental group consists of 8–10 male Sprague-Dawley or Wistar rats of approximately 30–40 g body weight at the start of the experiment. The agent being tested is administered by an appropriate route as single or multiple daily doses for a period of seven days. Prior to administration of the first dose, the rats are given a single dose of a fluorescent marker (tetracycline 25 mg/kg, or calcein 10 mg/kg) that labels the position of bone forming surfaces at that point in time. After dosing of compound has been completed, the rats are killed and both forelimbs are removed at the elbow, the foot is removed at the ankle and the skin removed. The sample is frozen and mounted vertically on a microtome chuck. Cross sections of the midshaft region of the ulna are cut in the cryostat. The rate of bone resorption is measured morphometrically in the medial-dorsal portion of the cortical bone. The measurement is done as follows: the amount of bone resorbed at the periosteal surface is equal to the distance by which the periosteal surface has advanced towards the fluorescent label which had been incorporated at the endosteal bone formation surface on day zero; this distance is calculated by subtracting the width of bone between the label and the periosteal surface on day 7 from the width on day zero; the resorption rate in microns per day is calculated by dividing the result by 7.

HUMAN OSTEOCLAST RESORPTION ASSAY ("PIT ASSAY")

Aliquots of osteoclastoma-derived cell suspensions are removed from liquid nitrogen strorage, warmed rapidly at 37° C. and washed ×1 in RPMI-1640 medium by centrifugation (1000 rpm, 5 mins at 40° C.).

Aspirate the medium and replace it with murine anti-HLA-DR antibody, diluted 1:3 in RPMI-1640 medium. Incubate for 30 mins on ice and mix the cell suspension frequently.

The cells are washed ×2 with cold RPMI-1640 by centrifugation (1000 rpm, 5 mins at 40° C.) and the cells are transferred to a sterile 15 ml centrifuge tube. The number of mononuclear cells are enumerated in an improved Neubauer counting chamber.

Sufficient magnetic beads (5/mononuclear cell), coated with goat anti-mouse IgG, are removed from their stock bottle and placed into 5 ml of fresh medium (this washes away the toxic azide preservative). The medium is removed by immobilizing the beads on a magnet and is replaced with fresh medium.

The beads are mixed with the cells and the suspension is incubated for 30 mins on ice. The suspension is mixed frequently.

The bead-coated cells are immobilized on a magnet and the remaining cells (osteoclast-rich fraction) are decanted into a sterile 50 ml centrifuge tube.

Fresh medium is added to the bead-coated cells to dislodge any trapped osteoclasts. This wash process is repeated ×10. The bead-coated cells are discarded.

The osteoclasts are enumerated in a counting chamber, using a large-bore disposable plastic pasteur to charge the chamber with the sample.

The cells are pelleted by centrifugation and the density of osteoclasts adjusted to $1.5 \times 10^4$/ml in EMEM medium, supplemented with 10% fetal calf serum and 1.7 g/liter of sodium bicarbonate.

3 ml aliquots of the cell suspension (per treatment) are decanted into 15 ml centrifuge tubes. The cells are pelleted by centrifugation.

To each tube 3 ml of the appropriate treatment are added (diluted to 50 uM in the EMEM medium). Also included are appropriate vehicle controls, a positive control (87MEM1 diluted to 100 ug/ml) and an isotype control (IgG2a diluted to 100 ug/ml). Incubate at 37° C. for 30 mins.

0.5 ml aliquots of the cells are seeded onto sterile dentine slices in a 48-well plate and incubated at 37° C. for 2 hours. Each treatment is screened in quadruplicate.

The slices are washed in six changes of warm PBS (10 ml/well in a 6-well plate) and then placed into fresh treatment or control. Incubate at 37° C. for 48 hours.

Tartrate Resistant Acid DhosDhatase (TRAP) Procedure (Selective Stain for Cells of the Osteoclast Lineage).

The slices are washed in phosphate buffered saline and fixed in 2% gluteraldehyde (in 0.2M sodium cacodylate) for 5 mins.

They are washed in water and incubated in TRAP buffer for 5 mins at 37° C.

Following a wash in cold water they are incubated in cold acetate buffer/fast red garnet for 5 mins at 4° C.

Excess buffer is aspirated, and the slices are air dried following a wash in water.

The TRAP positive osteoclasts are enumerated by brightfield microscopy and are then removed from the surface of the dentine by sonication.

Pit volumes are determined using the Nikon/Lasertec ILM21W confocal microscope.

INHIBITION OF RGD-MEDIATED GPIIb-IIIa BINDING

Purification of GPIIb-IIIa

Ten units of outdated, washed human platelets (obtained from Red Cross) were lyzed by gentle stirring in 3% octylglucoside, 20 mM Tris-HCl, pH 7.4, 140 mM NaCl, 2 mM $CaCl_2$ at 4° C. for 2 h. The lysate was centrifuged at 100,000 g for 1 h. The supernatant obtained was applied to a 5 mL lentil lectin sepharose 4B column (E.Y. Labs) preequilibrated with 20 mM Tris-HCl, pH 7.4, 100 mM NaCl, 2 mM $CaCl_2$, 1% octylglucoside (buffer A). After 2 h incubation, the column was washed with 50 mL cold buffer A. The lectin-retained GPIIb- IIIa was eluted with buffer A containing 10% dextrose. All procedures were performed at 4° C. The GPIIb- IIIa obtained was >95% pure as shown by SDS polyacrylarnide gel electrophoresis.

Incorporation of GPIIb-IIIa in Liposomes.

A mixture of phosphatidylserine (70%) and phosphatidylcholine (30%) (Avanti Polar Lipids) were dried to the walls of a glass tube under a stream of nitrogen. Purified GPIIb-IIIa was diluted to a final concentration of 0.5 mg/mL and mixed with the phospholipids in a protein:phospholipid ratio of 1:3 (w:w). The mixture was resuspended and sonicated in a bath sonicator for 5 min. The mixture was then dialyzed overnight using 12,000–14,000 molecular weight cutoff dialysis tubing against a 1000-fold excess of 50 mM Tris-HCl, pH 7.4, 100 mM NaCl, 2 mM CaCl2 (with 2 changes). The GPIIb-IIIa-containing liposomes were centrifuged at 12,000 g for 15 min and resuspended in the dialysis buffer at a final protein concentration of approximately 1 mg/mL. The liposomes were stored at −70C. until needed.

Competitive Binding to GPIIb-IIIa

The binding to the fibrinogen receptor (GPIIb-IIIa) was assayed by an indirect competitive binding method using [$^3$H]-SK&F-107260 as an RGD-type ligand. The binding assay was performed in a 96-well filtration plate assembly (Millipore Corporation, Bedford, Mass.) using 0.22 um hydrophilic durapore membranes. The wells were precoated with 0.2 mL of 10 $\mu$g/mL polylysine (Sigma Chemical Co., St. Louis, Mo.) at room temperature for 1 h to block nonspecific binding. Various concentrations of unlabeled benzadiazapines were added to the wells in quadruplicate. [$^3$H]-SK&F-107260 was applied to each well at a final concentration of 4.5 nM, followed by the addition of 1 $\mu$g of the purified platelet GPIIb-IIIa-containing liposomes. The mixtures were incubated for 1 h at room temperature. The GPIIb-IIIa-bound [3H]-SK&F-107260 was seperated from the unbound by filtration using a Millipore filtration manifold, followed by washing with ice-cold buffer (2 times, each 0.2 mL). Bound radioactivity remaining on the filters was counted in 1.5 mL Ready Solve (Beckman Instruments, Fullerton, Calif.) in a Beckman Liquid Scintillation Counter (Model LS6800), with 40% efficiency. Nonspecific binding was determined in the presence of 2 $\mu$M unlabeled SK&F-107260 and was consistently less than 0.14% of the total radioactivity added to the samples. All data points are the mean of quadruplicate determinations.

Competition binding data were analyzed by a nonlinear least-squares curve fitting procedure. This method provides the IC50 of the antagonists (concentration of the antagonist which inhibits specific binding of [$^3$H]-SK&F-107260 by 50% at equilibrium). The IC50 is related to the equilibrium dissociation constant (Ki) of the antagonist based on the Cheng and Prusoff equation: $Ki=IC50/(1+L/Kd)$, where L is the concentration of [3H]-SK&F-107260 used in the competitive binding assay (4.5 nM), and $K_d$ is the dissociation constant of [3H]-SK&F-107260 which is 4.5 nM as determined by Scatchard analysis Compounds of the present invention inhibit the vitronectin binding to SK&F 007260 with a Ki at the vitronectin receptor that is about ten-fold greater than that for the fibrinogen receptor. Preferred compounds have a Ki at the vitronectin receptor that is thirty-fold greater than that at the fibrinogen receptor. The most preferred compounds have a Ki at the vitronectin receptor that is a hundred-fold greater than that at the fibrinogen receptor.

The examples which follow are intended to in no way limit the scope of this invention, but are provided to illustrate how to make and use the compounds of this invention. Many other embodiments will be readily apparent to those skilled in the art.

EXAMPLES

GENERAL

Nuclear magnetic resonance spectra were recorded at either 250 or 400 MHz using, respectively, a Bruker AM 250 or Bruker AC 400 spectrometer. $CDCl_3$ is deuteriochloroform, $DMSO-d_6$ is hexadeuteriodimethylsulfoxide, and $CD_3OD$ is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Continuous wave infrared (IR) spectra were recorded on a Perkin-Elmer 683 infrared spectrometer, and Fourier transform infrared (FTIR) spectra were recorded on a Nicolet Impact 400 D infrared spectrometer. IR and FTIR spectra were recorded in transmission mode, and band positions are reported in inverse wavenumbers ($cm^{-1}$). Mass spectra were taken on either VG 70 FE, PE Syx API III, or VG ZAB HF instruments, using fast atom bombardment (FAB) or electrospray (ES) ionization techniques. Elemental analyses were obtained using a Perkin-Elmer 240C elemental analyzer. Melting points were taken on a Thomas-Hoover melting point apparatus and are uncorrected. All temperatures are reported in degrees Celsius.

Analtech Silica Gel GF and E. Merck Silica Gel 60 F-254 thin layer plates were used for thin layer chromatography. Both flash and gravity chromatography were carried out on E. Merck Kieselgel 60 (230–400 mesh) silica gel. Analytical and preparative HPLC. were carried out on Rainin or Beckman chromatographs. ODS refers to an octadecylsilyl derivatized silica gel chromatographic support. 5 $\mu$Apex-ODS indicates an octadecylsilyl derivatized silica gel chromatographic support having a nominal particle size of 5 $\mu$, made by Jones Chromatography, Littleton, Colo. YMC. ODS-AQ® is an ODS chromatographic support and is a registered trademark of YMC. Co. Ltd., Kyoto, Japan. PRP-1® is a polymeric (styrene-divinylbenzene) chromatographic support, and is a registered trademark of Hamilton Co., Reno, Nev.) Celite® is a filter aid composed of acid-washed diatomaceous silica, and is a registered trademark of Manville Corp., Denver, Colo.

Methyl (±)-7-carboxy-4-methy-3-oxo-2,3,4,5-tetrahydro-1H-1,4-benzodiazepine-2-acetate, methyl (2S)-7-carboxy-4-methyl-3-oxo-2,3,4,5-tetrahydro-1H-1,4-benzodiazepine-2-acetate, methyl (2R)-7-carboxy-4-methy-3-oxo-2,3,4,5-tetrahydro-1H-1,4-benzodiazepine-2-acetate, methyl (±)-7-carboxy-4-isopropyl-3-oxo-2,3,4,5-tetrahydro-1H-1,4-benzodiazepine-2-acetate, methyl (±)-7-carboxy-3-oxo-2-(2-phenylethyl)-2,3,4,5-tetrahydro-1H-1,4-benzodiazepine-2-acetate, and methyl (±)-8-carboxy-2-methyl-3-oxo-2,3,4,5-tetrahydro-1H-2-benzazepine-4-acetate were prepared by the method of Bondinell, et al., WO 93/00095. 2-(Aminomethyl)imidazole was prepared according to the procedure in *Annalen* 1968, 718, 249.

Preparation 1

Preparation of methyl (±)-7-carboxy-4-(2-methoxyethyl)-3-oxo-2,3,4,5-tetrahydro-1H-1,4-benzodiazepine-2-acetate a) tert-Butyl 3-[(2-methoxyethyl)amino]methyl4-nitrobenzoate A mixture of tert-butyl 3-methy-4-nitrobenzoate (WO 93/00095; 14.96 g, 63.05 mmol), NBS (16.83 g, 94.58 mmol), benzoyl peroxide (1.53 g, 6.31 mmol), and CCl$_4$ (315 mL) was heated at reflux. After 18.5 h, the reaction was cooled thoroughly in ice and filtered to remove the precipitated succinimide. The filtrate was concentrated to leave a yellow oil.

This yellow oil was dissolved in dry THF (315 mL), and 2-methoxyethylamine (16.4 mL, 189.2 mmol) was added all at once. The orangish-yellow solution was stirred at RT for 40 min, then was concentrated to remove the THF. The residue was diluted with Et$_2$O (630 mL) and washed sequentially with 1.0 N NaOH (125 mL) and H$_2$O (125 mL). The combined aqueous layers were back-extracted with Et$_2$O (300 mL), and the combined organic layers were washed with brine (125 mL) and dried (MgSO$_4$). Concentration and silica gel chromatography (3:2 EtOAc/hexanes) gave the title compound (10.30 g, 53%) as a yellow oil: TLC R$_f$ (1:1 EtOAc/hexanes) 0.43; $^1$H NMR (250 MHz, CDCl$_3$) δ 8.22 (d, J=1.7 Hz, 1H), 7.99 (dd, J=8.4, 1.7 Hz, 1H), 7.92 (d, J=8.4 Hz, 1H), 4.08 (s, 2H), 3.51 (t, J=5.1 Hz, 1H), 3.36 (s, 3H), 2.82 (t, J=5.1 Hz, 2H), 1.61 (s, 9H); FTIR (CCl$_4$) 1723, 1530, 1369, 1302, 1162, 1116, 842 cm$^{-1}$; MS (ES) m/e 311 (M+H)$^+$, 255 (M+H—C$_4$H$_8$)$^+$.

b) tert-Butyl 3-[[N-(2-methoxyethyl)-N-(tert-butoxycarbonyl)]amino]methyl4-nitrobenzoate Di-tert-butyl dicarbonate (7.97 g, 36.51 mmol) was added all at once to a solution of tert-butyl 3-[(2-methoxyethyl) amino]methyl-4-nitrobenzoate (10.30 g, 33.19 mmol) in CHCl$_3$ (165 mL) at RT. After 16 h, the reaction was concentrated and reconcentrated from hexanes (to remove CHCl$_3$). Silica gel chromatography (20% EtOAc/hexanes) gave the title compound (13.21 g, 97%) as a yellow oil: TLC R$_f$ (20% EtOAc/hexanes) 0.49; $^1$H NMR (250 MHz, CDCl$_3$) δ 7.85–8.15 (m, 3H), 4.75–4.95 (m, 2H), 3.35–3.65 (m, 4H), 3.25 (bs s, 3H), 1.60 (s, 9H), 1.15–1.80 (m, 9H); FTIR (CCl$_4$) 1723, 1701, 1531, 1368, 1304, 1161, 1119 cm$^{-1}$; MS (ES) m/e 428.2 (M+NH$_4$)$^+$, 411.2 (M+H)$^+$, 355.2 (M+H—C$_4$H$_8$)$^+$, 311.2 (M+H—C$_4$H$_8$—CO$_2$)$^+$.

c) tert-Butyl 4-amino-3-[[N-(2-methoxyethyl)-N-(tert-butoxycarbonyl)]amino]methyl benzoate 10% Pd/C (3.42 g, 3.22 mmol) was added to a solution of tert-butyl 3-[[N-(2-methoxyethyl)-N-(tert-butoxycarbonyl)] amino]methyl-4-nitrobenzoate (13.21 g, 32.18 mmol) in EtOAc (320 mL), and the mixture was shaken on a Parr apparatus at RT under H$_2$ (55 psi). After 4 h, the reaction was filtered through Celite®, and the filtrate was concentrated to afford the title compound (12.16 g, 99%) as a colorless foam: TLC R$_f$ (20% EtOAc/hexanes) 0.34; $^1$H NMR (250 MHz, CDCl$_3$) δ 7.68–7.77 (m, 2H), 6.56 (d, J=8.9 Hz, 1H), 5.00 (br s, 2H), 4.46 (s, 2H), 3.38–3.52 (m, 2H), 3.32 (s, 3H), 3.20–3.35 (m, 2H), 1.57 (s, 9H), 1.48 (s, 9H); FTIR (CCl$_4$) 3490, 3340, 3230, 1703, 1673, 1642, 1367, 1284, 1149, 1170 cm$^{-1}$; MS (ES) m/e 403.2 (M+Na)$^+$, 381.2 (M+H)$^+$, 325.2 (M+H—C$_4$H$_8$)$^+$, 281 (M+H—C$_4$H$_8$—CO$_2$)$^+$, 269.0 (M+H—2×C$_4$H$_8$)$^+$, 225.0 (M+H—2×C$_4$H$_8$—CO$_2$)$^+$.

d) t-Butyl (±)4-[2-(1,4-dimethoxy-1,4-dioxobutyl)amino]-3-[[N-(2-methoxyethyl)-N-(tert-butoxycarbonyl)]amino] methylbenzoate A solution of tert-butyl 4-amino-3-[[N-(2-methoxyethyl)-N-(tert-butoxycarbonyl)]amino]methylbenzoate (12.16 g, 31.96 mmol) and dimethylacetylene dicarbolate (4.3 mL, 35.2 mmol) in MeOH (65 mL) was heated at reflux for 45 min, then was cooled to RT. The resulting solution was combined with MeOH (260 mL) and 10% Pd/C (6.80 g, 6.4 mmol), and the mixture was shaken on a Parr apparatus at RT under H$_2$ (50 psi). After 6.5 h, the reaction was filtered through Celite®, and the filtrate was concentrated on the rotavap. The residue was reconcentrated from CHCl$_3$ (to remove MeOH), then was chromatographed on silica gel (30% EtOAc/hexanes). The title compound (15.03 g, 90%) was obtained as a faintly yellow oil: TLC R$_f$ (30% EtOAc/hexanes) 0.39; $^1$H NMR (250 MHz, CDCl$_3$) δ 7.82 (dd, J=8.6, 2.0 Hz, 1H), 7.72 (d, J=2.0 Hz, 1H), 6.63 (d, J=8.6 Hz, 1H), 6.35–6.55 (m, 1H), 4.55–4.70 (m, 1H), 4.52 (1/2 AB, J=15.1 Hz, 1H), 4.40 (1/2 AB, J=15.1 Hz, 1H), 3.71 (s, 3H), 3.69 (s, 3H), 3.35–3.50 (m, 2H), 3.31 (s, 3H), 3.20–3.30 (m, 2H), 2.98 (dd, J=16.2, 6.7 Hz, 1H), 2.84 (dd, J=16.2, 6.8 Hz, 1H), 1.56 (s, 9H), 1.48 (s, 1H); FTIR (CCl4) 3312, 1748, 1704, 1670, 1610, 1367, 1297, 1142, 1172 cm$^{-1}$; Me (ES) m/e 547.2 (M+Na)$^+$, 525.2 (M+H)$^+$, 469.2 (M+H—C$_4$H$_8$)$^+$, 425.2 (M+H—C$_4$H$_8$—CO$_2$)$^+$.

e) Methyl (±)-7-carboxy-4-(2-methoxyethyl)-3-oxo-2,3,4,5-tetrahydro-1H-1,4-benzodiazepine-2-acetic acid TFA (140 mL) was added all at once to a solution of t-butyl (±)-4-[2-(1,4-dimethoxy-1,4-dioxobutyl)amino]-3-[[N-(2-methoxyethyl)-N-(tert-butoxycarbonyl)]amino] methylbenzoate (15.03 g, 28.65 mmol) in anhydrous CH$_2$Cl$_2$ (140 mL) at 0° C., and the faintly yellow solution was warmed to RT. After 2 h, the solution was concentrated on the rotavap, and the residue was reconcentrated from toluene (to remove residual TFA). The resulting oil was combined with toluene (280 mL) and Et$_3$N (20 niL, 143 mmol), and the mixture was heated to reflux. A light yellow, homogeneous solution was produced. After 23.5 h, the reaction was concentrated on the rotavap to leave a solid residue. This was dissolved in a minimum of MeOH (ca. 720 mL) at reflux, diluted with H$_2$O (720 mL), and acidified with glacial AcOH (8 mL). The solution was cooled to RT, then was cooled in the refrigerator. After several h, more glacial AcOH (24 mL) was added. The mixture was kept in the refrigerator overnight then was filtered. The solid was washed sequentially with MeOH and Et$_2$O, then was dried in high vacuum to afford the title compound (6.40 g, 66%) as a nearly colorless powder: mp 228–230° C.; TLC R$_f$(10% MeOH/CHCl$_3$) 0.51; $^1$H NMR (250 MHz, DMSO-d$_6$) δ 7.59 (d, J=1.9 Hz, 1H), 7.54 (dd, J=8.5, 1.9 Hz, 1H), 6.50–6.60 (m, 2H), 5.43 (d, J=16.6 Hz, 1H), 5.12–5.22 (m, 1H), 4.04 (d, J=16.6 Hz, 1H), 3.60 (s, 3H), 3.20–3.70 (m, 4H), 3.08 (s, 3H), 2.83 (dd, J=16.7, 8.8 Hz, 1H), 2.65 (dd, J=16.7, 5.3 Hz, 1H); MS (ES) m/e 359.0 (M+Na)$^+$, 337.0 (M+H)$^+$. The mother liquors were concentrated on the rotavap to ca. 500 mL, cooled, and filtered to afford additional title compound (1.51 g, total=7.91 g, 82%) as a light yellow solid: mp 226–229.5° C.

Preparation 2

Using the procedures of Preparation 1, except substituting 3,4-methylenedioxyphenethylamine for 2-methoxyethylamine, the following compound was prepared:

a) Methyl (±)-7-carboxy-4-[2-(3,4-methylenedioxyphenyl)ethyl]-3-oxo-2,3,4,5-tetrahydro-1H-1,4-benzodiazepine-2-acetate. $^1$H NMR (DMSO-d$_6$) δ 7.51 (dd, J=8.6, 2 Hz, 1H), 7.45 (s, 1H), 6.57 (m, 2H), 6.49 (m, 2H), 5.87 (s, 2H), 5.32 (d, J=16.5 Hz, 1H), 5.07 (m, 1H), 3.78 (d, J=16.5 Hz, 1H), 3.62 (s, 3H), 3.56 (m, 2H), 2.88 (dd, J=16.7, 8.8 Hz, 1H), 2.60 (m, 3H).

Preparation 3

Preparation of methyl (±)-7-carboxy-3-oxo-2,3,4,5-tetrahydro-1H-1,4-benzodiazepine-2-acetate a) tert-Butyl 3-[[bis-(t-butoxycarbonyl)]amino]methyl-4-nitrobenzoate Di-tert-butyliminodicarboxylate (4.35 g, 20.0 mmol) was added to a suspension of sodium hydride (0.48 g, 20.0 mmol) in anhydrous DMF (30 mL) at RT. After 30 minutes, a solution of t-butyl 3-bromomethyl-4-nitrobenzoate (6.3 g, 20 mmol) in DMF (15 mL) was added rapidly dropwise. After 16 h, the solvent was evaporated and the residue partitioned between EtOAc (200 mL) and water (40 mL). The organic layer was extracted with water (3×50 mL) and brine (40 mL) and dried finally over Na$_2$SO$_4$. Removal of solvent gave the crude product which was purified on flash chromatography (15:85; EtOAc:Hexane) to give the title compound (81.5%): MS (ES) m/e 453 (M+H)$^+$; $^1$H NMR (400 MHz, CDCl$_3$) δ 7.97–8.10 (m, 3H), 5.16 (s, 2H), 1.62 (s, 9H), 1.49 (s, 18H).

b) tert-Butyl 4-amino-3-[[bis-(t-butoxycarbonyl)]amino]methylbenzoate

A solution of tert-butyl 3-[[bis-(t-butoxycarbonyl)]amino]methyl-4-nitrobenzoate (4.2 g, 9.3 mmol) in ethanol (150 mL) was hydrogenated at 40 psi in the presence of 10% Pd on C (0.40 g). After 30 minutes, catalyst was filtered and solvent removed to give the title compound in essentially quantitative yield: MS (ES) m/e 423 (M+H)$^+$; $^1$H NMR (400 MHz, CDCl$_3$) δ 7.82 (s, 1H), 7.71 (d, J=8.4 Hz, 1H), 6.56 (d, J=8.4 Hz, 1H), 4.92 (br s, 2H), 4.68 (s, 2H), 1.62 (s, 9H), 1.49 (s, 18H).

c) (E/Z) tert-Butyl 4-[2-(1,4-dimethoxy-1,4-dioxo-2-butenyl)amino]-3-[[bis-(t-butoxycarbonl)]amino]methylbenzoate A solution of tert-butyl 4-amino-3-[[bis-(t-butoxycarbonyl)]amino]methyl benzoate (3.9 g, 9.2 mmol) and dimethylacetylene dicarboxylate (1.34 g, 9.4 mmol) was refluxed 1 h and evaporated to dryness to give the title compound: MS (ES) m/e 565.2 (M+H)$^+$; $^1$H NMR (400 MHz, CDCl$_3$) δ 9.69 (s, 1H), 7.91 (s, 1H), 7.77 (m, 1H), 6.75 (d, J=7.3 Hz, 1H), 5.56 (s, 1H), 4.92 (s, 2H), 3.77 (s, 3H), 3.59 (s 3H), 1.62 (s, 9H), 1.49 (s, 18H).

d) tert-Butyl (±)-4-[2-(1,4-dimethoxy-1,4-dioxobutyl)amino]-3-[[bis-(t-butoxycarbonyl)]amino]methylbenzoate A solution of (E/Z) tert-butyl 4-[2-(1,4-dimethoxy-1,4-dioxo-2-butenyl)amino]-3-[[bis-(t-butoxycarbonyl)]amino]methylbenzoate (5.2 g, 9.2 mmol) in methanol (150 mL) was hydrogenated at 40 psi in the presence of 10% Pd/C (0.75 g). After 2 h, the catalyst was removed by filtration, and the solvent was removed to provide the crude product. Purification by flash chromatography gave the title compound (80%). MS (ES) m/e 567.2 (M+H)$^+$; $^1$H NMR (400 MHz, CDCl$_3$) δ 7.82 (s, 1H), 6.66 (d, J=8.5 Hz, 1H), 6.39 (d, J=8.5 Hz, 1H), 4.70 (d, J=4.5 Hz, 2H), 4.61 (m, 1H), 3.72 (s, 6H), 2.82–2.99 (m, 2H), 1.62 (s, 9H), 1.49 (s, 18H).

e) (±)-4-[2-(1,4-Dimethoxy-1,4-dioxobutyl)amino]-3-(aminomethyl)benzoic acid, bis-(trifluoroacetate)

A solution of tert-butyl 4-[2-(1,4-dimethoxy-1,4-dioxobutyl)amino]-3-[[bis-(t-butoxycarbonyl)]amino]methylbenzoate (4.0 g, 7.1 mmol) in a mixture of methylene chloride (100 mL) and trifluoroacetic acid (25 mL) was kept 16 h at RT. The solvents were evaporated and the residue was triturated with ether to give the title compound in essentially quantitative yield: MS (ES) m/e 310.2 (M+H)$^+$; $^1$H NMR (400 MHz, DMSO-d$_6$) δ 8.25 (br s, 3H), 7.89 (s, 1H), 7.79 (d, J=8.4 Hz, 1H), 6.75 (d, J=8.4 Hz, 1H), 6.25 (d, J=8.4 Hz, 1H), 4.65 (m, 1H), 4.05 (s, 2H), 3.69 (, 3H), 3.65 (s, 3H), 2.89–3.07 (m, 2H).

f) Methyl (±)-7-carboxy-3-oxo-2,3,4,5-tetrahydro-1H-1,4-benzodiazepine-2-acetate was added to a solution of 4-[2-(1,4-dimethoxy-1,4-dioxobutyl)amino]-3-(aminomethyl)benzoic acid, bis-(trifluoroacetate) (4.0 g, 7.0 mmol) at −10° C. under argon. After 30 minutes, the cold solution was quenched with acetic acid (1.5 mL). The reaction mixture was kept one h at −20° C. and filtered. The filter cake was slurried in water (30 mL) and filtered to provide the title compound (65%): MS (ES) m/e 279.0 (M+H)$^+$; $^1$H NMR (400 MHz, DMSO-d$_6$) δ 8 8.21 (t, J=5.4 Hz, 1H), 7.55 (m, 2H), 6.55 (d, J=8.4 Hz, 1H), 6.45 (s, 1H), 5.05 (m, 2H), 3.76 (dd, J=15.8, 7.5 Hz, 1H), 2.82 (dd, 16.8, 9.8 Hz, 1H), 2.65 (dd, J=16.8, 4.5 Hz, 1H).

Preparation 4

Preparation of 2-(methylaminomethyl)benzimidazole dihydrochloride a) 2-[(tert-Butoxycarbonyl)sarcosyl]aminoaniline A solution of phenylenediamine (100 g, 0.924 mole) and Boc-sarcosine (175 g, 0.924 mole) in DMF (1750 mL) was cooled to −10° C. under argon, and a solution of DCC (190.8 g, 0.924 mole) in CH$_2$Cl$_2$ (1750 mL) was added in a slow stream over 1 hr. The temperature rose to 0° C. during the addition. The reaction was stirred overnight while the temperature was allowed to rise to RT. The white precipitate was removed by filtration, and the filtrate was diluted with H$_2$O (3.5 L) and saturated brine (1 L). The CH$_2$Cl$_2$ layer was separated and the aqueous phase was extracted with EtOAc (2×1 L). The combined organic layers were washed with H$_2$O (1 L) and brine (0.5 L), then were concentrated to a yellow residue (341 g). This was triturated with EtOAc to afford the title compound (179.4 g, 70%): mp 134–136° C.

b) 2-[(N-tert-Butoxycarbonyl-N-methyl)aminomethyl] benzimidazole

A solution of 2-[(tert-butoxycarbonyl)sarcosyl] aminoaniline (178.4 g, 0.639 mole) in THF (900 mL) and AcOH (900 mL) was heated to reflux under argon for 1 hr, then a vacuum was carefully applied to the reaction, and most of the THF was removed by distillation. The residual solution was poured into stirred ice water, and conc. $NH_4OH$ (1150 mL) was added to adjust the pH to 10. An oil formed which crystallized on stirring overnight. The solid was filtered and dried at 50° C. at atmospheric pressure for two days to leave a yellow-white solid (167 g, 100%): mp 140–150° C. Further drying at RT and atmospheric pressure gave the crude title compound (162 g, 97%).

c) 2-(Methylamiinomethyl)benzimidazole dihydrochloride

A solution of 4 M HCl/dioxane (616 mL, 2.46 mole) and anisole (134 mL, 1.23 mole) was cooled to 0° C. under argon, and a solution of 2-[(N-tert-butoxycarbonyl-N-methyl)aminomethyl]benzimidazole (161 g, 0.616 mole) in $CH_2Cl_2$ (800 mL) was added in a slow stream over 30 min. The temperature rose to 8° C. during the addition, and a white precipitate began to form before the addition was complete. The reaction was stirred for 20 min, then the title compound (66.6 g, 46%) was collected by filtration: mp 250–255° C. (dec.). Anal. Calcd for $C_9H_{11}N_3 \cdot 2$ HCl: C, 46.17; H, 5.60; N, 17.95. Found: C, 46.33; H, 5.68; N, 17.55. The filtrate was diluted with $Et_2O$, and the mixture was allowed to stand overnight. Filtration gave additional title compound (62 g; total yield 128.6 g, 89%) as a pink solid: mp 248–253° C. (dec.).

Example 1

Preparation of (±)-7-[[[(2-benzimidazolyl)methyl] amino]carbonyl]-4-methyl-3-oxo-2,3,4,5-tetrahydro-1H-1,4-benzodiazepine-2-acetic acid a) Methyl (±)-7-[[[(2-benzimidazolyl)methyl]amino] carbonyl]-4-methyl-3-oxo-2,3,4,5-tetrahydro-1H-1,4-benzodiazepine-2-acetate A mixture of methyl (±)-7-carboxy-4-methyl-3-oxo-2,3,4,5-tetrahydr1H-1,4-benzodiazpine-2-acetate (0.57 g, 1.82 mmol) and thionyl chloride (15 mL) was refluxed for 1 h. The resulting orange solution was concentrated to dryness to leave a yellow-orange foam. This was dissolved in $CH_2Cl_2$ (10 mL) and added dropwise to a solution containing 2-(aminomethyl)benzimidazole dihydrochloride (1.2 g, 5.46 mmol), pyridine (0.72 g, 9.1 mmol), and triethylamine (0.55 g, 5.46 mmol) in $CH_2Cl_2$ (15 mL) at 0° C. under argon. The reaction mixture was then stirred in RT under argon. After 25.5 h, $CH_2Cl_2$ (200 mL) and 5% $NaHCO_3$ (50 mL) were added to the reaction mixture to give a light yellow precipitate which was filtered and air-dried to give the title compound (0.11 g, 14%). The filtrate was separated and the organic layer was washed sequentially with 5% $NaHCO_3$ (50 mL) and $H_2O$ (50 mL), then was concentrated on the rotavap. After trituration with $CH_2Cl_2$ and air-drying, a yellowish solid was collected to yield more of the title compound (0.35 g, 45%): $^1H$ NMR (250 MHz, $CDCl_3$/$DMSO-d_6$) δ 6.30–8.70 (m, 9H), 5.52 (d, J=16 Hz, 1H), 5.14 (m, 1H), 4.67 (d, J=5 Hz, 2H), 3.80 (d, J=17 Hz, 1H), 3.63 (s, 3H), 2.97 (s, 3H), 2.85 (dd, J=16, 9 Hz, 1H), 2.64 (dd, J=17, 5 Hz, 1H); MS (ES) m/e 422.2 $(M+H)^+$.

b) (±)-7-[[[(2-Benzimidazolyl)methyl]amino]carbonyl]4-methyl-3-oxo-2,3,4,5-tetrahydro-1H-1,4-benzodiazepine-2-acetic acid 1.0 N LiOH (0.57 mL, 0.57 mmol) was added dropwise at RT to a mixture of methyl (±)-7-[[[(2-benzimidazolyl) methyl]amino]carbonyl]4-methyl-3-oxo-2,3,4,5-tetrahydro-1H-1,4-benzodiazepine-2-acetate (0.11 g, 0.26 mmol) in THF (4 mL) and $H_2O$ (5 mL). The resulting light brownish-yellow solution was stirred for 21.5 h, then was concentrated on the rotavap. The resulting residue was lyophilized to give the crude product (0.11 g, 100%) as a yellowish powder. Preparative HPLC. (PRP-1® column, step gradient, 10–20% $CH_3CN/H_2O$-0.1% TFA) afforded the title compound: $^1H$ NMR (250 MHz, $DMSO-d_6$) δ 6.45–9.06 (m, 9H), 5.53 (d, J=16 Hz, 1H), 5.13 (m, 1H), 4.86 (d, J=5 Hz, 2H), 3.87 (d, J=17 Hz, 1H), 2.95 (s, 3H), 2.80 (dd, J=17, 9 Hz, 1H), 2.57 (dd, J=17, 5 Hz, 1H); MS (ES) m/e 408.2 $(M+H)^+$. Anal. Calcd for $C_{21}H_{21}N_5O_4 \cdot 4/3$ $CF_3CO_2H \cdot H_2O$: C, 49.22; H, 4.25; N, 12.13. Found: C, 49.24; H, 4.22; N, 12.11.

Example 2

Preparation of (±)-7-[[[(2-benzimidazolyl)methyl] amino]carbonyl]-3-oxo-4-(2-phenylethyl)-2,3,4,5-tetrahydro-1H-1,4-benzodiazepine-2-acetic acid a) Methyl (±)-7-[[[(2-benzimidazolyl)methyl]amino] carbonyl]-3-oxo-4-(2-phenylethyl)-2,3,4,5-tetrahydro-1H-1,4-benzodiazepine-2-acetate EDC. (230 mg, 1.2 mmol) was added to a stirred solution of methyl (±)-7-carboxy-3-oxo-4-(2-phenylethyl)-2,3,4,5-tetrahydro-1H-1,4-benzodiazepine-2-acetate (382.4 mg, 1.0 mmol), 2-(aminomethyl)benzimidazole dihydrochloride (264 mg, 1.2 mmol), $HOBT \cdot H_2O$ (162 mg, 1.2 mmol), and diisopropylethylamine (0.70 mL, 4.0 mmol) in anhydrous DMF (5 mL) at RT. After 19 h, the reaction was concentrated on the rotavap (high vacuum), and the residue was partitioned between $H_2O$ (5 mL) and EtOAc (20 mL). The layers were separated and the organic layer was washed with $H_2O$ (5 mL). Drying ($MgSO_4$), concentration, and silica gel chromatography (load with 5% $MeOH/CHCl_3$; gradient: 5% MeOH in 1:1 $EtOAc/CHCl_3$ (300 mL), then 10% MeOH/EtOAc (400 mL), then 10% $MeOH/CHCl_3$) gave the title compound (414.9 mg, 81%) as an off-white solid: TLC (10% MeOH/EtOAc) $R_f$0.62; $^1H$ NMR (250 MHz, $DMSO-d_6$) δ 8.72 (br t, J=5.6 Hz, 1H), 7.35–7.75 (m, 4H), 7.00–7.35 (m, 7H), 6.56 (d, J=8.4 Hz, 1H), 6.37 (br d, J=3.5 Hz, 1H), 5.42 (d, J=16.6 Hz, 1H), 5.08–5.20 (m, 1H), 4.52–4.75 (m, 2H), 3.93 (d, J=16.6 Hz, 1H), 3.45–3.72 (m, 2H), 3.61 (s, 3H), 2.83 (dd, J=16.7, 8.9 Hz 1H), 2.60–2.75 (m, 3H); MS (ES) 512.2 $(M+H)^+$.

b) (±)-7-[[[(2-Benzimidazolyl)methyl]amino]carbonyl]-3-oxo-4-(2-phenylethyl)-2,3,4,5-tetrahydro-1H-1,4-benzodiazepine-2-acetic acid A mixture of methyl (±)-7-[[[(2-benzimidazolyl)methyl] amino]carbonyl]-3-oxo-4-(2-phenylethyl)-2,3,4,5-tetrahydro-1H-1,4-benzodiazepine-2-acetate (413.1 mg, 0.81 mmol), 1.0 N LiOH (0.97 mL, 0.97 mmol), THF (4 mL), and $H_2O$ (3 mL) was stirred at 40–45° C. for 20 min, and the resulting solution was stirred at RT for 17 h. Acidification with TFA (0.19 mL, 2.4 mmol) and concentration left an off-white solid. Recrystallization from $CH_3CN/H_2O$ gave the title compound (343.2 mg, 69%) as a colorless powder: HPLC (PRP-1®, 30% $CH_3CN/H_2O$-0.1% TFA) K'=1.5; $^1H$ NMR (400 MHz, $CD_3OD$) δ 7.68–7.75 (m, 2H), 7.60 (dd, J=8.6, 2.2 Hz, 1H), 7.51–7.58 (m, 2H), 7.49 (d, J=2.2 Hz, 1H), 7.07–7.22 (m, 5H), 6.61 (d, J=8.6 Hz, 1H), 5.46 (d, J=16.8 Hz, 1H), 5.18 (dd, J=9.0, 5.1 Hz, 1H), 4.95 (s, 2H), 3.81 (d, J=16.8 Hz, 1H), 3.61–3.78 (m, 2H), 2.94 (dd, J=16.8, 9.0 Hz, 1H), 2.71–2.83 (m, 2H), 2.65 (dd, J=16.8, 5.1 Hz, 1H); MS (ES) m/e 498.4 $(M+H)^+$. Anal. Calcd for $C_{28}H_{27}N_5O_4 \cdot CF_3CO_2H \cdot 0.25$ $H_2O$: C, 58.49; H, 4.66; N, 11.37. Found: C, 58.52; H, 4.47; N, 11.04.

Example 3

Preparation of (±)4-isopropyl-7-[[[(2-benzimidazolyl)methyl]amino]carbonyl]-3-oxo-2,3,4,5-tetrahydro-1H-1,4-benzodiazepine-2-acetic acid a) Methyl (±)-4-isopropyl-7-[[[(2-benzimidazolyl)methyl]amino]carbonyl]-3-oxo-2,3,4,5-tetrahydro-1H-1,4-benzodiazepine-2-acetate EDC (173 mg, 0.90 mmol) was added to a stirred solution of methyl (±)-7-carboxy-4-isopropyl-3-oxo-2,3,4,5-tetrahydro-1H-1,4-benzodiazepine-2-acetate (240.3 mg, 0.75 mmol), 2-(aminomethyl)benzimidazole dihydrochloride (198 mg, 0.90 mmol), HOBT.H$_2$O (122 mg, 0.90 mmol), and diisopropylethylamine (0.52 mL, 3.0 mmol) in anhydrous DMF (4 mL) at RT. After 20 h, the reaction was concentrated on the rotavap (high vacuum), and the residue was diluted with H$_2$O (5 mL) to afford a gummy precipitate. EtOAc (3 mL) was added and the mixture was stirred briskly. The precipitate remained gummy, but changed in form so that it was suspended as a mass in the solvents. The solvents were drawn off with a pipet and the residue was suspended in MeOH (3 mL) and EtOAc (6 mL). The mixture was stirred briskly at RT for several min, then was cooled in ice and filtered. The filter pad was washed with EtOAc and dried in high vacuum to leave the title compound (275.1 mg, 82%) as an off-white powder: $^1$H NMR (250 MHz, 20% CD$_3$OD/CDCl3) δ 7.45–7.70 (m, 4H), 7.15–7.35 (m, 2H), 6.56 (d, J=9.1 Hz, 1H), 5.22 (d, J=16.9 Hz, 1H), 5.13 (app t, 1H), 4.72–4.92 (m, 1H), 4.72 (s, 2H), 4.03 (d, J=16.9 Hz, 1H), 3.74 (s, 3H), 3.00 (d, J=16.4, 7.7 Hz, 1H), 2.67 (dd, J=16.4, 6.0 Hz, 1H), 1.21 (d, J=6.7 Hz, 3H), 1.03 (d, J=6.8 Hz, 3H); MS (ES) 450.2 (M+H)$^+$.

b) (±)-4-Isopropyl-7-[[[(2-benzimidazolyl)methyl]amino]carbonyl]-3-oxo-2,3,4,5-tetrahydro-1H-1,4-benzodiazepine-2-acetic acid A mixture of methyl (±)-4-isopropyl-7-[[[(2-benzimidazolyl)methyl]amino]carbonyl]-3-oxo-2,3,4,5-tetrahydro-1H-1,4-benzodiazepine-2-acetate (275.1 mg, 0.61 mmol), 1.0 N LiOH (0.73 mL, 0.73 mmol), THF (3 mL), and H$_2$O (2.3 mL) was stirred at 35° C. for 45 min, and the resulting solution was stirred at RT. After 17.5 h, the solution was filtered, and the filtrate was neutralized with 1.0 N HCl (0.73 mL). Since the product did not precipitate, the solution was acidified with TFA (0.2 mL) and concentrated. The resulting solid was triturated with H$_2$O to leave a nearly colorless solid, which was dissolved with warming in 1:1 CH$_3$CN/H$_2$O. The solution was cooled to RT and diluted with several volumes of H$_2$O/0.1% TFA. ODS chromatography (20% CH$_3$CN/H$_2$O-0.1% TFA), concentration, and lyophilization gave the title compound (293.4 mg, 80%) as a colorless powder: HPLC (PRP-1®, 20% CH$_3$CN/H$_2$O-0.1% TFA) K'=2.5; $^1$H NMR (400 MHz, CD$_3$OD) δ 7.70–7.76 (m, 2H), 7.65 (d, J=2.2 Hz, 1H), 7.61 (dd, J=8.5, 2.2 Hz, 1H), 7.53–7.60 (m, 2H), 6.62 (d, J=8.5 Hz, 1H), 5.33 (d, J=16.9 Hz, 1H), 5.21 (dd, J=8.9, 5.2 Hz, 1H), 4.97 (d, J=1.9 Hz, 2H), 4.72–4.85 (m, 1H), 4.10 (d, J=16.9 Hz, 1H), 2.96 (dd, J=16.8, 8.9 Hz, 1H), 2.65 (dd, J=16.8, 5.2 Hz, 1H), 1.21 (d, J=6.7 Hz, 3H), 1.03 (d, J=6.8 Hz, 3H); MS (ES) m/e 436.2 (M+H)$^+$. Anal. Calcd for C$_{23}$H$_{25}$N$_5$O$_4$.1.25 CF$_3$CO$_2$H.1.25 H$_2$O: C, 51.00; H, 4.83; N, 11.66. Found: C, 51.12; H, 4.91; N, 11.37.

Example 4

Preparation of (±)-7-[[[N-(2-benzothiazolyl)methyl-N-methyl]amino]carbonyl]4-methyl-3-oxo-2,3,4,5-tetrahydro-1H-1,4-benzodiazepine-2-acetic acid a) 2-Bromomethylbenzothiazole A mixture of 2-methylbenzothiazole (2.0 g, 13.40 mmol), N-bromosuccinimide (2.39 g, 13.40 mmol), and AIBN (0.5 g, 3.04 mmol) in CCl$_4$ (40 mL) was refluxed for 12 h, then the mixture was cooled and filtered. The filtrate was concentrated and purified by silica gel chromatography (5% EtOAc/hexane) to give the title compound (2.19 g, 72%) as a yellow oil: $^1$H NMR (250 MHz, DMSO-d$_6$): δ 5.12 (s, 2H), 7.5 (m, 2H), 8.01 (dd, J=7.9, 1.8 Hz, 1H), 8.15 (dd, J=7.9, 1.8 Hz 1H).

b) 2-[(Methylamino)methyl]benzothiazole

To a stirred solution of 2-bromomethylbenzothiazole (0.4 g. 1.75 mmol) in THF (4 mL) was added 40% aqueous methylamine (0.30 g, 8.77 mmol). Stirring was continued overnight, then the mixture was concentrated. The residue was taken up in H$_2$O, neutralized with 2.5 N NaOH, and extracted with CH$_2$Cl$_2$. The organic extracts were dried (MgSO$_4$) and concentrated to give the title compound (0.36 g, 80%) as a brown oil: $^1$H NMR (250 MHz, DMSO-d$_6$): δ 2.70 (s, 3H), 4.71 (s, 2H), 7.55 (m, 2H), 8.0 (d, J=7.9 Hz, 1H), 8.17 (d, J=7.9 Hz, 1H).

c) Methyl (±)-7-[[[N-(2-benzothiazolyl)methyl-N-methyl]amino]carbonyl]4-methyl-3-oxo-2,3,4,5-tetrahydro-1H-1,4-benzodiazepine-2-acetate A mixture of methyl (±)-7-carboxy-4-methyl-3-oxo-2,3,4,5-tetrahydro-1H-1,4-benzodiazepine-2-acetate (0.25 g, 0.855 mmol), 2-[(methylamino)methyl]benzothiazole (0.228 g, 1.283 mmol), EDC (0.31 g, 1.0026 mmol), HOBT.H$_2$O (0.14 g, 1.026 mmol), and diisopropylethylamine (0.30 mL, 1.711 mmol) in dry DMF (5 mL) was stirred at RT in 20 h. The reaction mixture was concentrated, and the residue was taken up in H$_2$O and extracted with CH$_2$Cl$_2$. The combined organic extracts were dried (MgSO$_4$) and concentrated. Silica gel chromatography (5% MeOH/CH$_2$Cl$_2$) gave the title compound (0.289 g, 75%) as a yellow oil: $^1$H NMR (400 MHz, DMSO-d$_6$): δ 2.65 (dd, J=16.8, 5.0 Hz, 1H), 2.82 (dd, J=16.8, 8.9 Hz, 1H), 2.90 (s, 3H), 3.15 (s, 3H), 3.62 (s, 3H), 3.90 (d, J=16.1 Hz, 1H), 4.90 (s, 2H), 5.13 (m, 1H), 5.45 (d, J=16.1 Hz, 1H), 6.29 (d, J=3.6 Hz, 1H), 6.57 (d, J=8.3 Hz, 1H), 7.19 (d, J=8.3 Hz, 1H), 7.21 (s, 1H), 7.45 (t, J=7.4 Hz, 1H), 7.52 (t, J=7.4 Hz, 1H), 8.00 (d, J=7.9 Hz, 1H), 8.10 (d, J=7.9 Hz, 1H).

d) (±)-7-[[[N-(2-Benzothiazolyl)methyl-N-methyl]amino]carbonyl]-4-methyl-3-oxo-2,3,4,5-tetrahydro-1H-1,4-benzodiazepine-2-acetic acid 2.5 N NaOH (3.0 mL) was added to a stirred solution of methyl (±)-7-[[[N-(2-benzothiazolyl)methyl-N-methyl]amino]carbonyl]-4-methyl-3-oxo-2,3,4,5-tetrahydro-1H-1,4-benzodiazepine-2-acetate (0.289 g, 0,639 mmol) in MeOH (3 mL) at RT. After 3 h, the mixture was concentrated, and the residue was acidified to pH 4. The colorless solid was collected and triturated in Et$_2$O to give the title compound (0.250 g, 89%) as a colorless solid: $^1$H NMR (400 MHz, DMSO-d$_6$) δ 2.55 (dd, J=16.8, 5.0 Hz, 1H), 2.75 (dd, J=16.8, 8.9 Hz, 1H), 2.91 (s, 3H), 3.1 (s, 3H), 3.9 (d, J=16.1 Hz, 1H), 4.9 (d, J=5.7 Hz, 2H), 5.10 (m, 1H), 5.45 (d, J=16.1 Hz, 1H), 6.29 (d, J=3.6 Hz, 1H), 6.57 (d, J=8.3 Hz, 1H), 7.19 (d, J=8.3 Hz, 1H), 7.21 (s, 1H), 7.45 (t, J=7.4 Hz, 1H), 7.52 (t, J=7.4 Hz, 1H), 8.00 (d, J=7.9 Hz, 1H), 8.10 (d, J=7.9 Hz, 1H); IR (KBr) 3500, 3286, 3100, 3000, 1735, 1719, 1662, 1652, 1614, 1595, 1482, 1392, 827,765 cm$^{-1}$; MS (ES) m/e 439.2 (M+H)$^+$. Anal. Calcd for C$_{22}$H$_{22}$N$_4$O$_4$S 1.5 H$_2$O: C, 56.76; H, 5.41; N, 12.03. Found: C, 56.37; H, 5.23; N, 11.86.

Example 5

Preparation of (±)-7-[[[N-(2-benzoxazolyl)methyl-N-methyl]amino]carbonyl]-4-methyl-3-oxo-2,3,4,5-tetrahydro-1H-1,4-benzodiazepine-2-acetic acid a) 2-Bromomethylbenzoxazole Following the procedure of Example 4(a), except using 2-methylbenzoxazole in place of 2-methylbenzothiazole, the title compound (2.22 g, 70%) was prepared as a yellow oil: $^1$H NMR (250 MHz, DMSO-$d_6$) δ 5.17 (s, 2H), 7.55 (m, 2H), 8.01 (d, J=7.9, 1.8 Hz, 1H), 8.20 (dd, J=7.9, 1.8 Hz, 1H).

b) 2-[(Methylamino)methyl]benzoxazole

Following the procedure of Example 4(b), except using 2-bromomethyl benzoxazole in place of 2-bromomethylbenzothiazole, the title compound (0.250 g, 71%) was prepared as a brown oil: $^1$H NMR (400 MHz, DMSO-$d_6$) δ 2,75 (s, 3H), 4.71 (s, 2H), 7.60 (m, 2H), 8.01 (d, J=7.9 Hz, 1H), 8.17 (d, J=7.9 Hz, 1H).

c) Methyl-(±)-7-[[[N-(2-benzoxazolyl)methyl-N-methyl]amino]carbonyl]-4-methyl-3-oxo-2,3,4,5-tetrahydro-1H-1,4-benzodiazepine-2-acetate Following the procedure of Example 4(c), except using 2-[(methylamino) methyl]benzoxazole in place of 2-[(methylamino)methyl]benzothiazole, the title compound (0.342 g, 91%) was prepared as a brown oil: $^1$H NMR (DMSO-$d_6$) δ 2,65 (dd, J=16.8, 5.0 Hz, 1H), 2,82 (dd, J=16.8, 8.9 Hz, 1H), 2.91 (s, 3H), 3,15 (s, 3H), 3,61 (s, 3H), 3.90 (d, J=16.1 Hz, 1H), 4,91 (s, 2H), 5.15 (m, 1H), 5.47 (d, J=16.1 Hz, 1H), 6.30 (d, J=3,6 Hz, 1H), 6.57 (d, J=8.3 Hz, 1H), 7.20 (m, 2H), 7.40 (m, 2H), 7.72 (t, J=7.4 Hz, 2H), 7.95 (s, 1H).

d) (±)-7-[[[N-(2-Benzoxazolyl)methyl-N-methyl]amino]carbonyl]-4-methyl-3-oxo-2,3,4,5-tetrahydro-1H-1,4-benzodiazepine-2-acetic acid Methyl-(±)-7-[[[N-(2-benzoxazolyl)methyl-N-methyl]amino]carbonyl]-4-methyl-3-oxo-2,3,4,5-tetrahydro-1H-1,4-benzodiazepine-2-acetate was saponified following the procedure of Example 4(d). Purification by silica gel chromatography (2:8:1 MeOH/CH$_2$Cl$_2$/Et$_3$N) gave the title compound (0.231 g, 70%) as an off-white solid: $^1$H NMR (400 MHz, DMSO-$d_6$) δ 2.45 (dd, J=16.8, 5.0 Hz, 1H), 2,70 (dd, J=16.8, 8.9 Hz, 1H), 2.90 (s, 3H), 3,15 (s, 3H), 3.91 (d, J=16.1 Hz, 1H), 4.90 (d, J=5.7 Hz, 2H), 5.07 (m, 1H), 5.45 (d, J=16.1 Hz, 1H), 6.30 (d, J=3.6 Hz, 1H), 658 (d, J=8.3 Hz, 1H), 7.20 (m, 2H), 7.40 (m, 2H), 7.70 (m, 2H); IR (KBr) 3370, 3100, 3000, 1728, 1653, 1612, 1575, 1485, 1455, 1397, 831, 765 cm$^{-1}$; MS (ES) m/e 421 (M—H)$^-$. Anal. Calcd for C$_{22}$H$_{22}$N$_4$O$_5$ 1.25 H$_2$O: C, 59.39; H, 5.45; N, 12.50. Found: C, 59.43; H, 5.23; N, 12.14.

Example 6

Preparation of (±)-7-[[[N-[-2-(5(6)-chlorobenzimidazolyl)methyl]-N-methyl]amino]carbonyl]-4-methyl-3-oxo-2,3,4,5-tetrahydro-1H-1,4-benzodiazepine-2-acetic acid a) 2-[[(N-tert-butoxycarbonyl-N-methyl)amino]methyl]-5(6)-chlorobenzimidazole To a stirred and cooled (0° C.) mixture of Boc-sarcosine (2.0 g, 10.571 mmol) and Et$_3$N (1.12 g, 11.01 mmol) in anhydrous THF (25 mL) was added isobutylchloroformate (1.51 g, 11.01 mmol). After 1 h, 4-chloro-1,2-phenylenediamine (1.43 g, 10.571 mmol) was added. Stirring was continued for 2 h, then acetic acid (10 mL) was added, and the reaction was heated to reflux. After 4 h, the mixture was cooled, concentrated, neutralized with 2.5 N NaOH, and extracted with CH$_2$Cl$_2$. Drying (MgSO$_4$), concentration, and silica gel chromatography (1% MeOH/CH$_2$Cl$_2$) gave the title compound (2.10 g, 67%) as a brown foam: $^1$H NMR (250 MHz, DMSO-$d_6$): δ 1.45 (s, 9H), 2.95 (s, 3H), 4.60 (s, 2H), 7.10 (d, J=9.3 Hz, 1H), 7.50 (d J=9.3 Hz, 1H), 7.60 (s, 1H).

b) 5(6)-Chloro-2-[(methylamino)methyl]benzimidazole

To a stirred solution of 2-[[(N-tert-butoxycarbonyl-N-methyl)amino]methyl]-5(6)-chlorobenzimidazole (2.10 g, 7.101 mmol) in anhydrous CH$_2$Cl$_2$ (20 mL) was added TFA (2.2 mL, 28.404 mmol). After stirring overnight, the mixture was concentrated, neutralized with 2.5 N NaOH, and extracted with CH$_2$Cl$_2$. The combined organic extracts were washed with brine, dried (MgSO$_4$), and concentrated to give the title compound (1.25 g, 90%) as a brown oil: $^1$H NMR (250 MHz, DMSO-$d_6$) δ 2.35 (s, 3H), 3.88 (s, 2H), 7.17 (d, J=9.3 Hz, 1H), 7.50 (d, J=9.3 Hz, 1H), 7.55 (s, 1H).

c) Methyl (±)-7-[[[N-[2-(5(6)-chlorobenzimidazolyl)methyl]-N-methyl]amino]carbonyl]-4-methyl-3-oxo-2,3,4,5-tetrahydro-1H-1,4-benzodiazepine-2-acetate Following the procedure of Example 4(c), except substituting 5(6)-chloro-2-[(methylamino)methyl]benzimidazole for 2-[(methylamino)methyl]benzothiazole, the title compound (0.262 g, 59%) was obtained as an off-white solid after silica gel chromatography (5% MeOH/CH$_2$Cl$_2$): $^1$H NMR (250 MHz, DMSO-$d_6$) δ 2.65 (dd, J=16.8, 5.0 Hz, 1H), 2.82 (dd, J=16.8, 8.9 Hz, 1H), 2.91 (s, 3H), 3.15 (s, 3H), 3.61 (s, 3H), 3.91 (d, J=16.1 Hz, 1H), 4.80 (d, J=5.7 Hz, 2H), 5.15 (m, 1H), 5.47 (d, J=16.1 Hz, 1H), 6.25 (d, J=3.6 Hz, 1H), 6.55 (d, J=8.3 Hz, 1H), 7.20 (m, 2H), 7.60 (m, 2H).

d) (±)-7-[[[N-[2-(5(6)-Chlorobenzimidazolyl)methyl]-N-methyl)amino] carbonyl]-4-methyl-3-oxo-2,3,4,5-tetrahydro-1H-1,4-benzodiazepine-2-acetic acid Methyl (±)-7-[[[N-[2-(5(6)-chlorobenzimidazolyl)methyl]-N-methyl]amino]carbonyl]-4-methyl-3-oxo-2,3,4,5-tetrahydro-1H-1,4-benzodiazepine-2-acetate was saponified following the procedure of Example 4(d). Trituration with EtOH/Et$_2$O gave the title compound (0.100 g, 69%) as a colorless solid: $^1$H NMR (400 MHz, DMSO-$d_6$) δ 2.55 (dd, J=16.8, 5.0 Hz, 1H), 2.75 (dd, J=16.8, 8.9 Hz, 1H), 2.91 (s, 3H), 3.10 (s, 3H), 3.90 (d, J=16.1 Hz, 1H), 4.9 (s, 2H), 5.10 (m, 1H), 5.45 (d, 16.1 Hz, 1H), 6.25 (s, 1H), 6.57 (d, J=8.3 Hz, 1H), 7.20 (m, 3H), 7.50 (d, J=9.3 Hz, 1H), 7.60 (s, 1H), 12.3 (br s, 1H), 12.5 (br s, 1H); MS (ES) m/e 456.0 (M+H)$^+$. Anal. Calcd for C$_{22}$H$_{22}$ClN$_5$O$_4$: C, 56.30; H, 5.05; N, 14.92. Found: C, 56.27; H, 5.30; N, 15.14.

Example 7

Preparation of (±)-7-[[[(2-indolyl)methyl]amino]carbonyl]-4-methyl-3-oxo-2,3,4,5-tetrahydro-1H-1,4-benzodiazepine-2-acetic acid a) Indole-2-carboxamide A mixture of ethyl indole-2-carboxylate (5 g, 26.5 mmol) and ammonium hydroxide (30 mL) was heated at 80° C. in a sealed glass vessel overnight. The reaction was cooled and the title compound (3.06 g, 73%) was collected by filtration as a colorless solid: $^1$H NMR (400 MHz, DMSO-$d_6$) δ 7.95 (br, 1H), 7.61 (d, 1H), 7.41 (d, 1H), 7.36 (br, 1H), 7.12, (t, 1H), 7.01 (t, 1H).

b) 2-Cyanoindole

A solution of indole-2-carboxamide (3.02 g, 18.8 mmol) in dichlorophenylphosphine oxide (20 mL) was heated at 80° C. overnight. The cooled reaction mixture was then poured over 100 mL ice and the pH was adjusted to 11 with 50% aqueous sodium hydroxide. Extraction with ethyl acetate followed by concentration in vacuo gave an off-white solid which was purified by silica gel chromatography (1% MeOH/CH$_2$Cl$_2$) to yield the title compound (2.41 g, 90%): $^1$H NMR (400 MHz, DMSO-$d_6$) δ 7.68 (d, 1H), 7.46 (d, 1H), 7.36 (s, 1H), 7.34 (t, 1H), 7.14 (t, 1H).

c) 2-Aminomethylindole

LAH (42 mL, 1M solution in THF) was added dropwise through a syringe to a solution of 2-cyanoindole (2.0 g, 14.1 mmol) in anhydrous THF (20 mL) with cooling, and the resulting solution was stirred at RT under argon for 5 h. $H_2O$ was added dropwise with cooling to destroy excess LAH, and the colorless precipitate was removed by filtration and washed with THF. The filtrate was dried ($K_2CO_3$) and concentrated to afford the title compound (2.11 g, quantitative) as a yellow solid: 1H NMR (400 MHz, DMSO-$d_6$) δ 7.41 (d, 1H), 7.29 (d, 1H), 6.97 (t, 1H), 6.91 (t, 1H), 6.20 (s, 1H), 3.82 (s, 2H), 2. 18 (br, 1H).

d) Methyl (±)-7-[[[(2-indolyl)methyl]amino]carbonyl]-4-methyl-3-oxo-2,3,4,5-tetrahydro-1H-1,4-benzodiazepine-2-acetate EDC (1.53 g, 7.99 mmol) was added to a solution of methyl (±)-7-carboxy-4-methyl-3-oxo-2,3,4,5-tetrahydro-1H-1,4-benzodiazepine-2-acetate (2.13 g, 7.26 mmol), 2-aminomethylindole (1.06 g, 7.26 mmol), HOBT.$H_2O$ (1.08 g, 7.99 mmol) and diisopropylethylamine (1.53 mL, 8.71 mmol) in anhydrous DMF (10 mL) at RT. After 20 h the reaction was concentrated on the rotavap (high vacuum). The residue was taken up in EtOAc and washed sequentially with $H_2O$ and 10% $Na_2CO_3$ (2×30 mL). Drying (MgSO$_4$), concentration, and silica gel chromatography (2% MeOH/$CH_2Cl_2$) gave the title compound (1.8 g, 60%): $^1$H NMR (400 MHz, DMSO-$d_6$) δ 8.56 (t, 1H), 7.95 (s, 1H), 7.59 (s, 1H), 7.56 (d, 1H), 7.43 (d, 1H), 7.33 (d, 1H), 7.01 (t, 1H), 6.93 (t, 1H), 6.55 (d, 1H), 6.33 (br, 1H), 6.25 (s, 1H), 5.49 (d, 1H), 5.14 (t, 1H), 4.56 (d, 2H), 3.82 (d, 1H), 3.61 (s, 3H), 2.92 (s, 3H), 2.75 (dd, 1H), 2.53 (d, 1H); MS(ES) m/e 421.2 (M+H)$^+$.

e) (±)-7-[[[(2-Indolyl)methyl]amino]carbonyl]-4-methyl-3-oxo-2,3,4,5-tetrahydro-1H-1,4-benzodiazepine-2-acetic acid 1.0 N NaOH (1 mL, 1.0 mmol) was added dropwise to a solution of methyl (±)-7-[[[(2-indolyl)methyl]amino]carbonyl]-4-methyl-3-oxo-2,3,4,5-tetrahydro-1H-1,4-benzodiazepine-2-acetate (0.35 g, 0.83 mmol) in THF (5 mL) and MeOH (2 mL) at RT. The resulting mixture was stirred for 20 h then was concentrated. The residue was dissolved in $H_2O$ (20 mL) and acidified with TFA. ODS chromatography (27% $CH_3CN/H_2O$-0.1% TFA), concentration and lyophilization gave the title compound (100 mg, 30%) as an off-white solid: HPLC (ODS, 5–60% $CH_3CN/H_2O$-0. 1% TFA gradient elution over 20 min) K'=10.2; $^1$H NMR (400 MHz, DMSO-$d_6$) δ 8.55 (t, 1H), 7.57 (s, 1H), 7.56 (d, 1H), 7.43 (d, 1H), 7.33 (d, 1H), 7.01 (t, 1H), 6.93 (t, 1H), 6.55 (d, 1H), 6.33 (br, 1H), 6.25 (s, 1H), 5.49 (d, 1H), 5.08 (t, 1H), 4.55 (d, 2H), 3.82 (d, 1H), 2.92 (s, 3H), 2.75 (dd, 1H), 2.53 (d, 1H); MS (ES) m/e 407.2(M+H)$^+$. Anal. Calcd for $C_{22}H_{22}N_4O_4.H_2O$: C, 62.25; H, 5.70; N, 13.20. Found: C, 62.66; H, 5.64; N, 12.99.

Example 8

Preparation of (2S)-7-[[[(2-Benzimidazolyl)methyl]amino]carbonyl]-4-methyl-3-oxo-2,3,4,5-tetrahydro-1H-1,4-benzodiazepine-2-acetic acid a) Methyl (2S)-7-[[[(2-benzimidazolyl)methyl]amino]carbonyl]-4-methyl-3-oxo-2,3,4,5-tetrahydro-1H-1,4-benzodiazepine-2-acetate EDC (1.15 g, 6.02 mmol) was added to a solution of methyl (2S)-7-carboxy-4-methyl-3-oxo-2,3,4,5-tetrahydro-1H-1,4-benzodiazepine-2-acetate (2.11 g, 5.02 mmol), 2-aminomethylbenzimidazole dihydrochloride (1.15 g, 6.02 mmol), HOBT.$H_2O$ (811 mg, 6.02 mmol), and diisopropylethylamine (1.76 mL, 10 mmol) in anhydrous DMF (25 mL) at RT. After 21 h, the reaction was concentrated on the rotavap (high vacuum), and the residue was taken up in $CH_2Cl_2$ (240 mL) and washed with $H_2O$. The organic layer was dried ($Na_2SO_4$), dissolved in xylenes, and reconcentrated to remove residual DMF. The crude product was chromatographed on silica gel (MeOH/CHCl$_3$) to give the title compound (1.1 g, 52%).

b) (2S)-7-[[[(2-Benzimidazolyl)methyl]amino]carbonyl]-4-methyl-3-oxo-2,3,4,5-tetrahydro-1H-1,4-benzodiazepine-2-acetic acid 1 N NaOH (4.75 mL, 4.75 mmol) was added to a cold solution of methyl (2S)-7-[[[(2-benzimidazolyl) methyl]amino]carbonyl]-4-methyl-3-oxo-2,3,4,5-tetrahydro-1H-1,4-benzodiazepine-2-acetate (1.0 g, 2.38 mmol), MeOH (10 mL) and $H_2O$ (5 mL). The solution was stirred at room temperature for 18 hr and concentrated. ODS chromatography ($CH_3CN/H_2O$-0.1% TFA) gave the tidle compound (0.91 g, 94%): HPLC (5 Altex Ultrasphere ODS, 4.5 mm×25 cm, 5%–60% $CH_3CN/H_2O$-0.1% TFA gradient over 20 min) K'=5.7; $^1$H NMR (400 MHz, DMSO-$d_6$) δ 8.7–8.9 (t, 1H), 6.3–7.6 (m, 8H), 5.4–25.6 (d, 1H), 5.0–5.1 (q, 1H), 4.5–4.7 (d 2H), 3.8–3.9 (d, 1H), 2.9–3.0 (s, 3H), 2.7–2.9 (dd, 2H); MS (ES) m/e 408.2 (M+H)$^+$. Anal. Calcd for $C_{21}H_{21}N_5O_4$. 3.5 $H_2O$: C, 53.61; H, 6.00; N, 14.89. Found: C, 53.38; H, 6.00; N, 14.55. $[α]^D$–237° (c 0.1).

Example 9

Preparation of (2R)-7-[[[(2-Benzimidazolyl)methyl]amino]carbonyl]-4-methyl-3-oxo-2,3,4,5-tetrahydro-1H-1,4-benzodiazepine-2-acetic acid a) Methyl (2S)-7-[[[(2-benzimidazolyl)methyl]amino]carbonyl]-2,3,4,5-tetrahydro-4-methyl-3-oxo-1H-1,4-benzodiazepine-2-acetate Following the procedure of Example 8(a), substituting methyl (2R)-7-carboxy-4-methyl-3-oxo-2,3,4,5-1H-1,4-benzodiazepine-2-acetate for the (2S) isomer, the title compound (0.37 g, 86%) was prepared.

b) (2R)-7-[[[(2-Benzimidazolyl)methyl]amino]carbonyl]-4-methyl-3-oxo-2,3,4,5-tetrahydro-1H-1,4-benzodiazepine-2-acetic acid Following the procedure of Example 8(b), the compound of Example 9(a) is saponified to yield the title compound (0.20 g, 57%): HPLC (5 Altex Ultrasphere ODS, 4.5 mm×25 cm, 12% $CH_3CN/H_2O$-0.1% TFA) K'=4.7; $^1$H NMR (400 MHz, DMSO-$d_6$) δ 8.7–8.9 (t, 1H), 6.3–7.6 (m, 8H), 5.4–5.6 (d, 1H), 5.0–5.1 (q, 1H), 4.5–4.7 (d 2H), 3.8–3.9 (d, 1H), 2.9–3.0 (s, 3H), 2.7–2.9 (dd, 2H); MS (ES) m/e 408.2 (M+H)$^+$. Anal. Calcd for $C_{21}H_{21}N_5O_4.3.75 H_2O$: C, 53.10; H, 6.05; N,14.74. Found: C, 52.86; H, 6.03; N, 14.39. $[α]^D$=+205° (c 0.1).

Example 10

Preparation of (±)-7-[[[(2-benzimidazolyl)methyl]amino]carbonyl]-9-chloro-4-methyl-3-oxo-2,3,4,5-tetrahydro-1H-1,4-benzodiazepine-2-acetic acid a) Methyl (±)-7-carboxy-9-chloro-4-methyl-3-oxo-2,3,4,5 -tetrahydro-1H-1,4-benzodiazepine-2-acetate A solution of (±)-7-carboxy4-methyl-3-oxo-2,3,4,5-tetrahydro-1H-1,4-benzodiazepine-2-acetate (1.0 g, 3.4 mmol), NCS (0.683 g, 4.0 mmol) in DMF (15 mL) was heated to 50° C. for 18 h. Water (150 mL) was added and the heterogeneous system was filtered. The solid was triturated with $CH_2Cl_2$/MeOH (9:1; 20 mL) for 1 h. Filtration and drying in vacuo gave the title compound (0.61 g, 55%): $^1$H NMR (400 MHz, DMSO-$d_6$) δ 7.6–7.8 (m, 2H), 4.0–5.8 (m, 4H), 3.6–3.7 (s, 3H), 2.8–3.0 (m, 5H); MS (ES) m/e 327.0 (M+H)$^+$.

b) Methyl (±)-7-[[[(2-benzimidazolyl)methyl]amino]carbonyl]-9-chloro-4-methyl-3-oxo-2,3,4,5-tetrahydro-1H-1,4-benzodiazepine-2-acetate Following the procedure of Example 8(a), substituting methyl (±)-7-carboxy-9-chloro-4-methyl-3-oxo-2,3,4,5-tetrahydro-1H-1,4-benzodiazepine-2-acetate for methyl (2S)-7-carboxy-4-methyl-3-oxo-2,3,4,5-tetrahydro-1H-1,4-benzodiazepine-2-acetate, and substituting 2-aminomethylbenzimidazole dihydrochloride for 4-(1-piperidinyl)piperidine, the title compound (0.68 g, 81%) was prepared.

c) (±)-7-[[[(2-Benzimidazolyl)methyl]amnino]carbonyl]-9-chloro-4-methyl-3-oxo-2,3,4,5-tetrahydro-1H-1,4-benzodiazepine-2-acetic acid Following the procedure of Example 8(b), methyl (±)-7-[[[(2-benzimidazolyl)methyl]amino]carbonyl]-9-chloro-4-methyl-3-oxo-2,3,4,5-tetrahydro-1H-1,4-benzodiazepine-2-acetate was saponified and purified to give the title compound (0.53 g, 84%): HPLC (5 Altex Ultrasphere ODS, 4.5 mm×25 cm, 5%–60% $CH_3CN/H_2O$-0.1% TFA gradient over 20 min) K'=6.5; $^1$H NMR (400 MHz, DMSO-$d_6$) δ 8.8–9.0 (t, 1H), 7.0–8.0 (m, 8H), 3.9–5.7 (m, 6H), 2.9–3.0 (s, 3H), 2.7–2.9 (m, 2H); MS (ES) m/e 442.2 (M+H)$^+$. Anal. Calcd for $C_{21}H_{20}ClN_5O_4$·1.25 $H_2O$: C, 54.31; H, 4.88; N, 15.08. Found: C, 54.77; H, 4.73; N, 14.68.

Example 11

Preparation of (±)-8-[[[(2-Benzimidazolyl)methyl]amino]carbonyl]-2-methyl-3-oxo-2,3,4,5-tetrahydro-1H-2-benzazepine-4-acetic acid a) Methyl (±)-8-[[[(2-benzinidazolyl)methyl]amino]carbonyl]-2-methyl-3-oxo-2,3,4,5-tetrahydro-1H-2-benzazepine-4-acetate To a solution stirred under argon at room temperature of methyl (±)-8-carboxy-2-methyl-3-oxo-2,3,4,5-tetrahydro-1H-2-benzazepine-4-acetate (0.30 g, 1 mmol), 2-aminomethylbenzimidazole dihydrochloride (0.27 g, 1.2 mmol), HOBT·$H_2O$ (0.17 g, 1.2 mmol), diisopropylethylamine (0.53 g, 4 mmol), and DMF (5 mL) was added EDC (0.24 g, 1.2 mmol). The resulting mixture was stirred for 18 h, then was concentrated to dryness, and the residue was partitioned between EtOAc and $H_2O$. The organic phase was washed twice with $H_2O$ and once with brine, dried (MgSO$_4$), and concentrated. The residue was recrystallized from boiling EtOAc to give the title compound (0.16 g, 37%) as a colorless solid: $^1$H NMR (CDCl$_3$) δ 9.95 (m, 1H), 7.86 (d, J=8 Hz, 1H), 7.79 (s, 1H), 7.52 (m, 2H), 7.28 (m, 2H), 7.07 (d, J=8.1 Hz, 1H), 5.16 (d, J=16.4 Hz, 1H), 4.82 (m, 2H), 3.78 (m, 1H), 3.69 (s, 3H), 3.65 (d, J=16.6 Hz, 1H), 3.10–2.90 (m 3H), 2.87 (s, 3H), 2.40 (dd, J=16.9, 5.4 Hz, 1H).

b) (±)-8-[[[(2-Benzimidazolyl)methyl]amino]carbonyl]-2-methyl-3-oxo-2,3,4,5-tetrahydro-1H-2-benzazepine-4-acetic acid A solution of methyl (±)-8-[[[(2-benzimidazolyl)methyl]amino]carbonyl]-2-methyl-3-oxo-2,3,4,5-tetrahydro-1H-2-benzazepine-4-acetate (0.10 g, 0.24 mmol), LiOH·$H_2O$ (0.013 g, 0.31 mmol), THF (2 mL), and $H_2O$ (2 mL) was stirred at RT for 18 h, then was concentrated to dryness. The residue was dissolved in $H_2O$, and the solution was brought to pH 4–5 with 3N HCl. The resulting precipitate was collected by filtration and dried. Recrystallization from boiling isopropanol gave the title compound (0.035 g, 36%) as a colorless solid: $^1$H NMR (DMSO-$d_6$) δ 9.13 (t, J=5.7 Hz, 1H), 7.79 (m, 1H), 7.48 (m, 2H), 7.23 (d, J=7.9 Hz, 1H), 7.14 (m, 2H), 5.32 (d, J=16.9 Hz, 1H), 4.69 (d, J=5.7 Hz, 2H), 4.03 (d, J=16.7 Hz, 1H), 3.79 (m, 1H), 3.14 (dd, J=18, 2 Hz, 1H), 2.90 (s, 3H), 2.70 (m, 2H), 2.38 (dd, J=11.4, 3 Hz, 1H); MS (ES) m/e 407 (M+H)$^+$. Anal. Calcd for $C_{22}H_{22}N_4O_4$·1.5 $H_2O$·0.5 $C_3H_8O$: C, 60.90; H, 6.31; N, 12.09. Found: C, 60.68; H, 6.05; N, 12.05.

Example 12

Preparation of (±)-8-[[[N-(2-benzimidazolyl)methyl-N-methyl]amino]carbonyl]-2-methyl-3-oxo-2,3,4,5-tetrahydro-1H-2-benzazepine-4-acetic acid a) Methyl (±)-8-[[[N-(2-benzinidazolyl)methyl-N-methyl]amino]carbonyl]-2-methyl-3-oxo-2,3,4,5-tetrahydro-1H-2-benzazepine-4-acetate Following the procedure of Example 11(a), methyl (±)-8-carboxy-2-methyl-3-oxo-2,3,4,5-tetrahydro-1H-2-benzazepine-4-acetate was coupled with 2-(methylamino)methylbenzimidazole. Chromatography on silica gel (5% MeOH/$CH_2Cl_2$) gave the title compound (67%) as a colorless foam: $^1$H NMR (CDCl$_3$) δ 7.62 (m, 2H), 7.30 (m, 4H), 7.16 (d, J=8.3 Hz, 1H), 5.31 (d, J=16.4 Hz, 1H), 4.92 (d, J=14.5 Hz, 1H), 4.87 (d, J=14.5 Hz, 1H), 3.88 (m, 2H), 3.71 (s, 3H), 3.02 (s, 3H), 3.16 (s, 3H), 3.15–2.90 (m, 3H), 2.43 (dd, J=16.9, 5.3 Hz, 1H).

b) (±)-8-[[[N-(2-Benzimidazolyl)methyl-N-methyl]amino]carbonyl]-2-methyl-3-oxo-2,3,4,5-tetrahydro-1H-2-benzazepine-4-acetic acid Following the procedure of Example 11(b), methyl (±)-8-[[[N-(2-benzimidazolyl)methyl-N-methyl]amino]carbonyl]-2-methyl-3-oxo-2,3,4,5-tetrahydro-1H-2-benzazepine-4-acetate was saponified. Extraction with $CH_2Cl_2$, concentration, and drying gave the title compound (52%) as a colorless solid: $^1$H NMR (DMSO-$d_6$) δ 7.59 (m, 1H), 7.47 (d, J=8 Hz, 1H), 7.35 (m, 2H), 7.15 (m, 3H), 5.25 (d, J=16 Hz, 1H), 4.87 (d, J=14 Hz, 1H), 4.08 (d, J=16 Hz, 1H), 3.78 (m, 1H), 3.10 (m, 1H), 3.35 (s, 3H), 3.03 (s, 3H), 2.85–2.65 (m, 2H), 2.35 (dd, J=16, 5 Hz, 1H); MS (ES) m/e 421.2 (M+H)$^+$. Anal. Calcd for $C_{23}H_{24}N_4O_4$·HCl·1.2 $CH_2Cl_2$·$H_2O$: C, 50.82; H, 5.18; N, 9.79. Found: C, 50.96; H, 5.48; N, 9.55.

Example 13

Preparation of (±)-7-[[[N-(2-benzimidazolyl)methyl-N-methly]amino]carbonyl]-3-oxo-4-(2-phenylethyl)-2,3,4,5-tetrahydro-1H-1,4-benzodiazepine-2-acetic acid a) Methyl (±)-$^7$-[[[N-(2-benzimidazolyl)methyl-N-methyl]amino]carbonyl]-3-oxo-4-(2-phenylethyl)-2,3,4,5-tetrahydr-1H-1,4-benzodiazepine-2-acetate Following the procedure of Example 11(a), methyl (±)-7-carboxy-3-oxo-4-(2-phenylethyl)-2,3,4,5-tetrahydro-1H-1,4-benzodiazepine acetate and 2-(methylamino)methylbenzimidazole were coupled. Chromatography on silica gel (1%–5% MeOH/$CH_2Cl_2$) gave the title compound (57%) as a colorless solid: $^1$H NMR (CDCl$_3$) δ 7.62 (m, 2H), 7.35–7.00 (m, 9H), 6.46 (d, J=8 Hz, 1H), 5.24, (d, J=16.6 Hz, 1H), 5.03 (m, 1H), 4.95 (d, J=14.6 Hz, 1H), 4.82 (d, J=14.6 Hz, 1H), 4.51 (d, J=5 Hz, 1H), 3.82 (m, 1H), 3.74 (s, 3H), 3.58 (m, 2H), 3.17 (s, 3H), 2.99 (dd, J=16, 6.8 Hz, 1H), 2.81 (m, 2H), 2.67 (dd, J=16, 6.3 Hz, 1H).

b) (±)-7-[[[N-(2-Benzimidazolyl)methyl-N-methyl]amino]carbonyl]-3-oxo-4-(2-phenylethyl)-2,3,4,5-tetrahydro-1H-1,4-benzodiazepine-2-acetic acid Methyl (±)-7-[[[N-(2-benzimidazolyl)methyl-N-methyl]amino]carbonyl]-3-oxo-4-(2-phenylethyl)-2,3,4,5- tetrahydro-1H-1,4-benzodiazepine-2-acetate was saponified according to the procedure of Example 11(b). Recrystallization from boiling isopropanol gave the title compound (57%) as a colorless solid: $^1$H NMR (DMSO-d$_6$) δ 7.58 (m, 1H), 7.47 (m, 1H), 7.35–7.10 (m, 8H), 6.55 (d, J=8 Hz, 1H), 6.23 (m, 1H), 5.37 (d, J=16 Hz, 1H), 5.05 (m, 1H), 4.77 (s, 2H), 3.95 (m, 1H), 3.58 (m, 2H), 3.05 (s, 3H), 2.65 (m, 2H), 2.58 (m, 1H); MS (ES) m/e 512.2 (M+H)$^+$. Anal. Calcd for C$_{29}$H$_{29}$N$_5$O$_4$.2H$_2$O: C, 63.61; H, 6.07; N, 12.79. Found: C, 63.33; H, 6.18; N, 12.58.

Example 14

Preparation of (±)-7-[[[N-(2-benzimidazolyl)methyl-N-methyl]amino]methyl]-1,4-dimethyl-3-oxo-2,3,4,5-tetrahydro-1H-1,4-benzodiazepine-2-acetic acid a) Methyl (±)-1-(tert-butoxycarbonyl)-7-carboxy-4-methyl-3-oxo-2,3,4,5-tetrahydro-1H-1,4-benzodiazepine-2-acetate A mixture of methyl (±)-7-carboxy-4-methyl-3-oxo-2,3,4,5-tetrahydro-1H-1,4-benzodiazepine-2-acetate (1 g, 3.42 mmol), di-tert-butyl dicarbonate (1.48 g, 6.8 mmol) and 4-dimethylaminopyridine (42 mg, 0.3 mmol) in anhydrous CH$_3$CN (30 mL) was stirred at RT for 3 h. More di-tert-butyl dicarbonate (0.65 g, 3 mmol) was then added to the clear yellow solution and the reaction was stirred at RT for an additional h. The reaction mixture was then quenched with water, the CH$_3$CN was removed in vacuo, and the residue was extracted with EtOAc. The organic layers were washed sequentially with saturated NH$_4$Cl and H$_2$O, then were dried (MgSO$_4$) and concentrated in vacuo. Silica gel chromatography (7/3 hexane/EtOAc-1% AcOH) gave the title compound (1.05 g, 78%) as a white solid: $^1$H NMR (CDCl$_3$, 400 MHz) δ 1.55 (s, 9H), 2.69 (dd, J=16, 5 Hz, 1H), 2.98 (dd, J=16, 5 Hz, 1H), 3.10 (s, 3H), 3.65–3.68 (m, 1H), 3.72 (s, 3H), 5.16 (dd, J=5, 5 Hz, 1H), 5.45 (d, J=16.4 Hz, 1H), 6.52 (d, J=8.4 Hz, 1H), 7.59 (d, J=1.4 Hz, 1H), 7.78 (dd, J=8.4, 1.4 Hz, 1H).

b) Methyl (±)-7-formyl-4-methyl-3-oxo-2,3,4,5-tetrahydro-1H-1,4-benzodiazepine-2-acetate Methyl (±)-1-(tert-butoxycarbonyl)-7-carboxy-4-methyl-3-oxo-2,3,4,5-tetrahydro-1H-1,4-benzodiazepine-2-acetate (400 mg, 1.02 mmol) was suspended in toluene and SOCl$_2$ (3 mL) was added. The reaction was heated at 80° C. for 3 h. The resulting solution was concentrated to dryness to leave a pale yellow solid. The acid chloride thus obtained was then suspended in THF (2 mL), and 2,6-lutidine (109 mg, 1.02 mmol) was added, followed by 10% Pd/C (40 mg). The resulting suspension was stirred under a H$_2$ atmosphere overnight, then was filtered through a short pad of Celite®. The filtrate was diluted with EtOAc and the solution was washed sequentially with 5% HCl and H$_2$O. Drying (MgSO$_4$) and concentration gave the title compound (139 mg, 60%) as a pale yellow solid, which was used in the next step without further purification: $^1$H NMR (CDCl$_3$, 400 MHz) δ 2.70 (dd, J=15.6, 6.8 Hz, 1H), 3.01 (dd, J=15.6, 6.4 Hz, 1H), 3.08 (s, 3H), 3.75–3.82 (m, 1H), 3.76 (s, 3H), 5.17 (dd, J=6.8, 6.4 Hz, 1H), 5.47 (d, J=16.4 Hz, 1H), 6.59 (d, J=8.4 Hz, 1H), 7.50 (s, 1H), 7.58 (d, J=8.4 Hz, 1H).

c) Methyl (±)-7-[[[N-(2-benzimidazolyl)methyl-N-methyl]amino]methyl]-1,4-dimethyl-3-oxo-2,3,4,5-tetrahydro-1H-1,4-benzodiazepine-2-acetate Methyl (±)-7-formyl-4-methyl-3-oxo-2,3,4,5-tetrahydro-1H-1,4-benzodiazepine-2-acetate (125 mg, 0.45 mmol) was suspended in anhydrous MeOH, then sodium acetate (111 mg, 1.35 mmol), 2-(aminomethyl)benzimidazole dihydrochloride (100 mg, 0.45 mmol) and 4 Å molecular sieves were added. After 30 min., sodium cyanoborohydride (32 mg, 0.49 mmol) was added in 2 portions over a period of 30 min. The reaction mixture was allowed to stir at RT overnight, then the MeOH was removed under vacuum. Formaldehyde (37 wt. % in H$_2$O, 3 mL) was added, followed by CH$_3$CN (3 mL), AcOH, and sodium cyanoborohydride (34 mg, 0.49 mmol). After 40 min. the reaction was concentrated under reduced pressure. The residue was diluted with CH$_2$Cl$_2$, and the solution was washed with saturated NaHCO$_3$. Drying (MgSO$_4$), concentration, and silica gel chromatography (55% CH$_2$Cl$_2$/20% EtOAc/20% hexane/5% MeOH) gave the title compound (55 mg, 29%): $^1$H NMR (CDCl$_{3, 400}$ MHz) δ 2.33 (s, 3H), 2.63 (dd, J=16.0, 5.0 Hz, 1H), 2.74 (s, 3H), 3.03 (dd, J=16.0, 8.8 Hz, 1H), 3.07 (s, 3H), 3.57 (br s, 2H), 3.68 (s, 3H), 3.87 (br s, 2H), 3.87 (d, J=16.4 Hz, 1H), 4.71 (dd, J=8.8 Hz, 5.0, 1H), 5.20 (d, J=16.4 Hz, 1H), 6.94–6.97 (m, 2H), 7.20–7.26 (m, 5H), 7.57 (bs, 1H); MS(ES) m/e 436 (M+H)$^+$.

d) (±)-7-[[[N-(2-Benzimidazolyl)methyl-N-methyl]amino]methyl]-1,4-dimethyl-3-oxo-2,3,4,5-tetrahydro-1H-1,4-benzodiazepine-2-acetic acid LiOH (5.8 mg, 0.17 mmol) was added at RT to a solution of methyl (±)-7-[[[N-(2-benzimidazolyl)methyl-N-methyl]amino]methyl]-1,4-dimethyl-3-oxo-2,3,4,5-tetrahydro-1H-1,4-benzodiazepine-2-acetate (50 mg, 0.115 mmol) in THF (2 mL) and H$_2$O(3 mL). The reaction mixture was heated at 50° C. for 30 min, then was concentrated in vacuo. The resulting residue was lyophilized to afford a pale yellow solid which was purified by preparative HPLC (11% CH$_3$CN/H$_2$O-0.1% TFA) to afford the title compound (30 mg, 31%): $^1$H NMR (CD$_3$OD, 400 MHz) 62.57 (m, 1H), 2.58 (s, 3H), 2.76 (s, 3H), 2.95 (dd, J=16, 8 Hz, 1H), 3.04 (s, 3H), 3.93 (d, J=16.3 Hz, 1H), 4.07 (br s, 2H), 4.38 (br s, 2H), 4.67 (dd, J=8.4, 7.0 Hz, 1H), 5.18 (d, J=16.3 Hz, 1H), 6.91 (d, J=8.4 Hz, 1H), 7.12 (s, 1H), 7.26 (d, J=8.4 Hz, 1H), 7.42 (m, 2H), 7.64 (m, 2H); MS(ES) m/e 422 (M+H)$^+$. Anal. Calcd. for C$_{25}$H$_{27}$N$_5$O$_3$.3.5 CF$_3$CO$_2$H: C, 42.51; H, 3.98; N, 8.26. Found: C, 42.58; H, 4.27; N, 7.89.

Example 15

Preparation of (±)-7-[[[N-(2-benzimidazolyl)methyl-N-methyl]amino]carbonyl]-4-methyl-3-oxo-2,3,4,5-tetrahydro-1H-1,4-benzodiazepine-2-acetic acid a) 2-(Methylaminomethyl)benzimidazole dihydrochloride Methylamine (5.0 g, 0.16 mole) was dissolved in a solution of Et$_2$O (100 mL) and EtOH (5 mL) at 0° C., and 2-chloromethylbenzimidazole (13.4 g, 0.08 mole) was added in small portions. The reaction mixture was stirred at RT for 3 h, then was allowed to stand at RT overnight. More Et$_2$O (200 mL) was added, and the reaction was cooled in an ice bath for 3 h before filtering off the precipitate. The filtrate was saturated with HCl and filtered, and the filtrate was concentrated. Silica gel chromatography (step gradient, 10–25% MeOH/CH$_2$Cl$_2$) yielded the title compound (2.5 g, 13%): $^1$H NMR (250 MHz, 5:1 DMSO-d$_6$/CDCl$_3$) δ 7.13–7.54 (m, 4H), 4.11 (s, 2H), 2.50 (s, 3H); MS (ES) m/e 162.0 (M+H)$^+$.

b) Methyl (±)-7-[[[N-(2-benzimidazolyl)methyl-N-methyl]amino]carbonyl]4-methyl-3-oxo-2,3,4,5-tetrahydro-1H-1,4-benzodiazepine-2-acetate Following the procedure of Example 1(a), except substituting 2-(methylamino methyl)benzimidazole dihydrochloride (1.2 g, 5.13 mmol) for the 2-(aminomethyl) benzimidazole dihydrochloride, the crude title compound was prepared. Silica gel chromatography (10% MeOH/CH$_2$Cl$_2$) yielded the title compound (0.29 g, 39%) as an off-white solid: $^1$H NMR (250 MHz, CDCl$_3$) δ 6.44–7.62 (m, 9H), 5.41 (d, J=16.2 Hz, 1H), 5.07 (m, 1H), 4.81 (m, 2H), 4.52 (d, J=5.2 Hz, 2H), 3.73 (s, 3H), 3.68 (d, J=16.6 Hz, 1H), 3.04 (s, 3H), 2.96 (s, 3H), 2.93 (dd, J=17.1, 6.5 Hz, 1H), 2.67 (dd, J=17.1, 6.3 Hz, 1H); MS (ES) m/e 436.2 (M+H)$^+$.

c) (±)-7-[[[N-(2-Benzimidazolyl)methyl-N-methyl]amino]carbonyl]4-methyl-3-oxo-2,3,4,5-tetrahydro-1H-1,4-benzodiazepine-2-acetic acid Following the procedure of Example 1(b), the compound of Example 15(b) was saponified and purified to give the title compound (0.21 g, 80%): MS (ES) m/e 422.2 (M+H)$^+$. Anal. Calcd for C$_{22}$H$_{23}$N$_5$O$_4$.4/3 CF$_3$CO$_2$H.H$_2$O: C, 47.93; H, 4.22; N, 10.96. Found: C, 47.88; H, 4.35; N, 10.96.

Example 16

Preparation of (±-7-[[[2-(2-benzimidazolyl)ethyl]amino]carbonyl]-4-methyl-3-oxo-2,3,4,5-tetrahydro-1H-1,4-benzodiazepine-2-acetic acid a) 2-Aminoethylbenzimidazole diacetate A mixture containing 2-cyanomethylbenzimidazole (2.0 g, 12.7 mmol), 10% Pd/C (1.0 g), and AcOH (40 mL) was hydrogenated at 42 psi for 6 h in a Parr apparatus. The reaction mixture was filtered through a bed of Celite® and concentrated to give the title compound (3.4 g, 95%): $^1$H NMR (250 MHz, CDCl$_3$) δ 7.04–28.13 (m, 7H), 3.17–3.39 (m, 4H); MS (ES) m/e 162.0 (M+H)$^+$.

b) Methyl (±)-7-[[[2-(2-benzimidazolyl)ethyl]amino]carbonyl]-4-methyl-3-oxo-2,3,4,5-tetrahydro-1H-1,4-benzodiazepine-2-acetate Following the procedure of Example 1(a), except substituting 2-aminoethyl benzimidazole diacetate (1.44 g, 5.13 mmol) for the 2-(aminomethyl)benzimidazole dihydrochloride, the crude title compound was prepared. Silica gel chromatography (9% MeOH/CH$_2$Cl$_2$) yielded the title compound (0.64 g, 86%) as an off-white solid: $^1$H NMR (250 MHz, CDCl$_3$) δ 6.20–8.23 (m, 9H), 5.50 (d, J=16.2 Hz, 1H), 5.11 (m, 1H), 3.70–3.81 (m, 3H), 3.64 (s, 3H), 3.11 (t, J=7.2 Hz, 2H), 2.98 (s, 3H), 2.86 (dd, J=16.8, 8.0 Hz, 1H), 2.63 (dd, J=16.8, 5.0 Hz, 1H); MS (ES) m/e 436.2 (M+H)$^+$.

c) (±)-7-[[[2-(2-Benzimidazolyl)ethyl]amino]carbonyl]-4-methyl-3-oxo-2,3,4,5-tetrahydro-1H-1,4-benzodiazepine-2-acetic acid Following the procedure of Example 1(b), the compound of Example 16(b) was saponified and purified to give the title compound (7.8 mg, 10%): MS (ES) m/e 422.0 (M+H)$^+$. Anal. Calcd for C$_{22}$H$_{23}$N$_5$O$_4$.2 CF$_3$CO$_2$H.2.5 H$_2$O: C, 44.96; H, 4.35; N, 10.08. Found: C, 44.79; H, 4.21; N, 10.08.

Example 17

Preparation of (±)-7-[[(2-benzimidazolyl)amino]carbonyl]-4-methyl-3-oxo-2,3,4,5-tetrahydro-1H-1,4-benzodiazepine-2-acetic acid a) Methyl (±)-7-[[(2-benzimidazolyl)amino]carbonyl]-4-methyl-3-oxo-2,3,4,5-tetrahydro-1H-1,4-benzodiazepine-2-acetate Following the procedure of Example 1(a), except substituting 2-amino benzimidazole (0.68 g, 5.13 mmol) for the 2-(aminomethyl)benzimidazole dihydrochloride, the crude title compound was prepared. Silica gel chromatography (7% MeOH/CH$_2$Cl$_2$) yielded the title compound (0.48 g, 69%) as an off-white solid: $^1$H NMR (250 MHz, CDCl$_3$) δ 6.50–8.16 (m, 9H), 5.47 (d, J=16.3 Hz, 1H), 5.24 (m, 1H), 3.82 (d, J=4.5 Hz, 1H), 3.65 (s, 3H), 2.60–3.01 (m, 6H); MS (ES) m/e 408.2 (M+H)$^+$.

b) (±)-7-[[(2-Benzimidazolyl)amino]carbonyl]-4-methyl-3-oxo-2,3,4,5-tetrahydro-1H-1,4-benzodiazepine-2-acetic acid Following the procedure of Example 1(b), the compound of Example 32(a) was saponified and purified to give the title compound (50 mg, 55%): MS (ES) m/e 394.2 (M+H)$^+$. Anal. Calcd for C$_{20}$H$_{19}$N$_5$O$_4$.4/3 CF$_3$CO$_2$H: C, 49.91; H, 3.76; N, 12.84. Found: C, 49.92; H, 3.83; N, 12.93.

Example 18

Preparation of (2S)-7-[[[N-(2-benzimidazolyl)methyl-N-methyl]amino]carbonyl]-4-methyl-3-oxo-2,3,4,5-tetrahydro-1H-1,4-benzodiazepine-2-acetic acid a) Methyl (2S)-7-[[[N-(2-benzimidazolyl)methyl-N-methyl]amino]carbonyl]-4-methyl-3-oxo-2,3,4,5-tetrahydro-1H-1,4-benzodiazepine-2-acetate Diisopropylethylamine (0.29 g, 2.25 mmol) was added in one portion to a stirred mixture of 2-(methylaminomethyl)benzimidazole bis(trifluoroacetate) (1.8 mmol), methyl (2S)-7-carboxy-4-methyl-3-oxo-2,3,4,5-tetrahydro-1H-1,4-benzodiazepine-2-acetate (0.44 g, 1.50 mmol), EDC (0.34 g, 1.8 mmol) and HOBT.H$_2$O (0.24 g, 1.8 mmol) in DMF (8 mL) at RT under argon. After 24 h, the solution was poured into a mixture of ice-water (90 g) and 5% NaHCO$_3$ (10 mL). The resulting precipitate was filtered and air-dried. Flash chromatography (silica gel, MeOH/CH$_2$Cl$_2$) yielded the title compound (79%): $^1$H NMR (400 MHz, CDCl$_3$) δ 6.51–7.60 (m, 9H), 5.41 (d, J=16.4 Hz, 1H), 5.07 (m, 1H), 4.82 (t, J=15.0 Hz, 2H), 4.50 (d, J=4.8 Hz, 1H), 3.74 (s, 3H), 3.68 (d, J=16.6 Hz, 1H), 3.15 (s, 3H), 2.96 (s, 3H), 2.93 (dd, J=17.1, 6.5 Hz, 1H), 2.67 (dd, J=16.1 6.5 Hz, 1H); MS (ES) m/e 436.2 (M+H)$^+$.

b) (2S)-7-[[[N-(2-Benzimidazolyl)methyl-N-methyl]amino]carbonyl]-4-methyl-3-oxo-2,3,4,5-tetrahydro-1H-1,4-benzodiazepine-2-acetic acid Following the procedure of Example 1(b), the compound of Example 18(a) was saponified and purified to give the title compound (0.11 g, 91%): MS (ESMS) m/e 422.2 (M+H)$^+$. Anal. Calcd for C$_{22}$H$_{23}$N$_5$O$_4$.3 H$_2$O: C, 55.57; H, 6.15; N, 14.73. Found: C, 55.30; H, 6.13; N, 14.39.

Example 19

Preparation of (±)-4-Methyl-7-[[[N-(2-(1-methyl) benzimidazolyl)methyl-N-methyl]amino]carbonyl]-3-oxo-2,3,4,5-tetrahydro-1H-1,4-benzodiazepine-2-acetic acid a) 2-[[N-(tert-Butoxycarbonyl)-N-methyl]aminomethyl]benzimidazole Di-tert-butyl dicarbonate (1.12 g, 5.13 mmol) was added dropwise at 0° C. to a mixture containing 2-(methylaminomethyl)benzimidazole dihydrochloride (1.0 g, 4.27 mmol), dioxane (25 mL), H$_2$O (25 mL), and 1 N NaOH (12.8 mL, 12.8 mmol). After 2 h, the reaction was warmed to RT and stirred for 21 h. The solvent was evaporated on the rotavap, and the pH was adjusted to 5 using 1 M NaHSO$_4$. The mixture was extracted with CH$_2$Cl$_2$ (2×80 mL), and the combined organic layers were washed with brine (30 mL) and dried (MgSO$_4$). Concentration gave the title product (0.7 g, 64%): $^1$H NMR (400 MHz, CDCl$_3$) δ 7.59 (b, 2H), 7.26 (m, 3H), 4.57 (s, 2H), 2.98 (s, 3H), 1.50 (s, 9H); MS (ES) m/e 262.0 (M+H)$^+$.

b) 1-Methyl-2-[[N-(tert-butoxycarbonyl)-N-methyl]aminomethyl]benzimidazole

A mixture of 2-[[N-(tert-butoxycarbonyl)-N-methyl]aminomethyl]benzimidazole (0.51 g, 1.95 mmol), NaH (0.12 g, 5.0 mmol), DMF (5 mL), and THF (20 mL) was stirred at RT under argon for 5 min, then methyl iodide (0.83 g, 5.86 mmol) was added. The reaction mixture was stirred at RT for 170 min, then was concentrated on the rotavap. The residue was diluted with $CH_2Cl_2$ (100 mL), and the mixture was washed sequentially with $H_2O$ (30 mL), 5% $NaHCO_3$ (30 mL), and brine (30 mL). Drying ($Na_2SO_4$) and concentration gave the title compound (0.51, 94%): $^1H$ NMR (250 MHz, $CDCl_3$) δ 7.23–7.77 (m, 4H), 4.79 (s, 2H), 3.82 (s, 3H), 2.86 (s, 3H), 1.50 (s, 9H); MS (ES) m/e 276.2 $(M+H)^+$.

c) 1-Methyl-2-(methylaminomethyl)benzimidazole bis (trifluoroacetate)

A mixture of 1-methyl-2-[[N-(tert-butoxycarbonyl)-N-methyl]aminomethyl]benzimidazole (0.51 g, 1.85 mmol) in 25% $TFA/CH_2Cl_2$ (20 mL) was stirred at RT under argon for 20 min. The solvent was removed on the rotavap and the residue was recrystallized from $Et_2O/CH_2Cl_2$ to give tidle compound (0.69 g, 92%): $^1H$ NMR (250 MHz, 5:1 $CDCl_3$:DMSO-$d_6$) δ 7.24–7.68 (m, 4H), 4.56 (s, 2H), 3.84 (s, 3H), 2.84 (s, 3H); MS (ES) m/e 176.0 $(M+H)^+$.

d) Methyl (±)-4-methyl-7-[[[N-(2-(1-methyl) benzimidazolyl)methyl-N-methyl]amino]carbonyl]-3-oxo-2,3,4,5-tetrahydro-1H-1,4-benzodiazepine-2-acetate Following the procedure of Example 18(a), except substituting 1-Methyl-2-(methylaminomethyl)benzimidazole bis(trifluoroacetate) for 2,6-diaminopyridine, the title compound (0.53 g, 77%) was prepared: $^1H$ NMR (250 MHz, $CDCl_3$) δ 6.50–7.80 (m, 9H), 5.43 (d, J=16.4 Hz, 1H), 5.03–5.10 (m, 3H), 4.42 (d, J=4.7 Hz, 1H), 3.88 (s, 3H), 3.74 (s, 3H), 3.68 (d, J=16.6 Hz, 1H), 3.13 (s, 3H), 3.06 (s, 3H), 2.99 (dd, J=16.2, 6.7 Hz, 1H), 2.66 (dd, J=16.2, 6.5 Hz, 1H); MS (ES) m/e 450.2 $(M+H)^+$.

e) (±)-4-Methyl-7-[[[N-(2-(1-methyl)benzimidazolyl) methyl-N-methyl]amino]carbonyl]-3-oxo-2,3,4,5-tetrahydro-1H-1,4-benzodiazepine-2-acetic acid Following the procedure of Example 1(b), the compound of Example 19(d) was saponified and purified to give the title compound (0.13 g, 60%): MS (ES) m/e 436.2 $(M+H)^+$. Anal. Calcd for $C_{23}H_{25}N_5O_4$·1.5 $H_2O$: C, 59.73; H, 6.10; N, 15.14. Found: C, 59.39; H, 6.05; N, 14.96.

Example 20

Preparation of (±)-7-[[[(2-(5(6)-methoxy) benzimidazolyl)methyl]amino]carbonyl]-4-methyl-3-oxo-2,3,4,5-tetrahydro-1H-1,4-benzodiazepine-2-acetic acid a) N-[N-(Benzyloxycarbonyl)glycyl]-4-methoxy-2-nitroaniline N-(Benzyloxycarbonyl)glycine (2.72 g, 13.13 mmol) was dissolved in $CH_2Cl_2$ and an excess of thionyl chloride at room temperature. After 2 h, the reaction was evaporated under vacuum and the residue was stripped with toluene twice and dried under vacuum. The white solid was taken into $CH_2Cl_2$ and 4-methoxy-2-nitroaniline (2.1819 g, 12.98 mmol) was added as a solid, followed by triethylamine (2.0 mL, 1.455 g, 14.38 mmol). The reaction was stirred at RT for 24 h, then was evaporated under vacuum. The residue was dissolved in EtOAc and washed with aqueous 1N $NaHCO_3$. The EtOAc layer was dried ($MgSO_4$) and concentrated under vacuum. Thin layer chromatography analysis (1:1:1 hexanes/$Et_2O/CH_2Cl_2$) showed good conversion to the acylated material. The crude material was dissolved in 2:1:1 hexanes/$Et_2O/CH_2Cl_2$ initially, with the addition of enough $Et_2O/CH_2Cl_2$ and sonication/heating to dissolve all the solid material. Silica gel chromatography (2:1:1 hexanes/$Et_2O$/ $CH_2Cl_2$ (2 L), then 1:1:1 hexanes/$Et_2O/CH_2Cl_2$ (1.5 L), then $Et_2O/CH_2Cl_2$) gave the title compound (3.3387 g, 72%): $^1H$ NMR (250 MHz, $CDCl_3$) δ 3.85 (s, 3H), 4.06 (d, 2H), 5.18 (s, 2H), 5.61 (t, 1H), 7.2–7.4 (m, 6H), 7.65 (d, 1H), 8.63 (d, 1H).

b) 2-[N-[(Benzyloxycarbonyl)amino]methyl]-5(6)-methoxybenzimidazole

N-[N-(Benzyloxycarbonyl)glycyl]4-methoxy-2-nitroaniline (1.0 g, 2.87 mmol) was dissolved in glacial acetic acid, and iron powder was added. The mixture was heated in an oil bath at about 65° C. with stirring. After 24 h, the reaction was evaporated under vacuum. The residue was evaporated with toluene, dried under vacuum, and adsorbed onto silica gel. Chromatography on a dry silica gel column (1:1 $Et_2O/CH_2Cl_2$ (1.5 L) followed by 5% MeOH/ $CH_2Cl_2$) gave the title compound (1.0063 g, 94%): $^1H$ NMR (250 MHz, $CDCl_3$) 8 3.78 (s, 3H), 4.57 (s, 2H), 5.05 (s, 2H), 6.8–7.5 (m, 8H), 10.85 (br. s., 1H); MS (ES) m/e 312.0 $(M+H)^+$.

c) 2-(Aminomethyl)-5(6)-methoxybenzimidazole

2-[N-[(Benzyloxycarbonyl)amino]methyl]-5(6)-methoxybenzimidazole (1.0063 g, 3.23mmol) was dissolved in MeOH, and 10% Pd/C was added. The reaction was stirred at RT under $H_2$ (balloon pressure) for 17 h, then was filtered through a bed of Celite®. The filtrate was evaporated under vacuum to yield the title compound (411.7 mg, 72%) as an oil: $^1H$ NMR (250 MHz, $CDCl_3$) δ 3.75 (s, 3H), 4.05 (s, 2H), 5.59 (br s, 2H), 6.82 (dd, 1H), 6.97 (d, 1H), 7.40 (d, 1H).

d) Methyl (±)-7-[[[(2-(5(6)-methoxy)benzimidazolyl) methyl]amino]carbonyl]-4-methyl-3-oxo-2,3,4,5-tetrahydro-1H-1,4-benzodiazepine-2-acetate Methyl (±)-7-carboxy-4-methyl-3-oxo-2,3,4,5-tetrahydro-1H-1,4-benzodiazepine-2-acetate (245.4 mg, 0.84 mmol) was dissolved in DMF. A solution of EDC (169.3 mg, 0.88 mmol) in DMF was added, followed by HOBT.$H_2O$ (112.1 mg, 0.83 mmol). A solution of 2-(Aminomethyl)-5(6)-methoxybenzimidazole (1.434 mg, 0.81 mmol) in DMF was then added, followed by diisopropylethylamine (0.2 mL, 1.44 mmol). The reaction was stirred at RT for 5 d, then was concentrated under vacuum. The residue was evaporated once with toluene. The crude material was partitioned between $H_2O$ and EtOAc. The aqueous phase was back-extracted with EtOAc, and the combined organic layers were dried ($MgSO_4$) and concentrated. TLC (10% MeOH/$CHCl_3$) showed two major products. Silica gel chromatography ($CHCl_3$ (0.25 L), then 3% MeOH/$CHCl_3$) gave three fractions; fraction 3 gave the title compound (112.9 mg, 31%): $^1H$ NMR (250 MHz, $CD_3OD$) δ 3.06 (s, 3H), 3.70 (s, 3H), 3.80 (s, 3H), 4.74 (s, 2H), 5.28 (t, 1H), 5.51 (d, 1H), 6.58 (d, 1H), 6.85 (d, 1H), 7.00 (s, 1H), 7.48 (d, 1H), 7.5–7.65 (m, 2H); MS (ES) m/e 452.2 $(M+H)^+$.

e) (±)-7-[[[(2-(5(6)-Methoxy)benzimidazolyl)methyl] amino]carbonyl]-4-methyl-3-oxo-2,3,4,5-tetrahydro-1H-1, 4-benzodiazepine-2-acetic acid Methyl (±)-7-[[[(2-(5(6)-methoxy)benzimidazolyl) methyl] amino]carbonyl]-4-methyl-3-oxo-2,3,4,5-tetrahydro-1H-1,4-benzodiazepine-2-acetate (112.9 mg, 0.25 mmol) was dissolved in MeOH, and aqueous 1N sodium hydroxide (0.5 mL, 0.5 mmol) was added. The reaction was stirred at RT for two d, then was warmed in an oil bath at about 65° C. The solution was concentrated and the residue was redissolved in aqueous MeOH. The solution was neutralized with aqueous 1N hydrochloric acid (0.5 mL, 0.5 mmol) and the mixture was evaporated under vacuum to remove most of the MeOH. The precipitate which formed was collected on a sintered glass funnel and dried under high vacuum to afford the title compound (103.1 mg, 94%): TLC (3:1:1 n-BuOHlAcOH/lH$_2$O) $R_f$=0.62; MS (ES) m/e 438.2

(M+H)⁺. Anal Calcd for $C_{22}H_{23}N_5O_5 \cdot 2\,H_2O$: C, 55.81; H, 5.75; N, 14.70. Found: C, 55.69; H, 5.59; N, 14.41.

Example 21

Preparation of (±)-7-[[[N-[2-(4-azabenzimidazolyl)]methyl-N-methyl]amino]carbonyl]-4-methyl-3-oxo-2,3,4,5-tetrahydro-1H-1,4-benzodiazepine-2-acetic acid a) 2-Amino-3-[[N-(benzyloxycarbonyl)sarcosyl]amino]pyridine N-(Benzyloxycarbonyl)sarcosine (4.1 g, 18.5 mmol) was dissolved in dry THF, and triethylamine (3 mL, 21.6 mmol) was added, followed by isobutylchloroformate (2.5 mL, 19.27 mmol). The solution was cooled to about −20° C. for 15 minutes, then a solution of 2,3-diaminopyridine (2.0767 g, 19.03 mmol) in dry THF was added slowly. The reaction was kept stirring between −10° C. to −20° C. for 15 minutes, then was allowed to warm to RT. After 3 d, the reaction was evaporated under vacuum, and the residue was partitioned between EtOAc and 1N NaHCO₃. The EtOAc phase was dried (MgSO₄) and evaporated under vacuum. The residue was dissolved in glacial AcOH and was stirred in a oil bath at 70° C. After 24 h, the reaction was removed from the oil bath, allowed to cool to RT, and concentrated under vacuum. The residue was evaporated with toluene, then was chromatographed on silica gel (CHCl₃, then 3% MeOH/CHCl₃, then 5% MeOH/CHCl₃) to afford the title compound (1.13 g, 19%): ¹H NMR (250 MHz, CDCl₃) δ 3.05 (s, 3H), 3.99 (s, 2H), 4.82 (br s, 1H), 6.5–6.65 (m, 1H), 7.32 (s, 5H), 7.87 (d, 1H), 8.84 (br s, 1H); MS (ES) m/e 315.4 (M+H)⁺.

b) 2-[[N-(Benzyloxycarbonyl)-N-methylamino]methyl]4-azabenzimidazole

2-Amino-3-[[N-(benzyloxycarbonyl)sarcosyl]amlno]pyridine (513 mg, 1.63 mmol) was taken up in glacial AcOH (25 mL) and the reaction was heated in an oil bath set at 100–105° C. After 24 h, the reaction was evaporated under vacuum and the residue was concentrated from toluene. Silica gel chromatography (CHCl₃, then 2% MeOH/CHCl₃, then 4% MeOH/CHCl₃) gave the title compound (385 mg, 80%): ¹H NMR (250 MHz, CDCl₃) δ 3.07 (s. 3H), 4.83 (s, 2H), 5.17 (s, 2H), 7.1–7.4 (m, 6H), 8.03 (d, 1H), 8.46 (d, 1H); MS (ES) m/e 297.2 (M+H)⁺.

c) 2-(Methylamino)methyl-4-azabenzimidazole

2-[[N-(Benzyloxycarbonyl)-N-methylamino]methyl]4-azabenzimidazole (385.5 mg, 1.30 mmol) was dissolved in MeOH, and 10% Pd/C was added. The mixture was stirred at RT under H₂ (balloon pressure) for 4 h, then the catalyst was removed by filtration through a bed of Celite®. The clear, colorless filtrate was evaporated under vacuum to afford the title compound (237.0 mg, 100%): ¹H NMR (250 MHz, CDCl₃/CD₃OD) δ 2.48 (s, 3H), 4.06 (s, 2H), 5.38 (br s, 1H), 7.15–8.35 (m, 4H).

d) Methyl (±)-7-[[[N-[2-(4-azabenzimidazolyl)]methyl-N-methyl]amino]carbonyl]-4-methyl-3-oxo-2,3,4,5-tetrahydro-1H-1,4-benzodiazepine-2-acetate EDC (263.1 mg, 1.37 mmol) was added to a suspension of methyl (±)-7-carboxy-4-methyl-3-oxo-2,3,4,5-tetrahydro-1H-1,4-benzodiazepine-2-acetate (392.2 mg, 1.34 mmol) and HOBT·H₂O (195.5 mg, 1.45 mmol) in DMF in a dried 100 mL round-bottomed flask. The white suspension slowly dissolved to afford a clear, colorless solution. A solution of 2-(methylamino)methyl-4-azabenzimidazole (237.0 mg, 1.3 mmol) in DMF and added, followed by diisopropylethylamine (0.3 mL, 1.72 mmol). The reaction was stirred at RT for 4 d, then was evaporated under high vacuum. The residue was concentrated from toluene and was chromatographed on silica gel (CHCl₃, then 5% MeOH/CHCl₃, then 10% MeOH/CHCl₃) to afford the title compound (183.3 mg, 32%): ¹H NMR (250 MHz, CDCl₃/CD₃OD) δ 3.04 (s, 3H), 3.17 (s, 3H), 3.72 (s, 3H), 4.13 (s, 2H), 5.13 (dd, 1H), 5.49 (d, 1H), 6.54 (d, 1H), 7.2–7.5 (m, 5H), 8.37 (br s, 1H); MS(ES) m/e 437.2 (M+H)⁺.

e) (±)-7-[[[N-[2-(4-azabenzimidazolyl)]methyl-N-methyl]amino]carbonyl]-4-methyl-3-oxo-2,3,4,5-tetrahydro-1H-1,4-benzodiazepine-2-acetic acid Methyl (±)-7-[[[N-[2-(4-azabenzimidazolyl)]methyl-N-methyl]amino]carbonyl]4-methyl-3-oxo-2,3,4,5-tetrahydro-1H-1,4-benzodiazepine-2-acetate (183 mg, 0.42 mmol) was dissolved in MeOH, and 1N sodium hydroxide (1.5 mL, 1.5 mmol) was added. The reaction was stirred at RT until complete by TLC, then was neutralized with 1N HCl (1.5 mL, 1.5 mmol). The reaction was evaporated under vacuum, and the residue was partially dissolved in MeOH and precipitated with H₂O. The mixture was evaporated under vacuum to remove most of the MeOH, and the resulting aqueous suspension was allowed to stand at RT for about 1 h before being filtered on a sintered glass funnel. The isolated material was dried in a vacuum dessicator under high vacuum to afford the title compound (154.5 mg): MS(ES) m/e 423.2 (M+H)⁺. Anal. Calcd for $C_{21}H_{22}N_6O_4 \cdot 2.75\,H_2O$: C, 53.44; H, 5.87; N, 17.81. Found: C, 53.52; H, 5.62; N, 17.23.

Example 22

Preparation of (±)-7-[[[N-[2-(5(6)-Azabenzimidazolyl)]methyl-N-methyl]amino]carbonyl]-4-methyl-3-oxo-2,3,4,5-tetrahydro-1H-1,4-benzodiazepine-2-acetic acid a) 2-[[N-(Benzyloxycarbonyl)-N-methylamino]methyl]-5(6)-azabenzimidazole N-(Benzyloxycarbonyl)sarcosine (4.07 g, 18.24 mmol) was dissolved in dry THF, and triethylamine (3.0 mL, 21.57 mmol) was added, followed by isobutylchloroformate (2.5 mL, 19.27 mmol). The white mixture was cooled in an acetone/dry ice bath to about −20° C. After 20 minutes, a solution of 3,4-diaminopyridine (2.0319 g, 18.62 mmol) in THF was added. The yellow solution was kept stirring at −10 to −20° C. for 15 min, then was allowed to warm slowly to RT. After 3 d, the reaction was evaporated under vacuum, and the residue was partitioned between EtOAc and 1.0 N NaHCO₃. The combined EtOAc layers were dried (MgSO₄) and concentrated. The clear, slightly tan colored residue was dissolved in glacial AcOH, and the solution was stirred in an oil bath at 70° C. After 24 h, the reaction was allowed to cool to RT and was concentrated. The residue was concentrated from toluene, then was chromatographed on silica gel (CHCl₃, then 2% MeOH/CHCl₃, then 4% MeOH/CHCl₃). Two fractions were collected. Fraction 1 (530 mg, 5.5%) appeared to be the diacylated material (MS(ES) m/e 520.2 (M+H)⁺). Fraction 2 contained the title compound (761 mg, 14%): ¹H NMR (250 MHz, CDCl₃) δ 3.07 (s, 3H), 4.77 (s, 2H), 5.07 (s, 2H), 7.2–7.3 (m, 5H), 7.44 (d, 1H), 8.95 (s, 1H); MS (ES) m/e 297.2 (M+H)⁺.

b) 2-(Methylamino)methyl-5(6)-azabenzimidazole

2-[[N-(Benzyloxycarbonyl)-N-methylamino]methyl]-5(6)-azabenzimidazole (685.5 mg, 2.31 mmol) was dissolved in MeOH, and 10% Pd/C was added. The mixture was stirred briskly at RT under H₂ (balloon pressure) for 4 h, then was filtered through Celite® to remove the catalyst. A clear, colorless filtrate was evaporated under vacuum to leave the title product (381 mg, 100%).

c) Methyl (±)-7-[[[N-[2-(5(6)-azabenzimidazolyl)]methyl-N-methyl]amino]carbonyl]-4-methyl-3-oxo-2,3,4,5-tetrahydro-1H-1,4-benzodiazepine-2-acetate EDC (263.1 mg, 1.37 mmol) was added to a suspension of methyl (±)-7-carboxy4-methyl-3-oxo-2,3,4,5-tetrahydro-1H-1,4-benzodiazepine-2-acetate (697.3 mg, 2.39 mmol) and HOBT.H$_2$O (345.5 mg, 2.56 mmol) in DMF in a dried 100 mL round-bottomed flask. The white suspension began to dissolve. After about 15 minutes, a solution of 2-(methylamino)methyl-5(6)-azabenzimidazole (380.6 mg, 2.35 mmol) in DMF was added. The reaction was stirred at RT for 20 h, then was concentrated under vacuum. Silica gel chromatography (CHCl$_3$, then 5% MeOH/CHCl$_3$, then 10% MeOH/CHCl$_3$) gave the title compound (679 mg, 66%): $^1$H NMR (250 MHz, CDCl$_3$) δ 3.00 (s, 3H), 3.12 (s, 3H), 3.48 (s, 3H), 3.66 (s, 3H), 5.07 (m, 1H), 5.40 (d, 1H), 6.35 (br s, 1H), 7.05 (br s, 1H), 7.12 (s, 1H), 7.47 (d, 1H), 8.36 (d, 1H), 8.94 (s, 1H).

d) (±)-7-[[[N-[2-(5(6)-Azabenzimidazolyl)]methyl-N-methyl]amnino]carbonyl]-4-methyl-3-oxo-2,3,4,5-tetrahydro-1H-1,4-benzodiazepine-2-acetic acid Methyl (±)-7-[[[N-[2-(5(6)-azabenzimidazolyl)]methyl-N-methyl]amino]carbonyl]-4-methyl-3-oxo-2,3,4,5-tetrahydro-1H-1,4-benzodiazepine-2-acetate (679.0 mg, 1.56 mmol) was dissolved in MeOH, and 1N NaOH (3.0 mL, 3.0 mmol) was added. A clear, yellow solution formed almost immediately. The reaction was stirred at RT for 24 h, then was neutralized with 1N aqueous HCl (3.0 mL, 3.0 mmol). The reaction was concentrated and the residue was suspended in H$_2$O. The mixture was sonicated, and the colorless precipitate was collected and dried in a vacuum dessicator to leave the title compound (471 mg, 71%): MS (ES) mle 423.2 (M+H)$^+$. Anal. Calcd for C$_{21}$H$_{22}$N$_6$O$_4$.2.25 H$_2$O: C, 54.48; H, 5.77; N, 18.15. Found: C, 54.67; H, 5.58; N, 17.64.

Example 23

Preparation of (±)-7-[[[(2-imidazolyl)methyl]amino]carbonyl]-4-methyl-3-oxo-2,3,4,5-tetrahydro-1H-1,4-benzodiazepine-2-acetate a) Methyl (±)-7-[[[(2-imidazolyl)methyl]amnino]carbonyl]4-methyl-3-oxo-2,3,4,5-tetrahydro-1H-1,4-benzodiazepine-2-acetate A mixture of methyl (±)-7-carboxy-4-methyl-3-oxo-2,3,4,5-tetrahydro-1H-1,4-benzodiazepine-2-acetate (584 mg, 2.0 mmol), 2-(aminomethyl)imidazole (2.2 mmol, prepared according to *Annalen* 1968, 718, 249), HOBT.H$_2$O (270 mg, 2 mmol), triethylamine (1.0 mL, 7.2 mmol), and EDC (383 mg, 2 mmol) in anhydrous DMF (40 mL) was stirred at RT overnight. The reaction was concentrated in vacuum, and the resulting residue was diluted with 5% K$_2$CO$_3$. CH$_2$Cl$_2$ extraction, drying (MgSO$_4$), and concentration gave the title compound (0.76 g, 86%): MS (ES) m/e 372 (M+H)$^+$.

b) (±)-7-[[[(2-Imidazolyl)methyl]amino]carbonyl]-4-methyl-3-oxo-2,3,4,5-tetrahydro-1H-1,4-benzodiazepine-2-acetic acid The compound of Example 23(a) (0.7 g, 1.6 mmol) was suspended in MeOH (10 mL) and THF (5 mL), and 1.0 N NaOH (6 mL) was added. The reaction was stirred at RT for 2 d, then was concentrated in vacuum. The residue was diluted with H$_2$O, and the pH was adjusted to 5 to 6 with 1.5 N HCl. Lyophilization gave the title compound: MS (ES) m/e 358 (M+H)$^+$. Anal. Calcd for C$_{17}$H$_{19}$N$_5$O$_4$.1.75 CF$_3$CO$_2$H: C, 44.21; H, 3.75; N, 12.57. Found: C, 44.21; H, 3.96; N, 12.54.

Example 24

Preparation of (±)-7-[[[2-(benzimidazolyl)methyl]methylamino]carbonyl]-4-(2-methoxyethyl)-3-oxo-2,3,4,5-tetrahydro-1H-1,4-benzodiazepine-2-acetic acid a) Methyl (±)-7-[[[2-(benzimidazolyl)methyl]methylamino]carbonyl]4-(2-methoxyethyl)-3-oxo-2,3,4,5-tetrahydro-1H-1,4-benzodiazepine-2-acetate EDC (138 mg, 0.72 mmol) was added to a solution of methyl (±)-7-carboxy-4-(2-methoxyethyl)-3-oxo-2,3,4,5-tetrahydro-1H-1,4-benzodiazepine-2-acetate (202 mg, 0.6 mmol), 2-(methylaminomethyl)benzimidazole dihydrochloride (0.72 mmol), HOBt.H$_2$O (97 mg, 0.72 mmol), and diisopropylethylamine (0.42 mL, 2.4 mmol) in anhydrous DMF (3 mL) at RT. The reaction was stirred at RT for 22.5 h, then was concentrated on the rotavap. The residue was reconcentrated from xylenes (to remove DMF), then was diluted with H$_2$O (2 mL). CHCl$_3$ extraction, drying (MgSO4), concentration, and chromatography on silica gel (5% MeOH/CHCl$_3$) gave the title compound (265.7 mg, 92%) as an off-white solid: TLC R$_f$ (5% MeOH/CHCl$_3$) 0.39; $^1$H NMR (400 MHz, CDCl$_3$) δ 7.68–7.82 (m, 1H), 7.37–7.51 (m, 1H), 7.15–7.35 (m, 4H), 6.45–6.57 (m, 1H), 5.38 (d, J=16.5 Hz, 1H), 5.04–5.14 (m, 1H), 4.82 (½ AB, J=14.6 Hz, 1H), 4.74 (½ AB, J=14.6 Hz, 1H), 4.53 (d, J=5.0 Hz, 1H), 3.99 (d, J=16.5 Hz, 1H), 3.74 (s, 3H), 3.65–3.83 (m, 1H), 3.37–3.61 (m, 3H), 3.22 (s, 3H), 3.15 (s, 3H), 2.98 (dd, J=16.0, 6.2 Hz, 1H), 2.68 (dd, J=16.0, 6.7 Hz, 1H); MS (ES) m/e 480.2 (M+H)$^+$, 319.0 (M+H−161)$^+$.

b) (±)-7-[[[2-(Benzimidazolyl)methyl]methylamino]carbonyl]-4-(2-methoxyethyl)-3-oxo-2,3,4,5-tetrahydro-1H-1,4-benzodiazepine-2-acetic acid 1.0 N LiOH (0.66 mL, 0.66 mmol) was added to a solution of methyl (±)-7-[[[2-(benzimidazolyl)methyl]methylamino]carbonyl]-4-(2-methoxyethyl)-3-oxo-2,3,4,5-tetrahydro-1H-1,4-benzodiazepine-2-acetate (265.7 mg, 0.55 mmol) in THF (2.8 mL) and H$_2$O (2.1 mL) at RT. The light yellow solution was stirred at RT for 17 h, then was concentrated to dryness on the rotavap. The residue was dissolved in H$_2$O (2 mL), and the solution was neutralized with 1.0 N HCl (0.66 mL). The solid precipitate was collected by suction filtration and recrystallized from H$_2$O/CH$_3$CN to afford the title compound (147.0 mg, 55%): HPLC (PRP-1, 15% CH$_3$CN/H$_2$O-0.1% TFA) K'=4.3; $^1$H NMR (400 MHz, DMSO-d$_6$) δ 7.59 (d, J=7.6 Hz, 1H), 7.47 (d, J=7.1 Hz, 1H), 7.08–7.25 (m, 4H), 6.53 (d, J=8.2 Hz, 1H), 6.13–6.26 (m, 1H), 5.42 (d, J=16.3 Hz, 1H), 5.00–5.12 (m, 1H), 4.70–4.86 (m, 2H), 3.88–4.03 (m, 1H), 3.44–3.60 (m, 2H), 3.22–3.40 (m, 2H), 3.33 (s, 3H), 3.08 (s, 3H), 2.76 (dd, J=16.7, 8.8 Hz, 1H), 2.53 (dd, J=16.7, 5.1 Hz, 1H, partially obscured by residual solvent signal); MS (ES) 466.2 (M+H)+, 305.0 (M+H−161)+. Anal. Calcd for C$_{24}$H$_{27}$N$_5$O$_5$.H$_2$O: C, 59.62; H, 6.04; N, 14.48. Found: C, 59.62; H, 6.18; N, 14.46.

Example 25

Preparation of (±)-7-[[[2-(4-Azabenzimidazolyl)methyl]methylamino]carbonyl]-4-(2-methoxyethyl)-3-oxo-2,3,4,5-tetrahydro-1H-1,4-benzodiazepine-2-acetic acid a) Methyl (±)-7-[[[2-(4-azabenzimidazolyl)methyl]methylanino]carbonyl]-4-(2-methoxyethyl)-3-oxo-2,3,4,5-tetrahydro-1H-1,4-benzodiazepine-2-acetate EDC (115 mg, 0.60 mmol) was added to a solution of methyl (±)-7-carboxy-4-(2-methoxyethyl)-3-oxo-2,3,4,5-tetrahydro-1H-1,4-benzodiazepine-2-acetate (168.2 mg, 0.50 mmol), 4-aza-2-(methylaminomethyl)benzimidazole (0.62 mmol), HOBt.H$_2$O (81 mg, 0.60 mmol), and diisopropylethylamine (0.17 mL, 1.0 mmol) in anhydrous DMF (2.5 mL) at RT. The reaction was stirred at RT for 20 h, then was concentrated on the rotavap, and the residue was diluted with H$_2$O (2 mL). CHCl$_3$ extraction (3×5 mL), drying (MgSO$_4$), concentration, and reconcentration from xylenes (to remove DMF) left a light yellow oil. Chromatography on silica gel (10% MeOH/CHCl$_3$) gave the title compound (225.4 mg, 94%) as a colorless foam: TLC R$_f$ (10% MeOH/CHCl$_3$) 0.39; $^1$H NMR (400 MHz, CDCl$_3$) two components; data for the major component only. δ 8.47 (m, 1H), 7.98–8.06 (m, 1H), 7.17–7.37 (m, 3H), 6.43–6.57 (m, 1H), 5.38 (d, J=16.6 Hz, 1H), 5.04–5.13 (m, 1H), 4.85 (½ AB, J=14.7 Hz, 1H), 4.78 (½ AB, J=14.7 Hz, 1H), 4.53 (d, J=4.9 Hz, 1H), 4.00 (d, J=16.6 Hz, 1H), 3.74 (s, 3H), 3.65–3.81 (m, 1H), 3.35–3.61 (m, 3H), 3.23 (s, 3H), 3.16 (s, 3H), 2.98 (dd, J=15.9, 6.2 Hz, 1H), 2.68 (dd, J=15.9, 6.7 Hz, 1H); MS (ES) m/e 503.2 (M+Na)$^+$, 481.2 (M+H)$^+$, 319.0 (M+H–162)$^+$.

b) (±)-7-[[[2-(4-Azabenzimidazolyl)methyl]methylamino]carbonyl]-4-(2-methoxyethyl)-3-oxo-2,3,4,5-tetrahydro-1H-1,4-benzodiazepine-2-acetic acid 1.0 N LiOH (0.56 mL, 0.56 mmol) was added to a solution of methyl (±)-7-[[[2-(4-azabenzimidazolyl)methyl]methylamino]carbonyl]4-(2-methoxyethyl)-3-oxo-2,3,4,5-tetrahydro-1H-1,4-benzodiazepine-2-acetate (225.4 mg, 0.47 mmol) in THF (2.4 mL) and H$_2$O (1.8 mL) at RT. The solution was stirred at RT for 16.5 h, then was acidified with TFA (0.11 mL) and concentrated to dryness on the rotavap. ODS chromatography (step gradient: 12% CH$_3$CN/H$_2$O-0.1% TFA, then 20% CH$_3$CN/H$_2$O-0.1% TFA), concentration to a small volume, and lyophilization gave the title compound (167.2 mg, 55%) as a light yellow powder: HPLC (PRP-1®, 12% CH$_3$CN/H$_2$O-0.1% TFA) K'=2.7; $^1$H NMR (400 MHz, DMSO-d$_6$) δ 8.48 (d, J=4.9 Hz, 1H), 8.22 (d, J=8.0 Hz, 1H), 7.38–7.50 (m, 1H), 7.15–7.30 (m, 2H), 6.54 (d, J=8.1 Hz, 1H), 6.10–6.45 (m, 1H), 5.43 (d, J=16.5 Hz, 1H), 5.02–5.14 (m, 1H), 4.82–4.99 (m, 2H), 3.95 (br d, J=16.5 Hz, 1H), 3.44–3.63 (m, 2H), 3.23–3.40 (m, 2H), 3.13 (br s, 3H), 3.08 (s, 3H), 2.76 (dd, J=16.7, 8.8 Hz, 1H), 2.53 (dd, J=16.7, 5.0 Hz, 1 H, partially obscured by residual solvent signal); MS (ES) m/e 467.2 (M+H)$^+$, 305.0 (M+H–162)$^+$. Anal. Calcd for C$_{23}$H$_{26}$N$_6$O$_5$.1.5 CF$_3$CO$_2$H.0.5 H$_2$O: C, 48.30; H, 4.44; N, 13.00. Found: C, 48.09; H, 4.38; N, 12.95.

Example 26

Preparation of (±)-7-[[[2-(1-methylindolyl)methyl]methylamino]carbonyl]-4-methyl-3-oxo-2,3,4,5-tetrahydro-1H-1,4-benzodiazepine-2-acetic acid a) Ethyl 1-methylindole-2-carboxylate Iodomethane (4.98 mL, 80 mmol) was added dropwise to a mixture containing ethyl indole-2-carboxylate (1.89 g, 10 mmol) and sodium hydride (1.2 g, 60% dispersion, prewashed by hexane) in anhydrous THF (60 mL) in a flame dried flask under argon at 0° C. After 4 h at RT the reaction was concentrated on the rotavap. The residue was taken into EtOAc and washed sequentially with H$_2$O and saturated NaCl. Drying (MgSO$_4$) and concentration gave the title compound (1.01 g, 50%) as a pale yellow solid.

b) 1-Methyl-2-(methylaminocarbonyl)indole

A mixture of ethyl 1-methylindole-2-carboxylate (4.06 g, 20 mmol) and methylamine (50 mL) was heated at 80° C. in a sealed glass vessel overnight. The reaction was cooled and the title compound (2.4 g, 64%) was collected by filtration as a colorless solid. MS (ES) m/e 189.0 (M+H)$^+$.

c) 1-Methyl-2-(methylamino)methylindole

LAH (50 mL, 1M solution in THF) was added dropwise through a syringe to a solution of 1-methyl-2-(methylaminocarbonyl)indole (2.33 g, 12.4 mmol) in anhydrous THF (10 mL) with cooling, and the resulting solution was stirred at RT under argon overnight. H$_2$O was added dropwise with cooling to destroy excess LAH, and the colorless precipitate was removed by filtration and washed with THF. The filtrate was dried (K$_2$CO$_3$), concentrated, and purified by silica gel flash chromatography to afford the title compound (430 mg, 20% yield) as a yellow solid. MS (ES) m/e 175 (M+H)$^+$.

d) Methyl (±)-7-[[[2-(1-methylindolyl)methyl]methylamino]carbonyl]-4-methyl-3-oxo-2,3,4,5-tetrahydro-1H-1,4-benzodiazepine-2-acetate EDC (508 mg, 2.65 mmol) was added to a solution of methyl (±)-7-carboxy-4-methyl-3-oxo-2,3,4,5-tetrahydro-1H-1,4-benzodiazepine-2-acetate (774 mg, 2.65 mmol), 1-methyl-2-(methylamino)methylindole (420 mg, 2.41 mmol), HOBT.H$_2$O (358 mg, 2.65 mmol) and diisopropylethylamine (0.54 mL, 2.89 mmol) in anhydrous DMF (10 mL) at RT. After 20 h the reaction was concentrated on the rotavap (high vacuum). The residue was taken up in EtOAc and washed sequentially with H$_2$O (3×30 mL) and 10% Na$_2$CO$_3$ (2×30 mL). Drying (MgSO$_4$), concentration, and silica gel chromatography (1% MeOH/CH$_2$Cl$_2$) gave the title compound (809 mg, 75%) as a white solid. MS(ES) m/e 449.2 (M+H)$^+$.

e) (±)-7-[[[2-(1-Methylindolyl)methyl]methylamino]carbonyl]-4-methyl-3-oxo-2,3,4,5-tetrahydro-1H-1,4-benzodiazepine-2-acetic acid 1.0 N NaOH (2 mL, 2 mmol) was added dropwise to a solution of methyl (±)-7-[[[2-(1-methylindolyl)methyl]methylamino]carbonyl]-4-methyl-3-oxo-2,3,4,5-tetrahydro-1H-1,4-benzodiazepine-2-acetate (600 mg, 1.34 mmol) in MeOH (10 mL) at RT. The resulting mixture was stirred for 20 h then was concentrated. The residue was dissolved in H$_2$O (10 mL) and acidified with 1.0 N HCl with cooling. The precipitated solid was collected by filtration to give the title compound (400 mg, 69%) as a white solid. MS (ES) m/e 435.2 (M+H)$^+$. Anal. Calcd for C$_{24}$H$_{26}$N$_4$O$_4$.0.75 H$_2$O: C, 64.34; H, 6.19; N, 12.51. Found: C, 64.16; H, 6.13; N, 12.50.

Example 27

Preparation of (±)-7-[[[2-(1-methylindolyl)methyl]amino]carbonyl]-4-methyl-3-oxo-2,3,4,5-tetrahydro-1H-1,4-benzodiazepine-2-acetic acid a) 1-Methylindole-2-carboxamide A mixture of ethyl 1-methylindole-2-arboxylate (5.9 g, 29 mmol) and ammonium hydroxide (50 mL) was heated at 80° C. in a sealed glass vessel overnight. The reaction was cooled and the title compound (2.2 g, 44%) was collected by filtration as a colorless solid. MS (ES) m/e 175.0 (M+H)$^+$.

b) 1-Methyl-2-(aminomethyl)indole

Following the procedure of Example 26(c), except substituting 1-methylindole-2-carboxamide for 1-methyl-2-(methylaminocarbonyl)indole, the title compound (86%) was obtained as a yellow brownish solid. MS (ES) m/e 161.0 (M+H)$^+$.

c) Methyl (±)-7-[[[2-(1-methylindolyl)methyl]amino]carbonyl]4-methyl-3-oxo-2,3,4,5-tetrahydro-1H-1,4-benzodiazepine-2-acetate Following the procedure of Example 26(d), except substituting 1-methyl-2-(aminomethyl)indole for the 1-methyl-2-(methylamino)methylindole, the title compound (50%) was prepared: MS (ES) m/e 435.2 (M+H)$^+$.

d) (±)-7-[[[2-(1-Methylindolyl)methyl]amino]carbonyl]-4-methyl-3-oxo-2,3,4,5-tetrahydro-1H-1,4-benzodiazepine-2-acetic acid Following the procedure of Example 26(e), methyl (±)-7-[[[2-(1-methylindolyl)methyl]amino]carbonyl]4-methyl-3-oxo-2,3,4,5-tetrahydro-1H-1,4-benzodiazepine-2-acetate was saponified to give the title compound as a colorless solid: MS (ES) m/e 358 (M+H)$^+$. Anal. Calcd for $C_{23}H_{24}N_4O_4$.3 HCl.0.875 $H_2O$: C, 50.63; H, 5.31; N, 10.26. Found: C, 51.00; H, 5.02; N, 9.89.

Example 28

Preparation of 7-[[[2RS-indolinyl)methyl]amino]carbonyl]4-methyl-3-oxo-2,3,4,5-tetrahydro-1H-1,4-benzodiazepine-2S-acetic acid a) Methyl (±)-indoline-2-carboxylate Thionyl chloride (2.86 mL, 39 mmol) was added to a solution of (±)-indoline-2-carboxylic acid (4.26 g, 26 mmol) in methanol (30 mL) at 0° C. The resulting mixture was stirred at RT for 18 h. The solvent was removed in vacuo and the residue was taken into $CH_2Cl_2$ and washed sequentially with $H_2O$ and saturated NaCl. Drying ($MgSO_4$) and concentration gave the title compound (4.31 g, 94%) as a pale yellow oil.

b) (±)-Indoline-2-carboxamide

Gaseous $NH_3$ was bubbled into a solution of methyl (±)-indoline-2-carboxylate (4.3 g, 24.2 mmol) in methanol (50 mL) at RT for 30 min. The reaction was stirred for 18 h, then was filtered to afford the title compound (3.35 g 85%) as a colorless solid: MS (ES) m/e 163.0 (M+H)$^+$.

c) (±)-2-(Aminomethyl)indoline

LAH (20 mL, 1M solution in THF) was added dropwise through a syringe to a solution of (±)-indoline-2-carboxamide (2.2 g, 13.6 mmol) in anhydrous THF (20 mL) with cooling, and the resulting solution was refluxed under argon for 5 h. More LAH (20 mL) was added, and reflux was continued for another 6 h. 10% aqueous THF was added dropwise with cooling to destroy excess LAH, and then $Et_2O$ was added. After stirring for 10 min, the colorless precipitate was removed by filtration and washed with THF. The filtrate was dried ($K_2CO_3$), concentrated, and purified by silica gel flash chromatography (90:10:0.2 $CH_2Cl_2$/MeOH/Et$_3$N). The title compound (1.02 g, 51%) was obtained as an amber oil: MS (ES) m/e 149.0 (M+H)$^+$.

d) Methyl 7-[[[(2RS-indolinyl)methyl]amino]carbonyl]-4-methyl-3-oxo-2,3,4,5-tetrahydro-1H-1,4-benzodiazepine-2S-acetate Following the procedure of Example 26(d), except substituting (±)-2-(aminomethyl)indoline for the 1-methyl-2-(methylamino)methylindole, the title compound (44%) was prepared: MS (ES) m/e 423.0 (M+H)$^+$.

e) 7-[[[(2RS-Indolyl)methyl]amino]carbonyl]4-methyl-3-oxo-2,3,4,5-tetrahydro-1H-1,4-benzodiazepine-2S-acetic acid Following the procedure of Example 26(e), methyl 7-[[[(2RS-indolinyl)methyl]amino]carbonyl]-4-methyl-3-oxo-2,3,4,5-tetrahydro-1H-1,4-benzodiazepine-2S-acetate was saponified to give the title compound as a colorless solid. MS (ES) m/e 409.2 (M+H)$^+$. Anal. Calcd for $C_{22}H_{24}N_4O_4$.1 HCl.0.5 $H_2O$: C, 58.21; H, 5.77; N, 12.34. Found: C, 58.36; H, 5.56; N, 12.26.

Example 29

Preparation of (±)-7-[[[(2-imidazolyl)methyl]amino]carbonyl]-3-oxo-4-(2-phenylethyl)-2,3,4,5-tetrahydro-1H-1,4-benzodiazepine-2-acetic acid a) Methyl (±)-7-[[[(2-imidazolyl)methyl]amino]carbonyl]-3-oxo-4-(2-phenylethyl)-2,3,4,5-tetrahydro-1H-1,4-benzodiazepine-2-acetate Methyl (±)-7-carboxy-3-oxo-2-(2-phenylethyl)-2,3,4,5-tetrahydro-1H-1,4-benzodiazepine-2-acetate (400 mg, 1.04 mmol) was suspended in anhydrous toluene (5 mL), then thionyl chloride (3 mL) was added and the reaction mixture was heated to reflux for 1.5 h. The solvent was then eliminated and more toluene was added (2×5 mL) and then distilled off. The acid chloride thus obtained was dissolved in dry DMF (8 mL) and diisopropylethylamine (506 mg, 3.9 mmol), DMAP (12.2, 0.1 mmol) and 2-(aminomethyl)imidazole dihydrochloride (222 mg, 1.3 mmol) were added. The reaction mixture was allowed to stir at RT overnight, then the solvent was removed under vacuum. The residue was purified by silica gel flash column chromatography (95% $CH_2Cl_2$/5% methanol) to produce the title compound (120 mg, 26%). $^1$H NMR (CDCl$_3$, 400 MHz) δ 2.62 (dd, J=16.2, 6.2 Hz, 1H), 2.76 (m, 2H), 2.94 (dd, J=16.2, 7.4 Hz, 1H), 3.6–3.71 (m, 3H), 3.70 (s, 3H), 4.45 (s, 2H), 5.02 (dd, J=7.2, 6.4 Hz, 1H), 5.27 (d, J=16.6 Hz, 1H), 6.47 (d, J=8.5, 1H), 6.89 (s, 2H), 7.06–7.16 (m, 5H), 7.31 (br s, 1H), 7.49 (d, J=8.5 Hz, 1H).

b) (±)-7-[[[(2-Imidazolyl)methyl]amino]carbonyl]-3-oxo-4-(2-phenylethyl)-2,3,4,5-tetrahydro-1H-1,4-benzodiazepine-2-acetic acid LiOH (16 mg, 0.38 mmol) was added at RT to a solution of methyl (±)-7-[[[(2-imidazolyl)methyl]amino]carbonyl]-3-oxo-4-(2-phenylethyl)-2,3,4,5-tetrahydro-1H-1,4-benzodiazepine-2-acetate (98 mg, 0.21 mmol) in dioxane (3 mL) and $H_2O$ (3 mL). The reaction mixture was heated at 65° C. for 3 h then the organic solvent was removed in vacuo. The aqueous residue was acidified with 1M HCl solution (0.38 mL) to obtain a white solid which was filtered, dissolved in hot methanol, and precipitated with ether. The thus obtained white solid was collected to yield the title compound (72 mg, 78%). $^1$H NMR (DMSO-d$_{6, 400}$ MHz) δ 2.59 (dd, J=16.2, 5.0 Hz, 1H), 2.77 (dd, J=7.7, 6.8 Hz, 2H), 2.92 (dd, J=16.5, 8.8 Hz, 1H), 3.63–3.75 (m, 2H), 3.79 (d, J=16.5 Hz, 1H), 4.61 (s, 2H), 5.13 (dd, J=8.8, 5.0 Hz, 1H), 5.45 (d, J=16.5 Hz, 1H), 6.57 (d, J=8.6 Hz, 1H), 7.07 (s, 2H), 7.10–7.19 (m, 5H), 7.41 (s, 1H), 7.54 (d, J=8.4 Hz, 1H). MS (ES) m/e 448 (M+H)$^+$. Anal. Calcd. for $C_{24}H_{25}N_5O_4 \cdot H_2O$: C, 61.92; H, 5.85; N, 15.04. Found: C, 61.69; H, 5.60; N, 14.86.

Example 30

Preparation of (±)-7-[[[(2-benzimidazolyl)methyl]amino]methyl]4-methyl-3-oxo-2,3,4,5-tetrahydro-1H-1,4-benzodiazepine-2-acetic acid a) Methyl (±)-7-[[[(2-benzimidazolyl)methyl]amino]methyl]-4-methyl-3-oxo-2,3,4,5-tetrahydro-1H-1,4-benzodiazepine-2-acetate Methyl (±)-7-formyl-4-methyl-3-oxo-2,3,4,5-tetrahydro-1H-1,4-benzodiazepine-2-acetate (180 mg, 0.65 mmol) (prepared as in Example 14(b)) was suspended in anhydrous methanol, then sodium acetate (160 mg, 1.95 mmol), 2-(amino methyl)benzimidazole dihydrochloride (143 mg, 0.65 mmol) and 4 Å molecular sieves were added. After 30 min., sodium cyanoborohydride (45 mg, 0.71 mmol) was added in 2 portions over a period of 30 min. The reaction mixture was allowed to stir at RT overnight, then the methanol was removed under vacuum. The residue was diluted with $CH_2Cl_2$, and the solution was washed with saturated $NaHCO_3$. Drying ($MgSO_4$), concentration, and silica gel chromatography (90% $CH_2Cl_2$/9% methanol/1% NEt3) gave the title compound (133 mg, 49%): $^1H$ NMR ($CDCl_3$, 400 MHz) δ 2.67 (dd, J=16.1, 6.1 Hz, 1H), 2.96 (dd, J=16.1, 6.8 Hz, 1H), 3.05 (s, 3H), 3.68 (d, J=16.4 Hz), 3.72 (br s, 2H), 3.75 (s, 3H), 4.11 (br s, 2H, 4.97 (dd, J=6.8 Hz, 6.1, 1H), 5.35 (d, J=16.4 Hz, 1H), 6.54 (d, J=8.1 Hz, 1H), 6.87 (s, 1H), 7.05 (d, J=8.2 Hz, 1H), 7.20–7.26 (m, 2H), 7.57 (m, 2H); MS(ES) m/e 408 $(M+H)^+$.

b) (±)-7-[[[(2-Benzimidazolyl)methyl]amino]methyl]-4-methyl-3-oxo-2,3,4,5-tetrahydro-1H-1,4-benzodiazepine-2-acetic acid LiOH (14.6 mg, 0.34 mmol) was added at RT to a solution of methyl (±)-7-[[[(2-benzimidazolyl)methyl]amino]methyl]-4-methyl-3-oxo-2,3,4,5-tetrahydro-1H-1,4-benzodiazepine-2-acetate (133 mg, 0.31 mmol) in dioxane (3 mL) and $H_2O$ (1 mL). The reaction mixture was stirred at RT overnight then the organic solvent was removed in vacuo. The aqueous residue was acidified with 1M HCl solution (0.38 mL) to obtain a white solid which was purified by ODS chromatography (10% acetonitrile/$H_2O$-0.1% TFA) to afford the title compound (65 mg, 51%): $^1H$ NMR (DMSO-$d_6$, 400 MHz) δ 2.51 (m, 1H), 2.73 (m, 1H), 2.91 (s, 3H), 3.69 (bs, 2H), 3.76 (d, J=16.6 Hz, 1H), 3.97 (br s, 2H), 4.97 (m, 1H), 4.45 (d, J=16.6 Hz, 1H), 5.77 (m, 1H), 6.52 (d, J=8.1 Hz, 1H), 6.97 (s, 1H), 7.02 (d, J=8.1 Hz, 1H), 7.20 (m, 2H), 7.52 (m, 2H); MS (ES) m/e 394 $(M+H)^+$. Anal. Calcd. for $C_{21}H_{23}N_5O_3 \cdot 2 CF_3CO_2H \cdot H_2O$: C, 46.95; H, 4.26; N, 10.95. Found: C, 46.81; H, 4.00; N, 10.84.

Example 31

Preparation of (±)-7-[[[(2-benzimidazolyl)methyl]amino]carbonyl]-1,4-dimethyl-3-oxo-2,3,4,5-tetrahydro-1H-1,4-benzodiazepine-2-acetic acid a) Methyl (±)-7-[[[(2-Benzimidazolyl)methyl]amino]carbonyl]-1,4-dimethyl-3-oxo-2,3,4,5-tetrahydro-1H-1,4-benzodiazepine-2-acetate Following the procedure of Example 2(a), except substituting methyl (t)-7-carboxy-1,4-dimethyl-3-oxo-2,3,4,5-tetrahydro-1H-1,4-benzodiazepine-2-acetate for the methyl (±)-7-carboxy-3-oxo-4-(2-phenylethyl)-2,3,4,5-tetrahydro-1H-1,4-benzodiazepine-2-acetate, the title compound was prepared (60%): MS (ES) m/e 435 $(M+H)^+$; $^1H$ NMR (250 MHz, $CDCl_3$) δ 9.82 (m, 1H), 7.81 (d, J=7.9 Hz, 1H), 7.62 (s, 1H), 7.5 (m, 2H), 7.22 (m, 2H), 6.79 (d, J=7.9 Hz, 1H), 5.09 (d, J=7.9 Hz, 1H), 1H), 4.76–5.01 (m, 3H), 3.61 (s, 3H), 3.59 (d, J=16.6 Hz, 1H), 3.1 (m, 1H), 2.90 (s, 3H), 2.81 (s, 3H), 2.65 (m, 1H).

b) (±)-7-[[[(2-Benzimidazolyl)methyl]amino]carbonyl]-1,4-dimethyl-3-oxo-2,3,4,5-tetrahydro-1H-1,4-benzodiazepine-2-acetic acid A solution of methyl (±)-7-[[[(2-benzimidazolyl)methyl]aamino]carbonyl]-1,4-dimethyl-3-oxo-2,3,4,5-tetrahydro-1H-1,4-benzodiazepine-2-acetate (0.080 g, 0.18 mmol) in a mixture of methanol (10 mL), water (1.0 mL) and 1.0 M NaOH (0.75 mL) was heated at 50° C. for 2 h, cooled to RT, and evaporated to dryness. The residue was dissolved in water (5.0 mL) and the solution acidified to pH 5 with 0.25 N HCl to precipitate the title compound (55%): MS (ES) m/e 422 $(M+H)^+$; Anal. Calcd for $C_{22}H_{23}N_5O_4 \cdot 2.3 H_2O$: C, 57.09; H, 6.01; N, 15.13. Found: C, 57.29; H, 5.79; N, 14.82. $^1H$ NMR (400 MHz, DMSO-$d_6$) δ 8.93 (br t, J=5.6 Hz, 1H), 7.78 (d, J=8.4 Hz, 1H), 7.73 (s, 1H), 7.49 (m, 2H), 7.12 (m, 2H), 6.98 (d, J=8.4 Hz, 1H), 5.30 (d, J=16.6 Hz, 1H), 4.85 (m, 1H), 4.68 (d, J=5.4 Hz, 2H), 4.10 (d, J=16.6 Hz, 1H), 2.98 (s, 3H), 2.92 (m, 3H), 2.80 (s, 3H), 2.60 (dd, J=16.7, 8.9 Hz, 1H).

Example 32

Preparation of (±)-7-[[[(2-benzimidazolyl)methyl]methylamino]carbonyl]-3-oxo-2,3,4,5-tetrahydro-1H-1,4-benzodiazepine-2-acetic acid a) Methyl (±)-7-[[[(2-benzimidazolyl)methyl]methylamino]carbonyl]-3-oxo-2,3,4,5-tetrahydro-1H-1,4-benzodiazepine-2-acetate Following the procedure of Example 15(b), except substituting methyl 7-carboxy-3-oxo-2,3,4,5-tetrahydro-1H-1,4-benzodiazepine-2-acetate for the methyl (±)-7-carboxy4-methyl-3-oxo-2,3,4,5-tetrahydro-1H-1,4-benzodiazepine-2-acetate, the crude title compound was prepared. Chromatography (silica gel, 7% MeOH/$CH_2Cl_2$) yielded the title compound (35%): MS (ES) m/e 422.2 $(M+H)^+$.1H NMR (400 MHz, $CDCl_3$) δ 7.45 (m, 1H), 7.38 (m, 4H), 7.15 (d, J=8.4 Hz, 1H), 6.90 (s, 1H), 6.50 (d, J=8.4 Hz, 1H), 5.35 (s, 3H), 4.95 (m, 1H), 4.65 (m, 1H), 3.71 (s, 3H), 3.65 (m, 1H), 3.48 (s, 3H), 3.07 (m, 1H), 2.75 (dd, J=16.4, 8.4 Hz, 1H).

b) (±)-7-[[[(2-Benzimidazolyl)methyl]methylamino]carbonyl]-3-oxo-2,3,4,5-tetrahydro-1H-1,4-benzodiazepine-2-acetic acid A solution of methyl (±)-7-[[[(2-benzimidazolyl)methyl]methylamino]carbonyl]-3-oxo-2,3,4,5-tetrahydro-1H-1,4-benzodiazepine-2-acetate (0.040 g, 0.09 mmol) in a mixture of methanol (7.0 mL), water (0.7 mL), and 1.0 M NaOH (0.7 mL) was kept 16 h at RT. Trifluoroacetic acid (0.5 mL) was added and the solvents were removed to give the crude product. Purification by semi-preparative HPLC (YMC ODS-AQ, 15:85; acetonitrile:water, 0.1% TFA) gave the title compound: MS (ES) m/e 408.2 $(M+H)^+$; $^1H$ NMR (250 MHz, DMSO-$d_6$) δ 8.19 (br t, J=4.5 Hz, 1H), 7.72 (m, 2H), 7.38 (m, 2H), 7.28 (d, J=8.4 Hz, 1H), 7.15 (s, 1H), 6.62 (d, J=8.4 Hz, 1H), 6.22 (br s, 1H), 5.05 (m, 1H), 4.95 (s, 2H), 3.74 (dd, 15.8, 7.4 Hz, 1H), 3.15 (s, 3H), 2.75 (dd, J=16.4, 8.5 Hz, 1H), 2.50 (m, 1H).

Example 33

Preparation of (2S)-7-[[[N-butyl-N-benzimidazol-2-yl)methyl]amino]carbonyl]-3-oxo-4-methyl-2,3,4,5-tetrahydro-1H-1,4-benzodiazepine-2-acetic acid a) N-BOC-2-methylbenzimidazole To a stirred mixture of 2-methylbenzimidazole (15 g, 113.5 mmol), triethylamine (12 g, 119.2 mmol), and DMAP (cat.) in dry $CH_2Cl_2$ (150 mL) was added $(Boc)_2O$. After 24 h, the mixture was concentrated. The residue was taken up in $H_2O$, stirred and filtered to give a white solid (26.3 g, 100%): mp 71–72° C.; $^1H$ NMR (250 MHz, $CDCl_3$) δ 1.71 (s, 9H), 2.83 (s, 3H), 7.29 (m, 2H), 7.65 (m, 1H), 7.91 (m, 1H).

b) 1-BOC-2-bromomethylbenzimidazole

Following the procedure in Example 4(a), except substituting N-BOC-2-methylbenzimidazole for 2-methylbenzothiazole, the title compound was prepared as a yellow oil (12.88 g, 77%): $^1H$ NMR (250 MHz, $CDCl_3$): δ 1.79 (s, 9H), 4.95 (s, 2H), 7.40 (m, 2H), 7.75 (m, 1H), 8.01 (m, 1H).

c) 2-(1-Butylamino)methylbenzimidazole

To a stirred solution of 1-BOC-2-bromomethylbenzimidazole (2.00 g, 6.4 rnmol) in dry THF (20 mL) was added n-butylamine (1.2 g, 15.4 mmol). After stirring at RT overnight, the mixture was concentrated. The residue was taken up in $H_2O$ and extracted with $CH_2Cl_2$. The organic extracts were dried over $MgSO_4$ and concentrated to give a brown residue, which was dissolved in $CH_2Cl_2$ (15 mL) and treated with TFA (5 mL). The resulting mixture was stirred at RT overnight then was concentrated. The residue was taken up in $H_2O$, and the solution was neutralized with 2.5 N NaOH. $CH_2Cl_2$ extraction, drying ($MgSO_4$), concentration, and silica gel chromatography (2% MeOH/$CH_2Cl_2$) gave the title compound as a yellow oil (0.91 g, 70%): $^1H$ NMR (250 MHz, $CDCl_3$) δ 0.79 (t, J=7.2 Hz, 3H), 1.23 (m, 2H), 1.54 (m, 2H), 3.35 (t, J=7.2 Hz, 2H), 4.55 (s, 2H), 7.25 (m, 2H), 7.48 (m, 1H), 7.75 (m, 1H).

d) Methyl-(S)-7-[[[N-(2-benzimidazolyl)methyl-N-(n-butyl)]amino]carbonyl]-4-methyl-3-oxo-2,3,4,5-tetrahydro-1H-1,4-benzodiazepine-2-acetate To a stirred mixture of 2-(1-butylamino) methylbenzimidazole (0.14 g, 0.6671 mmol), methyl (S)-7-carboxy4-methyl-3-oxo-2,3,4,5-tetrahydro-1H-1,4-benzodiazepine-2-acetate (0.15 g, 0.5132 mmol), HOBT.$H_2O$ (0.083 g, 0.6158 mmol), and (i-Pr)$_2$NEt (0.133 g, 1.0263 mmol) in dry MeCN (5 mL) was added EDC (0.183 g, 0.6158 mmol). After stirring at RT overnight, the mixture was concentrated. The residue was taken up in $H_2O$ and extracted with $CH_2Cl_2$. The combined organic layers were washed sequentially with saturated $NaHCO_3$ and brine, then were dried ($MgSO_4$) and concentrated to give the title compound as a yellow foam (0.232 g, 95%): $^1H$ NMR (250 MHz, $CDCl_3$) δ 0.79 (t, J=7.2 Hz, 3H), 1.23 (m, 2H), 1.54 (m, 2H), 2.54 (dd, J=16.8 Hz, 5.0 Hz, 1H), 2.75 (dd, J=16.8 Hz, 8.9 Hz, 1H), 2.86 (s, 3H), 3.32 (t, J=7.2 Hz, 2H), 3.60 (s, 3H), 3.72 (d, J=16.1 Hz, 1H), 4.75 (s, 2H), 5.05 (m, 1H), 5.48 (d, J=16.1 Hz, 1H), 6.20 (d, J=3.6 Hz, 1H), 6.55 (d, J=8.9 Hz, 1H), 7.16 (m, 4H), 7.53 (m, 2H).

e) (S)-7-[[[N-(2-Benzimidazolyl)methyl-N-(n-butyl)] amino]carbonyl]-4-methyl-3-oxo-2,3,4,5-tetrahydro-1H-1,4-benzodiazepine-2-acetic acid Following the procedure in Example 11(b), methyl-(S)-7-[[[N-(2-benzimidazolyl)methyl-N-(n-butyl)]amino] carbonyl]-4-methyl-3-oxo-2,3,4,5-tetrahydro-1H-1,4-benzodiazepine-2-acetate was saponified to give an off white solid. Trituration in hot EtOH gave the title compound as a white solid (0.15 g, 60%): mp 160–162° C. (dec); $^1H$ NMR (400 MHz, DMSO-$d_6$) δ 0.79 (t, J=7.2 Hz, 3H), 1.23 (m, 2H), 1.54 (m, 2H), 2.54 (dd, J=16.8 Hz, 5.0 Hz, 1H), 2.75 (dd, J=16.8 Hz, 8.9 Hz, 1H), 2.86 (s, 3H), 3.32 (t, J=7.2 Hz, 2H), 3.72 (d, J=16.1 Hz, 1H), 4.75 (s, 2H), 5.05 (m, 1H), 5.48 (d, J=16.1 Hz, 1H), 6.20 (d, J=3.6 Hz, 1H), 6.55 (d, J=8.9 Hz, 1H), 7.16 (m, 4H), 7.53 (m, 2H); MS (ES) m/e 464 (M+H)$^+$; IR (KBr) 3400, 3000–3100, 2800–3100, 1712, 1671, 1655, 1630, 1611, 1271, 828 cm$^{-1}$. Anal. Calcd for $C_{25}H_{29}N_5O_4$.0.75 $H_2O$: C, 62.95; H, 6.44; N, 14.68. Found: C, 62.75; H, 6.40; N, 14.41.

Example 34

Preparation of (S)-7-[[[N-(2-benzimidazolyl)methyl-N-(2-phenylethyl)]amino]carbonyl]-4-methyl-3-oxo-2,3,4,5-tetrahydro-1H-1,4-benzodiazepine-2-acetic acid a) 2-(2-Phenylethylamino)methylbenzimidazole Following the procedure of Example 33(c), except substituting 2-phenylethylamine for n-butylamine, the title compound (0.100 g, 31%) was prepared as a brown oil following silica gel flash chromatography (5% MeOH/$CH_2Cl_2$): $^1H$ NMR (250 MHz, $CDCl_3$) δ 2.82 (t, J=7.5 Hz, 2H), 2.97 (t, J=7.5 Hz, 2H), 4.10 (s, 2H), 7.21 (m, 5H), 7.35 (m, 2H), 7.52 (m, 2H).

b) Methyl (S)-7-[[[N-(2-benzimidazolyl)methyl-N-(2-phenylethyl)]amino]carbonyl]-4-methyl-3-oxo-2,3,4,5-tetrahydro-1H-1,4-benzodiazepine-2-acetate Following the procedure of Example 33(d), except substituting 2-(2-phenylethylamino)methylbenzimidazole for 2-(1-butylamino)methylbenzimidazole, the title compound (0.195 g, 97%) was prepared as an off-white foam following silica gel flash chromatography (2–5% MeOH/$CH_2Cl_2$): $^1H$ NMR (250 MHz, DMSO-$d_6$) δ 2.54 (dd, J=16.5, 5.0 Hz, 1H), 2.75 (dd, J=16.5, 8.9 Hz, 1H), 2.85 (s, 3H), 2.90 (t, J=7.5 Hz, 2H), 3.60 (t, J=7.5 Hz, 2H), 3.65 (s, 3H), 3.78 (d, J=16.3 Hz, 1H), 4.78 (s, 2H), 5.05 (m, 1H), 5.42 (d, J=16.3 Hz, 1H), 6.18 (d, J=3.5 Hz, 1H), 6.54 (d, J=8.9 Hz, 1H), 7.10 (m, 7H), 7.26(m, 2H), 7.48 (m, 1H), 7.60 (m, 1H), 12.30 (s, 1H).

c) (S)-7-[[[N-(2-Benzimidazolyl)methyl-N-(2-phenylethyl)] amino]carbonyl]-4-methyl-3-oxo-2,3,4,5-tetrahydro-1H-1,4-benzodiazepine-2-acetic acid Following the procedure of Example 11(b), methyl (S)-7-[[[N-(2-benzimidazolyl)methyl-N-(2-phenylethyl)] amino]carbonyl]-4-methyl-3-oxo-2,3,4,5-tetrahydro-1H-1,4-benzodiazepine-2-acetate was saponified. Recrystallization from EtOH gave the title compound (0.070 g, 40%) as an off white solid: MS (ES) m/e 512 (M+H)$^+$; IR (KBr) 3300–3500, 3000–3100, 2800–300, 1631, 1647, 1652, 1618, 1405, 698 cm$^{-1}$. Anal. Calcd for $C_{29}H_{29}N_5O_4$.2.5 $H_2O$: C, 62.58; H, 6.16; N, 12.58. Found: C, 62.92, H, 6.02, N, 12.28.

Example 35

Preparation of (S)-7-[[[N-(2-benzimidazolyl)methyl-N-carboxymethyl]amino]carbonyl]-4-methyl-3-oxo-2,3,4,5-tetrahydro-1H-1,4-benzodiazepine-2-acetic acid a) N-[(2-Benzimizazolyl)methyl]glycine benzyl ester Following the procedure in Example 33(c), except substituting glycine benzyl ester HCl for n-butylamine, the title compound (1.00 g, 60%) was prepared as an off white solid: $^1H$ NMR (250 MHz, $CDCl_3$) δ 3.86 (s, 2H), 4.31 (s, 2H), 5.23 (s, 2H), 7.23 (m, 5H), 7.35 (m, 2H), 7.55 (m, 2H).

b) Methyl-(S)-7-[[[N-(2-benzimidazolyl)methyl-N-(benzyloxycarbonyl)methyl]amino]carbonyl]-4-methyl-3-oxo-2,3,4,5-tetrahydro-1H-1,4-benzodiazepine-2-acetate Following the procedure in Example 33(d), except substituting N-[(2-benzimizazolyl)methyl]glycine benzyl ester for 2-(1-butylamino)methylbenzimidazole, the title compound (0.95 g, 81%) was prepared as a yellow foam: $^1H$ NMR (250 MHz, $CDCl_3$) δ 2.54 (dd, J=16.5, 3.5 Hz, 1H), 2.75 (dd, J=16.5, 8.9 Hz, 1H), 2.87 (s, 3H), 3.65 (s, 3H), 3.78 (d, J=16.3 Hz, 1H), 4.30 (s, 2H), 4.86 (s, 2H), 5.05 (m, 1H), 5.23 (s, 2H), 5.45 (d, J=16.3 Hz, 1H), 6.55 (d, J=8.9 Hz, 1H), 7.10 (m, 2H), 7.23 (m, 5H), 7.55 (m, 2H), 7.81 (m, 2H).

c) Methyl-(S)-7-[[[N-(2-benzimidazolyl)methyl-N-carboxymethyl]amino]carbonyl]-4methyl-3-oxo-2,3,4,5-tetrahydro-1H-1,4-benzodiazepine-2-acetate A solution of methyl-(S)-7-[[[N-(2-benzimidazolyl) methyl-N-(benzyloxycarbonyl)methyl]amino]carbonyl]-4-methyl-3-oxo-2,3,4,5-tetrahydro-1H-1,4-benzodiazepine-2-acetate (0.185 g, 0.333 mmol) in methanol (5 mL) was hydrogenated over 10% Pd/C at RT overnight. The catalyst was removed by filtration through Celite®, and the filtrate was concentrated to give a yellow foam. Trituration with acetone gave the title compound (0.140 g, 90%) as an off white solid. $^1H$ NMR (250 MHz, $CDCl_3$) δ 2.54 (dd, J=16.5, 3.5 Hz, 1H), 2.75 (dd, J=16.5, 8.9 Hz, 1H), 2.87 (s, 3H), 3.65 (s, 3H), 3.78 (d, J=16.3 Hz, 1H), 4.86 (s, 2H), 5.05 (m, 1H), 5.23 (s, 2H), 5.45 (d, J=16.3 Hz, 1H), 6.55 (d, J=8.9 Hz, 1H), 7.10 (m, 2H), 7.55 (m, 2H), 7.81 (m, 2H).

d) (S)-7-[[[N-(2-Benzimidazolyl)methyl-N-carboxymethyl] amino]carbonyl]-4-methyl-3-oxo-2,3,4,5-tetrahydro-1H-1,4-benzodiazepine-2-acetic acid A solution of Example 35(b) in methanol (5 mL) was hydrogenated at RT in 10% Pd/C overnight. The catalyst was filtered through Celite. The filtrate was concentrated to give a yellow foam which was triturated in acetone to give the title compound as an off white solid (0.140 g, 90%): MS (ES) m/e 465 (M+H)$^+$: Anal. Calcd for $C_{23}H_{23}N_5O_6 \cdot 1.2$ $H_2O$: C, 56.92; H, 5.26; N, 14.38. Found: C, 57.09; H, 5.33; N, 14.00.

Example 36

Preparation of (S)-7-[[[N-(2-benzimidazolyl)methyl-N-cyclohexyl]amino]carbonyl -4-methyl-3-oxo-2,3,4,5-tetrahydro-1H-1,4-benzodiazepine-2-acetic acid a) 2-(Cyclohexylamino)methylbenzimidazole Following the procedure of Example 33(c), except substituting cyclohexylamine for n-butylamine, the title compound (0.191 g, 52%) was prepared as a brown oil: $^1$H NMR (250 MHz, CDCl$_3$) δ 1.35 (m, 4H), 1.75 (m, 4H), 2.21 (m, 2H), 2.78 (m, 1H), 4.31 (s, 2H), 7.21 (m, 2H), 7.51 (m, 2H).

b) Methyl-(S)-7-[[[N-(2-benzimidazolyl)methyl-N-cyclohexyl]amino]carbonyl]-4-methyl-3-oxo-2,3,4,5-tetrahydro-1H-1,4-benzodiazepine-2-acetate Following the procedure of Example 33(d), except substituting 2-(Cyclohexylamino)methylbenzimidazole for 2-(1-butylamino)methylbenzimidazole, the title compound (0.174 g, 50%) was prepared as a yellow foam: $^1$H NMR (250 MHz, CDCl$_3$) δ 1.15 (m, 4H), 1.60 (m, 4H), 1.85 (m, 2H), 2.65 (dd, J=16.5, 3.5 Hz, 1H), 2.98 (dd, J=16.5, 8.9 Hz, 1H), 3.07 (s, 3H), 3.71 (d, J=16.3 Hz, 1H), 4.48 (d, J=3.5 Hz, 1H), 4.67 (s, 2H), 5.10 (m, 1H), 5.47 (d, J=16.3 Hz, 1H), 6.51 (d, J=8.9 Hz, 1H), 7.15 (m, 3H), 7.22 (m, 2H), 7.31 (m, 1H), 7.65 (m, 1H).

c) (S)-7-[[[N-(2-Benzidazolyl)methyl-N-cyclohexyl]amino carbonyl]4-methyl-3-oxo-2,3,4,5-tetrahydro-1H-1,4-benzodiazepine-2-acetic acid Following the procedure of Example 4(d), methyl-(S)-7-[[[N-(2-benzimidazolyl)methyl-N-cyclohexyl]amino]carbonyl]-4-methyl-3-oxo-2,3,4,5-tetrahydro-1H-1,4-benzodiazepine-2-acetate was saponified. The title compound (0.100 g, 60%) was obtained as an off white solid: $^1$H NMR (400 MHz, DMSO-d$_6$) δ 1.15 (m, 4H), 1.55 (m, 4H), 1.93 (m, 2H), 2.54 (dd, J=16.5, 3.5 Hz, 1H), 2.78 (dd, J=16.5, 8.9 Hz, 1H), 2.91 (s, 3H), 3.83 (d, J=16.3 Hz, 1H), 3.85 (m, 1H), 4.97 (s, 2H), 5.07 (m, 1H), 5.48 (d, J=16.3 Hz, 1H), 6.56 (d, J=8.9 Hz, 1H), 7.20 (s, 1H), 7.25 (d, J=8.9 Hz, 1H), 7.50 (m, 2H), 7.82 (m, 2H); MS (ES) m/e 489 (M+H)$^+$. Anal. Calcd for $C_{27}H_{31}N_5O_4 \cdot H_2O$: C, 63.90; H, 6.55; N, 13.80. Found: C, 63.91; H, 6.27; N, 13.60.

Example 37

Preparation of (±)-7-[[[2-(5-nitrobenzimidazolyl) methyl]methylamino]carbonyl]-4-methyl-3-oxo-2,3,4,5-tetrahydro-1H-1,4-benzodiazepine-2-acetic acid a) 2-[[N-(tert-Butoxycarbonyl)-N-methyl]aminomethyl]-5-nitrobenzimidazole BOC sarcosine (2.555 g, 13.51 mmol) was weighed into a dry 250 mL roundbottom flask, purged with argon. The material was dissolved in dry THF (20 miL). Et$_3$N (3 mL, 21.6 mmol) was added, followed by isobutylchloroformate (1.8 mL, 13.88 mmol). The reaction was stirred at RT under argon for 30 minutes, then was cooled to −20° C, and 4-nitrophenylenediamine (2.0423 g, 13.34 mmol) was added as a solid. After the addition was complete, the cooling bath was removed and the reaction was allowed to warm to RT. After 20 h, the reaction was concentrated under vacuum. The material was dissolved in EtOAc and extracted with 1.0 N NaHCO$_3$. The organic phase was dried (MgSO$_4$), filtered and concentrated under vacuum. The residue was dissolved in glacial AcOH and heated to 75° C. in an oil bath. After 24 h, the reaction was concentrated under vacuum. The residue was reconcentrated from toluene. The material was flash chromatographed (silica gel, 1:2 CH$_2$Cl$_2$/Et$_2$O, 1:1 CH$_2$Cl$_2$/Et$_2$O, 5% MeOH/CH$_2$Cl$_2$) to give the title compound (2.05 g, 51%). Both fractions had identical mass spectral data: MS(ES) m/e 307.0 (M+H)$^+$; $^1$H NMR (250 MHz, CDCl$_3$) δ 8.61–7.46 (m, 5H), 4.65 (s, 2H), 3.04 (s, 3H), 1.50 (S, 9H).

b) 2-(Methylamino)methyl-5-nitrobenzimidazole

2-[N-(tert-Butoxycarbonyl)-N-methyl]aminomethyl-5-nitrobenzimidazole (904.8 mg, 2.96 mmol) was treated with 4 N HCl in dioxane. The reaction was stirred at RT for 1 h, then was concentrated under vacuum. The yellow slurry was reconcentrated from toluene. The residue was dried under high vacuum, leaving the title compound (830.5 mg) as a light yellow solid. This material was used without further purification.

c) Methyl (±)-7-[[[2-(5-nitrobenzimidazolyl)methyl] methylarnino]carbonyl]-4-methyl-3-oxo-2,3,4,5-tetrahydro-1H-1,4-benzodiazepine-2-acetate Methyl (±)-7-carboxy-4-methyl-3-oxo-2,3,4,5-tetrahydro-1H-1,4-benzodiazepine-2-acetate (511.8 mg, 1.75 mmol) was weighed into a dry 200 mL roundbottom flask. Dry DMF was added, followed by HOBt.H$_2$O (258.1 mg, 1.91 mmol) and EDC (351.5 mg, 1.83 mmol). The mixture was stirred at RT until all solids had dissolved, then a solution of 2-(methylamino)methyl-5-nitrobenzimidazole (492.5 mg, 1.76 mmol) and diisopropylethylamine (1.0 mL, 5.74 mmol) in DMF was added at RT. The reaction was stirred at RT for 24 h then was concentrated under vacuum. The residue was reconcentrated from toluene, then was chromatographed on silica gel (CHCl$_3$ (0.25 L), then 3% MeOH/CHCl$_3$ (1 L), then 5% MeOH/CHCl$_3$ (1 L)) to afford the title compound (847.5 mg, quantitative): MS (ES) m/e 481.0 (M+H)$^+$.

d) (±)-7-[[[2-(5-Nitrobenzimidazolyl)methyl]methylamino]carbonyl]-4-methyl-3-oxo-2,3,4,5-tetrahydro-1H-1,4-benzodiazepine-2-acetic acid Methyl (±)-7-[[[2-(5-nitrobenzimidazolyl)methyl]methylamino]carbonyl]-4-methyl-3-oxo-2,3,4,5-tetrahydro-1H-1,4-benzodiazepine-2-acetate (386.3 mg, 0.080 mmol) was suspended in MeOH, and 1.0 N NaOH (2.5 mL, 2.5 mmol) was added. The reaction was stirred at RT for 18 h, then was warmed in an oil bath set at 70° C. After 4 h, the reaction was cooled to RT and neutralized with 1.0 N HCl (2.5 mL). The solution was concentrated under vacuum. After most of the MeOH had evaporated, a yellow precipitate formed. The precipitate was collected on a sintered glass funnel and dried in a desiccator under vacuum to afford the title compound (317.3 mg, 85%). $^1$H NMR (250 MHz, CDCl$_3$) δ 8.55–6.60 (m, 6H), 5.50 (d, 1H), 5.15 (dd, 1H), 4.91 (s, 2H), 3.20 (s, 3H), 3.09 (s, 3H); MS (ES) m/e 467.2 (M+H)$^+$. Anal. Calcd for $C_{22}H_{22}N_6O_6 \cdot HCl$: C, 52.54; H, 4.61; N, 16.71. Found: C, 52.63; H, 4.83; N, 16.53.

Example 38

Preparation of (±)-7-[[[2-(5-aminobenzimidazolyl) methyl]methylamino]carbonyl]-4-methyl-3-oxo-2,3,4,5-tetrahydro-1H-1,4-benzodiazepine-2-acetic acid a) (±)-7-[[[2-(5-Aminobenzimidazolyl)methyl]methylamino]carbonyl]4-methyl-3-oxo-2,3,4,5-tetrahydro-1H-1,4-benzodiazepine-2-acetic acid Methyl (±)-7-[[[2-(5-nitrobenzimidazolyl)methyl]methylamino]carbonyl]-4-methyl-3-oxo-2,3,4,5-tetrahydro-1H-1,4-benzodiazepine-2-acetate (367.4 mg, 0.76 mmol) was suspended in MeOH, and 10% Pd/C catalyst was added. The mixture was stirred briskly at RT under H$_2$ (balloon).

After 4.5 h, the catalyst was removed by filtration through Celite®. The filtrate was concentrated under vacuum, and the residue was dissolved in MeOH. 1.0 N NaOH (2.5 mL, 2.5 mmol) and H$_2$O (10 mL) were added. The reaction was stirred at RT for 24 h, then was neutralized with 1.0 N HCl (2.5 mL). Concentration in vacuum left a dark residue, which was dissolved in MeOH. Activated carbon (Norit®) was added, and the mixture was heated at reflux on the steam bath. The activated carbon was removed by filtration through Celite®, and the filtrate was concentrated to about 50 mL. The precipitate was collected on a sintered glass funnel and dried in a vacuum desiccator to give the title compound (158.0 mg) as a red powder: HPLC (PRP-1®, 10% CH$_3$CN/H$_2$O-0.1% TFA) $t_R$=4.64; MS (ES) m/e 437.2 (M+H)$^+$; $^1$H NMR (250 MHz, CD$_3$OD) δ 7.42–6.56 (m, 6H), 5.54 (d, 1H), 5.15 (dd, 1H), 4.80 (s, 2H), 3.13 (s, 3H), 3.05 (s, 3H). Anal. Calcd for C$_{22}$H$_{24}$N$_6$O$_4$.0.75 HCl 1.75 H$_2$O: C, 53.35; H, 5.75; N, 16.97. Found: C, 53.91; H, 6.00; N, 16.36.

Example 39

Preparation of (±)-7-[2-(1,2,3,4-tetrahydro-9H-pyrido[3,4-b]indolyl)carbonyl]-4-methyl-3-oxo-2,3,4,5-tetrahydro-1H-1,4-benzodiazepine-2-acetic acid a) Methyl (±)-7-[2-(1,2,3,4-tetrahydro-9H-pyrido[3,4-b]indolyl)carbonyl]4-methyl-3-oxo-2,3,4,5-tetrahydro-1H-1,4-benzodiazepine-2-acetate Methyl (±)-7-carboxy-4-methyl-3-oxo-2,3,4,5-tetrahydro-1H-1,4-benzodiazepine-2-acetate (308.5 mg, 1.06 mmol) was weighed into a 250 mL roundbottom flask. Dry DMF was added, followed by HOBt.H$_2$O (159.1 mg, 1.18 mmol) and EDC (248.3 mg, 1.30 mmol). Diisopropylethylamine (0.20 mL, 1.15 mmol) was added, followed by a solution of 1,2,3,4-tetrahydro-9H-pyrido[3,4b]indole (187.6 mg, 1.09 mrol) in DMF. The reaction was stirred at RT for 24 h, then was concentrated under vacuum. Chromatography (silica gel, step gradient, 2% MeOH/CHCl$_3$, 3% MeOH/CHCl$_3$) gave the title compound as a clear, colorless oil (484.7 mg): $^1$H NMR (250 MHz, CDCl$_3$) δ 9.09 (br s, 1H), 7.47–7.04 (m, 7H), 6.49 (d, 1H), 5.37 (d, 1H), 5.05 (dd, 1H), 4.77 (s, 2H), 3.69 (s, 3H), 2.99 (s, 3H); MS (ES) m/e 447.2 (M+H)$^+$.

b) (±)-7-[2-(1,2,3,4-tetrahydro-9H-pyrido[3,4-b]indolyl)carbonyl]4-methyl-3-oxo-2,3,4,5-tetrahydro-1H-1,4-benzodiazepine-2-acetic acid Methyl (±)-7-[2-(1,2,3,4-tetrahydro-9H-pyrido[3,4-b]indolyl)carbonyl]-4-methyl-3-oxo-2,3,4,5-tetrahydro-1H-1,4-benzodiazepine-2-acetate (484.7 mg, 1.09 mmol) was dissolved in MeOH, and 1.0 N NaOH (2.0 mL, 2.0 mmol) was added. The reaction was stirred at RT for 24 h, then was heated in an oil bath set at 75° C. After 4 h, the reaction was neutralized with 1.0 N HCl and concentrated under vacuum. The resultant precipitate was collected and reprecipitated from methanol/water to afford the title compound (380 mg., 80%) as a colorless powder: MS (ES) m/e 433.2 (M+H)$^+$. Anal. Calcd for C$_{24}$H$_{24}$N$_4$O$_4$.1.5 H$_2$O: C, 62.73; H, 5.92; N, 12.19. Found: C, 62.56; H, 5.55; N, 11.91.

Example 40

Preparation of (S)-7-[[[2-(5.6-methylendioxybenzimidazolyl)methyl]methylamino]carbonyl]-4-methyl-3-oxo-2,3,4,5-tetrahydro-1H-1,4-benzodiazepine-2-acetic acid a) 2-[[N-(Benzyloxycarbonyl)-N-methyl]aminomethyl]-5,6-methylenedioxybenzimidazole Cbz-sarcosine (310.0 mg, 1.39 mmol) was dissolved in dry THF (10 mL) in a 250 mL roundbottom flask under argon. Isobutylchloroformate (0.2 mL, 1.54 mmol) was added, followed by Et$_3$N (0.25 mL, 1.80 mmol). The reaction was stirred at RT under argon for 30 min, then was cooled to −10° C. to −20° C. A solution of 1,2-diamino-4,5-methylenedioxybenzene (0.2 g, 1.314 mmol) in dry THF was added, and the reaction was allowed to warm to RT. After 18 h, the reaction was concentrated under vacuum. The white solid residue was dissolved in EtOAc, and the solution was washed with 1.0 N NaHCO$_3$. The organic layer was dried (MgSO$_4$), filtered, and concentrated under vacuum. The residue was dissolved in glacial AcOH and heated an oil bath set at 70° C. After 24 h, the reaction was concentrated under vacuum. The residue was reconcentrated from toluene, then was chromatographed on silica gel (1:1 CH$_2$Cl$_2$/Et$_2$O). The material obtained in this way (two components co-eluted) was redissolved in glacial AcOH and heated to 100° C. TLC of the reaction after 24 h still showed two products. Concentration and chromatography (silica gel, 1:1 CHCl$_3$/Et$_2$O) gave the title compound (145.0 mg, 32.7%): MS (ES) m/e 340.0 (M+H)$^+$; $^1$H NMR (250 MHz, CDCl$_3$) δ 7.32 (s, 5H), 7.27 (s, 1H), 7.11 (s, 1H), 5.94 (s, 2H), 5.13 (s, 2H), 4.58 (s, 2H), 3.03 (s, 3H).

b) 2-(Methylamino)methyl-5,6-methylenedioxybenzimidazole

2-[[N-(Benzyloxycarbonyl)-N-methyl]aminomethyl]-5,6-methylenedioxybenzimidazole (145.0 mg, 0.43 mmol) was dissolved in MeOH, and 10% Pd/C was added. The mixture was stirred briskly at RT under H$_2$ (balloon). After 4 h, the reaction was filtered through Celite®, and the filtrate was concentrated under vacuum to afford the title compound (70.8 mg, 80.2%).

c) Methyl (S)-7-[[[2-(5,6-methylendioxybenzimidazolyl)methyl]methylamino]carbonyl]-4-methyl-3-oxo-2,3,4,5-tetrahydro-1H-1,4-benzodiazepine-2-acetate EDC (76.2 mg, 0.40 mmoi) was added to a solution of methyl (2S)-7-carboxy4-methyl-3-oxo-2,3,4,5-tetrahydro-1H-1,4-benzodiazepine-2-acetate (0.35 mmol) and HOBt.H$_2$O (57.9 mg, 0.43 mmol) in dry DMF, and the reaction was stirred at RT. Diisopropylethylamine (0.150 mL, 0.86 mmol) was added, followed by a solution of 2-(methylamino)methyl-5,6-methylenedioxybenzimidazole (70.8 mg, 0.35 mmol) in dry DMF. The reaction was stirred at RT for 24 h, then was concentrated under vacuum. Chromatography (silica gel, step gradient, CHCl$_3$, 1:1 MeOH/CHCl$_3$) and rechromatography (2% MeOH/CHCl$_3$, 10% MeOH/CHCl$_3$) gave the title compound (102.5 mg, 61.1%): $^1$H NMR (250 MHz, CDCl$_3$) δ 7.18–7.13 (m, 3H), 6.82 (s, 1H), 6.49 (s, 1H), 5.97 (s, 2H), 5.40 (d, 1H), 5.05 (dd, 1H), 4.7–4.56 (m, 2H), 3.73 (s, 3H), 3.13 (s, 3H), 3.01 (s, 3H).

d) (S)-7-[[[2-(5,6-Methylendioxybenzimidazolyl)methyl]methylamino]carbonyl]-4-methyl-3-oxo-2,3,4,5-tetrahydro-1H-1,4-benzodiazepine-2-acetic acid Methyl (S)-7-[[[2-(5,6-methylendioxybenzimidazolyl)methyl]methylamino]carbonyl]-4-methyl-3-oxo-2,3,4,5-tetrahydro-1H-1,4-benzodiazepine-2-acetate (102.5 mg, 0.21 mmol) was dissolved in MeOH, and 1.0 N NaOH (0.5 mL, 0.5 mmol) was added. The reaction was stirred at RT for 48 h, then was neutralized with 1.0 N HCl. Concentration under vacuum left a residue which was diluted with water and allowed to stand at RT overnight. The resultant precipitate was collected by filtration and dried under high vacuum to yield the title compound (29.0 mg, 30%): HPLC $t_R$=11.67; (PRP-1®, gradient elution over 20 min, 5–50% CH$_3$CN/H$_2$O-0.1% TFA) MS (ES) m/e 466.2 (M+H)$^+$.

Example 41

Preparation of (S)-7-[[[2-(4,6-diazabenzimidazolyl) methyl]methylamino]carbonyl]-4-methyl-3-oxo-2,3, 4,5-tetrahydro-1H-1,4-benzodiazepine-2-acetic acid a) 2-[[N-(tert-Butoxycarbonyl)-N-methyl]aminomethyl]-4, 6-diazabenzimidazole Boc-sarcosine (3.6 g, 19.1 mmol) was dissolved in dry THF in a flame-dried 250 mL roundbottom flask, and $Et_3N$ (6 mL, 43.14 mmol) was added. The solution was cooled to 0° C. to −5° C., and isobutylchloroformate (2.5 mL, 1.93 mmol) was added. The white mixture was stiffed at −5° C. for 15 midn, then was cooled to −20° C. to −30° C., and 4,5-diamiinopyrimidine (2.1 g, 19.15 mmol.) was added as a solid. The cooling bath was removed and the reaction was allowed to warm to RT. After 24 h, the reaction was concentrated under vacuum. The residue was dissolved in EtOAc and washed with 1.0 $NaHCO_3$. The organic layer was dried ($MgSO_4$), filtered, and concentrated under vacuum. The residue was redissolved in glacial AcOH and heated in an oil bath set at 70° C. After 24 h, the reaction was cooled to RT, concentrated under vacuum, and reconcentrated from toluene. Flash chromatography column (silica gel, step gradient, 5% $MeOH/CHCl_3$, 10% $MeOH/CHCl_3$) gave the title compound (1.66 g, 33%): $^1H$ NMR (250 MHz, $CDCl_3$) δ 9.11 (s, 1H), 9.09 (s, 1H), 3.92 (s, 2H), 2.90–2.95 (m, 3H), 1.40–1.45 (m, 9H); MS (ES) m/e 264 $(M+H)^+$.

b) 2-(Methylamino)methyl-4,6-diazabenzimidazole

2-[[N-(tert-Butoxycarbonyl)-N-methyl]aminomethyl]-4, 6-diazabenzimidazole (1.13 g, 4.29 mmol) was treated with 4 N HCl in dioxane. A suspension formed, and more 4 N HCl in dioxane was added. The heterogeneous mixture was stiffed at RT for 2 h, then was concentrated under vacuum. The residue was dissolved in MeOH and the product was precipitated with $Et_2O$. The precipitate was collected on a sintered glass funnel and dried in a vacuum desiccator to yield the title compound (328.5 mg, 46.9%) as a white powder. TLC $R_f$ 0.36 (3:1:1 n-BuOH/HOAc/$H_2O$); $^1H$ NMR (250 MHz, $CD_3OD$) 8 9.56 (s, 1H), 9.33 (s, 1H), 4.81 (s, 2H), 2.99 (s, 3H); MS (ES) m/e 164.0 $(M+H)^+$.

c) Methyl (S)-7-[[[2-(4,6-diazabenzimidazolyl)methyl] methylamino]carbonyl]-4-methyl-3-oxo-2,3,4,5-tetrahydro-1H-1,4-benzodiazepine-2-acetate Methyl (S)-7-carboxy-4-methyl-3-oxo-2,3,4,5-tetrahydro-1H-1,4-benzodiazepine-2-acetate (262.6 mg, 0.55 mmol) was suspended in $CH_3CN$ (10 mL), and $HOBt.H_2O$ (86.7 mg, 0.64 mmol) was added, followed by EDC (115.5 mg, 0.60mmol). Diisopropylethylamine (150 mL, 0.86 mmol) was added, affording a homogeneous solution. A solution of 2-(methylamino)methyl-4,6-diazabenzimidazole (99.0 mg, 0.61 mmol) and diisopropylethylamine (150 mL, 0.86 mmol) was added, and the reaction was stirred at RT. After 3 d, the solvents were evaporated under vacuum, and the residue was reconcentrated from toluene. Chromatography (silica gel, step gradient, 5% $MeOH/CHCl_3$, 10% $MeOH/CHCl_3$) yielded the title compound (190 mg, 79.%): MS (ES) m/e 438.2 $(M+H)^+$; $^1H$ NMR (250 MHz, $CDCl_3$) δ 9.06 (s, 1H), 9.03 (s, 1H), 7.90–7.15 (m, 3H), 6.45 (d, 1H), 5.40 (d, 1H), 4.93 (dd, 1H), 3.71 (s, 3H), 3.16 (s, 3H), 2.98 (s, 3H).

d) (S)-7-[[[2-(4,6-Diazabenzimidazolyl)methyl] methylamino]carbonyl]4-methyl-3-oxo-2,3,4,5-tetrahydro-1H-1,4-benzodiazepine-2-acetic acid 1.0 N NaOH (1.5 mL, 1.5 mmol) was added to a solution of methyl (S)-7-[[[2-(4,6-diazabenzimidazolyl)methyl] methylamino]carbonyl]-4-methyl-3-oxo-2,3,4,5-tetrahydro-1H-1,4-benzodiazepine-2-acetate (190.3 mg, 0.44 mmol) in MeOH (5 mL) and $H_2O$ (5 mL). The reaction was stirred at RT for 24 h, then was neutralized with 1.0 N HCl (1.5 mL). The reaction was concentrated to dryness under vacuum, and the residue was purified by chromatography (ODS, step gradient, 5% $CH_3CN/H_2O$-0.1% TFA, 10% $CH_3CN/H_2O$-0.1% TFA, 20% $CH_3CN/H_2O$-0.1% TFA). One fraction was collected and concentrated under vacuum. The residue was reconcentrated from toluene and dried under vacuum, then was dissolved in MeOH and precipitated with $Et_3N$. The white precipitate was collected on a sintered glass funnel and dried in a vacuum desiccator to afford the title compound as a white powder (126.5 mg, 67.9%): HPLC $t_R$ 0.41; (ODS, gradient elution over 20 min, 5–50% $CH_3CN/H_2O$-0.1% TFA); MS (ES) m/e 424.2 $(M+H)^+$. Anal. Calcd for $C_{20}H_{21}N_7O_4$.0.5 $CF_3CO_2H$: C, 52.50; H, 4.51; N, 20.41. Found: C, 52.62; H. 4.88; N, 20.01.

Example 42

Preparation of (S)-7-[[[2-(4-azabenzimidazolyl) methyl]methylamino]carbonyl]-4-methyl-3-oxo-2,3, 4,5-tetrahydro-1H-1,4-benzodiazepine-2-acetic acid a) 2-[[N-(Benzyloxycarbonyl)-N-methyl]aminomethyl]4-azabenzimidazole A solution of Cbz-sarcosine (5 g, 22.4 mmol) and $Et_3N$ (4 mL, 28.76 mmol) in dry THF was cooled to 0° C. in an ice bath, and isobutylchloroformate (3.0 mL, 23.13 mmol) was added. The reaction was stirred at RT for 15 min, then was added to a solution of 2,3-diaminopyridine (2.5 g, 22.7 mmol) in dry THF at −25° C. The reaction was stirred at −20° C. for 30 min, then was allowed to warm to RT. After 24 h, the reaction was concentrated under vacuum. The residue was taken up in EtOAc and washed with 1.0 N $NaHCO_3$. The organic layer was dried ($MgSO_4$), filtered and concentrated under vacuum. The residue was dissolved in glacial AcOH (200 mL) and heated in an oil bath set at 109° C. After 20 h, the reaction was concentrated under vacuum, and the residue was reconcentrated from toluene. Chromatography (Silica gel, step gradient, $CHCl_3$, 3% MeOH/ $CHCl_3$, 5% $MeOH/CHCl_3$) gave the title compound (2.2 g, 33%), which was recrystallized from $Et_2O$: MS (ES) m/e 296.2 $(M+H)^+$.

b) 2-(Methylamino)methyl-4-azabenzimidazole

2-[[N-(Benzyloxycarbonyl)-N-methyl]aminomethyl]-4-azabenzimidazole (551.3 mg, 1.86 mmol) was dissolved in MeOH, and 10% Pd/C was added. The mixture was stirred briskly at RT under $H_2$ (balloon). After 4 h, the reaction was filtered through Celite®, and the filtrate was concentrated under vacuum to afford the title compound (420.1 mg, quantitative): $^1H$ NMR (250 MHz, $CDCl_3$) δ 8.34–8.32 (m, 1H), 7.98–7.14 (m, 4H), 5.18–5.12 (m, 1H), 4.87 (s, 2H), 3.32 (s, 3H), c) Methyl (S)-7-[[[2-(4-azabenzimidazolyl)methyl] methylamino]carbonyl]4-methyl-3-oxo-2,3,4,5-tetrahydro-1H-1,4-benzodiazepine-2-acetate EDC (309.1 mg, 1.61 mmol) was added to a solution of methyl (S)-7-carboxy-4-methyl-3-oxo-2,3,4,5-tetrahydro-1H-1,4-benzodiazepine-2-acetate (504.6 mg, 1.54 mmol), diisopropylethylamine (0.30 mL, 1.78 mmol), and $HOBt.H_2O$ (228.2 mg, 1.69 mmol) in dry DMF at RT. After 10 minutes, 2-(methylamino)methyl-4-azabenzimidazole (3.08 mmol) neutralized with diisopropylethylamine (0.600 mL) was added, and the reaction was stirred at RT. After 20 h, the solvents were evaporated under vacuum, and the residue was reconcentrated from toluene. Chromatography (silica gel, step gradient, $CHCl_3$, 5% $MeOH/CHCl_3$, 10% $MeOH/CHCl_3$) gave the title compound (326.8 mg, 48.6%): MS (ES) m/e 437.2 $(M+H)^+$; $^1H$ NMR (250 MHz, $CDCl_3$) δ 8.39 (d, 1H), 8.00–7.20 (m, 5H), 5.50 (d, 1H), 5.15–4.80 (m, 3H), 3.70 (s, 3H), 3.10 (s, 3H), 2.93 (s, 3H).

d) (S)-7-[[[2-(4-Azabenzimidazolyl)methyl]methylamino]carbonyl]4-methyl-3-oxo-2,3,4,5-tetrahydro-1H-1,4-benzodiazepine-2-acetate 1.0 N NaOH (2.0 mL, 2.0 mmol) was added to a solution of methyl (S)-7-[[[2-(4-azabenzimidazolyl)methyl]methylamino]carbonyl]-4-methyl-3-oxo-2,3,4,5-tetrahydro-1H-1,4-benzodiazepine-2-acetate (326.8 mg, 0.75 mmol) in MeOH (10 mL) and H$_2$O (10 mL) at RT. After 26 h, the reaction was neutralized with 1.0 N HCl (2.0 mL, 2.0 mmol) and concentrated under vacuum. The residue was taken up in H$_2$O and the resultant white precipitate was collected on a sintered glass funnel, washed with H$_2$O and dried under vacuum to afford the title compound (218.1 mg, 69%) as a white powder: MS (ES) m/e 423.4 (M+H)$^+$. Anal. Calcd for C$_{21}$H$_{22}$N$_6$O$_4$·2 H$_2$O: C, 55.02; H, 5.72; N, 18.33. Found: C, 55.07; H, 5.55; N, 17.81.

Example 43

Preparation of 7-[1-[2R-(2-benzimidazolyl)pyrrolidinyl]carbonyl]-4-methyl-3-oxo-2,3,4,5-tetrahydro-1H-1,4-benzodiazepine-2S-acetic acid a) 1-tert-Butoxycarbonyl-2R-(2-benzimidazolyl)pyrrolidine A solution of BOC-D-proline (3.0 g, 14 mmol.) and Et$_3$N (2.5 mL, 18 mmol) in dry THF was cooled to 0° C. in an ice bath, and isobutylchloroformate (2.0 mL, 15 mmol) was added. The reaction was stirred at 0° C. for 20 min, then was removed from the cooling bath and allowed to warm to RT for 10 minutes. The white slurry was added to a solution of o-phenylenediamine (1.55 g, 4.3 mmol) in THF at −20 to −30° C. After the addition was complete, the reaction was removed from the cooling bath and allowed to proceed at RT. After 20 h, the reaction was concentrated under vacuum. The residue was taken up in EtOAc and washed with 1.0 N NaHCO$_3$. The organic layer was dried (MgSO$_4$), filtered and concentrated under vacuum. The residue was dissolved in glacial AcOH and heated in an oil bath set at 70–75° C. After 24 h, the AcOH was evaporated under vacuum, and the residue was reconcentrated from toluene. Recrystallization from EtOAc gave the title compound (1.1 g). The mother liquors were concentrated and the residue taken into Et$_2$O to afford additional title compound (1.47 g).

b) 2R-(2-benzimidazolyl)pyrrolidine 1-tert-Butoxycarbonyl-2R-(2-benzimidazolyl)pyrrolidine (1.0702 g, 3.72 mmol) was treated with 4 N HCl/dioxane. After 2 h at RT, the reaction was concentrated under vacuum, and the residue was treated with Et$_2$O. The white precipitate was collected and dried under vacuum to afford the title compound (958.1 mg, 99.1%): $^1$H NMR (250 MHz, CDCl$_3$) δ 7.89–7.85 (m, 2H), 7.68–7.65 (m, 2H), 5.38–5.31 (m, 1H), 3.67–3.61 (m, 2H), 3.33–3.31 (m, 1H), 2.88–2.21 [α]$_D$-4.9-(c 1.0, H$_2$O).

c) Methyl 7-[1-[2R-(2-benzimidazolyl)pyrrolidinyl]carbonyl]-4-methyl-3-oxo-2,3,4,5-tetrahydro-1H-1,4-benzodiazepine-2S-acetate EDC (74.4 mg, 0.39 mmol) was added to a solution of methyl (S)-7-carboxy-4-methyl-3-oxo-2,3,4,5-tetrahydro-1H-1,4-benzodiazepine-2-acetate (104.2 mg, 0.32 mmol.), diisopropylethylamine (0.06 mL, 0.34 mmol), and HOBt.H$_2$O (56.6 mg, 0.42 mmol) in dry DMF at RT. The reaction was stirred at RT, and a solution of 2R-(2-benzimidazolyl)pyrrolidine (89.7 mg, 0.35 mmol) and diisopropylethylamine (0.120 mL, 0.69 mmol) in DMF was added. After 20 h, the reaction was concentrated under vacuum, and the residue was reconcentrated from toluene. Chromatography (silica gel, step gradient, CHCl$_3$, 3% MeOH/CHCl$_3$, 5% MeOH/CHCl$_3$) gave the title compound (136.9 mg, 92.5%): $^1$H NMR (250 MHz, CDCl$_3$) δ 7.77 (d, 1H), 7.63 (d, 1H), 7.34–7.22 (m, 4H), 7.06–7.05 (m, 1H), 6.37 d, 1H), 5.55–5.49 (m, 1H), 5.30 (d, 1H), 5.08–5.00 (m, 1H), 3.68 (s, 3H), 2.92 (s, 3H), 2.55–1.70 (m, 4H), 1.22 (t, 3H); MS (ES) m/e 462.2 (M+H)$^+$.

d) 7-[1-[2R-(2-Benzimidazolyl)pyrrolidinyl]carbonyl]-4-methyl-3-oxo-2,3,4,5-tetrahydro-1H-1,4-benzodiazepine-2S-acetic acid 1.0 N NaOH (0.75 mL, 0.75 mmol) was added to a solution of methyl 7-[1-[2R-(2-benzimidazolyl)pyrrolidinyl]carbonyl]-4-methyl-3-oxo-2,3,4,5-tetrahydro-1H-1,4-benzodiazepine-2S-acetate (136.9 mg, 0.30 mmol) in MeOH (5 mL) and H$_2$O (5 mL) at RT. After 24 h, 1.0 N HCl (0.75 mL, 0.75 mmol) was added and the reaction mixture was concentrated under vacuum. Chromatography (ODS, step gradient, 0.1% TFA/H$_2$O, 20% CH$_3$CN/H$_2$O-0–0.1% TFA), concentration, and reconcentration from toluene left a residue, which was redissolved in H$_2$O. Lyophilization gave the title compound (92 mg): HPLC t$_R$=10.68 (ODS, gradient elution over 20 min, 5–50% CH$_3$CN/H$_2$O-0.1% TFA); MS (ES) m/e 448.2 (M+H)$^+$.

Example 44

Preparation of 7-[1-[2S-(2-benzimidazolyl)pyrrolidinyl]carbonyl]-4-methyl-3-oxo-2,3,4,5-tetrahydro-1H-1,4-benzodiazepine-2S-acetic acid a) 1-tert-Butoxycarbonyl-2S-(2-benzimidazolyl)pyrrolidine Following the procedure of Example 43(a), except substituting BOC-L-proline for the BOC-D-proline, the title compound (3.2 g, 74%) was prepared. $^1$H NMR (250 MHz, CDCl$_3$) δ 7.53 (br s, 1H), 7.19–7.16 (m, 4H), 5.14 (d, 1H), 3.50 (s, 2H), 2.87 (br s, 1H), 2.19–1.97 (m, 3H), 1.49 (s, 9H), 1.25 (br s, 2H); MS (ES) m/e 288.2 (M+H)$^+$.

b) 2S-(2-benzimidazolyl)pyrrolidine

Following the procedure of Example 43(b), except substituting 1-tert-butoxycarbonyl-2S-(2-benzimidazolyl)pyrrolidine for the 1-tert-butoxycarbonyl-2R-(2-benzimidazolyl)pyrrolidine, the title compound was prepared(1.7988 g, 98.4%): $^1$H NMR (250 MHz, CDCl$_3$) δ 7.89–7.86 (m, 2H), 7.69–7.65 (m, 2H), 5.30–5.40 (m, 1H), 3.68–3.63 (m, 2H), 3.33–3.32 (m, 1H), 2.20–2.89 (m, 4H), [α]$_D$+3.9-(c 1.0, H$_2$O).

c) Methyl 7-[1-[2S-(2-benzimidazolyl)pyrrolidinyl]carbonyl]-4-methyl-3-oxo-2,3,4,5-tetrahydro-1H-1,4-benzodiazepine-2S-acetate Following the procedure of Example 43(c), except substituting 2S-(2-benzimidazolyl)pyrrolidine for the 2R-(2-benzimidazolyl)pyrrolidine, the title compound (90.4 mg, 61%) was prepared: MS (ES) m/e 462.4 (M+H)$^+$.

d) 7-[1-[2S-(2-Benzimidazolyl)pyrrolidinyl]carbonyl]4-methyl-3-oxo-2,3,4,5-tetrahydro-1H-1,4-benzodiazepine-2S-acetic acid Following the procedure of Example 43(d), except substituting methyl 7-[1-[2S-(2-benzimidazolyl)pyrrolidinyl]carbonyl]4-methyl-3-oxo-2,3,4,5-tetrahydro-1H-1,4-benzodiazepine-2S-acetate for the methyl 7-[1-[2R-(2-benzimidazolyl)pyrrolidinyl]carbonyl]-4-methyl-3-oxo-2,3,4,5-tetrahydro-1H-1,4-benzodiazepine-2S-acetate, the title compound (65.8 mg, 75%) was prepared: HPLC t$_R$=10.63 (ODS, gradient elution over 20 min, 5–50% CH$_3$CN/H$_2$O-0.1% TFA); MS (ES) m/e 448.2 (M+H)$^+$.

Example 45

Preparation of (±)-7-[[[2-(4-azabenzimidazolyl)methyl]methylamino]carbonyl]-4-isopropyl-3-oxo-2,3,4,5-tetrahydro-1H-1,4-benzodiazepine-2-acetic acid a) Methyl (±)-7-[[[2-(4-azabenzimidazolyl)methyl]methylamino]carbonyl]-4-isopropyl-3-oxo-2,3,4,5-tetrahydro-1H-1,4-benzodiazepine-2-acetate Following the procedure of Example 42(c), except substituting methyl (±)-7-carboxy-4-isopropyl-3-oxo-2,3,4,5-tetrahydro-1H-1,4-benzodiazepine-2-acetate for the methyl (S)-7-carboxy-4-methyl-3-oxo-2,3,4,5-tetrahydro-1H-1,4-benzodiazepine-2-acetate, the title compound (226 mg, 96%) was prepared: TLC $R_f$ (5% MeOH/CHCl$_3$) 0.28; $^1$H NMR (250 MHz, CDCl$_3$) δ 8.45 (d, 1H), 7.96–7.10 (m, 5H), 6.40 (br s, 1H), 5.09–4.77 (m, 5H), 3.70 (s, 3H), 3.47 (s, 3H), 3.09 (s, 3H), 1.23 (t, 1H), 1.09 (d, 1H), 0.86 (br s, 1H).

b) (±)-7-[[[2-(4-Azabenzimidazolyl)methyl]methylamino]carbonyl]-4-isopropyl-3-oxo-2,3,4,5-tetrahydro-1H-1,4-benzodiazepine-2-acetic acid 1.0 N NaOH (1.5 mL, 1.5 mmol) was added to a solution of methyl (±)-7-[[[2-(4-azabenzimidazolyl)methyl]methylamino]carbonyl]-4-isopropyl-3-oxo-2,3,4,5-tetrahydro-1H-1,4-benzodiazepine-2-acetate (226.2 mg, 0.49 mmol) in MeOH (5 mL) and H$_2$O (5 mL) at RT. After 24 h, the reaction was neutralized with 1.0 N HCl and the solvents were evaporated under vacuum. ODS chomatograpby (0.1% TFA/H$_2$O, followed by 20% CH$_3$CN/H$_2$O-0.1% TFA), concentration, and reconcentration from toluene left a residue, which was redissolved in H$_2$O. Lyophilization gave impure title compound (181.9 mg) as a white powder, which was repurified by ODS chromatography (10% CH$_3$CN/H$_2$O-0.1% TFA, followed by 20% CH$_3$CN/H$_2$O-0.1% TFA). Concentration and reconcentration from toluene left a residue, which was dissolved in MeOH and precipitated with Et$_2$O. The precipitate was collected on a sintered glass funnel and dried in a vacuum desiccator to afford the title compound (65.5 mg): HPLC (ODS, gradient elution over 20 min, 5–50% CH$_3$CN/H$_2$O-0.1% TFA) $t_R$=12.32; MS (ES) m/e 451.2 (M+H)$^+$. Anal. Calcd for C$_{23}$H$_{26}$N$_6$O$_4$·0.5 CF$_3$CO$_2$H·0.75 H$_2$O: C, 55.33; H, 5.42; N, 16.13. Found: C, 55.43; H, 5.60; N, 16.01.

Example 46

Preparation of (S)-7-[[[2-(4-aza-5-methylbenzimidazolyl)methyl]methylamino]carbonyl]-4-methyl-3-oxo-2,3,4,5-tetrahydro-1H-1,4-benzodiazepine-2-acetic acid a) 2-Amino-6-methyl-3-nitropyridine 2-Amino-6-picoline (5.1 g, 47.1 mmol) was weighed into a 500 mL round bottom flask, and the flask was cooled to −30° C. Concentrated H$_2$SO$_4$ (20 mL) was added, which caused some fuiming to occur. Concentrated HNO$_3$ (10 mL, 160 mmol) was then added dropwise slowly. The reaction was allowed to warm to RT over 30 min, then was heated in an oil bath set at 80° C. After 90 min, the reaction was removed from the heating bath, and ice was added. 6.25 N NaOH (150 mL, 937.5 mmol) was added slowly, and the resulting yellow precipitate was collected on a sintered glass funnel. Drying in a vacuum desiccator gave the title compound (1.7 g, 24%): TLC $R_f$ (5% MeOH/CHCl$_3$) 0.77; $^1$H NMR (250 MHz, CDCl$_3$) δ 8.31 (d, 1H), 6.32 (d, 1H), 2.46 (s, 3H); MS (ES) m/e 154.0 (M+H)$^+$.

b) 2,3-Diamino-6-methylpyridine

2-Amino-6-methyl-3-nitropyridine (754 mg, 4.92 mmol) was suspended in MeOH, and 10% Pd/C was added. The mixture was stirred briskly at RT under H$_2$ (balloon). After 4 h, the reaction was filtered through Celite®, and the filtrate was concentrated under vacuum to afford the title compound (677 mg, quantitative): $^1$H NMR (250 MHz, CD$_3$OD) δ 6.82 (d, 1H), 6.36 (d, 1H), 2.25 (s, 3H).

c) 2-[[N-(Benzyloxycarbonyl)-N-methyl]aminomethyl]-5-methyl-4-azabenzimidazole

A solution of Cbz-sarcosine (1.8 g, 7.85 mmol) in dry THF at RT was treated with isobutylchloroformate (1.25 mL, 9.64 mmol), followed by Et$_3$N (3.0 mL, 21.57 mmol). After 30 min, a solution of 2,3-diamino-6-methylpyridine (882 mg, 7.16 mmol) in dry THF was added, and the reaction was stirred at RT. After 3 d, the reaction was concentrated under vacuum. The residue was taken up in EtOAc and washed with 1.0 N NaHCO$_3$. The organic layer was dried (MgSO$_4$), filtered, concentrated under vacuum, and reconcentrated from toluene. The residue was dissolved in glacial AcOH (100 mL) and heated in an oil bath set at 110° C. After 24 h, the reaction was concentrated under vacuum, and the residue was reconcentrated from toluene. Chromatography (silica gel, step gradient, CHCl$_3$, 2% MeOH/CHCl$_3$, 3% MeOH/CHCl$_3$) gave the title compound (1.0 g, 46.6%): $^1$H NMR (250 MHz, CDCl$_3$) δ 7.29 (s, 5H), 7.17 (s, 1H), 7.03 (d, 1H), 5.09 (s, 2H), 4.74 (s, 2H), 3.05 (s, 3H), 2.61 (s, 3H); MS (ES) m/e 311.0 (M+H)$^+$.

d) 2-(Methylamino)methyl-5-methyl-4-azabenzimidazole

2-[[N-(Benzyloxycarbonyl)-N-methyl]aminomethyl]-5-methyl-4-azabenzimidazole (1.0347 g, 0.33 mmol) was dissolved in MeOH, and 10% Pd/C was added. The mixture was stirred briskly at RT under H$_2$ (balloon). After 20 h, the reaction was filtered through Celite®, and the light yellow filtrate was concentrated under vacuum to afford the title compound (678.9 mg, quantitative) as a reddish colored material.

e) Methyl (S)-7-[[[2-(4-aza-5-methylbenzimidazolyl)methyl]methylamino]carbonyl]-4-methyl-3-oxo-2,3,4,5-tetrahydro-1H-1,4-benzodiazepine-2-acetate EDC (212.7 mg, 1.11 mmol) was added to a solution of methyl (S)-7-carboxy4-methyl-3-oxo-2,3,4,5-tetrahydro-1H-1,4-benzodiazepine-2-acetate (293.5 mg, 0.93 mmol), diisopropylethylamine (0.30 mL, 1.72 mmol), and HOBt.H$_2$O (143.5 mg, 1.06 mmol) in dry DMF at RT. After 30 minutes, a solution of 2-(methylamino)methyl-5-methyl4-azabenzimidazole (190.7 mg, 1.08 mmol) in dry DMF was added. The reaction was stirred at RT for 24 h, then was concentrated under vacuum, and the residue was reconcentrated from toluene. Chromatography (silica gel, step gradient, CHCl$_3$, 3% MeOH/CHCl$_3$, 5% MeOH/CHCl$_3$) gave the title compound (265 mg, 63%): $^1$H NMR (250 MHz, CDCl$_3$) δ 8.51 (br s, 1H), 7.86–7.05 (m, 5H), 5.34 (d, 1H), 5.06 (t, 1H), 3.69 (s, 3H), 3.08 (s, 3H), 2.62 (s, 3H); MS (ES) m/e 451.2 (M+H)$^+$.

f) (S)-7-[[[2-(4-Aza-5-methylbenzimidazolyl)methyl]methylamino]carbonyl]-4-methyl-3-oxo-2,3,4,5-tetrahydro-1H-1,4-benzodiazepine-2-acetic acid 1.0 N NaOH (2.0 mL, 2.0 mmol) was added to a solution of methyl (S)-7-[[[2-(4-aza-5-methylbenzimidazolyl)methyl]methylamino]carbonyl]-4-methyl-3-oxo-2,3,4,5-tetrahydro-1H-1,4-benzodiazepine-2-acetate (264.7 mg, 0.59 mmol) in MeOH (10 mL) and H$_2$O (10 mL) at RT. After 20 h, the reaction was neutralized with 1.0 N HCl (2.0 mL) and the solvents were evaporated under vacuum. The crude material was precipitated from water to give the title compound (49.8 mg): TLC R$_f$0.51 (3:1:1 n-BuOH/HOAc/H$_2$O); HPLC $t_R$=8.35 min (PRP-1®, gradient elution over 20 min, 5–50% CH$_3$CN/H$_2$O-0.1% TFA); MS (ES) m/e 437.2 (M+H)$^+$. Anal. Calcd for C$_{22}$H$_{24}$N$_6$O$_4$·0.75 H$_2$O·1.2 HCl: C, 42.56; H, 3.53; N, 11.03. Found: C, 42.20; H, 3.02; N, 11.36.

Example 47

Preparation of (S)-7-[[[2-(5,6-dimethoxybenzimidazolyl)methyl]methylamino]carbonyl]-4-methyl-3-oxo-2,3,4,5-tetrahydro-1H-1,4-benzodiazepine-2-acetic acid a) 2-[[N-(Benzyloxycarbonyl)-N-methyl]aminomethyl]-5,6-dimethoxybenzimidazole Cbz-sarcosine (1.4 g, 6.1 mmol) was dissolved in dry THF in a 100 mL roundbottom flask, and Et$_3$N (1.5 mL, 10.8 mmol) was added, followed by isobutylchloroformate (0.80 mL, 6.17 mmol). The reaction was stirred at RT, then was added to a solution of 4,5-dimethoxyphenylenediamine (6.06 mmol) in dry THF at −25° C. The Cbz-sarcosine, mixed-anhydride solution was added to the cooled phenylenediamine solution. The reaction was stirred at −25° C. for 10 min, then was allowed to warm to RT. After 20 h, the reaction was concentrated under vacuum. The residue was taken up in EtOAc and washed with 1.0 N NaHCO$_3$. The organic layer was dried (MgSO$_4$), filtered, concentrated under vacuum, and reconcentrated from toluene. The residue was dissolved in glacial AcOH (100 mL) and heated in an oil bath heated set at 110° C. After 24 h, the reaction was concentrated under vacuum. Flash chromatography (silica gel, step gradient, 2% MeOH/CHCl$_3$, 5% MeOH/CHCl$_3$) gave the title compound (1.7 g, 81%): $^1$H NMR (250 MHz, CDCl$_3$) δ 7.33 (s, 5H), 7.05 (s, 2H), 5.15 (s, 2H), 4.64 (s, 2H), 3.88 (s, 6H), 3.04 (s, 3H); MS (ES) m/e 356.2 (M+H)$^+$.

b) 2-(Methylamino)methyl-5,6-dimethoxybenzimidazole

2-[[N-(Benzyloxycarbonyl)-N-methyl]aminomethyl]-5,6-dimethoxybenzimidazole (1.7454 g, 4.91 mmol) was dissolved in MeOH, and 10% Pd/C was added. The mixture was stirred briskly at RT under H$_2$ (balloon). After 4 h, the reaction was filtered through Celite®, and the filtrate was concentrated under vacuum to afford the title compound.

c) Methyl (S)-7-[[[2-(5,6-dimethoxybenzimidazolyl)methyl]methylamino]carbonyl]4-methyl-3-oxo-2,3,4,5-tetrahydro-1H-1,4-benzodiazepine-2-acetate EDC (139.9 mg, 0.73 mmol) was added to a suspension of methyl (S)-7-carboxy4-methyl-3-oxo-2,3,4,5-tetrahydro-1H-1,4-benzodiazepine-2-acetate (198.5 mg, 0.68 mmol), and HOBt.H$_2$O (98.8 mg, 0.73 mmol) in CH$_3$CN at RT. After 15 minutes, diisopropylethylamine (0.200 mL, 1.15 mmol) was added, followed by a solution of 2-(methylamino)methyl-5,6-dimethoxybenzimidazole (147.3 mg, 0.67 mmol) in CH$_3$CN. The reaction was stirred at RT for 24 h, then the solvents were evaporated under vacuum. The residue was reconcentrated from toluene, then was chromatographed (silica gel, step gradient, CHCl$_3$, 3% MeOH/CHCl$_3$, 5% MeOH/CHCl$_3$) to afford the title compound (227 mg, 68%): $^1$H NMR (250 MHz, CDCl$_3$) δ 7.29–7.16 (m, 5H), 5.37 (d, 1H), 5.09 −5.03 (m, 1H), 4.864.72 (m, 3H), 3.90 (s, 6H), 3.71 (s, 3H), 3.12 (s, 3H); MS (ES) m/e 496 (M+H)$^+$.

d) (S)-7-[[[2-(5,6-dimethoxybenzimidazolyl)methyl]methylamino]carbonyl]-4-methyl-3-oxo-2,3,4,5-tetrahydro-1H-1,4-benzodiazepine-2-acetic acid 1.0 N NaOH (1.5 mL, 1.5 mmol) was added to a solution of methyl (S)-7-[[[2-(5,6-dimethoxybenzimidazolyl)methyl]methylamino]carbonyl]-4-methyl-3-oxo-2,3,4,5-tetrahydro-1H-1,4-benzodiazepine-2-acetate (227.1 mg, 0.46 mmol) in MeOH (10 mL) and H$_2$O (10 mL) at RT. After 24 h, the reaction was neutralized with 1.0 N HCl (1.5 mL, 1.5 mmol). After 30 min, a white precipitate had formed, which was collected on a sintered glass funnel and washed with water. The material was dried in a vacuum desiccator to afford the title compound (144.3 mg, 65%): MS (ES) m/e 482.2 (M+H)$^+$. Anal. Calcd for C$_{24}$H$_{27}$N$_5$O$_6$.1.75 H$_2$O.0.4 HCl: C, 54.64; H, 5.90; N, 13.27. Found: C, 54.69; H, 5.92; N, 12.67.

Example 48

Preparation of (±)8-[[2-(2-benzimidazolyl)acetyl]amino]-2-methyl-3-oxo-2,3,4,5-tetrahydro-1H-2-benzazepine-4-acetic acid a) Methyl (±)-8-[[2-(2-benzimidazolyl)acetyl]amino]-2-methyl-3-oxo-2,3,4,5-tetrahydro-1H-2-benzazepine-4-acetate Methyl (±)-8-amino-2-methyl-3-oxo-2,3,4,5-tetrahydro-1H-2-benzazepine-4-acetate was coupled with 2-benzimidazloylacetic acid according to the procedure of example 11(a). Purification by chromatography (silica gel, 2%–5% CH$_3$OH/CH$_2$Cl$_2$) gave the title compound as a colorless foam (31%): $^1$H NMR (CDCl$_3$) 7.55 (m, 1H), 7.44 (d, J=2 Hz, 1H), 7.38 (dd, J=8.3 Hz, J=2 Hz, 1H), 7.30 (m, 2H), 5.18 (d, J=16.3 Hz, 1H), 4.24 (s, 2H), 3.71 (m, 1H), 3.68 (s, 3H), 3.65 (d, J=16.3 Hz, 1H), 3.03 (m, 1H), 2.95 (s, 3H), 2.85 (m, 1H), 2.40 (dd, J=16.9, 6.3 Hz, 1H).

b) (±)-8-[[2-(2-Benzimidazolyl)acetyl]amino]-2-methyl-3-oxo-2,3,4,5-tetrahydro-1H-2-benzazepine-4-acetic acid Methyl (±)-8-[[2-(2-benzimidazolyl)acetyl]amino]-2-methyl-3-oxo-2,3,4,5-tetrahydro-1H-2-benzazepine-4-acetate was saponified according to the procedure of Example 24(b) to give the title compound as a white solid (47%): $^1$H NMR (DMSO-d$_6$) δ 10.38 (s, 1H), 7.49 (m, 3H), 7.42 (d, J=8.4 Hz, 1H), 7.15 (m, 2H), 7.06 (d, J=8.4 Hz, 1H), 5.24 (d, J=16.5 Hz, 1H), 3.96 (s, 2H), 2.35 (m, 1H), MS (ES) m/e 407.2 (M+H)$^+$. Anal. Calcd for C$_{22}$H$_{22}$N$_4$O$_4$.1.75 H$_2$O: C, 60.33; H, 5.87; N, 12.79. Found: C, 60.57; H, 5.49; N, 12.41.

Example 49

Preparation of (±)-8-[[[(2-benzimidazolyl)methyl]methylamino]carbonyl]-4-methyl-3-oxo-2,3,4,5-tetrahydro-1H-2-benzazepine-4-acetic acid a) Methyl (±)-8-[[[(2-benzimidazolyl)methyl]methylamino]carbonyl]4-methyl-3-oxo-2,3,4,5-tetrahydro-1H-2-benzazepine4-acetate Methyl (±)-8-carboxy-3-oxo-2,3,4,5-tetrahydro-1H-2-benzazepine-4-acetate was coupled with 2-(methylamino)methylbenzimidazole according to the procedure of Example 2(a). Purification by chromatography (silica gel, 1%–6% CH$_3$OH/CH$_2$Cl$_2$) gave the title compound as a white foam (76%): $^1$H NMR (CDCl$_3$) δ 7.62 (m, 2H), 7.43 (m, 1H), 7.30 (m, 2H), 7.13 (m, 2H), 5.06 (d, J=14.6 Hz, 1H), 4.86 (d, J=14.6 Hz, 1H), 4.77 (dd, J=16.6 Hz, J=4 Hz), 3.91 (dd, J=16.6, 6 Hz, 1H), 3.72 (s, 3H), 3.08 (s, 3H), 3.05 (m, 2H), 2.52 (dd, J=16.9, 5.7 Hz, 1H).

b) (±)-8-[[[(2-Benzimidazolyl)methyl]methylamino]carbonyl]-4-methyl-3-oxo-2,3,4,5-tetrahydro-1H-2-benzazepine-4-acetic acid Methyl (±)-8-[[[(2-benzimidazolyl)methyl]methylamino]carbonyl]4-methyl-3-oxo-2,3,4,5-tetrahydro-1H-2-benzazepine-4-acetate was saponified according to the procedure of Example 11(b) to give the title compound as a white solid (90%): $^1$H NMR (DMSO-d$_6$) δ 7.88 (m, 1H), 7.54 (m, 2H), 7.34 (d, J=7.9 Hz, 1H), 7.30 (s, 1H), 7.16 (m, 2H), 6.98 (m, 1H), 4.87 (m, 1H), 4.67 (m, 2H), 4.00 (m, 1H), 3.87 (m, 1H), 3.10 (m, 1H), 3.02 (s, 3H), 2.76 (m, 1H), 2.43 (m, 1H), 1.97 (m, 1H); MS (ES) m/e 407 (M+H)$^+$. Anal. Calcd for C$_{22}$H$_{21}$N$_4$O$_4$Li.2.375 H$_2$O: C, 58.05; H, 5.70: N, 12.31. Found: C, 57.85; H, 5.41; N, 12.66.

Example 50

Preparation of (S)-7-[[[(2-benzimidazolyl)methyl]methylamino]carbonyl]-3-oxo-4-(2-phenylethyl)-2,3,4,5-tetrahydro-1H-1,4-benzodiazepine-2-acetic acid a) Methyl (S)-7-carboxy-3-oxo-4-(2-phenylethyl)-2,3,4,5-tetrahydro-1H-1,4-benzodiazepine-2-acetate To a solution stirred under argon at RT of methyl (±)-7-carboxy-3-oxo-4-(2-phenylethyl)-2,3,4,5-tetrahydro-1H-1,4-benzodiazepine-2-acetate (9.0 g, 23 mmol) in $CH_3CN$ (100 mL) was added diazabicycloundecene (4.6 g, 30 mmol), followed by benzyl bromide (20 g, 116 mmol). The resulting solution was stirred for 1 h, then was concentrated. The residue was partitioned between 1.0 N HCl and EtOAc, and the layers were separated. The organic layer was washed with brine, dried ($MgSO_4$), and concentrated. The residue was purified by chromatography (silica gel, $CH_2Cl_2$) to give a pale yellow oil (7 g). Preparative HPLC (Whelk O-1, 50:50:1 hexane:$CHCl_3$:$CH_3OH$) gave an oil which was 97% of the desired (S)-enantiomer. Removal of racemate by crystallization (EtOAc) gave a colorless oil (3.2 g, 98% ee). This material was placed in a 500 mL Parr hydrogenation vessel with $CH_3OH$ (30 mL) and 10% Pd/C (0.45 g), and the mixture was shaken under $H_2$ (50 psi) for 6 h. The reaction mixture was then filtered and the filtrate was concentrated to give the title compound as a colorless foam (2.1 g, 47%): $^1H$ NMR ($CDCl_3$) δ 7.78 (dd, J=8.5, 1.9 Hz, 1H), 7.55 (d, J=1.9 Hz, 1H), 7.30–7.10 (m, 5H), 6.51 (d, J=8.5 Hz, 1H), 5.30 (d, J=16.6 Hz, 1H), 5.10 (t, J=6.5 Hz, 1H), 3.77 (s, 3H), 3.74 (m, 3H), 3.67 (d, J=16.6 Hz, 1H), 3.02 (dd, J=16, 6.8 Hz, 1H), 2.83 (t, J=7.1 Hz, 2H) 2.69 (dd, J=16, 6.5 Hz, 1H).

b) Methyl (S)-7-[[[(2-benzimidazolyl)methyl]methylanmino]carbonyl]-3-oxo-4-(2-phenylethyl)-2,3,4,5-tetrahydro-1H-1,4-benzodiazepine-2-acetate Methyl (S)-7-carboxy-3-oxo4-(2-phenylethyl)-2,3,4,5-tetrahydro-1H-1,4-benzodiazepine-2-acetate was coupled with 2-(methylamino)methylbenzimidazole according to the procedure of Example 2(a). Purification by chromatography on silica gel (1%–5% $CH_3OH/CH_2Cl_2$) gave the title compound (2.85 g, 99%) as a colorless foam: $^1H$ NMR ($CDCl_3$) δ 7.63 (m, 2H), 7.33 (m, 2H), 7.25–7.10 (m, 7H), 6.59 (d, J=8.3 Hz, 1H), 5.24 (d, J=16.7 Hz, 1H), 5.03 (m, 1H), 4.94 (d, J=14.6 Hz, 1H), 4.85 (d, J=14.6 Hz, 1H), 4.50 (d, J=4.7 Hz, 1H), 3.77 (m, 1H), 3.76 (s, 3H), 3.59 (d, J=16.7 Hz, 1H), 3.57 (m, 1H), 3.19 S, 3H), 2.99 (dd, J=16, 6.5 Hz, 1H, 2.81 (m, 2H), 2.67 (dd, J=16, 6.4 Hz, 1H).

c) (S)-7-[[[(2-Benzimidazolyl)methyl]methylamino]carbonyl]-3-oxo-4-(2-phenylethyl)-2,3,4,5-tetrahydro-1H-1,4-benzodiazepine-2-acetic acid Methyl (S)-7-[[[(2-benzimidazolyl)methyl]methylamino]carbonyl]-3-oxo-4-(2-phenylethyl)-2,3,4,5-tetrahydro-1H-1,4-benzodiazepine-2-acetate was saponified according to the procedure of Example 11(b) to give the title compound (1.8 g, 66%) as a white solid: $^1H$ NMR (DMSO-$d_6$) δ 7.54 (m, 2H), 7.30–7.10 (m, 9H), 6.54 (d, J=8.3 Hz, 1H), 6.30 (br s, 1H), 5.37 (d, J=16.2 Hz, 1H), 5.05 (m, 1H), 4.77 (s, 2H), 3.97 (br s, 1H), 3.51 (m, 3H), 3.05 (s, 3H), 2.65 (m, 3H), 2.49 (m, 1H). Anal. Calcd for $C_{29}H_{29}N_5O_4 \cdot H_2O$: C, 65.77; H, 5.90; N, 13.22. Found: C, 65.51; H, 5.84; N, 13.19.

Example 51

Preparation of (±)-7-[[[2-(benzimidazoyl)methyl]amino]carbonyl-4-[2-(3,4-methylenedioxyphenyl)ethy]-3-oxo-2,3,4,5-tetrahydro-1H-1,4-benzodiazepine-2-acetic acid a) Methyl (±)-7-[[[2-(benzimidazolyl)methyl]amino]carbonyl-4-[2-(3,4-methylenedioxyphenyl)ethyl]-3-oxo-2,3,4,5-tetrahydro-1H-1,4-benzodiazepine-2-acetate Methyl (±)-7-carboxyl-4-[2-(3,4-methylenedioxyphenyl)ethyl]-3-oxo-2,3,4,5-tetrahydro-1H-1,4-benzodiazepine-2-acetate was coupled with 2-(aminomethyl)benzimidazole dihydrochloride hydrate according to the procedure of Example 2(a). Purification by chromatography (silica gel, 1%–5% $CH_3OH/CH_2Cl_2$) followed by recrystallization ($CH_3OH$/EtOAc) gave the title compound as a tan solid (59%): $^1H$ NMR (DMSO-$d_6$) δ 8.72 (t, J=5 Hz, 1H), 7.61 (s, 1H), 7.56 (m, 2H), 7.43 (m, 1H), 7.13 (m, 2H), 6.76 (m, 2H), 6.57 (m, 2H), 6.37 (d, J=3.6 Hz, 1H), 5.95 (s, 2H), 5.42 (d, J=16.5 Hz, 1H), 5.13 (m, 1H), 4.64 (m, 2H), 3.92 (d, J=16.5 Hz, 1H), 3.61 (s, 3H), 3.58 (m, 2H), 2.83 (dd, J=16.6, 7.6 Hz, 1H), 2.65 (m, 3H).

b) (±)-7-[[[2-(Benzimidazolyl)methyl]amino]carbonyl-4-[2-(3,4-methylenedioxyphenyl)ethyl]-3-oxo-2,3,4,5-tetrahydro-1H-1,4-benzodiazepine-2-acetic acid Methyl (±)-7-[[[2-(benzimidazolyl)methyl]amino]carbonyl-4-[2-(3,4-methylenedioxyphenyl)ethyl]-3-oxo-2,3,4,5-tetrahydro-1H-1,4-benzodiazepine-2-acetate was saponified according to the procedure of Example 11 (b) to give the title compound (84%) as a white solid: $^1H$ NMR (DMSO-$d_6$) 8 8.76 (t, J=5 Hz, 1H), 7.58 (m, 2H), 7.48 (m, 2H), 7.13 (m, 2H), 6.76 (m, 2H), 6.58 (m, 2H), 5.94 (s, 2H), 5.40 (d, J=16.5 Hz, 1H), 5.06 (m, 1H), 4.64 (m, 2H), 3.91 (d, J=16.5 Hz, 1H), (m, 2H), 2.72 (m, 1H), 2.60 (t, J=8 Hz, 2H), 2.50 (m, 1); MS (ES) m/e 542 (M+H)$^+$. Anal. Calcd for $C_{29}H_{27}N_5O_6 \cdot 1.5\ H_2O$: C, 61.26; H, 5.32; N, 12.32. Found: C, 61.42; H, 5.22; N, 12.25.

Example 52

Preparation of (±)-7-[[[(4(5)-imidazolyl)methyl]amino]carbonyl]-4-methyl-3-oxo-2,3,4,5-tetrahydro-1H-1,4-benzodiazepine-2-acetic acid a) Methyl (±)-7-[[[(4(5)-imidazolyl)methyl]amino]carbonyl]-4-methyl-3-oxo-2,3,4,5-tetrahydro-1H-1,4-benzodiazepine-2-acetate Following the procedure of Example 23(a), except substituting 4(5)-(aminomethyl)imidazole (prepared according to *J. Pharm. Sci.* 1973, 403) for the 2-(aminomethyl)imidazole, and heating the reaction at 90–100° C. for 24 h, the title compound (21%) was prepared: MS (ES) m/e 372 (M+H)$^+$.

b) (±)-7-[[[(4(5)-Imidazolyl)methyl]amino]carbonyl]-4-methyl-3-oxo-2,3,4,5-tetrahydro-1H-1,4-benzodiazepine-2-acetic acid Following the procedure of Example 23(b), methyl (±)-7-[[[(4(5)-imidazolyl)methyl]amino]carbonyl]-4-methyl-3-oxo-2,3,4,5-tetrahydro-1H-1,4-benzodiazepine-2-acetate was saponified to give the title compound: MS (ES) m/e 358 (M+H)$^+$. Anal. Calcd for $C_{17}H_{19}N_5O_4 \cdot 1.15\ CF_3CO_2H \cdot 0.05\ H_2O$: C, 47.37; H, 4.17; N, 14.31. Found: C, 47.70; H, 3.91; N, 13.92.

Example 53

Preparation of (±)-[[[4-(2-phenylimidazolyl)methyl]amino]carbonyl]-4-methyl-3-oxo-2,3,4,5-tetrahydro-1H-1,4-benzodiazepine-2-acetic acid a) 4-Aminomethyl-2-phenylimidazole dihydrochloride Hydroxylamine hydrochloride (229 mg, 3.3 mmol) was added to a suspension of 2-phenylimidazole-4-carboxaldehyde (516 mg, 3 mmol; prepared according to *J. Chem. Soc. Perkin Trans. I* 1974, 1527) and sodium acetate (541 mg, 6.6 mmol) in absolute EtOH (5 mL) and $H_2O$ (5 mL) at RT. A yellow, homogeneous solution was produced. After 15 min, the reaction was concentrated on the rotavap to remove the EtOH, and the oily, aqueous mixture was extracted with 20% $MeOH/CHCl_3$ (10 mL) then with $CHCl_3$ (10 mL). The combined organic layers were dried ($MgSO_4$) and concentrated to leave a yellow foam.

The yellow foam was dissolved in absolute EtOH (9 mL), and 1.0 N HCl (6 mL, 6 mmol) and 10% Pd/C (0.32 g, 0.3 mmol) were added. The mixture was shaken on a Parr apparatus at RT under $H_2$ (50 psi) for 4 h, then was filtered through Celite®. The filtrate was concentrated on the rotavap to leave a light yellow solid. Recrystallization from absolute $EtOH/H_2O$ gave the title compound as a light pink solid (465 mg, 63%): mp 273–275° C. (dec.); $^1H$ NMR (250 MHz, $CD_3OD$) δ 7.93–8.12 (m, 2H), 7.80 (s, 1H), 7.50–7.76 (m, 3H), 4.40 (s, 2H); MS (ES) m/e 347.2 $(2M+H)^+$, 174.0 $(M+H)^+$, 157.0 $(M+H-NH_3)^+$.

b) Methyl (±)-[[[4-(2-phenylimidazolyl)methyl]amino]carbonyl]-4-methyl-3-oxo-2,3,4,5-tetrahydro-1H-1,4-benzodiazepine-2-acetate EDC (138 mg, 0.72 mmol) was added to a solution of methyl (±)-7-carboxy-4-methyl-3-oxo-2,3,4,5-tetrahydro-1H-1,4-benzodiazepine-2-acetate (175.4 mg, 0.6 mmol), 4-aminomethyl-2-phenylimidazole dihydrochloride (177.2 mg, 0.72 mmol), $HOBT \cdot H_2O$ (97.3 mg, 0.72 mmol), and diisopropylethylamine (0.52 mL, 3.0 mmol) in anhydrous DMF (3 mL) at RT. After 22 h, the reaction was concentrated on the rotavap (high vacuum), and the residue was partitioned between $H_2O$ and EtOAc. The layers were separated, and the aqueous was extracted with $CHCl_3$. The organic layers were combined, which caused an oil to separate. This was dissolved by addition of MeOH. Drying ($MgSO_4$), concentration, and reconcentration from xylenes (to remove DMF) left a yellow semisolid residue. Chromatography (silica gel, 10% $MeOH/CHCl_3$) gave the title compound (230 mg, 86%) as an oily foam which solidified to an off-white solid on treatment with EtOAc: TLC $R_f$ 0.42 (10% $MeOH/CHCl_3$); $^1H$ NMR (400 MHz, 10% $CD_3OD/CDCl_3$) δ 7.82 (d, J=7.3 Hz, 2H), 7.28–7.57 (m, 5H), 7.03 (s, 1H), 6.54 (d, J=8.5 Hz, 1H), 5.48 (d, J=16.6 Hz, 1H), 5.12 (t, J=6.8 Hz, 1H), 4.52 (s, 2H), 3.79 (d, J=16.6 Hz, 1H), 3.73 (s, 3H), 3.06 (s, 3H), 2.98 (dd, J=16.2, 7.6 Hz, 1H), 2.66 (dd, J=16.2, 6.0 Hz, 1H); MS (ES) m/e 470.2 (M+Na)+, 448.2 $(M+H)^+$.

c) (±)-[[[4-(2-Phenylimidazolyl)methyl]amino]carbonyl]-4-methyl-3-oxo-2,3,4,5-tetrahydro-1H-1,4-benzodiazepine-2-acetic acid A suspension of methyl (±)-[[[4-(2-phenylimidazolyl)methyl]amino]carbonyl]-4-methyl-3-oxo-2,3,4,5-tetrahydro-1H-1,4-benzodiazepine-2-acetate (229.6 mg, 0.51 mmol), 1.0 N LiOH (0.61 mL, 0.61 mmol), THF (2.6 mL), and $H_2O$ (2 mL) was stirred at RT. A homogeneous solution had formed within 15 min. After 2.5 h, the reaction was concentrated to about 1 mL and filtered. An extra portion of $H_2O$ (2 mL) was used in the filtration. The filtrate was neutralized with 1.0 N HCl (0.61 mL), and the solid was collected and washed with $H_2O$. The resulting solid was triturated with hot 1:1 $CH_3CN/H_2O$, filtrered, and washed sequentially with $CH_3CN$ and $H_2O$. Drying in high vacuum gave the title compound (187.4 mg, 82%) as a colorless powder: HPLC k' 1.6 (PRP-1®, 20% $CH_3CN/H_2O$-0.1% TFA); $^1H$ NMR (400 MHz, DMSO-$d_6$) δ 8.32–8.47 (m, 1H), 7.90 (d, J=7.5 Hz, 2H), 7.51–7.61 (m, 2H), 7.38–7.48 (m, 2H), 7.26–7.36 (m, 1H), 7.01 (br s, 1H), 6.54 (d, J=8.3 Hz, 1H), 6.30 (s, 1H), 5.48 (d, J=16.5 Hz, 1H), 5.02–5.12 (m, 1H), 4.38 (br s, 2H), 3.81 (d, J=16.5 Hz, 1H), 2.91 (s, 3H), 2.76 (dd, J=16.7, 9.1 Hz, 1H), 2.54 (dd, J=16.7, 4.9 Hz, 1H, partially obscured by residual solvent signal); MS (ES) m/e 434.2 $(M+H)^+$. Anal. Calcd for $C_{23}H_{23}N_5O_4 \cdot 0.75\ H_2O$: C, 61.81; H, 5.52; N, 15.67. Found: C, 62.05; H, 5.44; N, 15.59.

Example 54

Preparation of (±)-7-[[[2-(3-indolyl)ethyl]amino]carbonyl]-4-methyl-3-oxo-2,3,4,5-tetrahydro-1H-1,4-benzodiazepine-2-acetic acid a) Methyl (±)-7-[[[2-(3-Indolyl)ethyl]amino]carbonyl]4-methyl-3-oxo-2,3,4,5-tetrahydro-1H-1,4-benzodiazepine-2-acetate Following the procedure of Example 26(d), except substituting 3-(2-aminoethyl)indole for the 1-methyl-2-(methylamino)methylindole, the title compound was prepared (50%): MS (ES) m/e 435.2 $(M+H)^+$.

b) (±)-7-[[[2-(3-Indolyl)ethyl]amino]carbonyl]4-methyl-3-oxo-2,3,4,5-tetrahydro-1H-1,4-benzodiazepine-2-acetic acid Following the procedure of Example 26(e), methyl (±)-7-[[[2-(3-Indolyl)ethyl]amino]carbonyl]-4-methyl-3-oxo-2,3,4,5-tetrahydro-1H-1,4-benzodiazepine-2-acetate was saponified to give the title compound as a colorless solid. MS (ES) m/e 421.0 $(M+H)^+$. Anal. Calcd for $C_{23}H_{24}N_4O_4 \cdot 1.3\ H_2O$: C, 62.24; H, 6.04; N, 12.24. Found: C, 62.31; H, 5.61; N, 12.04.

Example 55

Preparation of (S)-7-[[[2-(4-phenylimidazolyl)methyl]amino]carbonyl]4-methyl-3-oxo-2,3,4,5-tetrahydro-1H-1,4-benzodiazepine-2-acetic acid a) Methyl (S)-7-[[[2-(4-phenylimidazolyl)methyl]amino]carbonyl]-4-methyl-3-oxo-2,3,4,5-tetrahydro-1H-1,4-benzodiazepine-2-acetate Following the procedure of Example 23(a) except substituting 2-(aminomethyl)-4-phenyl imidazole (*Aust. J. Chem.*, 1971, 24, 2389) for 2-(aminomethyl)imidazole, the title compound was prepared: MS (ES) m/e 448 $(M+H)^+$.

b) (S)-7-[[[2-(4-Phenylimidazolyl)methyl]amino]carbonyl]-4-methyl-3-oxo-2,3,4,5-tetrahydro-1H-1,4-benzodiazepine-2-acetic acid Following the procedure of Example 23(b) methyl (S)-7-[[[2-(4-phenylimidazolyl)methyl]amino]carbonyl]-4-methyl-3-oxo-2,3,4,5-tetrahydro-1H-1,4-benzodiazepine-2-acetate was saponified to give the title compound: MS (ES) m/e 434 $(M+H)^+$. Anal. Calcd for $C_{23}H_{23}N_5O_4 \cdot 0.5\ CF_3CO_2H \cdot 0.5\ HCl \cdot 1.75\ H_2O$: C, 47.01; H, 4.80; N 11.42. Found: C, 47.14; H, 4.17; N, 11.51.

Examples 56–75

Following the general procedures of Examples 1–55, the following compounds were prepared:

56. (+/−)-2,3,4,5-Tetrahydro-7-[[[benzimidazol-2-yl)methyl]methylamino]carbonyl]-4-(3,3-dimethylbutyl)-3-oxo-1H-1,4-benzodiazepine-2-acetic acid;

57. (−)-7-[[[6-Trifluoromethylbenzimidazoyl-2-ylmethyl]aminomethyl]carbonyl]-2,3,4,5-tetrahydro-4-methyl-3-oxo-benzodiazepine-2-acetic acid;

58. (−)-7-[[[4,7-Dimethoxybenzimidazoyl-2-ylmethyl] aminomethyl]carbonyl]-2,3,4,5-tetrahydro-4-methyl-3-oxo-benzodiazepine-2-acetic acid;
59. (+/−)-2,3,4,5-Tetrahydro-7-[[[(benzimidazol-2-yl) methylanino]carbonyl]-4-(3,3-dimethylbutyl)-3-oxo-1H-1,4-benzodiazepine-2-acetic acid;
60. (−)-7-[[[7-Methylbenzimidazol-2-ylmethyl] methylamino]carbonyl]-2,3,4,5-tetrahydro-4-methyl-3-oxo-1,4-benzodiazepine-2-acetic acid;
61. (2S)-[[[N-aminobutyl-N-(benzimidazlo-2-yl)methyl] amino]carbonyl]-3-oxo-4-methyl-2,3,4,5-tetrahydro-1H-1,4-benzodiazepine-2-acetic acidbis(trifluoroacetate)salt;
62. (2S)-[[[N-cyanomethyl-N-(benzimidazlo-2-yl)methyl] amino]carbonyl]-3-oxo4-methyl-2,3,4,5-tetrahydro-1H-1,4-benzodiazepine-2-acetic acid dihydrochloride salt;
63. (S)-2,3,4,5-Tetrahydro-7-[[[(benzimidazol-2-yl)] methyl]amino]carbonyl]-4-(4-phthalimidobutyl)-3-oxo-1,4-benzodiazepine-2-acetic acid;
64. (−)-7-[[[Imidazo[4,5B]-4,6-dimethylpyridyl-2-ylmethyl]aminomethyl]carbonyl]-2,3,4,5-tetrahydro4-methyl-3-oxo-benzodiazepine-2-acetic acid trifluoroacetate salt;
65. (+/−)-7-[[(2-Benzimidazol-2-ylmethyl)-N-methylamino]carbonyl]-2,3,4,5-tetrahydro-3-oxo-4-[2-(3',4'-methylenedioxyphenyl)ethyl]-1H-1,4-benzodiazepine-2-acetic acid;
66. (+/−)-2,3,4,5-Tetrahydro-7-[[[(Benzimidazol-2-yl) methyl]amino]carbonyl]-4-(2-methoxyethyl)-3-oxo-1H-1,4-benzodiazepine-2-acetic acid;
67. (S)-7-[[2-[1-Methylbenzimidazolyl] benzimidazolylmethylamino]carbonyl]-2,3,4,5-tetrahydro4-methyl-3-oxo-1H-1,4-benzodiazepine-2-acetic acid;
68. (S)-7-[[[N-Cyclohexyl-N-(benzimidazol-2-yl)methyl] amino]carbonyl]-3-oxo-2,3,4,5-tetrahydro-1H-1,4-benzodiazepine-2-acetic acid;
69. (S)-7-[[[2-Bis-(Benzimidazolylmethyl)aminocarbonyl]-2,3,4,5-tetrahydro-4-methyl-3-oxo-1H-1,4-benzodiazepine-2-acetic acid;
70 (+/−)-2,3,4,5-Tetrahydro-7-[[[imidazo[4,5-B]pyrid-2-yl] methyl]methylamino]carbonyl]-4-(3,3-dimethylbutyl)-3-oxo-1H-1,4-benzodiazepine-2-acetic acid;
71. (+/−)-7-[[(2-Benzimidazol-2-ylmethyl)-N-methylamino]carbonyl-2,3,4,5-tetrahydro-3-oxo-4-(2',2',2'-trifluoroethyl)-1H-1,4-benzodaizepine-2-acetic acid; 72. (+/−)-7-[[(2-Benzimidazolyl)acetyl]amino]-5-oxo-4-(2-phenylethyl)-2,3,4,5-tetrahydro-1H-1,4-benzodiazepine-2-acetic acid;
73. (+/−)-7-[[(2-Benzimidazol-2-ylmethyl)amino] carbonyl]-2,3,4,5-tetrahydro-3-oxo-4-(2',2',2'-trifluoroethyl)-1H-1,4-benzodiazepine-2-acetic acid;
74. (−)-7-[[[5,6-Difluorobenzimidazoyl-2-ylmethyl] aminomethyl]carbonyl]-2,3,4,5-tetrahydro-4-methyl-3-oxo-1,4-benzodiazepine-2-acetic acid; and
75. (+/−)-7-[[Bis-(Benzimidazol-2-ylmethyl)amino] carbonyl]-2,3,4,5-tetrahydro-4-phenylethyl-3-oxo-1H-1,4-benzodiazepine-2-acetic acidtris(trifluoroacetate)salt.

Example 76

Preparation of 4-[2-[[[1-[(Benzimidazol-2-yl) methyl]benzimidazol-2-yl]methyl]methylamino] acetyl]phenoxyacetic acid a) 4-[2-(BOC-methylamino)acetyl]phenol A solution of di-tert-butyl dicarbonate (5.96 g, 27.3 mmol) in 1,4-dioxane (25 mL) was added dropwise at 0° C. to a mixture of 4-[2-(methylamino)acetyl]phenol hydrochloride (5.0 g, 24.8 mmol), 1,4-dioxane (30 mL), H₂O (25 mL) and 1.0 N NaOH (25 mL, 25 mmol). After 24 h, the reaction was warmed to RT and stirred for 1.5 hr. More 1.0 N NaOH (25 mL, 25 mmol) was added, and the reaction was stirred for an additional 0.5 h at RT, then was evaporated on the rotavap. The residue was diluted with EtOAc (80 mL), and the mixture was acidified to pH 2 using 1.0 M NaHSO₄. The resulting mixture was extracted with EtOAc, and the combined organic layers were washed with H₂O and dried (Na₂SO₄). Filtration and concentration gave the title compound (6.49 g, 99%): $^1$H NMR (250 MHz, CDCl₃) δ 6.70–8.05 (m, 4 H), 4.53 (s, 2H), 2.98 (s, 3H), 1.50 (s, 9H).

b) Benzyl 4-[2-(BOC-methylamino)acetyl]phenoxyacetate

A mixture of 4-[2-(BOC-methylamino)acetyl]phenol (5.04 g, 19.0 mmol) and K₂CO₃ (2.63 g, 19.0 mmol) in acetone (100 mL) was stirred at reflux under argon for 1 h. The mixture was cooled to RT and benzyl bromoacetate (5.23 g, 22.8 mmol) was added. The reaction was heated at reflux for 18 h, then was cooled and filtered. The filter cake was washed with acetone, and the filtrate was concentrated on the rotavap. The residue was dissolved in CH₂Cl₂ (300 mL) and washed sequentially with H₂O (50 mL) and brine (50 mL). Drying (Na₂SO₄), concentration, and flash chromatography (silica gel, 1:3 EtOAc/hexanes) yielded the title compound (7.28 g, 93%): $^1$H NMR (250 MHz, CDCl₃) δ 6.85–7.95 (m, 9 H), 5.23 (s, 2H), 4.71 (s, 2H), 4.55 (d, 2H), 2.95 (d, 3H), 1.45 (d, 9H).

c) Benzyl 4-[2-(methylamino)acetyl]phenoxyacetate hydrochloride

A mixture of benzyl 4-[2-(BOC-methylamino)acetyl] phenoxyacetate (7.26 g, 17.57 mmol) and 4 M HCl in 1,4-dioxane (150 mL) was stirred for 1 h at RT. Evaporation on the rotavap and trituration with Et₂O afforded the title compound as a white powder (5.93 g, 97%): $^1$H NMR (250 MHz, CD₃OD) δ 7.05–8.00 (m, 9 H), 5.23 (s, 2H), 4.88 (s, 2H), 4.65 (s, 2H), 2.80 (s, 3H).

d) Benzyl 4-[2-[[[1-[(benzimidazol-2-yl)methyl] benzimidazol-2-yl]methyl]methylamino]acetyl] phenoxyacetate Et₃N (0.28 g, 2.78 mmol) was added slowly to a mixture of benzyl 4-[2-(methylamino)acetyl]phenoxyacetate hydrochloride (0.39 g, 1.11 mmol), 2-(chloromethyl) benzimidazole (0.24 g, 1.45 mmol), CH₃CN (20 mL), and CH₂Cl₂ (5 mL) at RT under argon. After 5 h, the reaction mixture was concentrated on the rotavap. The residue was dissolved in CH₂Cl₂ and washed sequentially with 5% NaHCO₃ and brine. Drying (MgSO₄), concentration, and flash chromatography (silica gel, step gradient, 7–15% MeOH/CH₂Cl₂) yielded the title compound as an off-white powder (0.08 g, 12%): MS (ES) m/e 574.2 [M+H]⁺.

e) 4-[2-[[[(1-[(Benzimidazol-2-yl)methyl]benzimidazol-2-yl]methyl]methylamino]acetyl]phenoxyacetic acid A mixture of benzyl 4-[2-[[[1-[(benzimidazol-2-yl) methyl]benzimidazol-2-yl]methyl]methylamino]acetyl] phenoxyacetate (0.08 g, 0.18 mmol) and 5% Pd/C (0.11 g) in MeOH (15 m L) was shaken on a Parr apparatus under H₂ (41 psi) for 1 h. The mixture was filtered through a bed of Celite®, and the filter pad was washed with glacial AcOH and MeOH. The filtrate was concentrated to give the crude product (0.07 g). Preparative HPLC (Hamilton PRP-1® column, step gradient, 10–30% CH₃CN/H₂O-0.1% TFA) afforded the title compound: MS (ES) m/e 484.2 [M+H]⁺. Anal. Calcd for C₂₇H₂₅N₅O₄.3 C₂HF₃O₂: C, 48.01; H, 3.42 N, 8.48. Found: C, 48.40; H, 3.72; N, 8.77.

Example 77

(±)4-[[2-[(Benzimidazol-2-yl)methyl]methylamino]-1-hydroxyethy]-1,2-phenylenedioxydiacetic acid a) N-Cbz-Adrenalone Adrenalone hydrochloride (28.6 g, 0.121 mole) was added to 2.0 N NaOH (200 mL, 0.2 mol) which was first cooled to 5° C. in an ice bath. 2.0 N NaOH (60 mL, 0.06 mole) in one addition funnel and a solution of benzyl chloroformate (17.3 mL, 0.121 mol) in toluene (18 mL) in another addition funnel were added at rates such that the reaction temperature remained between 5–10° C. and that addition of both solutions was completed simultaneously. The resulting brown solution was stirred at 5° C. for 75 min, then was diluted with $H_2O$ (230 mL) and acidified with 1.0 N HCl (536 mL). A gummy precipitate formed initially, but solidified on trituration with a glass rod followed by stirring for 30 min. The pale green solid was filtered, stirred briefly with $H_2O$, filtered, stirred briefly with EtOH, and filtered. The resulting solid was ground in a mortar with more EtOH, then was filtered and dried in vacuum to afford the title compound (28.6 g, 75%): mp 183–186° C.

b) Dimethyl 4-[2-(Cbz-methylamino)acetyl]-1,2-phenylenedioxydiacetate

A mixture of N-Cbz-adrenalone (23.6 g, 74.8 mmole), acetone (340 mL), and anhydrous $K_2CO_3$ (21.0 g, 152 mmole) was heated at reflux under argon. After 70 min, the beige suspension was cooled to RT, and methyl bromoacetate (17.9 mL, 189 mmole) was added. The resulting suspension was stirred at RT under argon for 16 hr, then was heated to 50° C. After 6 h, the mixture was cooled to RT and filtered, and the filtrate was concentrated to dryness. The residue was dissolved in $CH_2Cl_2$ and washed sequentially with $H_2O$ and 5% $K_2CO_3$. Drying ($Na_2SO_4$) and concentration gave the title compound as an oil which solidified on standing (26.35 g, 82%): mp 56–59° C.

c) Dimethyl 4-[2-(methylamino)-1-hydroxyethyl]-1,2-phenylenedioxydiacetate

Following the procedure of Example 76(e), except substituting dimethyl 4-[2-(Cbz-methylamino)acetyl]-1,2-phenylenedioxydiacetate (2.1 g, 4.57 mmol) for benzyl 4-[2-[[[1-[(benzimidazol-2-yl)methyl]benzimidazol-2-yl]methyl]methylamino]acetyl]phenoxyacetate and using EtOAc (50 mL) and MeOH (20 mL) as solvents, the title compound (1.34 g, 90%) was prepared: MS (ES) m/e 328.0 $[M+H]^+$.

d) Dimethyl (±)-4-[[2-[(benzimidazol-2-yl)methyl]methylamino]-1-hydroxyethy]-1,2-phenylenedioxydiacetate Following the procedure of Example 76(d), except substituting dimethyl 4-[2-(methylamino)-1-hydroxyethyl]-1,2-phenylenedioxydiacetate (1.37 g, 4.20 mmol) for benzyl 4-[2-(methylamino)acetyl]phenoxyacetate hydrochloride, the title compound was prepared (0.25g, 13%): MS (ES) m/e 458.2 $[M+H]^+$.

e) (±)-4-[[2-[(Benzimidazol-2-yl)methyl]methylamino]-1-hydroxyethyl]-1,2-phenylenedioxydiacetic acid A mixture of dimethyl (±)-4-[[2-[(benzimidazol-2-yl)methyl]methylamino]-1-hydroxyethyl]-1,2-phenylenedioxydiacetate (0.23 g, 0.5 mmol), THF (10 mL), $H_2O$ (10 mL), and 1.0 N LiOH (2.0 mL, 2.0 mmol) was stirred at RT for 26 h. The reaction mixture was concentrated on the rotavap, and the aqueous residue was acidified with 1.0 N AcOH (2 mL) with cooling in an ice bath. The resulting mixture was lyophilized to give the crude product (0.32 g). Preparative HPLC (Hamilton PRP-1® column, 10% $CH_3CN/H_2O$-0.1% TFA) afforded the title compound: MS (ES) m/e 430.2 $[M+H]^+$. Anal. Calcd for $C_{21}H_{23}N_3O_7 \cdot 7/2\ C_2HF_3O_2$: C, 39.73; H, 3.39 N, 4.97 Found: C, 39.47; H, 3.38; N, 4.86.

Example 78

4-[2-[[(Benzimidazol-2-yl)methyl]methylamino]acetyl]-1,2-phenylenedioxydiacetic acid a) 1-BOC-2-methylbenzimidazole A mixture of 2-methylbenzimidazole (1.5 g, 11.35 mmole), $Et_3N$ (1.66 mL, 11.92 mmole), DMAP (0.20 g, 1.6 mmole), and $(BOC)_2O$ (2.60 g, 11.92 mmole) in anhydrous $CH_2Cl_2$ (15 mL) was stirred at RT for 24 hr, then was concentrated. The residue was taken up in $H_2O$, stirred, and filtered to afford the title compound as a colorless solid (2.63 g, 100%): mp 71–72° C.

b) 1-BOC-2-(bromomethyl)benzimidazole

NBS (8.43 g, 47.4 mmol) and AIBN (2.1 g, 12.8 mmol) were added to a solution of 1-BOC-2-methylbenzimidazole (10.0 g, 43.1 mmol) in $CCl_4$ (120 mL) at reflux. After 21 h, the reaction was cooled and filtered. The filtrate was concentrated, and the resulting brown oil was chromatographed (silica gel, 15% EtOAc/hexanes) to afford the title compound: $^1$H NMR (400 MHz, $CDCl_3$) δ 7.94–8.01 (m, 1 H), 7.70–7.75 (m, 1 H), 7.31–7.44 (m, 2 H), 4.96 (s, 2 H), 1.75 (s, 9 H), c) 4-[2-(BOC-methylamino)acetyl]-1,2-dihydroxybenzene Following the procedure of Example 76(a), except substituting adrenalone hydrochloride (5.0 g, 23.0 mmol) for 4-[2-(methylamino)acetyl]phenol hydrochloride, the title compound (1.2 g, 19%) was prepared following flash chromatography (silica gel, 1:1 EtOAc/hexanes): MS (ES) m/e 282.2 $[M+H]^+$.

d) Dimethyl 4-[2-(BOC-methylamino)acetyl]-1,2-phenylenedioxydiacetate

Following the procedure of Example 76(b), except substituting 4-[2-(BOC-methylamino)acetyl]-1,2-dihydroxybenzene (0.9 g, 3.2 mmol) for 4-[2-(BOC-methylamino)acetyl]phenol and methyl bromoacetate (1.23 g, 8.0 mmol) for benzyl bromoacetate, the title compound (1.11 g, 81%) was prepared: MS (ES) m/e 426.2 $[M+H]^+$.

e) Dimethyl 4-[2-(methylamino)acetyl]-1,2-phenylenedioxydiacetate hydrochloride

Following the procedure of Example 76(c), except substituting dimethyl 4-[2-(BOC-methylamino)acetyl]-1,2-phenylenedioxydiacetate (1.11 g, 2.6 mmol) for benzyl 4-[2-(BOC-methylamino)acetyl]phenoxyacetate, the title compound was prepared (1.1 g, quantitative): MS (ES) m/e 326.0 $[M+H]^+$.

f) Dimethyl 4-[2-[[(1-BOC-benzimidazol-2-yl)methyl]methylamino]acetyl]-1,2-phenylenedioxydiacetate Following the procedure of Example 76(d), except substituting dimethyl 4-[2-(methylamino)acetyl]-1,2-phenylenedioxydiacetate hydrochloride (0.24 g, 0.66 mmol) for benzyl 4-[2-(methylamino)acetyl]phenoxyacetate hydrochloride, 1-BOC-2-(bromomethyl)benzimidazole (0.31 g, 0.99 mmol) for 2-(chloromethyl)benzimidazole, and using THF (5 mL) and $CH_2Cl_2$ (5 mL) as solvents, the title compound was prepared (0.14 g, 38%): MS (ES) m/e 556.2 $[M+H]^+$.

g) Dimethyl 4-[2-[[(benzimidazol-2-yl)methyl]methylamino]acetyl]-1,2-phenylenedioxydiacetate bis(trifluoroacetate)

A mixture of dimethyl 4-[2-[[(1-BOC-benzimidazol-2-yl)methyl]methylamino]acetyl]-1,2-phenylenedioxydiacetate (0.13 g, 0.23 mmol) in TFA 4 mL) and $CH_2Cl_2$ (12 mL) was stirred at RT under argon for 20 min. Removal of the solvents on the rotavap gave the title compound (0.18 g, quantitative): MS (ES) m/e 456.2 $[M+H]^+$.

h) 4-[2-[[(Benzimidazol-2-yl)methyl]methylamino]acetyl]-1,2-phenylenedioxydiacetic acid Following the procedure of Example 77(e), except substituting dimethyl 4-[2-[[(benzimidazol-2-yl)methyl]

methylamino]acetyl]-1,2-phenylenedioxydiacetate bis (trifluoroacetate) (0.16 g, 0.23 mmol) for dimethyl (±)4-[[2-[(benzimidazol-2-yl)methyl]methylamino]-1-hydroxyethyl]-1,2-phenylenedioxydiacetate, the title compound was prepared (0.08 g, 80%): MS (ES) m/e 428.2 [M+H]$^+$. Anal. Calcd for $C_{21}H_{21}N_3O_7.11/5\ C_2HF_3O_2.9/5\ H_2O$: C, 42.93; H, 3.80 N, 5.91. Found: C, 42.62; H, 3.52; N, 6.30.

Example 79

Preparation of 3-[[4-[[[(Benzimidazol-2-yl)methylamino]carbonyl]phenyl]amino]propionic Acid a) ethyl 3-[4-(carboxy)phenylamino]propionate A solution of 4-aminobenzoic acid (6.85 g, 0.05 mol) and ethyl acrylate (15 g, 0.15 mol) in acetic acid (40 mL) was heated to 100° C. for 15 h. The solid which formed was filtered, washed with hexane and dried to give of the title compound (7.5 g, 63%).

b) ethyl 3-[[4-[[[(benzimidazol-2-yl)methylamino]carbonyl]phenyl]amino]propionic acid The compound of Example 79(a) (0.3 g, 1.26 mmol) in thionyl chloride (10 mL) was heated to reflux for 10 min, cooled, concentrated in vacuo, and residual thionyl chloride was removed by addition of methylene chloride followed by concentration in vacuo. The residual oil was dissolved in methylene chloride and treated with 2-(aminomethyl) benzimidazole dihydrochloride hydrate (0.33 g, 1.5 mmol) and diisopropylethylamine (0.56 g, 4.3 mmol). The resulting mixture was stirred overnight, washed with water and the organic phase was dried (sodium sulfate) and concentrated in vacuo. The resulting pale yellow solid was chromatographed (silica gel, methanol-dichloromethane 3:97) and fractions containing the product were pooled and concentrated in vacuo to give the title compound. MS(ES) m/e 367 [M+H]$^+$.

c) 3-[[4-[[[(benzimidazol-2-yl)methy]amino]carbonyl]phenyl]amino]propionic acid

A solution of the compound of Example 79(b)(0.4 g, 1.1 mmol) in methanol (20 mL), water (2 mL) and 0.95N aqueous sodium hydroxide (2.5 mL) was stirred and heated to 50° C. for 2 h. The mixture was treated with trifluoroacetic acid (1 mL), concentrated in vacuo, and the residue was triturated with dichloromethane (4×100 mL). The resulting white solid was recrystallized from 20% acetonitrile/water-0.1% trifluoroacetic acid to give the title compound. MS(ES) m/e 339 [M+H]$^+$.

Example 80

Preparation of 4-[4-[1-(2-Methylbenzimidazoyl) piperidinyl]]-piperidineacetic acid sodium salt a) Methyl 4-[4-[1-(t-butyloxycarbonyl)piperidinyl]]piperidineacetate A mixture of t-butyl 1-(4,4'-bipiperidine)carboxylate (3.1 g, 10 mmol), prepared as described by Bondinell, et al. (WO 93/00095), methyl bromoacetate (1.7 g, 11 mmol), and triethylamine (2.3 g, 22 mmol) in DMF (15 mL) was heated ar 85° C. for 4 h. The reaction mixture was diluted with EtOAc (50 mL), partitioned between NaHCO$_3$ (5% soution, 100 mL) and extracted with EtOAc (2×50 mL). The combined organic extracts were washed with H$_2$O, saturated NaCl soution, dried over MgSO$_4$, and evaporated to give the titled compound (3.37 g, 99%). MS (ES) m/e 341.2 [m+H]$^+$.

b) Methyl 4-[4-(1-piperidinyl)]piperidineacetate

A mixture of Example 1(a) (3.37 g, 10 imnol) and 4M HCl in dioxane (20 mL) in CH$_2$Cl$_2$ (25 mL) was stirred at RT for 18 h. The resulting white suspension was filtered to give the titled compounds as the dihydrochloride (3.1 g, 99%).

c) Methyl 4-[4-[-1-(2-Methylbenzimidazoyl)piperidinyl]]-piperidineacetate

To a stirred solution of Example 1(b) (2 g, 6.4 mmol) and triethylamine (3.6 mL, 25.6 mmol) in CH$_2$Cl$_2$ (50 mL) was added in portions a suspension of 2-chloromethylbenzimidazole (1.1 g, 6.6 mmol) in CH$_2$Cl$_2$ (25 mL) at RT. After stirring for 4 h, the reaction mixture was diluted with CH$_2$Cl$_2$ (50 mL), partitioned between NaHCO$_3$ (5% soution, 100 mL) and extracted with CH$_2$Cl$_2$ (2×50 mL). The combined organic extracts were washed with H$_2$O, a saturated NaCl soution, dried over MgSO$_4$, and evaporated. The titled compound was purified by flash chromatograpy (SiO$_2$/6% MeOH/CH$_2$Cl$_2$) to yield the titled compound (0.36 g, 16%). $^1$H NMR (400 MHz, CDCl$_3$) δ 1.07 (m, 2H), 1.35 (m, 4H), 1.65 (t, J=9.1, 4H), 2.09 (q, J=10.9, 4H), 2.93 (m, 4H), 3.20 (s, 2H), 3.71 (s, 3H), 3.79 (s, 2H), 7.22 (m, 2H), 7.56 (bs, 2H). MS (ES) m/e 471.2 [m+H]$^+$.

d) 4-[4-[1-(2-Methylbenzimidazoyl)piperidinyl]]-piperidineacetic acid sodium salt To a stirred solution of Example 1(c) (0.45 g, 1.2 mmol) in MeOH (15 mL) was added 1N NaOH solution (8.5 mL, 8.5 mmol) at RT. After 18 h, the white suspension was filtered to white solid (0.2 g, mp >250° C., 43%,) as the titled compound. MS (ES) m/e 357.2 [m+H]$^+$. $^1$H NMR (400 MHz, CD$_3$OD) δ 1.10 (bm, 2H), 1.34 (bm, 4H), 1.73 (bm, 4H), 2.11 (bm, 4H), 3.05 (m, 6H), 3.77 (s, 2H), 7.21 (bm, 2H), 7.52 (bm, 2H). Anal. Calcd for $C_{20}H_{27}N_4O_2Na.0.375\ H_2O$: C, 62.36; H, 7.26, N, 14.54 Found: C, 62.38; H, 7.20: N, 14.32.

Example 81

1a) Benzyl 4-bromobutyrate:

To a stirred, cooled (0° C.) mixture of benzyl alcohol (1.0 g, 5.392 mmol) and pyridine (0.47 g, 5.9312 mmol) in anhydrous methylene chloride (10 mL) was added 4-bromobutyryl chloride (0.58 g, 5.9312 mmol). After stirring in 1 h at room temperature, the mixture was concentrated, taken up in H$_2$O, extracted with EtOAc, washed with brine, dried over MgSO$_4$, filtered and concentrated to give a colorless oil (1.38 g, 100%). $^1$H NMR (CDCl$_3$, 300 MHz): δ 2.24 (m, 2H), 2.59 (t, J=5.7 Hz, 2H), 3.48 (t, J=5.7 Hz, 2H), 5.14 (s, 2H), 7.38 (m, 5H).

1b) (S)-Benzyl 4-(N-t-Boc-tyrosine methyl ester)butyrate:

A mixture of Example 1a (1.57 g, 6.1177 mmol), N-t-Boc-tyrosine methyl ester (1.80 g, 6.1177 mmol), and CsCO$_3$ in dried DMF (10 mL) was stirred at RT in 20 h. The mixture was concentrated, taken up in H$_2$O, extracted with EtOAc. The organic extracts were washed by brine, dried over MgSO$_4$, filtered and concentrated to give 2.30 g brown oil of the title compound (79%). $^1$H NMR (300 MHz, CDCl$_3$) δ 1.47 (s, 9H), 2.15 (m, 2H), 2.59 (t, J=5.7 Hz, 2H), 3.03 (m, 2H), 3.70 (s, 3H), 3.97 (t, J=5.7 Hz, 2H), 4.55 (m, 1H), 4.97 (d, 5.8 Hz, 1H), 5.12 (s, 2H), 6.78 (d, J=2H), 7.05 (d, J=8.3 Hz, 2H), 7.41 (m, 5H).

1c) (S)-Benzyl 4-(tyrosine methyl ester)butyrate:

To a stirred solution of Example 1b (2.30 g, 4.8778 mmol) in dried CH$_2$Cl$_2$ (10 mL) was added 12 mL of TFA. After stirring at RT in 3 h, the mixture was concentrated, taken up in H$_2$O, neutralized by 2.5N NaOH, extracted with CH$_2$C12, dried over MgSO$_4$, filtered, and concentrated to give a brown oil (1.60 g, 88%). 1H NMR (300 MHz, CDCl$_3$) δ 2.15 (m, 2H), 2.55 (t, J=5.7 Hz, 2H), 2.95 (dd, J=13.8 Hz, 7.3 Hz, 1H), 3.13 (dd, J=13.8 Hz, 7.3 Hz, 1H), 3.70 (s, 3H), 3.97 (t, J=5.7 Hz, 1H), J=7.3 Hz, 1H), 5.15 (s, 2H), 6.80 (d, J=8.3 Hz, 2H), 7.10 (d, J=8.3 Hz, 2H), 7.35 (m, 5H).

1d) (S)-Benzyl 4-[(N-butylsulfonyl) tyrosine methyl ester] butyrate:

To a stirred mixture of Example 1c (1.60 g, 4.3079 mmol) and pyridine (0.41 g, 5.1695 mmol) in dried $CH_2Cl_2$ (15 mL) was added n-butylsulfonyl chloride (0.81 g, 5.1695 mmol). After stirring at RT in 2 h, the mixture was concentrated, taken up in $H_2O$, extracted with EtOAc. The organic extracts were washed by 2N HCl, saturated $NaHCO_3$, brine, dried over $MgSO_4$, filtered, and concentrated to give a brown oil (2.01 g, 95%). 1H NMR (300 MHz, $CDCl_3$) δ 0.89 (t, J=7.3 Hz, 3H), 1.37 (m, 2H), 1.65 (m, 2H), 2.20 (m, 2H), 2.60 (t, J=5.7 Hz, 2H), 2.72 (t, J=7.3 Hz, 2H), 2.95 (dd, J=13.8 Hz, 7.3 Hz, 1H), 3.10 (dd, J=13.8 Hz, 7.3 Hz, 1H), 3.77 (s, 3H), 3.93 (t, J=5.7 Hz, 2H), 4.30 (m, 1H), 4.70 (d, J=7.3 Hz, 1H), 5.12 (s, 2H), 6.80 (d, J=8.3 Hz, 2H), 7.03 (d, J=8.3 Hz, 2H), 7.35 (m, 5H).

1e) (S)-4-[(N-butylsulfonyl)tyrosine methyl ester]butyric acid:

A solution of Example 1d (0.781 g, 1.589 mmol) in MeOH (10 mL) was hydrogenated at 50 PSI in 10% Pd/C (0.50 g) in 3 h. The catalyst was filtered through celite. The filtrate was concentrated to give a white solid (0.59 g, 93%). 1H NMR (300 MHz, $CDCl_3$) δ 0.89 (t, J=7.3 Hz, 3H), 1.35 (m, 2H), 1.65 (m, 2H), 2.10 (m, 2H), 2.55 (t, J=5.7 Hz, 2H), 2.75 (t, J=7.3 Hz, 2H), 2.95 (dd, J=13.8 Hz, 7.3 Hz, 1H), 3.05 (dd, J=13.8 Hz, 7.3 Hz, 1H), 3.48 (s, 3H), 3.97 (t, J=5.7 Hz, 2H), 4.30 (m, 1H), 4.90 (d, J=7.3 Hz, 1H), 6.90 (d, J=8.3 Hz, 2H), 7.10 (d, J=8.3 Hz, 2H).

1f) (S)-N-butylsulfonyl-4-(3-(benzimidazol-2-yl)propyl) tyrosine methyl ester:

To a stirred, cooled (0° C.) mixture of Example 1e (0.595 g, 1.4823 mmol) and $Et_3N$ (0.16 g, 1.5565 mmol) in dried THF (7 mL) was added isobutylchloroformate (0.212 g, 1.5565 mmol). After stirring at O0° C. in 1 h, o-phenylenediamine (0.16 g, 14823 mmol) and 1 mL of HOAc was added. The reaction mixture was heated at reflux overnight. The mixture was cooled, diluted with EtOAc, washed by $H_2O$, saturated $NaHCO_3$, brine, dried over $MgSO_4$, concentrated and purified by flash column chromatograph (5% MeOH/$CH_2Cl_2$) to give a white foam (0.487 g, 69%). $^1$H NMR (300 MHz, $CDCl_3$) δ 0.89 (t, J=7.3 Hz, 3H), 1.35 (m, 2H), 1.65 (m, 2H), 2.30 (m, 2H), 2.80 (t, J=5.7 Hz, 2H), 2.95 (dd, J=13.8 Hz, 7.3 Hz, 1H), 3.10 (m, 3H), 3.0 (s, 3H), 3.98 (t, J=5.7 Hz, 2H), 4.35 (m, 1H), 4.90 (d, 7.3 Hz, 1H), 6.77 (d, j=8.3 Hz, 2H), 7.03 (d, J=8.3 Hz, 2H), 7.26 (m, 2H), 7.58 (m, 2H).

1g) (S)-N-Butylsulfonyl-p-[3-(2-benzimidazoyl)propyl] tyrosine:

To a stirred solution of Example 1f (0.487 g, 1.0285 mmol) in MeOH (5 mL) was added $LiOH.H_2O$ (0.09 g, 2.0571 mmol) in 24 h. The mixture was concentrated, diluted in $H_2O$, neutralized with 2.0N HCl. The off white solid was filtered, triturated in hot EtOH to give the title compound as a white solid (0.377 g, 80%, Mp: >230° C.). $^1$H NMR (300 MHz, DMSO-$d_6$) δ 0.75 (t, 7.3 Hz, 3H), 1.15 (m, 2H), 1.30 (m, 2H), 2.20 (m, 2H), 2.52 (m, 2H), 2.75 (dd, J=13.8 Hz, 7.3 Hz, 1H), 2.97 (dd, J=13.8 Hz, 7.3 Hz, 1H), 3.00 (t, J=5.7 Hz, 2H), 3.90 (m, 1H), 4.10 (t, J=5.7 Hz, 2H), 6.85 (d, 8.3 Hz, 2H), 7.10 (m, 2H), 7.20 (d, J=8.3 Hz, 2H), 7.50 (m, 2H), 7.61 (d, J=7.3 Hz, 1H). IR (cm$^{-1}$, KBr) 3300–3400, 3244, 3000–3100, 2800–300, 1634, 1612, 1512, 1466, 1384, 1245, 1148, 1110. MS (ESI, M+H)460.2. Anal. Calc. for $C_{23}H_{29}N_3O_5S$: C, 60.11; H, 6.36; N, 9.14; Found: C,60.01; H, 6.34; N, 9.01.

Example 82

Preparation of 4-[2-[[[1-[(Benzimidazol-2-yl) methyl]benzimidazol-2-yl]methy]methylamino] acetyl]phenoxyacetic acid a) 4-[2-(BOC-methylamino)acetyl]phenol A solution of di-tert-butyl dicarbonate (5.96 g, 27.3 mmol) in 1,4-dioxane (25 mL) was added dropwise at 0° C. to a mixture of 4-[2-(methylamino)acetyl]phenol hydrochloride (5.0 g, 24.8 mmol), 1,4-dioxane (30 mL), $H_2O$ (25 mL) and 1.0 N NaOH (25 mL, 25 mmol). After 24 hr, the reaction was warmed to RT and stiffed for 1.5 hr. More 1.0 N NaOH (25 mL, 25 mmol) was added, and the reaction was stirred for an additional 0.5 h at RT, then was evaporated on the rotavap. The residue was diluted with EtOAc (80 mL), and the mixture was acidified to pH 2 using 1.0 M $NaHSO_4$. The resulting mixture was extracted with EtOAc (2×50 mL), and the combined organic layers were washed with $H_2O$ (30 mL) and dried ($Na_2SO_4$). Filtration and concentration gave the title compound (6.49 g, 99%): $^1$H NMR (250 MHz, $CDCl_3$) δ 6.70–8.05 (m, 4 H), 4.53 (s, 2H), 2.98 (s, 3H), 1.50 (s, 9H).

b) Benzyl 4-[2-(BOC-methylamino)acetyl]phenoxyacetate

A mixture of 4-[2-(BOC-methylamino)acetyl]phenol (5.04 g, 19.0 mmol) and $K_2CO_3$ (2.63 g, 19.0 mmol) in acetone (100 mL) was stirred at reflux under argon for 1 h. The mixture was cooled to RT and benzyl bromoacetate (5.23 g, 22.8 mmol) was added. The reaction was heated at reflux for 18 h, then was cooled and filtered. The filter cake was washed with acetone, and the filtrate was concentrated on the rotavap. The residue was dissolved in $CH_2Cl_2$ (300 mL) and washed sequentially with $H_2O$ (50 mL) and brine (50 mL). Drying ($Na_2SO_4$), concentration, and silica gel flash chromatography (1:3 EtOAc/hexanes) yielded the title compound (7.28 g, 93%): $^1$H NMR (250 MHz, $CDCl_3$) δ 6.85–7.95 (m, 9 H), 5.23 (s, 2H), 4.71 (s, 2H), 4.55 (d, 2H), 2.95 (d, 3H), 1.45 (d, 9H).

c) Benzyl 4-[2-(methylamnino)acetyl]phenoxyacetate hydrochloride

A mixture of benzyl 4-[2-(BOC-methylamino)acetyl] phenoxyacetate (7.26 g, 17.57 mmol) and 4 M HCl in 1,4-dioxane (150 mL) was stirred for 1 h at RT. Evaporation on the rotavap and trituration with $Et_2O$ afforded the title compound (5.93 g, 97%) as a white powder: $^1$H NMR (250 MHz, $CD_3OD$) δ 7.05–8.00 (m, 9 H), 5.23 (s, 2H), 4.88 (s, 2H), 4.65 (s, 2H), 2.80 (s, 3H).

d) Benzyl 4-[2-[[[1-[(benzimidazol-2-yl)methyl] benzimidazol-2-yl]methyl]methylamino]acetyl] phenoxyacetate $Et_3N$ (0.28 g, 2.78 mmol) was added slowly to a mixture of benzyl 4-[2-(methylamino)acetyl]phenoxyacetate hydrochloride (0.39 g, 1.11 mmol), 2-(chloromethyl) benzimidazole (0.24 g, 1.45 mmol), $CH_3CN$ (20 mL), and $CH_2Cl_2$ (5 mL) at RT under argon. After 5 h, the reaction mixture was concentrated on the rotavap. The residue was dissolved in $CH_2Cl_2$ (100 mL) and washed sequentially with 5% $NaHCO_3$ (2×20 mL) and brine (20 mL). Drying ($MgSO_4$), concentration, and silica gel flash chromatography (step gradient, 7–15% MeOH/$CH_2Cl_2$) yielded the title compound (0.08 g, 12%) as an off-white powder: MS (ES) m/e 574.2 [M+H]$^+$.

e) 4-[2-[[[1-[(Benzimidazol-2-yl)methyl]benzimidazol-2-yl]methyl]methylamino]acetyl]phenoxyacetic acid A mixture of benzyl 4-[2-[[[1-[(benzimidazol-2-yl) methyl]benzimidazol-2-yl]methyl]methylamino]acetyl] phenoxyacetate (0.08 g, 0.18 mmol) and 5% Pd/C (0.11 g) in MeOH (15 mL) was shaken on a Parr apparatus under $H_2$ (41 psi) for 1 h. The mixture was filtered through a bed of celite®, and the filter pad was washed with glacial AcOH and MeOH. The filtrate was concentrated to give the crude product (0.07 g). Preparative HPLC (Hamilton PRP-1® column, step gradient, 10–30% $CH_3CN/H_2O$ containing 0.1% TFA) afforded the title compound: MS (ES) m/e 484.2 $[M+H]^+$. Anal. Calcd for $C_{27}H_{25}N_{5O4}·.3C_2HF3O_2$: C, 48.01; H, 3.42 N, 8.48. Found: C, 48.40; H, 3.72; N, 8.77.

Example 83

(±)4-[[2-[(Benzimidazol-2-yl)methyl] methylamninol-1-hydroxyethy]-1,2-phenylenedioxydiacetic acid a) N-Cbz-Adrenalone Adrenalone hydrochloride (28.6 g, 0.121 mole) was added to 2.0 N NaOH (200 mL, 0.2 mole) which was first cooled to 5° C. in an ice bath. 2.0 N NaOH (60 mL, 0.06 mole) in one addition funnel and a solution of benzyl chloroformate (17.3 mnL, 0.121 mole) in toluene (18 mL) in another addition funnel were added at rates such that the reaction temperature remained between 5–10° C. and that addition of both solutions was completed simultaneously. The resulting brown solution was stirred at 5° C. for 75 min, then was diluted with $H_2O$ (230 mL) and acidified with 1.0 N HCl (536 mL). A gummy precipitate formed initially, but solidified on trituration with a glass rod followed by stirring for 30 min. The pale green solid was filtered, stirred briefly with $H_2O$ (180 mL), filtered, stirred briefly with EtOH (135 mL), and filtered. The resulting solid was ground in a mortar with more EtOH (135 mL), then was filtered and dried in vacuum to afford the title compound (28.6 g, 75%): mp 183–186° C.

b) Dimethyl 4-[2-(Cbz-methylamino)acetyl]-1,2-phenylenedioxydiacetate

A mixture of N-Cbz-adrenalone (23.6 g, 74.8 mmole), acetone (340 mL), and anhydrous $K_2CO_3$ (21.0 g, 152 mmole) was heated at reflux under argon. After 70 min, the beige suspension was cooled to RT, and methyl bromoacetate (17.9 mL, 189 mmole) was added. The resulting suspension was stirred at RT under argon for 16 hr, then was heated to 50° C. After 6 hr, the mixture was cooled to RT and filtered, and the filtrate was concentrated to dryness. The residue was dissolved in $CH_2Cl_2$ (800 mL) and washed sequentially with $H_2O$ (160 mL) and 5% $K_2CO_3$ (2×100 mL). Drying ($Na_2SO_4$) and concentration gave the title compound (26.35 g, 82%) as an oil which solidified on standing: mp 56–59° C.

c) Dimethyl 4-[2-(methylamino)-1-hydroxyethyl]-1,2-phenylenedioxydiacetate

Following the procedure of Example 82(e), except substituting dimethyl 4-[2-(Cbz-methylamino)acetyl]-1,2-phenylenedioxydiacetate (2.1 g, 4.57 mmol) for benzyl 4-[2-[[[1-[(benzimidazol-2-yl)methyl]benzimidazol-2-yl] methyl]methylamino]acetyl]-phenoxyacetate and using EtOAc (50 mL) and MeOH (20 mL) as solvents, the title compound (1.34 g, 90%) was prepared: MS (ES) m/e 328.0 $[M+H]^+$.

d) Dimethyl (±)-4-[[2-[(benzimidazol-2-yl)methyl] methylamino]-1-hydroxyethyl]-1,2-phenylenedioxydiacetate Following the procedure of Example 82(d), except substituting dimethyl 4-[2-(methylamino)-1-hydroxyethyl]-1,2-phenylenedioxydiacetate (1.37 g, 4.20 mmol) for benzyl 4-[2-(methylamino)acetyl]phenoxyacetate hydrochloride, the title compound (0.25g, 13%) was prepared: MS (ES) m/e 458.2 $[M+H]^+$.

e) (±)4-[[2-[(Benzimidazol-2-yl)methyl]methylamino]-1-hydroxyethyl]-1,2-phenylenedioxydiacetic acid A mixture of dimethyl (±)-4-[[2-[(benzimidazol-2-yl) methyl]methylamino]-1-hydroxyethyl]-1,2-phenylenedioxydiacetate (0.23 g, 0.5 mmol), THF (10 mL), $H_2O$ (10 mL), and 1.0 N LiOH (2.0 mL, 2.0 mmol) was stirred at RT for 26 h. The reaction mixture was concentrated on the rotavap, and the aqueous residue was acidified with 1.0 N AcOH (2 mL) with cooling in an ice bath. The resulting mixture was lyophilized to give the crude product (0.32 g). Preparative HPLC (Hamilton PRP-1® column, 10% $CH_3CN/H_2O$ containing 0.1% TFA) afforded the title compound: MS (ES) m/e 430.2 $[M+H]^+$. Anal. Calcd for $C_{21}H_{23}N_3O_7·7/2$ $C_2HF_3O_2$: C, 39.73; H, 3.39 N, 4.97 Found: C, 39.47; H, 3.38; N, 4.86.

Example 84

4-[2-[[(Benzimidazol-2-yl)methyl]methylamino] acetyl]-1,2-phenylenedioxydiacetic acid a) 1-BOC-2-methylbenzimidazole A mixture of 2-methylbenzimidazole (1.5 g, 11.35 mmole), $Et_3N$ (1.66 mL, 11.92 mmole), DMAP (0.20 g, 1.6 mmole), and $(BOC)_2O$ (2.60 g, 11.92 mmole) in anhydrous $CH_2Cl_2$ (15 mL) was stirred at RT for 24 hr, then was concentrated. The residue was taken up in $H_2O$, stirred, and filtered to afford the title compound (2.63 g, 100%) as a colorless solid: mp 71–72° C.

b) 1-BOC-2-(bromomethyl)benzimidazole

NBS (8.43 g, 47.4 mmole) and AIBN (2.1 g, 12.8 mmole) were added to a solution of 1-BOC-2-methylbenzimidazole (10.0 g, 43.1 mmole) in $CCl_4$ (120 mL) at reflux. After 21 hr, the reaction was cooled and filtered. The filtrate was concentrated, and the resulting brown oil was chromatographed on silica gel (15% EtOAc/hexanes) to afford the title product: $^1H$ NMR (400 MHz, $CDCl_3$) δ 7.94–8.01 (m, 1 H), 7.70–7.75 (m, 1 H), 7.31–7.44 (m, 2 H), 4.96 (s, 2 H), 1.75 (s, 9 H), c) 4-[2-(BOC-methylamino)acetyl]-1,2-dihydroxybenzene Following the procedure of Example 82(a), except substituting adrenalone hydrochloride (5.0 g, 23.0 mmol) for 4-[2-(methylamino)acetyl]phenol hydrochloride, the title compound (1.2 g, 19%) was prepared following silica gel flash chromatography (1:1 EtOAc/hexanes): MS (ES) m/e 282.2 $[M+H]^+$.

d) Dimethyl 4-[2-(BOC-methylamino)acetyl]-1,2-phenylenedioxydiacetate

Following the procedure of Example 82(b), except substituting 4-[2-(BOC-methylamino)acetyl]-1,2-dihydroxybenzene (0.9 g, 3.2 mmol) for 4-[2-(BOC-methylamino)acetyl]phenol and methyl bromoacetate (1.23 g, 8.0 mmol) for benzyl bromoacetate, the title compound (1.11 g, 81%) was prepared: MS (ES) m/e 426.2 $[M+H]^+$.

e) Dimethyl 4-[2-(methylamino)acetyl]-1,2-phenylenedioxydiacetate hydrochloride

Following the procedure of Example 82(c), except substituting dimethyl 4-[2-(BOC-methylamino)acetyl]-1,2-phenylenedioxydiacetate (1.11 g, 2.6 mmol) for benzyl 4-[2-(BOC-methylamino)acetyl]phenoxyacetate, the title compound (1.1 g, quantitative) was prepared: MS (ES) m/e 326.0 $[M+H]^+$.

f) Dimethyl 4-[2-[[(1-BOC-benzimidazol-2-yl)methyl] methylamino]acetyl]-1,2-phenylenedioxydiacetate Following the procedure of Example 82(d), except substituting dimethyl 4-[2-(methylamino)acetyl]-1,2-phenylenedioxydiacetate hydrochloride (0.24 g, 0.66 mmol) for benzyl 4-[2-(methylamino)acetyl]phenoxyacetate hydrochloride, 1-BOC-2-(bromomethyl)benzimidazole (0.31 g, 0.99 mmol) for 2-(chloromethyl)benzimidazole, and using THF (5 mL) and $CH_2Cl_2$ (5 mL) as solvents, the title compound (0.14 g, 38%) was prepared: MS (ES) m/e 556.2 $[M+H]^+$.

g) Dimethyl 4-[2-[[(benzimidazol-2-yl)methyl]methylamino]acetyl]-1,2-phenylenedioxydiacetate bis(trifluoroacetate)

A mixture of dimethyl 4-[2-[[(1-BOC-benzimidazol-2-yl)methyl]methylamino]-acetyl]-1,2-phenylenedioxydiacetate (0.13 g, 0.23 mmol) in TFA 4 mL) and CH$_2$Cl$_2$ (12 mL) was stirred at RT under argon for 20 min. Removal of the solvents on the rotavap gave the title compound (0.18 g, quantitative): MS (ES) m/e 456.2 [M+H]$^+$.

h) 4-[2-[[(Benzimidazol-2-yl)methyl]methylamino]acetyl]-1,2-phenylenedioxydiacetic acid Following the procedure of Example 82(e), except substituting dimethyl 4-[2-[[(benzimidazol-2-yl)methyl]methylamino]acetyl]-1,2-phenylenedioxydiacetate bis(trifluoroacetate) (0.16 g, 0.23 mmol) for dimethyl (±)-4-[[2-[(benzimidazol-2-yl)methyl]methylamino]-1-hydroxyethyl]-1,2-phenylenedioxydiacetate, the title compound (0.08 g, 80%) was prepared: MS (ES) m/e 428.2 [M+H]$^+$. Anal. Calcd for C$_{21}$H$_{21}$N$_3$O$_7$.11/5 C$_2$HF$_3$O$_2$.9/5 H$_2$O: C, 42.93; H, 3.80 N, 5.91. Found: C, 42.62; H, 3.52; N, 6.30.

Example 85

Preparation of 3-[[(4-[[[(Benzimidazol-2-yl)methy]amino]carbonyl]phenyl]amino]propionic Acid a) ethyl 3-[4-(carboxy)phenylamino]propionate A solution of 4-aminobenzoic acid (6.85 g, 0.05 mol) and ethyl acrylate (15 g, 0.15 mol) in acetic acid (40 mL) was heated to 100° C. for 15 h. The solid which formed was filtered, washed with hexane and dried to give the title compound (7.5 g, 63%).

b) ethyl 3-[[4-[[[(benzimidazol-2-yl)methy]amino]carbonyl]phenyl]amino]propionic acid The compound of Example 85(a)(0.3 g, 1.26 mmol) in thionyl chloride (10 mL) was heated to reflux for 10 min, cooled, concentrated in vacuo, and residual thionyl chloride was removed by addition of methylene chloride followed by concentration in vacuo. The residual oil was dissolved in methylene chloride and treated with 2-(aminomethyl)benzimidazole dihydrochloride hydrate (0.33 g, 1.5 mmol) and diisopropylethylamine (0.56 g, 4.3 mmol). The resulting mixture was stirred overnight, washed with water and the organic phase was dried (sodium sulfate) and concentrated in vacuo. The resulting pale yellow solid was chromatographed (silica gel, methanol-dichloromethane 3:97) and fractions containing the product were pooled and concentrated in vacuo to give the title compound. MS(ES) m/e 367 [M+H]$^+$.

c) 3-[[4-[[[(benzimidazol-2-yl)methy]armino]carbonyl]phenyl]amino]propionic acid A solution of the compound of Example 85(b)(0.4 g, 1.1 mmol) in methanol (20 mL), water (2 mL) and 0.95N aqueous sodium hydroxide (2.5 mL) was stirred and heated to 50° C. for 2 h. The mixture was treated with trifluoroacetic acid (1 mL), concentrated in vacuo, and the residue was triturated with dichloromethane (4×100 mL). The resulting white solid was recrystallized from 20% acetonitrile/water-0.1% trifluoroacetic acid to give the title compound. MS(ES) m/e 339 [M+H]$^+$.

Example 86–92

Following the general procedures of Examples 1–55, the following compounds are parpared:

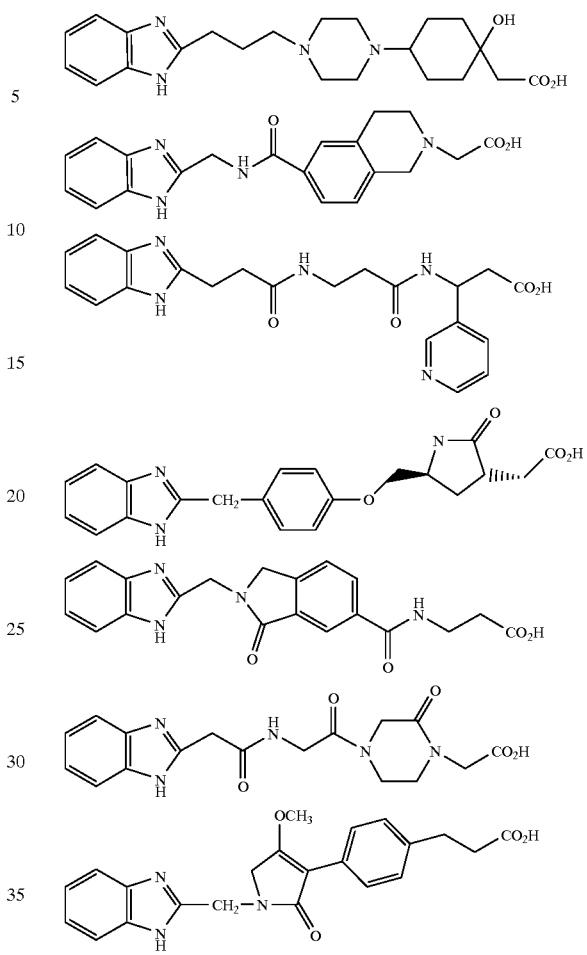

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

Example 93

Parenteral Dosage Unit Composition

A preparation which contains 20 mg of the compound of Example 1 as a sterile dry powder is prepared as follows: 20 mg of the compound is dissolved in 15 mL of distilled water. The solution is filtered under sterile conditions into a 25 mL multi-dose ampoule and lyophilized. The powder is reconstituted by addition of 20 mL of 5% dextrose in water (D5W) for intravenous or intramuscular injection. The dosage is thereby determined by the injection volume. Subsequent dilution may be made by addition of a metered volume of this dosage unit to another volume of D5W for injection, or a metered dose may be added to another mechanism for dispensing the drug, as in a bottle or bag for IV drip infusion or other injection-infusion system.

Example 94

Oral Dosage Unit Composition

A capsule for oral administration is prepared by mixing and milling 50 mg of the compound of Example 1 with 75 mg of lactose and 5 mg of magnesium stearate. The resulting powder is screened and filled into a hard gelatin capsule.

Example 95
Oral Dosage Unit Composition

A tablet for oral administration is prepared by mixing and granulating 20 mg of sucrose, 150 mg of calcium sulfate dihydrate and 50 mg of the compound of Example 1 with a 10% gelatin solution. The wet granules are screened, dried, mixed with 10 mg starch, 5 mg talc and 3 mg stearic acid; and compressed into a tablet.

The foregoing is illustrative of the making and using of this invention. This invention, however, is not limited to the precise embodiments described herein, but encompasses all modifications within the scope of the claims which follow.

What is claimed is:

1. A compound according to formula (I) or (II):

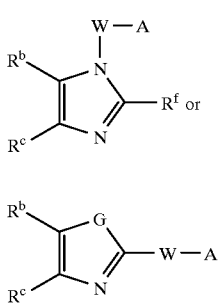

wherein

W is —(CHR$^g$)$_a$—U—(CHR$^g$)$_b$—V— or

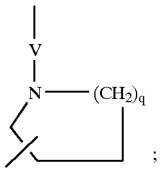

A is

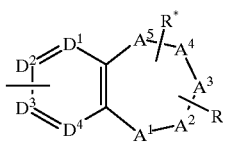

wherein:
$A^1$ to $A^5$ form an accessible substituted seven-membered ring, which may be saturated or unsaturated, provided that two of $A^1$ to $A^5$ are nitrogen atoms and the others are carbon atoms;
$D^1$ to $D^4$ are CH;
R is at least one substituent chosen from the group of $R^7$, or Q-C$_{1-4}$alkyl, Q-C$_{2-4}$alkenyl, Q-C$_{2-4}$alkynyl, optionally substituted by one or more of =O, $R^{11}$ or $R^7$;
R* is H, Q-C$_{1-6}$alkyl, Q-C$_{1-6}$oxoalkyl, Q-C$_{2-6}$alkenyl, Q-C$_{3-4}$oxoalkenyl, Q-C$_{3-4}$oxoalkynyl, Q-C$_{2-4}$alkynyl, C$_{3-6}$cycloalkyl, Ar or Het, optionally substituted by one or more of $R^{11}$;
Q is C$_{3-6}$cycloalkyl, Het or Ar;

$R^7$ is —COR$^8$, —COCR'$_2$R$^9$, —C(S)R$^8$, —S(O)$_m$OR', —S(O)$_m$NR'R", —PO(OR'), —PO(OR')$_2$, —B(OR')$_2$, —NO$_2$ and 5-tetrazolyl;
$R^8$ is —OR', —NR'R", —NR'SO$_2$R', —NR'OR', —OCR'$_2$C(O)OR', —OCR'$_2$OC(O)—R', —OCR'$_2$C(O)NR'$_2$, CF$_3$ or AA1;
$R^9$ is —OR', —CN, —S(O)$_r$R', S(O)$_m$NR'$_2$, —C(O)R'C(O)NR'$_2$ or —CO$_2$R';
$R^{11}$ is H, halo, —OR$^{12}$, —CN, —NR'R$^{12}$, —NO$_2$, —CF$_3$, CF$_3$S(O)$_r$—, —CO$_2$R', —CONR'$_2$, Q-C$_{0-6}$alkyl-, Q-C$_{1-6}$oxoalkyl-, Q-C$_{2-6}$alkenyl-, Q-C$_{2-6}$alkynyl, Q-C$_{0-6}$alkloxy-, Q-C$_{0-6}$alkylamino- or Q-C$_{0-6}$alkyl-S(O)$_r$—;
$R^{12}$ is R', —C(O)R', —C(O)NR'$_2$, —C(O)OR$^{15}$, —S(O)$_m$R' or S(O)$_m$NR'$_2$;
$R^{13}$ is R', —CF$_3$, —SR', or —OR';
$R^{14}$ is R', C(O)R', CN, NO$_2$, SO$_2$R' or C(O)OR$^{15}$;
$R^{15}$ is H, C$_{1-6}$alkyl or Ar—C$_{0-4}$alkyl;
R' is H, C$_{1-6}$alkyl, C$_{3-7}$cycloalkyl-C$_{0-4}$alkyl or Ar—C$_{0-4}$alkyl;
R" is R', —C(O)R' or —C(O)OR$^{15}$;
R'" is R"or AA2;
AA1 is an amino acid attached through its amino group and having its carboxyl group optionally protected, and AA2 is an amino acid attached through its carboxyl group, and having its amino group optionally protected;
m is 1 or 2;
n is 0 to 3;
p is 0 or 1;
t is 0 to 2;
U and V are absent or CO, CR$^g_2$, C(=CR$^g_2$), S(O)$_k$, O, NR$^g$, CR$^g$OR$^g$, CR$^g$(OR$^k$)CR$^g_2$, CR$^g_2$CR$^g$(OR$^k$), C(O)CR$^g_2$, CR$^g_2$C(O), CONR$^i$, NR$^i$CO, OC(O), C(O)O, C(S)O, OC(S), C(S)NR$^g$, NR$_g$C(S), S(O)$_2$NR$^g$, NR$^g$S(O)$_2$N=N, NR$^g$NR$^g$, NR$^g$CR$^g_2$, CR$^g_2$O, OCR$^g_2$, C≡C or CR$^g$=CR$^g$;
G is NR$^e$;
R$^g$ is H, C$_{1-6}$alkyl, Het-C$_{0-6}$alkyl, C$_{3-7}$cycloalkyl-C$_{0-6}$alkyl or Ar—C$_{1-6}$alkyl;
R$^k$ is R$^g$, —C(O)R$^g$, or —C(O)OR$^f$;
R$^i$ is H, C$_{1-6}$alkyl, Het-C$_{0-6}$alkyl, C$_{3-7}$cycloalkyl-C$_{0-6}$alkyl, Ar—C$_{0-6}$alkyl, or C$_{1-6}$alkyl substituted by one to three groups chosed from halogen, CN, NR$^g_2$, OR$^g$, SR$^g$, CO$_2$R$^g$, and CON(R$^g$)$_2$;
R$^f$ is H, C$_{1-6}$alkyl or Ar—C$_{1-6}$alkyl;
R$^e$ is H, C$_{1-6}$alkyl, Ar—C$_{1-6}$alkyl, Het-C$_{1-6}$alkyl, C$_{3-7}$cycloalkyl-C$_{1-6}$alkyl, or (CH$_2$)$_k$CO$_2$R$^g$;
k is 0, 1 or 2;
q is 1 or 2;
a is 0, 1 or 2;
b is 0, 1 or 2;
R$^b$ and R$^c$ are joined together to form a six membered aromatic carbocyclic ring, optionally substituted by up to three substituents chosen from halogen, CF$_3$, C$_{1-4}$alkyl, OR$^f$, S(O)$_k$R$^f$, COR$^f$, CO$_2$R$^f$OH, NO$_2$, N(R$^f$)$_2$, CO(NR$^f$)$_2$, and CH$_2$N(R$^f$)$_2$; or methylenedioxy;
or a pharmaceutically acceptable salt thereof.

2. A compound according to claim 1 wherein:
$A^1$ is CR$^1$R$^{1'}$, CR$^1$, NR$^1$, or N;
$A^2$ is CR$^2$R$^{2'}$, CR$^2$, NR$^2$;
$A^3$ is CR$^3$R$^{3'}$, CR$^3$, NR$^3$, or N;
$A^4$ is CR$^4$R$^{4'}$, CR$^4$, NR$^4$, or N;
$A^5$ is CR$^5$R$^{5'}$, CR$^5$, NR$^5$, or N;

$D^1$–$D^4$ are CH;

$R^1$ and $R^{1'}$ are R* or R, or together are =O;

$R^2$ and $R^{2'}$ are R*, R or =O;

$R^3$ and $R^{3'}$ are R*, R or =O;

$R^4$ and $R^{4'}$ are R*, R or =O;

$R^5$ and $R^{5'}$ are R*, R or =O; and x is 0, 1 or 2;

provided that two of $A^1$ to $A^5$ are nitrogen atoms and the others are carbon atoms.

3. A compound according to claim 2 wherein:

$A^1$ is $CR^1R^{1'}$, $CR^1$, $NR^1$, or N; $A^2$ is $CR^2R^{2'}$, $NR^2$ or $CR^2$; $A^3$ is $CR^3R^{3'}$; $A^4$ is $CR^4R^{4'}$, $NR^4$, or N; $A^5$ is $CR^5R^{5'}$, $CR^5$, $NR^5$, or N; $R^2$ or $R^4$ are R; $R^3, R^{3'}$ and $R^5, R^{5'}$ are =O or R*,H, provided that two of $A^1$ to $A^5$ are nitrogen atoms and the others are carbon atoms.

4. A compound according to claim 2 wherein:

$A^1$ is NR", or N; $A^2$ is $CR^2$ or $CR^2R^{2'}$; $A^3$ is $CR^3R^{3'}$; $A^4$ is $NR^4$; and $A^5$ is $CR^5R^{5'}$.

5. A compound according to claim 2 wherein:

$A^1$ is $NR^1$, $A^2$ is $CHCR^2$, $A^3$ is $CR^3R^{3'}$, $A^4$ is $NR^4$, and $A^5$ are C=O.

6. A compound according to claim 2 wherein:

$A^1$ and $A^4$ are C=O, $A^2$ is $NR^2$, $A^3$ is $CHR^{3'}$ and $A^5$ is $NR^5$.

7. A compound according to claim 2 wherein:

$A^1$ is $NR^1$, $A^2$ is $CHR^2$, $A^3$ is C=O, $A^4$ is NR' and $A^5$ is $CHR^5$.

8. A compound according to claim 3 wherein:

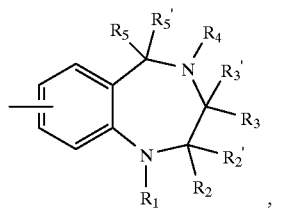
,
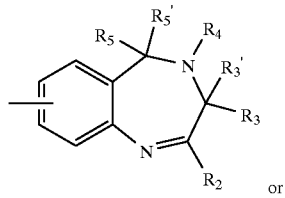
or
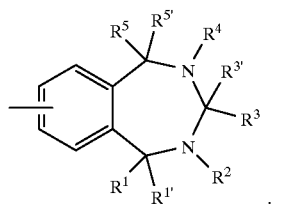
.

9. A compound according to claim 2 wherein:

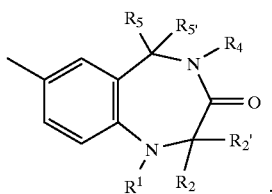

10. A compound according to claim 9 wherein:
$R^1$ is H or $C_{1-4}$alkyl; $R^2, R^{2'}$ are H,—$CH_2CO_2H$; and $R^5R^{5'}$ are H,H.

11. A compound which is:

(2S)-7-[[[N-(2-benzimidazolyl)methyl-N-methyl]amino]carbonyl]-4-methyl-3-oxo-2,3,4,5-tetrahydro-1H-1,4-benzodiazepine-2-acetic acid;

7-[[[2-(4-aza-5-methylbenzimidazolyl)methyl]methylamino]carbonyl]-4-methyl-3-oxo-2,3,4,5-tetrahydro-1H-1,4-benzodiazepine-2-acetic acid;

(±)-7-[[[2-(4-Azabenzimidazolyl)methyl]methylamino]carbonyl]-4-(2-methoxyethyl)-3-oxo-2,3,4,5-tetrahydro-1H-1,4-benzodiazepine-2-acetic acid;

(±)-7-[[[2-(benzimidazolyl)methyl]methylamino]carbonyl]-4-(2-methoxyethyl)-3-oxo-2,3,4,5-tetrahydro-1H-1,4-benzodiazepine-2-acetic acid;

7-[[[2-(4-azabenzimidazolyl)methyl]methylamino]carbonyl]-4-methyl-3-oxo-2,3,4,5-tetrahydro-1H-1,4-benzodiazepine-2-acetic acid;

(2S)-7-[[[N-butyl-N-benzimidazol-2-yl)methyl]amino]carbonyl]-3-oxo-4-methyl-2,3,4,5-tetrahydro-1H-1,4-benzodiazepine-2-acetic acid;

7-[[[(2-benzimidazolyl)methyl]methylamino]carbonyl]-3-oxo-4-(2-phenylethyl)-2,3,4,5-tetrahydro-1H-1,4-benzodiazepine-2-acetic acid;

7-[[[N-(2-benzimidazolyl)methyl-N-(2-phenylethyl)]amino]carbonyl]-4-methyl-3-oxo-2,3,4,5-tetrahydro-1H-1,4-benzodiazepine-2-acetic acid;

(±)-7-[[[2-(benzimidazolyl)methyl]amino]carbonyl-4-[2-(3,4-methylenedioxyphenyl)ethyl]-3-oxo-2,3,4,5-tetrahydro-1H-1,4-benzodiazepine-2-acetic acid;

(±)-7-[[[N-(2-benzimidazolyl)methyl-N-methyl]amino]carbonyl]-3-oxo-4-(2-phenylethyl)-2,3,4,5-tetrahydro-1H-1,4-benzodiazepine-2-acetic acid;

(±)-7-[[[(2-benzimidazolyl)methyl]amino]carbonyl]-4-methyl-3-oxo-2,3,4,5-tetrahydro-1H-1,4-benzodiazepine-2-acetic acid;

(±)-7-[[[(2-benzimidazolyl)methyl]amino]carbonyl]-3-oxo-4-(2-phenylethyl)-2,3,4,5-tetrahydro-1H-1,4-benzodiazepine-2-acetic acid;

(±)-4-isopropyl-7-[[[(2-benzimidazolyl)methyl]aamino]carbonyl]-3-oxo-2,3,4,5-tetrahydro-1H-1,4-benzodiazepine-2-acetic acid;

(±)-7-[[[N-[2-(5(6)-chlorobenzimidazolyl)methyl]-N-methyl]amino]carbonyl]-4-methyl-3-oxo-2,3,4,5-tetrahydro-1H-1,4-benzodiazepine-2-acetic acid;

(2S)-7-[[[(2-Benzimidazolyl)methyl]amino]carbonyl]-4-methyl-3-oxo-2,3,4,5-tetrahydro-1H-1,4-benzodiazepine-2-acetic acid;

(2R)-7-[[[(2-Benzimidazolyl)methyl]amino]carbonyl]-4-methyl-3-oxo-2,3,4,5-tetrahydro-1H-1,4-benzodiazepine-2-acetic acid;

(±)-7-[[[(2-benzimidazolyl)methyl]amino]carbonyl]-9-chloro-4-methyl-3-oxo-2,3,4,5-tetrahydro-1H-1,4-benzodiazepine-2-acetic acid;

(±)-7-[[[N-(2-benzimidazolyl)methyl-N-methyl]amino]carbonyl]-3-oxo-4-(2-phenylethyl)-2,3,4,5-tetrahydro-1H-1,4-benzodiazepine-2-acetic acid;

(±)-7-[[[N-(2-benzimidazolyl)methyl-N-methyl]amino] methyl]-1,4-dimethyl-3-oxo-2,3,4,5-tetrahydro-1H-1,4-benzodiazepine-2-acetic acid;

(±)-7-[[[N-(2-benzimidazolyl)methyl-N-methyl]amino] carbonyl]-4-methyl-3-oxo-2,3,4,5-tetrahydro-1H-1,4-benzodiazepine-2-acetic acid;

(±)-7-[[[2-(2-benzimidazolyl)ethyl]amino]carbonyl]-4-methyl-3-oxo-2,3,4,5-tetrahydro-1H-1,4-benzodiazepine-2-acetic acid;

(±)-7-[[(2-benzimidazolyl)amino]carbonyl]-4-methyl-3-oxo-2,3,4,5-tetrahydro-1H-1,4-benzodiazepine-2-acetic acid;

(2S)-7-[[[N-(2-benzimidazolyl)methyl-N-methyl]amino] carbonyl]-4-methyl-3-oxo-2,3,4,5-tetrahydro-1H-1,4-benzodiazepine-2-acetic acid;

(±)-4-Methyl-7-[[[N-(2-(1-methyl)benzimidazolyl)methyl-N-methyl]amino]carbonyl]-3-oxo-2,3,4,5-tetrahydro-1H-1,4-benzodiazepine-2-acetic acid;

(±)-7-[[[(2-(5(6)-methoxy)benzimidazolyl)methyl]amino] carbonyl]-4-methyl-3-oxo-2,3,4,5-tetrahydro-1H-1,4-benzodiazepine-2-acetic acid;

(±)-7-[[[N-[2-(4-azabenzimidazolyl)]methyl-N-methyl] amino]carbonyl]-4-methyl-3-oxo-2,3,4,5-tetrahydro-1H-1,4-benzodiazepine-2-acetic acid;

(±)-7-[[[N-[2-(5(6)-Azabenzimidazolyl)]methyl-N-methyl] amino]carbonyl]-4-methyl-3-oxo-2,3,4,5-tetrahydro-1H-1,4-benzodiazepine-2-acetic acid;

(±)-7-[[[2-(benzimidazolyl)methyl]methylamino]carbonyl]-4-(2-methoxyethyl)-3-oxo-2,3,4,5-tetrahydro-1H-1,4-benzodiazepine-2-acetic acid;

(±)-7-[[[2-(4-Azabenzimidazolyl)methyl]methylamino] carbonyl]-4-(2-methoxyethyl)-3-oxo-2,3,4,5-tetrahydro-1H-1,4-benzodiazepine-2-acetic acid;

(±)-7-[[[(2-benzimidazolyl)methyl]amino]methyl]-4-methyl-3-oxo-2,3,4,5-tetrahydro-1H-1,4-benzodiazepine-2-acetic acid;

(±)-7-[[[(2-benzimidazolyl)methyl]amino]carbonyl]-1,4-dimethyl-3-oxo-2,3,4,5-tetrahydro-1-1,4-benzodiazepine-2-acetic acid;

(±)-7-[[[(2-benzimidazolyl)methyl]methylamino]carbonyl]-3-oxo-2,3,4,5-tetrahydro-1H-1,4-benzodiazepine-2-acetic acid;

(2S)-7-[[[N-butyl-N-benzimidazol-2-yl)methyl]anino] carbonyl]-3-oxo-4-methyl-2,3,4,5-tetrahydro-1H-1,4-benzodiazepine-2-acetic acid;

7-[[[N-(2-benzimidazolyl)methyl-N-(2-phenylethyl)] amino]carbonyl]-4-methyl-3-oxo-2,3,4,5-tetrahydro-1H-1,4-benzodiazepine-2-acetic acid;

7-[[[N-(2-benzimidazolyl)methyl-N-carboxymethyl]amino] carbonyl]-4-methyl-3-oxo-2,3,4,5-tetrahydro-1H-1,4-benzodiazepine-2-acetic acid;

7-[[[N-(2-benzimidazolyl)methyl-N-cyclohexyl aminojcarbonyl]-4-methyl-3-oxo-2,3,4,5-tetrahydro-1H-1,4-benzodiazepine-2-acetic acid;

(±)-7-[[[2-(5-nitrobenzimidazolyl)methyl]methylamino] carbonyl]-4-methyl-3-oxo-2,3,4,5-tetrahydro-1H-1,4-benzodiazepine-2-acetic acid;

(±)-7-[[[2-(5-aminobenzimidazolyl)methyl]methylamino] carbonyl]-4-methyl-3-oxo-2,3,4,5-tetrahydro-1H-1,4-benzodiazepine-2-acetic acid;

7-[[[2-(5,6-methylendioxybenziinidazolyl)methyl] methylamino]carbonyl]-4-methyl-3-oxo-2,3,4,5-tetrahydro-1H-1,4-benzodiazepine-2-acetic acid;

7-[[[2-(4,6-diazabenzimidazolyl)methyl]methylamino] carbonyl]-4-methyl-3-oxo-2,3,4,5-tetrahydro-1H-1,4-benzodiazepine-2-acetic acid;

7-[[[2-(4-azabenzimidazolyl)methyl]methylamino] carbonyl]-4-methyl-3-oxo-2,3,4,5-tetrahydro-1H-1,4-benzodiazepine-2-acetic acid;

(±)-7-[[[2-(4-azabenzimidazolyl)methyl]methylamino] carbonyl]-4-isopropyl-3-oxo-2,3,4,5-tetrahydro-1H-1,4-benzodiazepine-2-acetic acid;

7-[[[2-(4-aza-5-methylbenzimidazolyl)methyl] methylamino]carbonyl]-4-methyl-3-oxo-2,3,4,5-tetrahydro-1H-1,4-benzodiazepine-2-acetic acid;

7-[[[2-(5,6-dimethoxybenzimidazolyl)methyl] methylamino]carbonyl]-4-methyl-3-oxo-2,3,4,5-tetrahydro-1H-1,4-benzodiazepine-2-acetic acid;

7-[[[(2-benzimidazolyl)methyl]methylarino]carbonyl]-3-oxo-4-(2-phenylethyl)-2,3,4,5-tetrahydro-1H-1,4-benzodiazepine-2-acetic acid;

(±)-7-[[[2-(benzimidazolyl)methyl]amino]carbonyl-4-[2-(3, 4-methylenedioxyphenyl)ethyl]-3-oxo-2,3,4,5-tetrahydro-1H-1,4-benzodiazepine-2-acetic acid;

(+/-)-2,3,4,5-Tetrahydro-7-[[[benzimidazol-2-yl)methyl] methylamino]carbonyl]-4-(3,3-dimethylbutyl)-3-oxo-1H-1,4-benzodiazepine-2-acetic acid;

(-)-7-[[[6-Trifluoromethylbenzimidazoyl-2-ylmethyl] aminomethyl]carbonyl]-2,3,4,5-tetrahydro-4-methyl-3-oxo-benzodiazepine-2-acetic acid;

(-)-7-[[[4,7-Dimethoxybenzimidazoyl-2-ylmethyl] aminomethyl]carbonyl]-2,3,4,5-tetrahydro-4-methyl-3-oxo-benzodiazepine-2-acetic acid;

(+/-)-2,3,4,5-Tetrahydro-7-[[[(benzimidazol-2-yl) methylamino]carbonyl]-4-(3,3-dimethylbutyl)-3-oxo-1H-1,4-benzodiazepine-2-acetic acid;

(-)-7-[[[7-Methylbenzimidazol-2-ylmethyl]methylamino] carbonyl]-2,3,4,5-tetrahydro-4-3-oxo-1,4-benzodiazepine-2-acetic acid;

(2S)-[[[N-aminobutyl-N-(benzimidazlo-2-yl)methyl] aamino]carbonyl]-3-oxo-4-methyl-2,3,4,5-tetrahydro-1H-1,4-benzodiazepine-2-acetic acidbis(trifluoroacetate) salt;

(2S)-[[[N-cyanomethyl-N-(benzimidazlo-2-yl)methyl] amino]carbonyl]-3-oxo-4-methyl-2,3,4,5-tetrahydro-1H-1,4-benzodiazepine-2-acetic acid dihydrochloride salt;

2,3,4,5-Tetrahydro-7-[[[(benzimidazol-2-yl)]methyl]amino] carbonyl]-4-(4-phthalimidobutyl)-3-oxo-1,4-benzodiazepine-2-acetic acid;

(+/-)-7-[[(2-Benzimidazol-2-ylmethyl)-N-methylamino carbonyl]-2,3,4,5-tetrahydro-3-oxo-4-[2-(3',4'-methylenedioxyphenyl)ethyl]-1H-1,4-benzodiazepine-2-acetic acid;

(+/-)-2,3,4,5-Tetrahydro-7-[[[(Benzimidazol-2-yl)methyl] amino]carbonyl]-4-(2-methoxyethyl)-3-oxo-1H-1,4-benzodiazepine-2-acetic acid;

7-[[[2-[1-Methylbenzimidazolyl] benzimidazolylmethylamino]carbonyl]-2,3,4,5-tetrahydro-4-methyl-3-oxo-1H-1,4-benzodiazepine-2-acetic acid;

7-[[[N-Cyclohexyl-N-(benziniidazol-2-yl)methyl]amino] carbonyl]-3-oxo-2,3,4,5-tetrahydro-1H-1,4-benzodiazepine-2-acetic acid;

7-[[[2-Bis-(Benzimidazolylmethyl)aminocarbonyl]-2,3,4,5-tetrahydro-4-methyl-3-oxo-1H-1,4-benzodiazepine-2-acetic acid;

(+/-)-7-[[(2-Benzimidazol-2-ylmethyl)-N-methylamino carbonyl-2,3,4,5-tetrahydro-3-oxo-4-(2',2',2'-trifluoroethyl)-1H-1,4-benzodiazepine-2-acetic acid;

(+/-)-7-[[(2-Benzimidazolyl)acetyl]amino]-5-oxo-4-(2-phenylethyl)-2,3,4,5-tetrahydro-1H-1,4-benzodiazepine-2-acetic acid;

(+/-)-7-[[(2-Benzimidazol-2-ylmethyl)ariino]carbonyl]-2,3, 4,5-tetrahydro-3-oxo-4-(2',2',2'-trifluoroethyl)-1H-1,4-benzodiazepine-2-acetic acid;

(-)-7-[[[5,6-Difluorobenzimidazoyl-2-ylmethyl] aminomethyl]carbonyl]-2,3,4,5-tetrahydro-4-methyl-3-oxo-1,4-benzodiazepine-2-acetic acid; and (+/−)-7-[[Bis-(Benzimidazol-2-ylmethyl)amino]carbonyl]-2,3,4,5-tetrahydro-4-phenylethyl-3-oxo-1H-1,4-benzodiazepine-2-acetic acidtris(trifluoroacetate)salt.

12. A pharmaceutical composition having vitronectin receptor inhibiting activity which comprises a pharmaceutically acceptable carrier and a compound according to formula (I) or (II) or (III) or (IV) or (V).

13. A method of inhibiting a vitronectin receptor in a mammal which comprises administering an effective amount of a compound according to formula (I) or (II) or (III) or (IV) or (V):

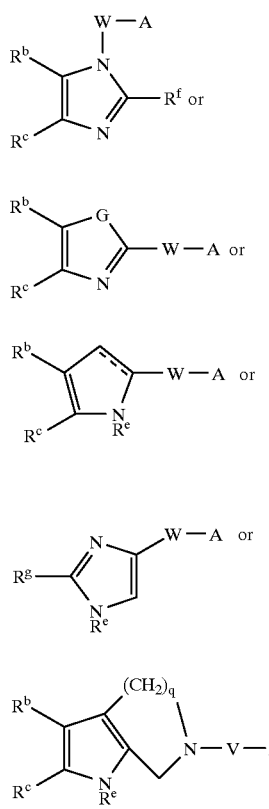

wherein:

W is $CHR^g_a$—U—$CHR^g_b$—V— or

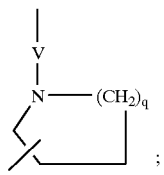

A is a fibrinogen receptor antagonist template;

U and V are absent or CO, $CR^g_2$, C(=$CR^g_2$), S(O)$_k$, O, $NR^g$, $CR^gOR^g$, $CR^g(OR^k)CR^g_2$, $CR^g_2CR^g(OR^k)$, C(O)$CR^g_2$, $CR^g_2C(O)$, $CONR^i$, $NR^iCO$, OC(O), C(O)O, C(S)O, OC(S), C(S)$NR^g$, $NR^g$C(S), S(O)$_2NR^g$, $NR^g$S(O)$_2$ N=N, $NR^gNR^g$, $NR^gCR^g_2$, $NR^gCR^g_2$, $CR^g_2O$, $OCR^g_2$, C≡C or $CR^g$=$CR^g$;

G is $NR^e$, S or O;

$R^g$ is H, $C_{1-6}$alkyl, Het-$C_{0-6}$alkyl, $C_{3-7}$cycloalkyl-$C_{0-6}$alkyl or Ar—$C_{0-6}$alkyl;

$R^k$ is $R^g$, —C(O)$R^g$, or —C(O)O$R^f$;

$R^i$ is H, $C_{1-6}$alkyl, Het-$C_{0-6}$alkyl, $C_{3-7}$cycloalkyl-$C_{0-6}$alkyl, Ar—$C_{0-6}$alkyl, or $C_{1-6}$alkyl substituted by one to three groups chosed from halogen, CN, $NR^g_2$, $OR^g$, $SR^g$, $CO_2R^g$, and CON($R^g$)$_2$;

$R^f$ is H, $C_{1-6}$alkyl or Ar—$C_{1-6}$alkyl;

$R^e$ is H, $C_{1-6}$alkyl, Ar—$C_{1-6}$alkyl, Het-$C_{1-6}$alkyl, $C_{3-7}$cycloalkyl-$C_{1-6}$alkyl, or (CH$_2$)$_k$CO$_2R^g$;

k is 0, 1 or 2;

q is 1 or 2;

a is 0, 1 or 2;

b is 0, 1 or 2;

$R^b$ and $R^c$ are independently selected from H, $C_{1-6}$alkyl, Ar—$C_{0-6}$alkyl, Het-$C_{0-6}$alkyl, or $C_{3-6}$cycloalkyl-$C_{0-6}$alkyl, halogen, CF$_3$, $OR^f$, S(O)$_kR^f$, $COR^f$, NO$_2$, N($R^f$)$_2$, CO($NR^f$)$_2$, CH$_2$N($R^f$)$_2$, or $R^b$ and $R^c$ are joined together to form a five or six membered aromatic or non-aromatic carbocyclic or heterocyclic ring, optionally substituted by up to three substituents chosen from halogen, CF$_3$, $C_{1-4}$alkyl, $OR^f$, S(O)$_kR^f$, $COR^f$, CO$_2R^f$OH, NO$_2$, N($R^f$)$_2$, CO($NR^f$)$_2$, and CH$_2$N($R^f$)$_2$; or methylenedioxy;

or a pharmaceutically acceptable salt thereof.

14. A method according to claim 13 wherein the compound inhibits the vitronectin receptor at a concentration of less than 50 micromolar.

15. A method according to claim 13 wherein the compound inhibits the vitronectin receptor at a concentration of less than 1 micromolar.

16. A method according to claim 13 wherein the compound inhibits the vitronectin receptor with a Ki at the vitronectin receptor that is ten-fold greater than the Ki for said compound at the fibrinogen receptor.

17. A method according to claim 13 wherein the compound inhibits the vitronectin receptor with a Ki at the vitronectin receptor that is thirty-fold greater than the Ki for said compound at the fibrinogen receptor.

18. A method according to claim 13 wherein the compound inhibits the vitronectin receptor with a Ki at the vitronectin receptor that is a hundred-fold greater than the Ki for said compound at the fibrinogen receptor.

* * * * *